(12) United States Patent
Chang et al.

(10) Patent No.: US 12,227,484 B2
(45) Date of Patent: Feb. 18, 2025

(54) INHIBITORS OF PARG

(71) Applicant: ARase Therapeutics Inc., Cambridge, MA (US)

(72) Inventors: Paul Chang, Cambridge, MA (US); Katherine Widdowson, Cambridge, MA (US); Lisa J. Ames, Cambridge, MA (US)

(73) Assignee: ARase Therapeutics Inc., Boston, MA (US)

( * ) Notice: Subject to any disclaimer, the term of this patent is extended or adjusted under 35 U.S.C. 154(b) by 0 days.

(21) Appl. No.: 18/168,322

(22) Filed: Feb. 13, 2023

(65) Prior Publication Data
US 2023/0265057 A1 Aug. 24, 2023

Related U.S. Application Data

(60) Provisional application No. 63/309,753, filed on Feb. 14, 2022.

(51) Int. Cl.
| | |
|---|---|
| C07D 239/80 | (2006.01) |
| C07D 405/12 | (2006.01) |
| C07D 405/14 | (2006.01) |
| C07D 409/12 | (2006.01) |
| C07D 417/04 | (2006.01) |
| C07D 417/14 | (2006.01) |
| C07D 487/12 | (2006.01) |

(52) U.S. Cl.
CPC ......... *C07D 239/80* (2013.01); *C07D 405/12* (2013.01); *C07D 405/14* (2013.01); *C07D 409/12* (2013.01); *C07D 417/04* (2013.01); *C07D 417/14* (2013.01); *C07D 487/12* (2013.01)

(58) Field of Classification Search
CPC .. C07D 239/80; C07D 405/12; C07D 405/14; C07D 409/12; C07D 417/04; C07D 417/14; C07D 487/12
See application file for complete search history.

(56) References Cited

U.S. PATENT DOCUMENTS

| | | |
|---|---|---|
| 5,118,594 A | 6/1992 | Lestina et al. |
| 2021/0380539 A1 | 12/2021 | McGonagle et al. |
| 2022/0332708 A1 | 10/2022 | Gardina et al. |
| 2023/0278998 A1 | 9/2023 | Xu et al. |
| 2024/0140954 A1 | 5/2024 | Zhuo et al. |

FOREIGN PATENT DOCUMENTS

| | | |
|---|---|---|
| CN | 117157299 | 5/2024 |
| TW | 202241908 | 11/2022 |
| WO | WO 2003/024955 | 3/2003 |
| WO | WO 2009/012242 | 1/2009 |
| WO | WO 2016/024185 | 2/2016 |
| WO | WO 2016/092326 | 6/2016 |
| WO | WO 2016/097749 | 6/2016 |
| WO | WO 2020/028221 | 2/2020 |
| WO | WO 2021/055744 | 3/2021 |
| WO | WO 2023/057389 | 4/2023 |
| WO | WO 2023/057394 | 4/2023 |
| WO | WO 2023/165571 | 9/2023 |
| WO | WO 2023/175184 | 9/2023 |
| WO | WO 2023/175185 | 9/2023 |
| WO | WO 2023/208092 | 11/2023 |
| WO | WO 2023/224998 | 11/2023 |
| WO | WO 2024/002284 | 1/2024 |
| WO | WO 2024/017306 | 1/2024 |
| WO | WO 2014/066491 | 5/2024 |

OTHER PUBLICATIONS

Chen; Bioinformatics 2005, 21, 4133-4139. https://doi.org/10.1093/bioinformatics/bti683 (Year: 2005).*
Chemical Abstracts STN Registry Database, Record for RN 1023477-61-3, "N-cyclopentyl-1,2,3,4-tetrahydro-1,3-dimethyl-2,4-dioxo-6-quinazolinesulfonamide". Entered STN May 29, 2008. (Year: 2008).*
Yamazaki; "Unique properties of Fluorine and Their relevance to Medicinal Chemistry and Chemical Biology" Chapter 1 in "Fluorine in Medicinal Chemistry and Chemical Biology" (Blackwell Publishing, 2009) pp. 3-46. (Year: 2009).*
Chemical Abstracts STN Registry Database, entry for RN 958716-37-5, "1,2,3,4-Tetrahydro-1,3-dimethyl-2,4-dioxo-N-(2-phenylcyclopropyl)-6-Quinazolinesulfonamide", Entered into STN Dec. 19, 2007. (Year: 2007).*
Chemical Abstracts STN Registry Database, entry for RN 2134699-54-8, "1,2,3,4-Tetrahydro-1-methyl-2,4-dioxo-N-(tetrahydro-3-methyl-3-furanyl)pyrido[2,3-d]pyrimidine-6-sulfonamide", Entered into STN Oct. 15, 2017. (Year: 2017).*
Waszkowycz; J. Med. Chem. 2018, 61, 23, 10767-10792. https://doi.org/10.1021/acs.jmedchem.8b01407 (Year: 2018).*
Slade; Genes & Dev. 2020, 34, 360-394. https://doi.org/10.1101/gad.334516.119 (Year: 2020).*
Chemical Abstracts STN Registry Database, record for RN 1378013-26-3, "rel-1,2,3,4-tetrahydro-1,3-dimethyl-N-[(1R,2S)-2-[(1-methylethyl)amino]cyclobutyl]-2,4-dioxo-6-quinazolinesulfonamide", Entered STN Jun. 13, 2012. (Year: 2012).*
National Center for Biotechnology Information. PubChem Compound Summary for CID 157019391, 3-methyl-2,4-dioxo-N-[(3S,4S)-4-(pyridin-4-ylmethyl)oxolan-3-yl]-1H-quinazoline-6-sulfonamide. https://pubchem.ncbi.nlm.nih.gov/compound/157019391. Create Date Nov. 29, 2021. Accessed Aug. 8, 2024. (Year: 2021).*
Bock et al., "RNA Regulation by Poly(ADP-Ribose) Polymerases," Mol. Cell, Jun. 18, 2015, 58(6):959-969.
Caiafa et al., "Epigenetics: poly(ADP-ribosyl)ation of PARP-1 regulates genomic methylation patterns," FASEB J., Mar. 2009, 23(3):672-678.

(Continued)

*Primary Examiner* — Daniel R Carcanague
(74) *Attorney, Agent, or Firm* — Fish & Richardson P.C.

(57) ABSTRACT

The present invention relates to sulfonamides and related compounds which are inhibitors of PARG and are useful in the treatment of cancer.

57 Claims, No Drawings

(56) References Cited

OTHER PUBLICATIONS

Chang et al., "Poly(ADP-ribose) is required for spindle assembly and structure," Nature, Dec. 2, 2004, 432(7017): 645-649.
Cohen et al., "Insights into the biogenesis, function, and regulation of ADPribosylation," Nat Chem Biol., Feb. 14, 2018, 14(3)236-243.
Curtin et al., "Therapeutic applications of PARP inhibitors: anticancer therapy and beyond," Mol Aspects Med., 2013, 34(6):1217-1256.
Dahl et al., "Fine-Tuning of Smad Protein Function by Poly(ADP-Ribose) Polymerasesand Poly(ADP-Ribose) Glycohydrolase during Transforming Growth Factor β Signaling," Plos One, Aug. 2014, 9(8):e103651(19 pages).
Guastafierro et al., "ADP-ribose polymer depletion leads to nuclear Ctcf re-localization and chromatin rearrangement(1)," Biochem J., Feb. 1, 2013, 449(3):623-630.
James et al., "First-in-Class Chemical Probes against Poly(ADP-ribose) Glycohydrolase (PARG) Inhibit DNA Repair with Differential Pharmacology to Olaparib," ACS Chemical Biology, Nov. 18, 2016, 11(11):3179-3190.
Le May et al., "Poly (ADP-Ribose) Glycohydrolase Regulates Retinoic Acid Receptor-Mediated Gene Expression," Mol Cell, Dec. 14, 2012, 48:785-798.
Leung et al., "Poly(ADP-ribose) regulates stress responses and microRNA activity in the cytoplasm," Mol Cell., May 20, 2011, 42(4):489-499.
Mortusewicz et al., "PARG is recruited to DNA damage sites through poly(ADP-ribose)-and PCNA-dependent mechanisms," Nucleic Acid Res., Jul. 2011, 39(12):5045-5056.
PCT International Search Report and Written Opinion in International Appln. No. PCT/US2023/062470, mailed on May 19, 2023, 18 pages.
International Preliminary Report on Patentability in International Appln. No. PCT/US2023/062470, mailed Aug. 29, 2024, 10 pages.
International Search Report and Written Opinion in International Appln. No. PCT/US2024/015371, mailed on May 28, 2024, 16 pages.

* cited by examiner

INHIBITORS OF PARG

CROSS-REFERENCE TO RELATED APPLICATION

This application claims the benefit of U.S. Provisional Application No. 63/309,753, filed Feb. 14, 2022.

FIELD OF THE INVENTION

The present invention relates to sulfonamides and related compounds which are inhibitors of PARG and are useful in the treatment of cancer.

BACKGROUND OF THE INVENTION

Cancer is a disease caused by abnormal and unregulated cell division. One of the hallmarks of cancer is the up or downregulation of cellular stress pathways which the cancer cells or tumor use for a proliferative advantage. These cellular stress pathways often include, but are not limited to, oxidative stress, DNA damage stress, DNA replicative stress, transcriptional stress, hypoxia, and others.

ADP-ribose, as well as the enzymes that generate ADP-ribose (Poly(ADP-ribose) polymerases or PARPs) and hydrolyze ADP-ribose (Poly(ADP-ribose) glycohydrolases or PARGs), play critical roles in regulating cellular stress responses. There are two forms of ADP-ribose in the cell, mono(ADP-ribose) (MAR) and Poly(ADP-ribose) (PAR). Both forms of ADP-ribose are generated by a family of 17 PARP proteins, whose key roles in the cell are to regulate cellular stress responses (Cohen M S, Chang P. Nat Chem Biol. 2018).

In humans, PARG exists as a single gene with 3 splicing isoforms. These isoforms function in and are localized to the nucleus, cytoplasm, and mitochondria. The best understood function for PARG is in DNA damage repair. However, PARG also regulates gene splicing, transcriptional and epigenetic pathways (Bock F J, Todorova T T, Chang P. Mol Cell 2015) (Le May, Litis et al. Mol Cell. 2012) (Dahl, Maturi et al. Plos One, 2014) (Guastafierro, Catizone et al. Biochem J 2013) (Caiafa, Guastafierro et al. FASEB J 2009), cell division (Chang and Mitchison Nature 2004), the cytoplasmic stress response (Leung, Chang et al. Mol Cell 2011), and other cellular stresses.

Modulation of both MAR and PAR levels have been shown to be effective treatments for multiple cancers. Inhibiting ADP-ribose synthesis through the use of PARP inhibitors can be used for the treatment of multiple cancer types. PARG inhibitors work by modulating cellular stress responses such as the DNA damage response (DDR) and the replicative stress response. DDR and replicative stress are very important cellular stress responses for cancers because they are a consequence of all cellular stress responses, thus many cancers have them.

Cancers accumulate DNA damage due to the upregulation of cellular stress pathways and subsequent errors in DNA replication. In cancers, single-strand breaks (SSBs) are the most common type of DNA damage lesion and PARG together with PARP1 play important roles in single strand break repair (SSBR) and another repair mechanism called base excision repair (BER). PARP1 recognizes the break, binds to it, and rapidly synthesizes PAR onto itself (automodification) and histone proteins. Multiple DNA repair proteins, including a master regulator XRCC1, bind to and are recruited to the newly synthesized PAR and then repair the break (Mortusewicz, Fouquerel et al. Nucleic Acid Res. 2011). Thus, the rapid increase in PAR acts as a key DNA repair signal. The signal initiated by PAR is transient as it becomes rapidly degraded by PARG. If PARG is absent or non-functional, PAR rapidly accumulates in the cancer cell and is toxic, resulting in cell death. When PARP1 is bound to or automodified by PAR, its catalytic activity is reduced and therefore PARG activity helps activate PARP1 and is an important regulator to keep the DNA damage repair signal "on" (Curtin and Szabo Mol Aspects Med. 2013).

PARG depletion by RNA interference (RNAi) has been shown to kill cancer cells and to result in tumor regression in multiple murine cancer models. Human and murine cells that are null or depleted for PARG display an increased sensitivity to DNA damaging agents demonstrating a general defect in DNA damage related stress responses upon inhibition or depletion of PARG. Other cancer relevant stress pathways have also been shown to be defective upon PARG knockdown, suggesting PARG is an attractive target for the treatment of multiple cancer types. In humans, PARG depletion kills lung, ovarian, breast, cervical, and pancreatic cancer cells in vitro. Xenograft models of these human cancers implanted into mice show tumor regression when PARG protein expression is knocked down. Together, these results demonstrate that PARG is an effective target for the treatment of multiple stress-dependent cancers, and potentially cancers where cellular stress responses are not obviously present. This invention seeks to provide cell permeable inhibitors of PARG.

SUMMARY OF THE INVENTION

The present invention is directed to a compound of Formula I:

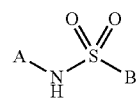

or a pharmaceutically acceptable salt thereof, wherein constituent members are defined below.

The present invention is further directed to a pharmaceutical composition comprising a compound of Formula I, or a pharmaceutically acceptable salt thereof, and at least one pharmaceutically acceptable carrier.

The present invention is further directed to a method of inhibiting the activity of PARG comprising contacting a compound of Formula I, or a pharmaceutically acceptable salt thereof, with PARG.

The present invention is further directed to a method of treating a disease or disorder in a patient in need of treatment, where the disease or disorder is characterized by overexpression or increased activity of PARG, comprising administering to the patient a therapeutically effective amount of a compound of Formula I, or a pharmaceutically acceptable salt thereof.

The present invention is further directed to a method of treating cancer in a subject in need thereof, the method comprising administering to the subject a therapeutically effective amount of an agent that inhibits PARG activity, such as a compound of Formula I, or a pharmaceutically acceptable salt thereof. The present disclosure also provides uses of the compounds described herein in the manufacture of a medicament for use in therapy. The present disclosure also provides the compounds described herein for use in therapy.

DETAILED DESCRIPTION

The present invention is directed to a compound of Formula I:

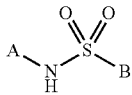
I or a pharmaceutically acceptable salt thereof, wherein:

A is a group having the formula:

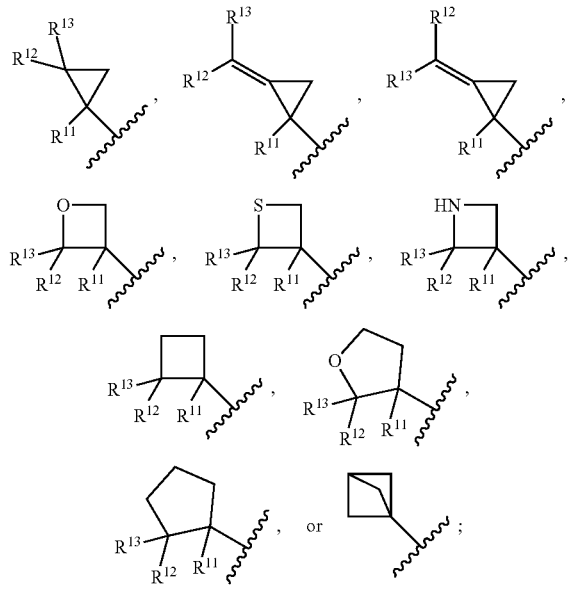

B is a group of formula (a), formula (b), or formula (c):

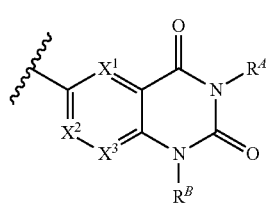
(a)

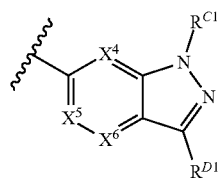
(b)

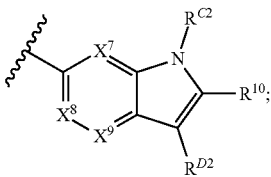
(c)

$X^1$ is N or $CR^1$;
$X^2$ is N or $CR^2$;
$X^3$ is N or $CR^3$;
$X^4$ is N or $CR^4$;
$X^5$ is N or $CR^5$;
$X^6$ is N or $CR^6$;
$X^7$ is N or $CR^7$;
$X^8$ is N or $CR^8$;
$X^9$ is N or $CR^9$;

wherein no more than two of $X^1$, $X^2$, and $X^3$ are simultaneously N;

wherein no more than two of $X^4$, $X^5$, and $X^6$ are simultaneously N;

wherein no more than two of $X^7$, $X^8$, and $X^9$ are simultaneously N;

$R^1$, $R^2$, $R^4$, $R^5$, $R^7$, and $R^8$ are each independently selected from H, halo, and $C_{1-4}$ alkyl;

$R^3$, $R^6$, and $R^9$ are each independently selected from H, halo, $NR^cR^d$, $OR^a$, $C_{6-10}$ aryl, $C_{3-7}$ cycloalkyl, 5-10 membered heteroaryl, and 4-10 membered heterocycloalkyl, wherein said $C_{6-10}$ aryl, $C_{3-7}$ cycloalkyl, 5-10 membered heteroaryl, and 4-10 membered heterocycloalkyl of $R^3$, $R^6$, and $R^9$ are each optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

$R^{10}$ is H, halo, $C_{1-4}$ alkyl, or $C_{1-4}$ haloalkyl;

$R^A$ and $R^B$ are each independently selected from H, $C_{1-4}$ alkyl, and $C_{2-6}$ alkenyl, wherein said $C_{1-4}$ alkyl and $C_{2-6}$ alkenyl of $R^A$ and $R^B$ are each optionally substituted with 1, 2, or 3 substituents independently selected from $Cy^1$, halo, $C_{1-4}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c2}R^{d2}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2 NR^{c1}R^{d1}$;

wherein at least one of $R^A$ and $R^B$ is other than H;

$R^{C1}$ and $R^{C2}$ are independently selected from $C_{1-6}$ alkyl, $C_{2-6}$ alkenyl, and 5-membered heteroaryl, wherein said $C_{1-6}$ alkyl, $C_{2-6}$ alkenyl, and 5-membered heteroaryl of $R^{C1}$ and $R^{C2}$ are each optionally substituted with 1, 2, 3, or 4 substituents independently selected from halo, $C_{1-6}$ alkyl, $C_{1-6}$ alkyl substituted with R', $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each R' is independently selected from halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^{D1}$ and $R^{D2}$ are independently selected from H, halo, and $C_{1-4}$ alkyl;

$R^{11}$ is H, CN, CCR", $CH_3$, $CH_2CN$, $CH_2OH$, $CHF_2$, or $CH_2F$;

R" is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $C(O)R^{b3}$, $C(O)NR^{c3}R^{d3}$, $C(O)OR^{a3}$, or $NR^{c3}R^{d3}$; $R^{12}$ is H or F;

$R^{13}$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, or $S(O)_2NR^{c3}R^{d3}$, wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^{13}$ is optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein when A is a group of formula:

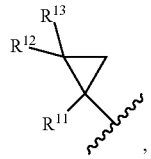

, then $R^{13}$ is other than H, $CH_3$, and CN;

or $R^{12}$ and $R^{13}$, together with the C atom to which they are attached, form a $C_3$ cycloalkyl or 3-membered heterocycloalkyl group comprising one heteroatom selected from N and O, optionally substituted with 1, 2, or 3 substituents independently selected from halo, $C_{1-4}$ alkyl, $C_{1-4}$haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $Cy^1$ is independently selected from $C_{6-10}$ aryl, $C_{3-7}$ cycloalkyl, 5-10 membered heteroaryl, and 4-10 membered heterocycloalkyl, each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{a1}$, $S(O)_2R^{b1}$, and $S(O)_2NR^{c1}R^{d1}$;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is optionally substituted with 1, 2, 3, 4, or 5 substituents independently selected from halo, $C_{1-4}$ alkyl, $C_{1-4}$haloalkyl, $C_{1-6}$ haloalkyl, $C_{2-6}$ alkenyl, $C_{2-6}$ alkynyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or $R^c$ and $R^d$, together with the N atom to which they are attached, form a 4-7 membered heterocycloalkyl group optionally substituted with 1, 2, or 3 substituents independently selected from halo, $C_{1-4}$ alkyl, $C_{1-4}$haloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or $R^{c1}$ and $R^{d1}$, together with the N atom to which they are attached, form a 4-7 membered heterocycloalkyl group optionally substituted with 1, 2, or 3 substituents independently selected from halo, $C_{1-4}$ alkyl, $C_{1-4}$haloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)$ $NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or $R^{c2}$ and $R^{d2}$, together with the N atom to which they are attached, form a 4-7 membered heterocycloalkyl group optionally substituted with 1, 2, or 3 substituents independently selected from halo, $C_{1-4}$ alkyl, $C_{1-4}$ haloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or $R^{c3}$ and $R^{d3}$, together with the N atom to which they are attached, form a 4-7 membered heterocycloalkyl group optionally substituted with 1, 2, or 3 substituents independently selected from halo, $C_{1-4}$ alkyl, $C_{1-4}$ haloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy; and each $R^e$, $R^{e1}$, $R^{e2}$, $R^{e3}$, and $R^{e4}$ is independently selected from H, $C_{1-4}$ alkyl, and CN.

The present invention is directed to a compound of Formula I:

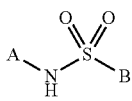

I or a pharmaceutically acceptable salt thereof, wherein:

A is a group having the formula:

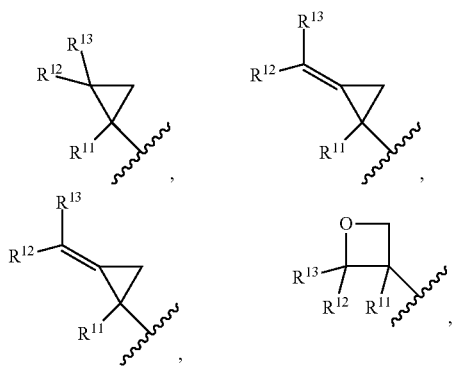

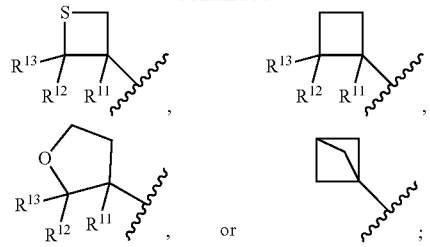

B is a group of formula (a), formula (b), or formula (c):

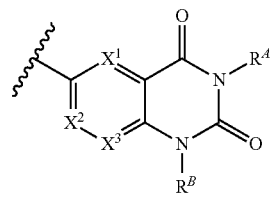

(a)

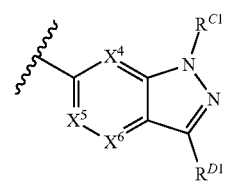

(b)

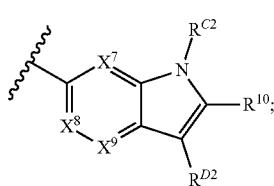

(c)

$X^1$ is N or $CR^1$;
$X^2$ is N or $CR^2$;
$X^3$ is N or $CR^3$;
$X^4$ is N or $CR^4$;
$X^5$ is N or $CR^5$;
$X^6$ is N or $CR^6$;
$X^7$ is N or $CR^7$;
$X^8$ is N or $CR^8$;
$X^9$ is N or $CR^9$;

wherein no more than two of $X^1$, $X^2$, and $X^3$ are simultaneously N;

wherein no more than two of $X^4$, $X^5$, and $X^6$ are simultaneously N;

wherein no more than two of $X^7$, $X^8$, and $X^9$ are simultaneously N;

$R^1$, $R^2$, $R^4$, $R^5$, $R^7$, and $R^8$ are each independently selected from H, halo, and $C_{1-4}$ alkyl;

$R^3$, $R^6$, and $R^9$ are each independently selected from H, $C_{6-10}$ aryl, $C_{3-7}$ cycloalkyl, 5-10 membered heteroaryl, and 4-10 membered heterocycloalkyl, wherein said $C_{6-10}$ aryl, $C_{3-7}$ cycloalkyl, 5-10 membered heteroaryl, and 4-10 membered heterocycloalkyl of $R^3$, $R^6$, and $R^9$ are each optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, C(O)

NR$^c$R$^d$, C(O)OR$^a$, OC(O)R$^b$, OC(O)NR$^c$R$^d$, C(=NR$^e$) NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

R$^{10}$ is H, halo, C$_{1-4}$ alkyl, or C$_{1-4}$ haloalkyl;

R$^A$ and R$^B$ are each independently selected from H, C$_{1-4}$ alkyl, and C$_{2-6}$ alkenyl, wherein said C$_{1-4}$ alkyl and C$_{2-6}$ alkenyl of R$^A$ and R$^B$ are each optionally substituted with 1, 2, or 3 substituents independently selected from Cy$^1$, halo, C$_{1-4}$ alkyl, C$_{2-6}$ alkenyl, C$_{2-6}$ alkynyl, C$_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O) NR$^{c1}$R$^{d1}$, NR$^{c1}$S(O)R$^{b1}$, NR$^{c1}$S(O)$_2$R$^{b1}$, NR$^{c1}$S(O)$_2$ NR$^{c1}$R$^{d1}$, S(O)R$^{b1}$, S(O)NR$^{c1}$R$^{d1}$, S(O)$_2$R$^{b1}$, and S(O)$_2$ NR$^{c1}$R$^{d1}$;

wherein at least one of R$^A$ and R$^B$ is other than H;

R$^{C1}$ and R$^{C2}$ are independently selected from C$_{1-6}$ alkyl, C$_{2-6}$ alkenyl, and 5-membered heteroaryl, wherein said C$_{1-6}$ alkyl, C$_{2-6}$ alkenyl, and 5-membered heteroaryl of R$^{C1}$ and R$^{C2}$ are each optionally substituted with 1, 2, 3, or 4 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a2}$, SR$^{a2}$, C(O)R$^{b2}$, C(O)NR$^{c2}$R$^{d2}$, C(O) OR$^{a2}$, OC(O)R$^{b2}$, OC(O)NR$^{c2}$R$^{d2}$, C(=NR$^{e2}$) NR$^{c2}$R$^{d2}$, NR$^{c2}$C(=NR$^{e2}$)NR$^{c2}$R$^{d2}$, NR$^{c2}$R$^{d2}$, NR$^{c2}$C (O)R$^{b2}$, NR$^{c2}$C(O)OR$^{a2}$, NR$^{c2}$C(O)NR$^{c2}$R$^{d2}$, NR$^{c2}$S (O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

R$^{D1}$ and R$^{D2}$ are independently selected from H, halo, and C$_{1-4}$ alkyl;

R$^{11}$ is CN, CH$_3$, CHF$_2$, or CH$_2$F;

R$^{12}$ is H or F;

R$^{13}$ is H, halo, C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O) NR$^{c3}$R$^{d3}$, C(=NR$^{e3}$)NR$^{c3}$R$^{d3}$, NR$^{c3}$C(=NR$^{e3}$) NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$ R$^{b3}$, or S(O)$_2$NR$^{c3}$R$^{d3}$, wherein said C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of R$^{13}$ is optionally substituted with 1, 2, 3, or 4 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O) NR$^{c3}$R$^{d3}$, S(O)$_2$R$^{b3}$, and S(O)$_2$NR$^{c3}$R$^{d3}$, wherein when A is a group of formula:

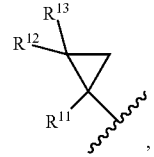

then R$^{13}$ is other than H, CH$_3$, and CN;

or R$^{12}$ and R$^{13}$, together with the C atom to which they are attached, form a C$_3$ cycloalkyl or 3-membered heterocycloalkyl group comprising one heteroatom selected from N and O, optionally substituted with 1, 2, or 3 substituents independently selected from halo, C$_{1-4}$ alkyl, C$_{1-4}$haloalkyl, CN, OR$^{a3}$, SR$^{a3}$, C(O)R$^{b3}$, C(O) NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C (O)OR$^{a3}$, C(=NR$^{e3}$)NR$^{c3}$R$^{d3}$, NR$^{c3}$C(=NR$^{e3}$) NR$^{c3}$R$^{d3}$, S(O)R$^{b3}$, S(O)NR$^{c3}$R$^{d3}$, S(O)$_2$R$^{b3}$, NR$^{c3}$S (O)$_2$R$^{b3}$, NR$^{c3}$S(O)$_2$NR$^{c3}$R$^{d3}$, and S(O)$_2$NR$^{c3}$R$^{d3}$;

each Cy$^1$ is independently selected from C$_{6-10}$ aryl, C$_{3-7}$ cycloalkyl, 5-10 membered heteroaryl, and 4-10 membered heterocycloalkyl, each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$) NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$ R$^{b1}$, and S(O)$_2$NR$^{c1}$R$^{d1}$;

each R$^a$, R$^b$, R$^c$, R$^d$, R$^{a1}$, R$^{b1}$, R$^{c1}$, R$^{d1}$, R$^{a2}$, R$^{b2}$, R$^{c2}$, R$^{d2}$, R$^{a3}$, R$^{b3}$, R$^{c3}$, and R$^{d3}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of R$^a$, R$^b$, R$^c$, R$^d$, R$^{a1}$, R$^{b1}$, R$^{c1}$, R$^{d1}$, R$^{a2}$, R$^{b2}$, R$^{c2}$, R$^{d2}$, R$^{a3}$, R$^{b3}$, R$^{c3}$, and R$^{d3}$ is optionally substituted with 1, 2, 3, 4, or 5 substituents independently selected from halo, C$_{1-4}$ alkyl, C$_{1-4}$haloalkyl, C$_{1-6}$ haloalkyl, C$_{2-6}$ alkenyl, C$_{2-6}$ alkynyl, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O) NR$^{c4}$R$^{d4}$, NR$^{c4}$C(O)OR$^{a4}$, C(=NR$^{e4}$)NR$^{c4}$R$^{d4}$, NR$^{c4}$C(=NR$^{e4}$)NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$, NR$^{c4}$S(O)$_2$NR$^{c4}$R$^{d4}$, and S(O)$_2$NR$^{c4}$R$^{d4}$;

or R$^c$ and R$^d$, together with the N atom to which they are attached, form a 4-7 membered heterocycloalkyl group optionally substituted with 1, 2, or 3 substituents independently selected from halo, C$_{1-4}$ alkyl, C$_{1-4}$haloalkyl, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{e4}$) NR$^{c4}$R$^{d4}$, NR$^{c4}$C(=NR$^{e4}$)NR$^{c4}$R$^{d4}$, S(O)R$^{b4}$, S(O) NR$^{c4}$R$^{d4}$, S(O)$_2$R$^{b4}$, NR$^{c4}$S(O)$_2$R$^{b4}$, NR$^{c4}$S(O)$_2$ NR$^{c4}$R$^{d4}$, and S(O)$_2$NR$^{c4}$R$^{d4}$;

or R$^{c1}$ and R$^{d1}$, together with the N atom to which they are attached, form a 4-7 membered heterocycloalkyl group optionally substituted with 1, 2, or 3 substituents independently selected from halo, C$_{1-4}$ alkyl, C$_{1-4}$ haloalkyl, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{e4}$) NR$^{c4}$R$^{d4}$, NR$^{c4}$C(=NR$^{e4}$)NR$^{c4}$R$^{d4}$, S(O)R$^{b4}$, S(O) NR$^{c4}$R$^{d4}$, S(O)$_2$R$^{b4}$, NR$^{c4}$S(O)$_2$R$^{b4}$, NR$^{c4}$S(O)$_2$ NR$^{c4}$R$^{d4}$, and S(O)$_2$NR$^{c4}$R$^{d4}$;

or R$^{c2}$ and R$^{d2}$, together with the N atom to which they are attached, form a 4-7 membered heterocycloalkyl group optionally substituted with 1, 2, or 3 substituents independently selected from halo, C$_{1-4}$ alkyl, C$_{1-4}$ haloalkyl, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{e4}$) NR$^{c4}$R$^{d4}$, NR$^{c4}$C(=NR$^{e4}$)NR$^{c4}$R$^{d4}$, S(O)R$^{b4}$, S(O) NR$^{c4}$R$^{d4}$, S(O)$_2$R$^{b4}$, NR$^{c4}$S(O)$_2$R$^{b4}$, NR$^{c4}$S(O)$_2$ NR$^{c4}$R$^{d4}$, and S(O)$_2$NR$^{c4}$R$^{d4}$;

or R$^{c3}$ and R$^{d3}$, together with the N atom to which they are attached, form a 4-7 membered heterocycloalkyl group optionally substituted with 1, 2, or 3 substituents independently selected from halo, C$_{1-4}$ alkyl, C$_{1-4}$ haloalkyl, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{e4}$) NR$^{c4}$R$^{d4}$, NR$^{c4}$C(=NR$^{e4}$)NR$^{c4}$R$^{d4}$, S(O)R$^{b4}$, S(O) NR$^{c4}$R$^{d4}$, S(O)$_2$R$^{b4}$, NR$^{c4}$S(O)$_2$R$^{b4}$, NR$^{c4}$S(O)$_2$ NR$^{c4}$R$^{d4}$, and S(O)$_2$NR$^{c4}$R$^{d4}$;

each R$^{a4}$, R$^{b4}$, R$^{c4}$, and R$^{d4}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl, wherein said C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl are each optionally substituted with 1, 2, or 3 substituents independently selected from OH, CN, amino, halo, C$_{1-6}$ alkyl, C$_{1-6}$ alkoxy, C$_{1-6}$ haloalkyl, and C$_{1-6}$ haloalkoxy; and each R$^e$, R$^{e1}$, R$^{e2}$, R$^{e3}$, and R$^{e4}$ is independently selected from H, C$_{1-4}$ alkyl, and CN.

In some embodiments, A is

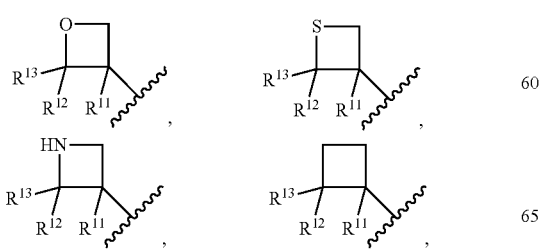

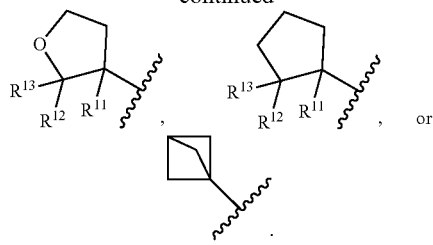

In some embodiments, A is

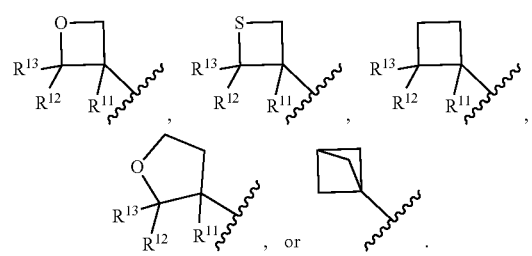

In some embodiments, A is a group having the formula:

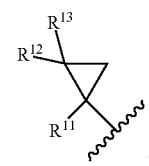

In some embodiments, A is a group having the formula:

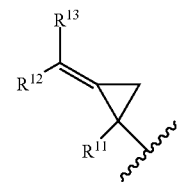

In some embodiments, A is a group having the formula:

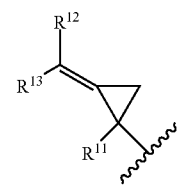

In some embodiments, A is a group having the formula:

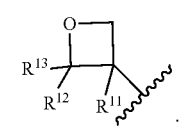

In some embodiments, A is a group having the formula:

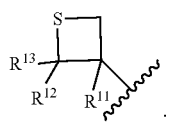

In some embodiments, A is a group having the formula:

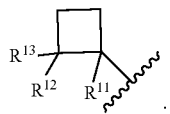

In some embodiments, A is a group having the formula:

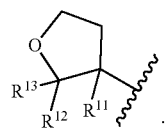

In some embodiments, A is a group having the formula:

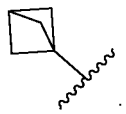

In some embodiments, A is a group having the formula:

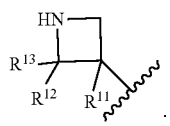

In some embodiments, A is a group having the formula:

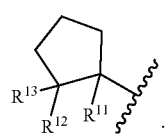

In some embodiments, A is selected from

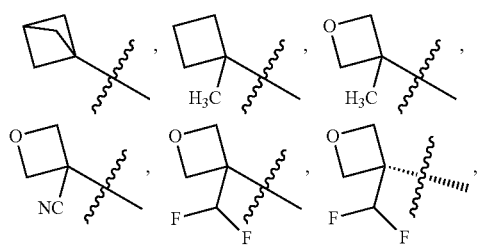

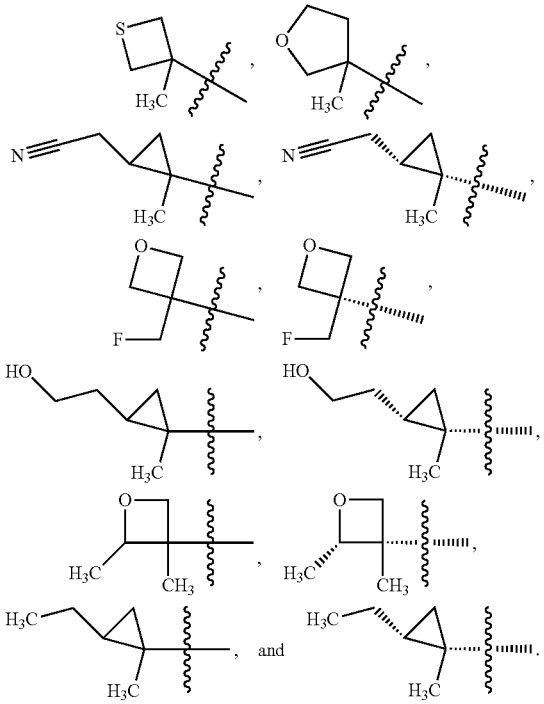

In some embodiments, A is selected from

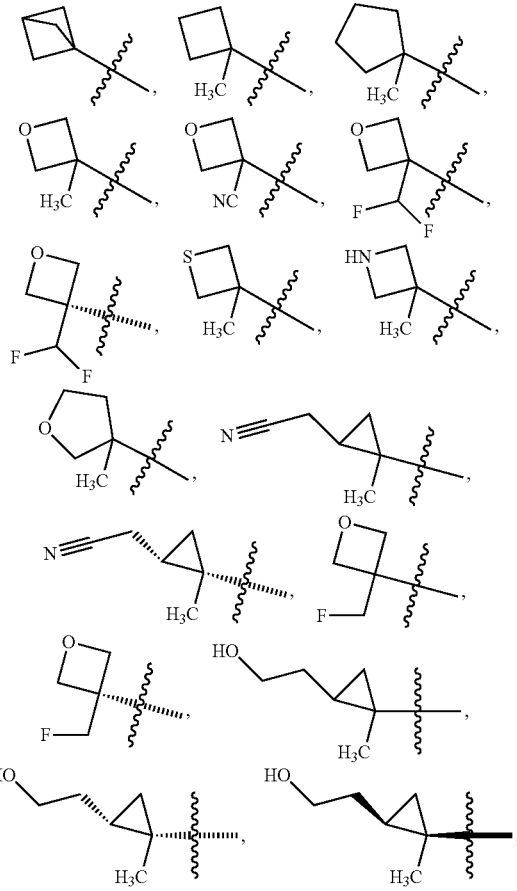

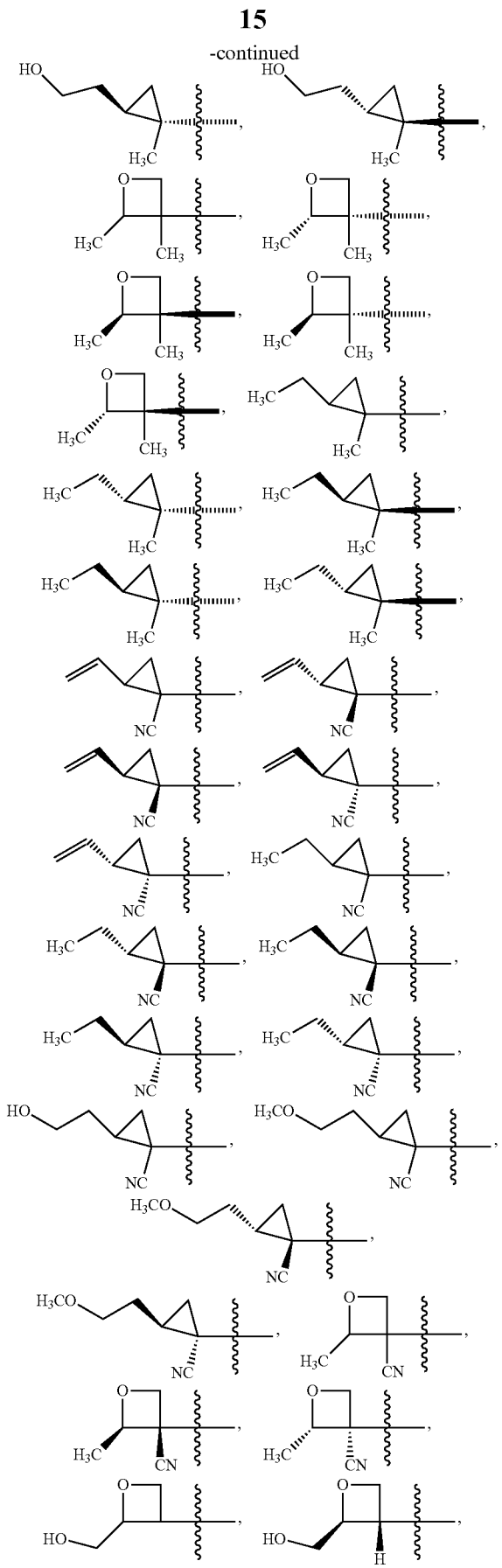
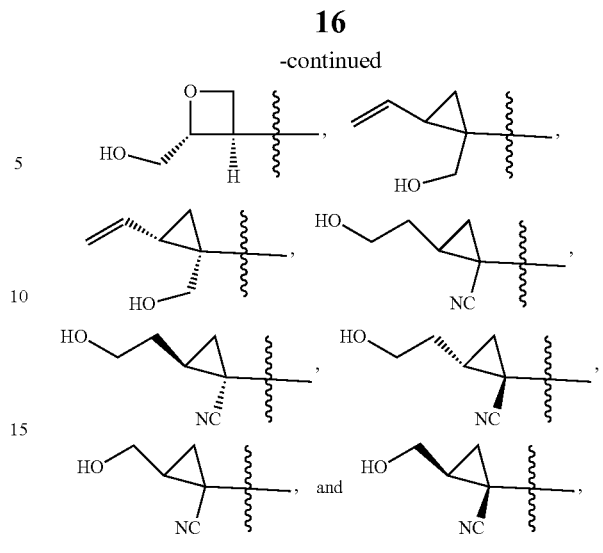
In some embodiments, when A is a group of formula:
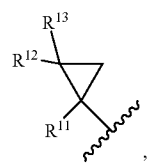
then $R^{13}$ is other than H, $CH_3$, fluoro, and CN.
In some embodiments, when A is a group of formula:
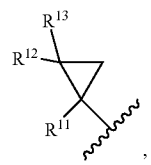
then $R^{13}$ is other than H, $CH_3$, and fluoro.
In some embodiments, B is a group of formula (a) or formula (b):
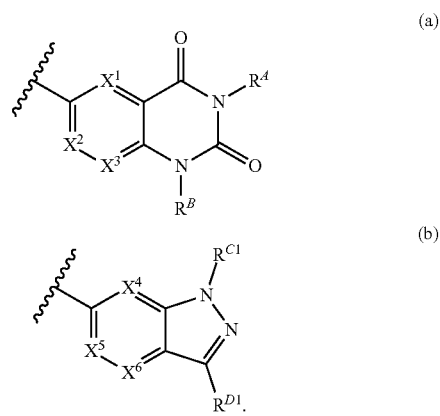

In some embodiments, B is of formula (a):

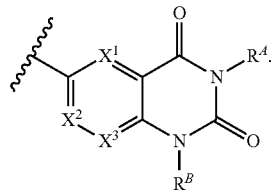

In some embodiments, B is of formula (b):

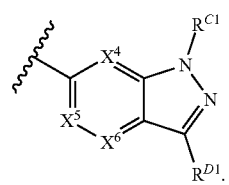

In some embodiments, B is of formula (c):

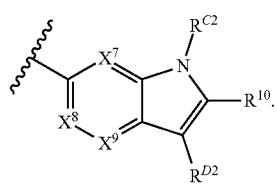

In some embodiments, A is

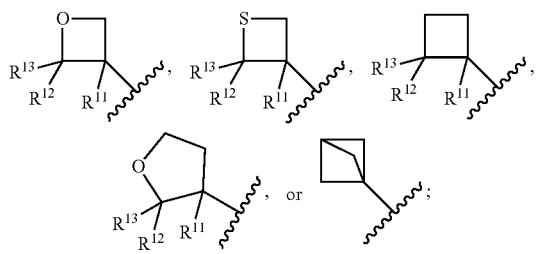

and
B is of formula (a):

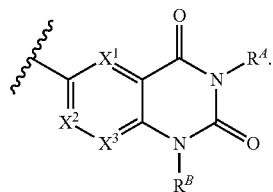

In some embodiments, A is

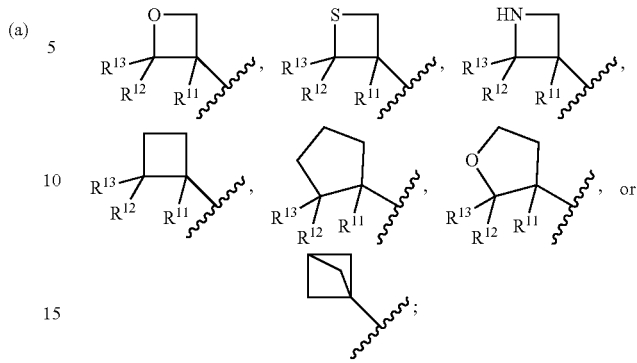

and
B is of formula (a):

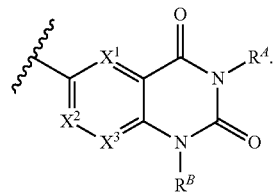

In some embodiments, A is

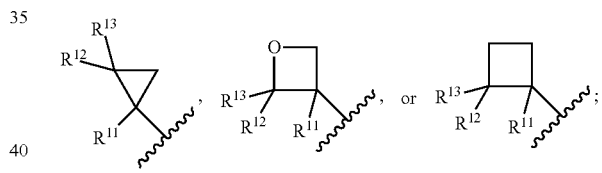

and
B is of formula (b):

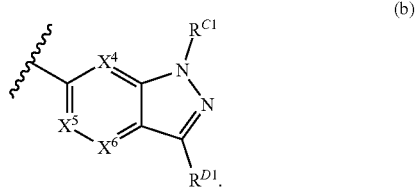

In some embodiments, $X^1$ is N. In some embodiments, $X^1$ is $CR^1$.
In some embodiments, $X^2$ is N. In some embodiments, $X^2$ is $CR^2$.
In some embodiments, $X^3$ is N. In some embodiments, $X^3$ is $CR^3$.
In some embodiments, $X^4$ is N. In some embodiments, $X^4$ is $CR^4$.
In some embodiments, $X^5$ is N. In some embodiments, $X^5$ is $CR^5$.
In some embodiments, $X^6$ is N. In some embodiments, $X^6$ is $CR^6$.

In some embodiments, $X^7$ is N. In some embodiments, $X^7$ is $CR^7$.

In some embodiments, $X^8$ is N. In some embodiments, $X^8$ is $CR^8$.

In some embodiments, $X^9$ is N. In some embodiments, $X^9$ is $CR^9$.

In some embodiments, $X^1$ is $CR^1$, $X^2$ is $CR^2$, and $X^3$ is $CR^3$.

In some embodiments, $X^4$ is $CR^4$, $X^5$ is $CR^5$, and $X^6$ is $CR^6$.

In some embodiments, $X^7$ is $CR^7$, $X^8$ is $CR^8$, and $X^9$ is $CR^9$.

In some embodiments, $R^1$ is H. In some embodiments, $R^1$ is halo. In some embodiments, $R^1$ is $C_{1-4}$ alkyl.

In some embodiments, $R^2$ is H. In some embodiments, $R^2$ is halo. In some embodiments, $R^2$ is $C_{1-4}$ alkyl.

In some embodiments, $R^3$ is H. In some embodiments, $R^3$ is $C_{6-10}$ aryl. In some embodiments, $R^3$ is $C_{3-7}$ cycloalkyl. In some embodiments, $R^3$ is 5-10 membered heteroaryl. In some embodiments, $R^3$ is 4-10 membered heterocycloalkyl. In some embodiments, $R^3$ is selected from $C_{6-10}$ aryl, $C_{3-7}$ cycloalkyl, 5-10 membered heteroaryl, and 4-10 membered heterocycloalkyl, substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, $R^3$ is halo. In some embodiments, $R^3$ is fluoro. In some embodiments, $R^3$ is chloro. In some embodiments, $R^3$ is bromo. In some embodiments, $R^3$ is iodo. In some embodiments, $R^3$ is $NR^cR^d$. In some embodiments, $R^3$ is $N(CH_3)_2$. In some embodiments, $R^3$ is $OR^a$. In some embodiments, $R^3$ is OH. In some embodiments, $R^3$ is $OCH_3$. In some embodiments, $R^4$ is H. In some embodiments, $R^4$ is halo. In some embodiments, $R^4$ is $C_{1-4}$ alkyl.

In some embodiments, $R^5$ is H. In some embodiments, $R^5$ is halo. In some embodiments, $R^5$ is $C_{1-4}$ alkyl.

In some embodiments, $R^6$ is H. In some embodiments, $R^6$ is $C_{6-10}$ aryl. In some embodiments, $R^6$ is $C_{3-7}$ cycloalkyl. In some embodiments, $R^6$ is 5-10 membered heteroaryl. In some embodiments, $R^6$ is 4-10 membered heterocycloalkyl. In some embodiments, $R^6$ is selected from $C_{6-10}$ aryl, $C_{3-7}$ cycloalkyl, 5-10 membered heteroaryl, and 4-10 membered heterocycloalkyl, substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, $R^6$ is $C_{6-10}$ aryl, $C_{3-7}$ cycloalkyl, 5-10 membered heteroaryl, and 4-10 membered heterocycloalkyl, wherein said $C_{6-10}$ aryl, $C_{3-7}$ cycloalkyl, 5-10 membered heteroaryl, and 4-10 membered heterocycloalkyl, optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, $R^6$ is halo. In some embodiments, $R^6$ is fluoro. In some embodiments, $R^6$ is chloro. In some embodiments, $R^6$ is bromo. In some embodiments, $R^6$ is iodo. In some embodiments, $R^6$ is $NR^cR^d$. In some embodiments, $R^6$ is $N(CH_3)_2$. In some embodiments, $R^6$ is $OR^a$. In some embodiments, $R^6$ is OH. In some embodiments, $R^6$ is $OCH_3$.

In some embodiments, $R^6$ is 4-10 membered heterocycloalkyl, optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, $R^6$ is piperazinyl, optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, $R^7$ is H. In some embodiments, $R^7$ is halo. In some embodiments, $R^7$ is $C_{1-4}$ alkyl.

In some embodiments, $R^8$ is H. In some embodiments, $R^8$ is halo. In some embodiments, $R^8$ is $C_{1-4}$ alkyl.

In some embodiments, $R^9$ is H. In some embodiments, $R^9$ is $C_{6-10}$ aryl. In some embodiments, $R^9$ is $C_{3-7}$ cycloalkyl. In some embodiments, $R^9$ is 5-10 membered heteroaryl. In some embodiments, $R^9$ is 4-10 membered heterocycloalkyl. In some embodiments, $R^9$ is selected from $C_{6-10}$ aryl, $C_{3-7}$ cycloalkyl, 5-10 membered heteroaryl, and 4-10 membered heterocycloalkyl, substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, $R^9$ is halo. In some embodiments, $R^9$ is fluoro. In some embodiments, $R^9$ is chloro. In some embodiments, $R^9$ is bromo. In some embodiments, $R^9$ is iodo. In some embodiments, $R^9$ is $NR^cR^d$. In some embodiments, $R^9$ is $N(CH_3)_2$. In some embodiments, $R^9$ is $OR^a$. In some embodiments, $R^9$ is OH. In some embodiments, $R^9$ is $OCH_3$.

In some embodiments, $R^1$ is H, $R^2$ is H, and $R^3$ is H.
In some embodiments, $R^4$ is H, $R^5$ is H, and $R^6$ is H.
In some embodiments, $R^7$ is H, $R^8$ is H, and $R^9$ is H.

In some embodiments, $R^{10}$ is H. In some embodiments, $R^{10}$ is halo. In some embodiments, $R^{10}$ is $C_{1-4}$ alkyl. In some embodiments, $R^{10}$ is $C_{1-4}$ haloalkyl.

In some embodiments, $R^A$ is H. In some embodiments, $R^A$ is $C_{1-4}$ alkyl. In some embodiments, $R^A$ is ethyl. In some embodiments, $R^A$ is $C_{2-6}$ alkenyl. In some embodiments, $R^A$ is selected from $C_{1-4}$ alkyl and $C_{2-6}$ alkenyl, substituted with 1, 2, or 3 substituents independently selected from $Cy^1$, halo, $C_{1-4}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^b$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^cC(O)R^{b1}$, $NR^cC(O)OR^{a1}$, $NR^cC(O)NR^{c1}R^{d1}$, $NR^{c1}S(O)R^{b1}$, $NR^{c1}S(O)_2R^{b1}$, $NR^cS(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, $R^A$ is $C_{1-4}$ alkyl, optionally substituted with 1, 2, or 3 substituents independently selected from $Cy^1$, halo, $C_{1-4}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, $R^A$ is $C_{1-4}$ alkyl, optionally substituted $Cy^1$.

In some embodiments, $R^A$ is $C_{2-6}$ alkenyl, optionally substituted with 1, 2, or 3 substituents independently selected from $Cy^1$, halo, $C_{1-4}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, $R^A$ is $C_{2-6}$ alkenyl, optionally substituted with 1, 2, or 3 substituents independently selected from $C(O)R^{b1}$, $C(O)NR^{c1}R^{d1}$, and $C(O)OR^{a1}$.

In some embodiments, $R^A$ is selected from $-CH_2CH_3$,

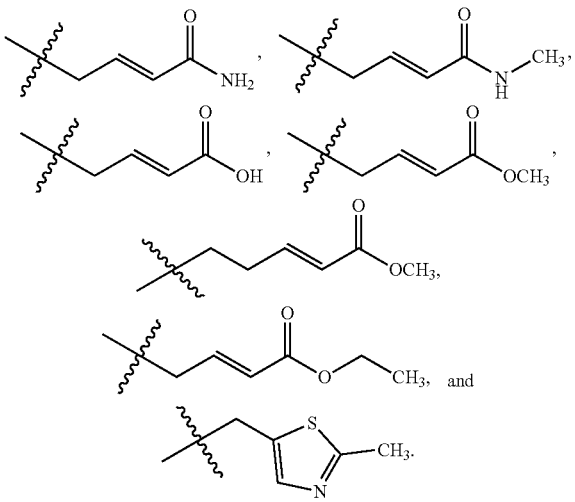

In some embodiments, $R^B$ is H. In some embodiments, $R^B$ is $C_{1-4}$ alkyl. In some embodiments, $R^B$ is $C_{2-6}$ alkenyl. In some embodiments, $R^B$ is selected from $C_{1-4}$ alkyl and $C_{2-6}$ alkenyl, substituted with 1, 2, or 3 substituents independently selected from $Cy^1$, halo, $C_{1-4}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, $R^B$ is selected from H and $C_{1-4}$ alkyl, wherein said $C_{1-4}$ alkyl is optionally substituted with 1, 2, or 3 substituents independently selected from $Cy^1$, halo, $C_{1-4}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, $R^B$ is $C_{1-4}$ alkyl, optionally substituted with 1, 2, or 3 substituents independently selected from $Cy^1$, halo, $C_{1-4}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^cC(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, $R^B$ is $C_{1-4}$ alkyl, optionally substituted with $Cy^1$.

In some embodiments, $R^B$ is selected from H, $-CH_2CH_3$,

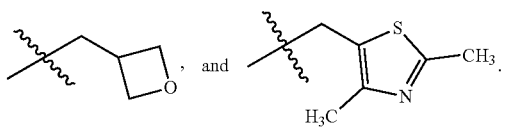

In some embodiments, $R^A$ is selected from $C_{1-4}$ alkyl and $C_{2-6}$ alkenyl, wherein said $C_{1-4}$ alkyl and $C_{2-6}$ alkenyl are each optionally independently substituted with 1, 2, or 3 substituents independently selected from $Cy^1$, $C(O)R^{b1}$, $C(O)NR^{c1}R^{d1}$, and $C(O)OR^{a1}$; and $R^B$ is selected from H and $C_{1-4}$ alkyl, wherein said $C_{1-4}$ alkyl is optionally substituted with $Cy^1$.

In some embodiments, $R^A$ and $R^B$ are each $C_{1-4}$ alkyl.

In some embodiments, $R^A$ and $R^B$ are each ethyl.

In some embodiments, $R^A$ is selected from $-CH_2CH_3$,

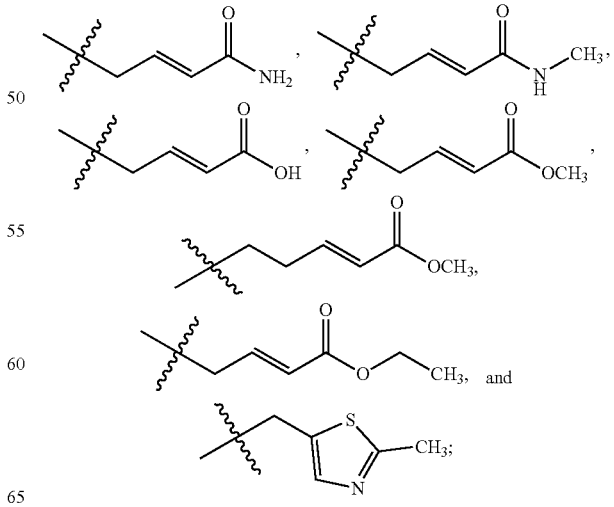

$R^B$ is selected from H, —CH$_2$CH$_3$,

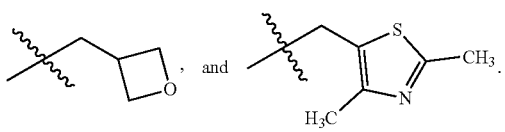

In some embodiments, $R^{C1}$ is C$_{1-6}$ alkyl. In some embodiments, $R^{C1}$ is C$_{2-6}$ alkenyl. In some embodiments, $R^{C1}$ is 5-membered heteroaryl. In some embodiments, $R^{C1}$ is selected from C$_{1-6}$ alkyl, C$_{2-6}$ alkenyl, and 5-membered heteroaryl, substituted with 1, 2, 3, or 4 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$.

In some embodiments, $R^{C1}$ is CH$_3$.

In some embodiments, $R^{C1}$ is 5-membered heteroaryl, optionally substituted with 1, 2, 3, or 4 substituents independently selected from halo, C$_{1-6}$ alkyl, C$_{1-6}$ alkyl substituted with R', C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$ C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$.

In some embodiments, $R^{C1}$ is 5-membered heteroaryl, optionally substituted with 1, 2, 3, or 4 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$.

In some embodiments, $R^{C1}$ is 1,3,4-thiadiazyl, optionally substituted with 1, 2, 3, or 4 substituents independently selected from halo, C$_{1-6}$ alkyl, C$_{1-6}$ alkyl substituted with R', C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$.

In some embodiments, $R^{C1}$ is 1,3,4-thiadiazyl, optionally substituted with 1, 2, 3, or 4 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$.

In some embodiments, $R^{C1}$ is 1,3,4-thiadiazyl. In some embodiments, $R^{C1}$ is 1,3,4-thiadiazyl substituted with C$_{1-6}$ alkyl. In some embodiments, $R^{C1}$ is 1,3,4-thiadiazyl substituted with methyl. In some embodiments, $R^{C1}$ is 1,3,4-thiadiazyl substituted with C$_{1-6}$ alkyl substituted with R'. In some embodiments, $R^{C1}$ is 1,3,4-thiadiazyl substituted with C$_{1-6}$ alkyl substituted with S(O)$_2$R$^{b2}$. In some embodiments, $R^{C1}$ is 1,3,4-thiadiazyl substituted with C$_{2-6}$ alkenyl. In some embodiments, $R^{C1}$ is 1,3,4-thiadiazyl substituted with C$_{3-7}$ cycloalkyl.

In some embodiments, $R^{C1}$ is 1,3,4-thiadiazyl substituted with C$_{1-6}$ haloalkyl.

In some embodiments, $R^{C1}$ is selected from CH$_3$,

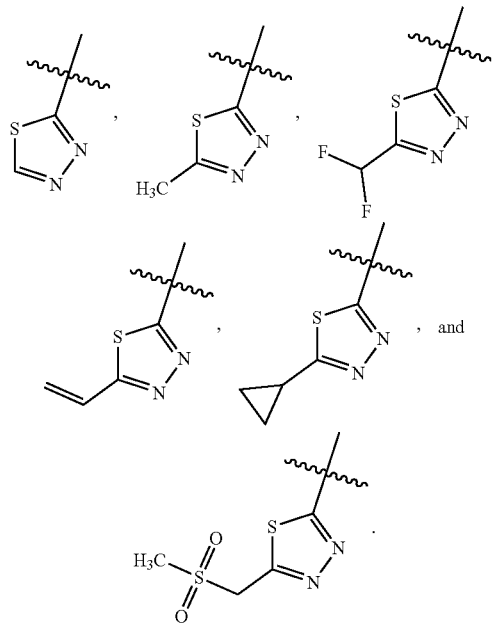

In some embodiments, $R^{C1}$ is

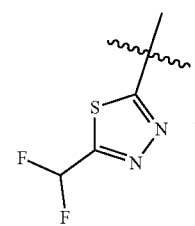

In some embodiments, $R^{C2}$ is $C_{1-6}$ alkyl. In some embodiments, $R^{C2}$ is $C_{2-6}$ alkenyl. In some embodiments, $R^{C2}$ is 5-membered heteroaryl. In some embodiments, $R^{C2}$ is selected from $C_{1-6}$ alkyl, $C_{2-6}$ alkenyl, and 5-membered heteroaryl, substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$ S(O)$_2$R$^{b2}$, and S(O)$_2$NR$^{c2}$R$^{d2}$.

In some embodiments, $R^{D1}$ is H. In some embodiments, $R^{D1}$ is halo. In some embodiments, $R^{D1}$ is $C_{1-4}$ alkyl.

In some embodiments, $R^{D2}$ is H. In some embodiments, $R^{D2}$ is halo. In some embodiments, $R^{D2}$ is $C_{1-4}$ alkyl.

In some embodiments, $R^{11}$ is CN, CH$_3$, CHF$_2$, or CH$_2$F. In some embodiments, $R^{11}$ is CN, CH$_3$, or CH$_2$F. In some embodiments, $R^{11}$ is CN. In some embodiments, $R^{11}$ is CH$_3$. In some embodiments, $R^{11}$ is CHF$_2$. In some embodiments, $R^{11}$ is CH$_2$F.

In some embodiments, $R^{11}$ is H. In some embodiments, $R^{11}$ is CH$_2$OH. In some embodiments, $R^{11}$ is CH$_2$CN. In some embodiments, $R^{11}$ is CCR". In some embodiments, $R^{11}$ is CCH.

In some embodiments, $R^{12}$ is H. In some embodiments, $R^{12}$ is F.

In some embodiments, $R^{13}$ is H. In some embodiments, $R^{13}$ is halo. In some embodiments, $R^{13}$ is $C_{1-6}$ alkyl. In some embodiments, $R^{13}$ is $C_{2-6}$ alkenyl. In some embodiments, $R^{13}$ is $C_{2-6}$ alkynyl. In some embodiments, $R^{13}$ is $C_{1-6}$ haloalkyl. In some embodiments, $R^{13}$ is $C_{6-10}$ aryl. In some embodiments, $R^{13}$ is $C_{3-7}$ cycloalkyl. In some embodiments, $R^{13}$ is 5-10 membered heteroaryl. In some embodiments, $R^{13}$ is 4-10 membered heterocycloalkyl. In some embodiments, $R^{13}$ is $C_{6-10}$ aryl-$C_{1-4}$ alkyl. In some embodiments, $R^{13}$ is $C_{3-7}$ cycloalkyl-$C_{1-4}$ alkyl. In some embodiments, $R^{13}$ is 5-10 membered heteroaryl-$C_{1-4}$ alkyl. In some embodiments, $R^{13}$ is 4-10 membered heterocycloalkyl-$C_{1-4}$ alkyl. In some embodiments, $R^{13}$ is CN. In some embodiments, $R^{13}$ is NO$_2$. In some embodiments, $R^{13}$ is OR$^{a3}$. In some embodiments, $R^{13}$ is SR$^{a3}$. In some embodiments, $R^{13}$ is C(O)R$^{b3}$. In some embodiments, $R^{13}$ is C(O)NR$^{c3}$R$^{d3}$. In some embodiments, $R^{13}$ is C(O)OR$^{a3}$. In some embodiments, $R^{13}$ is OC(O)R$^{b3}$. In some embodiments, $R^{13}$ is OC(O)NR$^{c3}$R$^{d3}$. In some embodiments, $R^{13}$ is C(=NR$^{e3}$)NR$^{c3}$R$^{d3}$. In some embodiments, $R^{13}$ is NR$^{c3}$C(=NR$^{e3}$)NR$^{c3}$R$^{d3}$. In some embodiments, $R^{13}$ is NR$^{c3}$R$^{d3}$. In some embodiments, $R^{13}$ is NR$^{c3}$C(O)R$^{b3}$. In some embodiments, $R^{13}$ is NR$^{c3}$C(O)OR$^{a3}$. In some embodiments, $R^{13}$ is NR$^{c3}$C(O)NR$^{c3}$R$^{d3}$. In some embodiments, $R^{13}$ is NR$^{c3}$S(O)R$^{b3}$. In some embodiments, $R^{13}$ is NR$^{c3}$S(O)$_2$R$^{b3}$. In some embodiments, $R^{13}$ is NR$^{c3}$S(O)$_2$NR$^{c3}$R$^{d3}$. In some embodiments, $R^{13}$ is S(O)R$^{b3}$. In some embodiments, $R^{13}$ is S(O)NR$^{c3}$R$^{d3}$. In some embodiments, $R^{13}$ is S(O)$_2$R$^{b3}$. In some embodiments, $R^{13}$ is S(O)$_2$NR$^{c3}$R$^{d3}$. In some embodiments, $R^{13}$ is selected from $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$.

In some embodiments, $R^{13}$ is $C_{1-6}$ alkyl, optionally substituted with 1, 2, 3, or 4 substituents independently selected from CN and OR$^{a3}$.

In some embodiments, $R^{13}$ is selected from H, ethyl, CH$_2$CN, and CH$_2$CH$_2$OH.

In some embodiments, $R^{13}$ is selected from H, methyl, ethyl, ethenyl, CH$_2$CN, CH$_2$OH, CH$_2$CH$_2$OH, and CH$_2$CH$_2$OCH$_3$.

In some embodiments, $R^{12}$ and $R^{13}$, together with the C atom to which they are attached, form a $C_3$ cycloalkyl group. In some embodiments, $R^{12}$ and $R^{13}$, together with the C atom to which they are attached, form a $C_3$ cycloalkyl group, substituted with 1, 2, or 3 substituents independently selected from halo, $C_{1-4}$ alkyl, $C_{1-4}$haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$.

In some embodiments, $R^{12}$ and $R^{13}$, together with the C atom to which they are attached, form a 3-membered heterocycloalkyl group comprising one N atom. In some embodiments, $R^{12}$ and $R^{13}$, together with the C atom to which they are attached, form a 3-membered heterocycloalkyl group comprising one N atom, substituted with 1, 2, or 3 substituents independently selected from halo, $C_{1-4}$ alkyl, $C_{1-4}$haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^3$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$. In some embodiments, $R^{12}$ and $R^{13}$, together with the C atom to which they are attached, form a 3-membered heterocycloalkyl group comprising one O atom. In some embodiments, $R^{12}$ and $R^{13}$, together with the C atom to which they are attached, form a 3-membered heterocycloalkyl group comprising one 0 atom, substituted with 1, 2, or 3 substituents independently selected from halo, $C_{1-4}$ alkyl, $C_{1-4}$haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$.

In some embodiments, $R^{12}$ and $R^{13}$ are each H.

In some embodiments, $R^{11}$, $R^{12}$, and $R^{13}$ are each H.

In some embodiments, $R^{11}$ is CN, CH$_3$, or CH$_2$F; $R^{12}$ is H; and $R^{13}$ is H.

In some embodiments, at least one Cy$^1$ is $C_{6-10}$ aryl. In some embodiments, at least one Cy$^1$ is $C_{3-7}$ cycloalkyl. In some embodiments, at least one Cy$^1$ is 5-10 membered heteroaryl. In some embodiments, at least one Cy$^1$ is 4-10 membered heterocycloalkyl, In some embodiments, at least one Cy$^1$ is selected from $C_{6-10}$ aryl, $C_{3-7}$ cycloalkyl, 5-10 membered heteroaryl, and 4-10 membered heterocycloalkyl, substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, at least one $Cy^1$ is 4-membered heterocycloalkyl. In some embodiments, at least one $Cy^1$ is oxetanyl. In some embodiments, at least one $Cy^1$ is

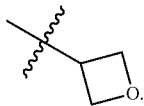

In some embodiments, at least one of $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is H. In some embodiments, at least one of $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is $C_{1-6}$ alkyl. In some embodiments, at least one of $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is $C_{1-6}$ haloalkyl. In some embodiments, at least one of $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is $C_{2-6}$ alkenyl. In some embodiments, at least one of $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is $C_{2-6}$ alkynyl. In some embodiments, at least one of $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is $C_{6-10}$ aryl. In some embodiments, at least one of $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is $C_{3-7}$ cycloalkyl. In some embodiments, at least one of $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is 5-10 membered heteroaryl. In some embodiments, at least one of $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is 4-10 membered heterocycloalkyl. In some embodiments, at least one of $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is $C_{6-10}$ aryl-$C_{1-4}$ alkyl. In some embodiments, at least one of $R^a$, $R^b$, $R^c$, $R^d$, $R^{a1}$, $R^{b1}$, $R^c$, $R^{d1}$, $R^{a2}$, $R^{b2}$, $R^{c2}$, $R^{d2}$, $R^{a3}$, $R^{b3}$, $R^{c3}$, and $R^{d3}$ is $C_{3-7}$ cycloalkyl-$C_{1-4}$ alkyl. In some embodiments, at least one of $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is 5-10 membered heteroaryl-$C_{1-4}$ alkyl. In some embodiments, at least one of $R^a$, $R^b$, $R^c$, $R^d$, $R^{a1}$, $R^{b1}$, $R^c$, $R^{d1}$, $R^{a2}$, $R^{b2}$, $R^{c2}$, $R^{d2}$, $R^{a3}$, $R^{b3}$, $R^{c3}$, and $R^{d3}$ is 4-10 membered heterocycloalkyl-$C_{1-4}$ alkyl. In some embodiments, at least one of $R^a$, $R^b$, $R^c$, $R^d$, $R^{a1}$, $R^{b1}$, $R^c$, $R^{d1}$, $R^{a2}$, $R^{b2}$, $R^{c2}$, $R^{d2}$, $R^{a3}$, $R^{b3}$, $R^{c3}$, and $R^{d3}$ is selected from $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, substituted with 1, 2, 3, 4, or 5 substituents independently selected from halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$.

In some embodiments, $R^c$ and $R^d$, together with the N atom to which they are attached, form a 4-7 membered heterocycloalkyl group. In some embodiments, $R^c$ and $R^d$, together with the N atom to which they are attached, form a 4-7 membered heterocycloalkyl group, substituted with 1, 2, or 3 substituents independently selected from halo, $C_{1-4}$ alkyl, $C_{1-4}$ haloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$.

In some embodiments, $R^{c1}$ and $R^{d1}$, together with the N atom to which they are attached, form a 4-7 membered heterocycloalkyl group. In some embodiments, $R^{c1}$ and $R^{d1}$, together with the N atom to which they are attached, form a 4-7 membered heterocycloalkyl group, substituted with 1, 2, or 3 substituents independently selected from halo, $C_{1-4}$ alkyl, $C_{1-4}$ haloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$.

In some embodiments, $R^{c2}$ and $R^{d2}$, together with the N atom to which they are attached, form a 4-7 membered heterocycloalkyl group. In some embodiments, $R^{c2}$ and $R^{d2}$, together with the N atom to which they are attached, form a 4-7 membered heterocycloalkyl group substituted with 1, 2, or 3 substituents independently selected from halo, $C_{1-4}$ alkyl, $C_{1-4}$ haloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^4)NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$.

In some embodiments, $R^{c3}$ and $R^{d3}$, together with the N atom to which they are attached, form a 4-7 membered heterocycloalkyl group. In some embodiments, $R^{c3}$ and $R^{d3}$, together with the N atom to which they are attached, form a 4-7 membered heterocycloalkyl group, substituted with 1, 2, or 3 substituents independently selected from halo, $C_{1-4}$ alkyl, $C_{1-4}$ haloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$.

In some embodiments, at least one of $R^{a4}$, $R^{b4}$, $R^{c4}$, and $R^{d4}$ is H. In some embodiments, at least one of $R^{a4}$, $R^{b4}$, $R^{c4}$, and $R^{d4}$ is $C_{1-6}$ alkyl. In some embodiments, at least one of $R^{a4}$, $R^{b4}$, $R^{c4}$, and $R^{d4}$ is $C_{1-6}$ haloalkyl. In some embodiments, at least one of $R^{a4}$, $R^{b4}$, $R^{c4}$, and $R^{d4}$ is $C_{2-6}$ alkenyl. In some embodiments, at least one of $R^{a4}$, $R^{b4}$, $R^{c4}$, and $R^{d4}$ is $C_{2-6}$ alkynyl. In some embodiments, at least one of $R^{a4}$, $R^{b4}$, $R^{c4}$, and $R^{d4}$ is $C_{6-10}$ aryl. In some embodiments, at least one of $R^{a4}$, $R^{b4}$, $R^{c4}$, and $R^{d4}$ is $C_{3-7}$ cycloalkyl. In some embodiments, at least one of $R^{a4}$, $R^{b4}$, $R^{c4}$, and $R^{d4}$ is 5-10 membered heteroaryl. In some embodiments, at least one of $R^{a4}$, $R^{b4}$, $R^{c4}$, and $R^{d4}$ is 4-10 membered heterocycloalkyl. In some embodiments, at least one of $R^{a4}$, $R^{b4}$, $R^{c4}$, and $R^{d4}$ is $C_{6-10}$ aryl-$C_{1-4}$ alkyl. In some embodiments, at least one of $R^{a4}$, $R^{b4}$, $R^{c4}$, and $R^{d4}$ is $C_{3-7}$ cycloalkyl-$C_{1-4}$ alkyl. In some embodiments, at least one of $R^{a4}$, $R^{b4}$, $R^{c4}$, and $R^{d4}$ is 5-10 membered heteroaryl-$C_{1-4}$ alkyl. In some embodiments, at least one of $R^{a4}$, $R^{b4}$, $R^{c4}$, and $R^{d4}$ is 4-10 membered heterocycloalkyl-$C_{1-4}$ alkyl. In some embodiments, at least one of $R^{a4}$, $R^{b4}$, $R^{c4}$, and $R^{d4}$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy.

In some embodiments, at least one of $R^e$, $R^{e1}$, $R^{e2}$, $R^{e3}$, and $R^{e4}$ is H. In some embodiments, at least one of $R^e$, $R^{e1}$, $R^{e2}$, $R^{e3}$, and $R^{e4}$ is $C_{1-4}$ alkyl. In some embodiments, at least one of $R^e$, $R^{e1}$, $R^{e2}$, $R^3$, and $R^{e4}$ is CN.

In some embodiments, provided herein is a compound of Formula (I), or a pharmaceutically acceptable salt thereof, having Formula IIA:

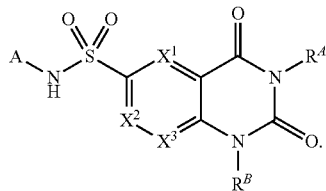

IIA

In some embodiments, provided herein is a compound of Formula (I), or a pharmaceutically acceptable salt thereof, having Formula IIB:

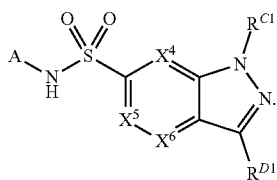

IIB

In some embodiments, provided herein is a compound of Formula (I), or a pharmaceutically acceptable salt thereof, having Formula IIC:

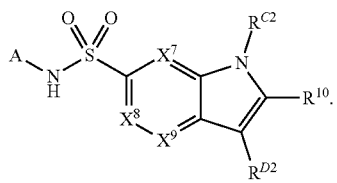

IIC

In some embodiments, provided herein is a compound of Formula (I), or a pharmaceutically acceptable salt thereof, having Formula IIA-1:

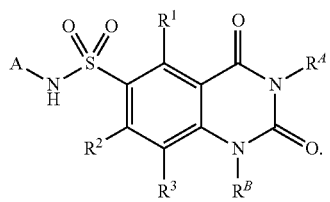

IIA-1

In some embodiments, provided herein is a compound of Formula (I), or a pharmaceutically acceptable salt thereof, having Formula IIA-2:

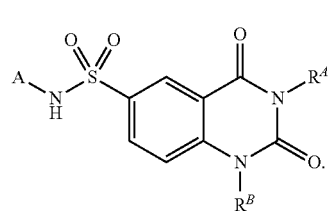

IIA-2

In some embodiments, provided herein is a compound of Formula (I), or a pharmaceutically acceptable salt thereof, having Formula IIA-3:

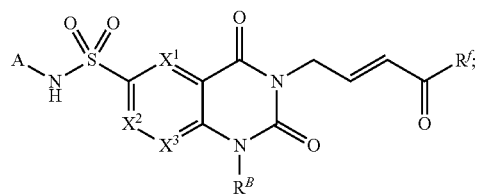

IIA-3 wherein $R^f$ is $R^{b1}$, $NR^{c1}R^{d1}$, or $OR^{a1}$.
In some embodiments, $R^f$ is $R^{b1}$.
In some embodiments, $R^f$ is $NR^{c1}R^{d1}$.
In some embodiments, $R^f$ is $OR^{a1}$.

In some embodiments, provided herein is a compound of Formula (I), or a pharmaceutically acceptable salt thereof, having Formula IIA-4:

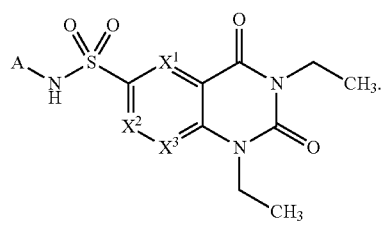

IIA-4

In some embodiments, provided herein is a compound of Formula (I), or a pharmaceutically acceptable salt thereof, having Formula IIB-1:

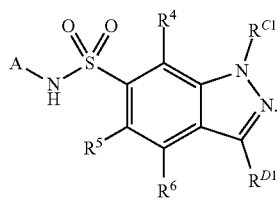

IIB-1

In some embodiments, provided herein is a compound of Formula (I), or a pharmaceutically acceptable salt thereof, having Formula IIB-2:

IIB-2

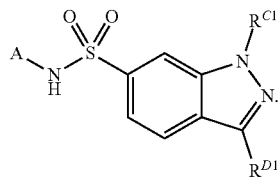

In some embodiments, provided herein is a compound of Formula (I), or a pharmaceutically acceptable salt thereof, having Formula IIB-2:

IIB-3

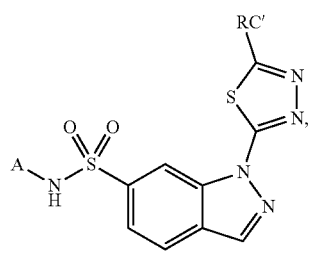

wherein $R^{C'}$ is selected from halo, $C_{1-6}$ alkyl, $C_{1-6}$ alkyl substituted with R', $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$.

In some embodiments, provided herein is a compound of Formula (I), or a pharmaceutically acceptable salt thereof, having Formula IIC-1:

IIC-1

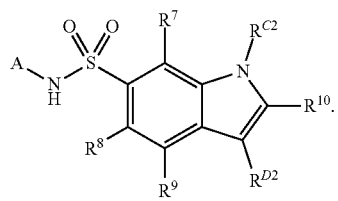

In some embodiments, provided herein is a compound of Formula (I), or a pharmaceutically acceptable salt thereof, having Formula IIC-2:

IIC-2

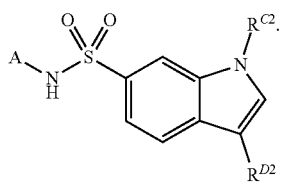

In some embodiments, provided herein is a compound of Formula (I), or a pharmaceutically acceptable salt thereof, having Formula IIIA:

IIIA

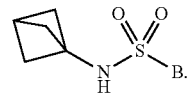

In some embodiments, provided herein is a compound of Formula (I), or a pharmaceutically acceptable salt thereof, having Formula IIIB:

IIIB

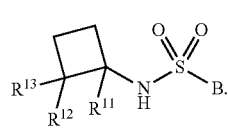

In some embodiments, provided herein is a compound of Formula (I), or a pharmaceutically acceptable salt thereof, having Formula IIIC:

IIIC

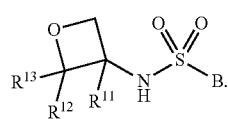

In some embodiments, provided herein is a compound of Formula (I), or a pharmaceutically acceptable salt thereof, having Formula IIID:

IIID

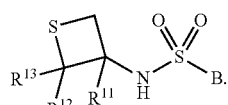

In some embodiments, provided herein is a compound of Formula (I), or a pharmaceutically acceptable salt thereof, having Formula IIIE:

IIIE

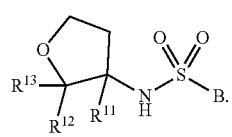

In some embodiments, provided herein is a compound of Formula (I), or a pharmaceutically acceptable salt thereof, having Formula IIIF:

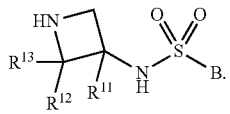

IIIF

In some embodiments, provided herein is a compound of Formula (I), or a pharmaceutically acceptable salt thereof, having Formula IIIG:

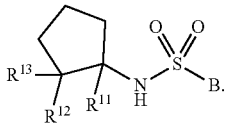

IIIG

In some embodiments, provided herein is a compound of Formula (I), or a pharmaceutically acceptable salt thereof, having Formula IVA:

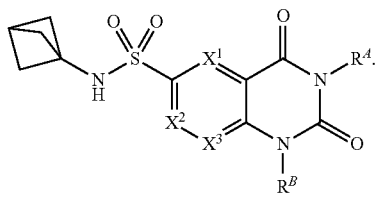

IVA

In some embodiments, provided herein is a compound of Formula (I), or a pharmaceutically acceptable salt thereof, having Formula IVB:

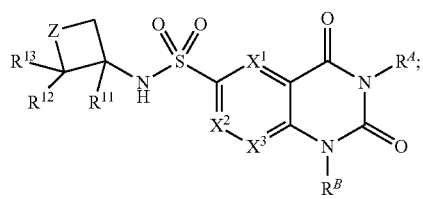

IVB wherein Z is $CH_2$, O, or S.

In some embodiments, provided herein is a compound of Formula (I), or a pharmaceutically acceptable salt thereof, having Formula IVB':

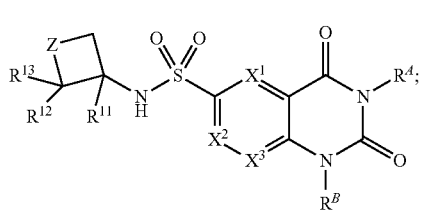

IVB' wherein Z is $CH_2$, N, O, or S.

In some embodiments, provided herein is a compound of Formula (I), or a pharmaceutically acceptable salt thereof, having Formula IVB-1:

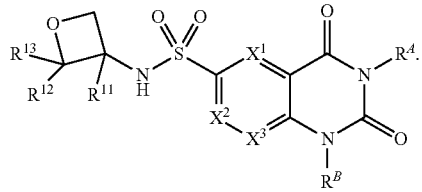

IVB-1

In some embodiments, provided herein is a compound of Formula (I), or a pharmaceutically acceptable salt thereof, having Formula IVB-2:

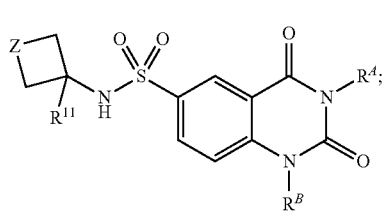

IVB-2 wherein Z is $CH_2$, O, or S.

In some embodiments, provided herein is a compound of Formula (I), or a pharmaceutically acceptable salt thereof, having Formula IVB-2':

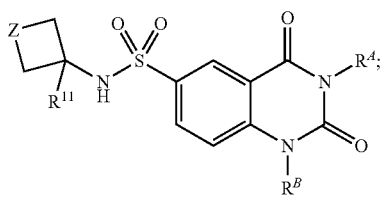

IVB-2' wherein Z is $CH_2$, N, O, or S.

In some embodiments, Z is $CH_2$.

In some embodiments, Z is N.

In some embodiments, Z is O.

In some embodiments, Z is S.

In some embodiments, provided herein is a compound of Formula (I), or a pharmaceutically acceptable salt thereof, wherein:

A is a group having the formula:

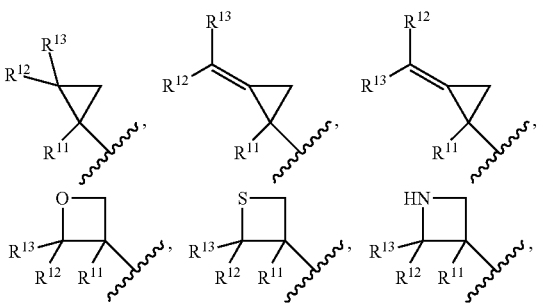

-continued

[chemical structures showing cyclobutyl with $R^{13}$, $R^{12}$, $R^{11}$ substituents; tetrahydrofuran with $R^{13}$, $R^{12}$, $R^{11}$; cyclopentyl with $R^{13}$, $R^{12}$, $R^{11}$; and bicyclobutyl]

B is a group of formula (a), formula (b), or formula (c):

(a) [pyrimidinedione-like ring with $X^1$, $X^2$, $X^3$, $N$-$R^A$, $N$-$R^B$]

(b) [pyrazole-fused ring with $X^4$, $X^5$, $X^6$, $N$-$R^{C1}$, $R^{D1}$]

(c) [pyrrole-fused ring with $X^7$, $X^8$, $X^9$, $N$-$R^{C2}$, $R^{10}$, $R^{D2}$]

$X^1$ is $CR^1$;
$X^2$ is $CR^2$;
$X^3$ is $CR^3$;
$X^4$ is $CR^4$;
$X^5$ is $CR^5$;
$X^6$ is $CR^6$;
$X^7$ is $CR^7$;
$X^8$ is $CR^8$;
$X^9$ is $CR^9$;

$R^1$, $R^2$, $R^4$, $R^5$, $R^7$, and $R^8$ are each independently selected from H, halo, and $C_{1-4}$ alkyl;

$R^3$, $R^6$, and $R^9$ are each independently selected from H, halo, $NR^cR^d$, $OR^a$, $C_{6-10}$ aryl, $C_{3-7}$ cycloalkyl, 5-10 membered heteroaryl, and 4-10 membered heterocycloalkyl, wherein said $C_{6-10}$ aryl, $C_{3-7}$ cycloalkyl, 5-10 membered heteroaryl, and 4-10 membered heterocycloalkyl of $R^3$, $R^6$, and $R^9$ are each optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

$R^{10}$ is H;

$R^A$ and $R^B$ are each independently selected from H, $C_{1-4}$ alkyl, and $C_{2-6}$ alkenyl, wherein said $C_{1-4}$ alkyl and $C_{2-6}$ alkenyl of $R^A$ and $R^B$ are each optionally substituted with 1, 2, or 3 substituents independently selected from $Cy^1$, halo, $C_{1-4}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

wherein at least one of $R^A$ and $R^B$ is other than H;

$R^{C1}$ and $R^{C2}$ are 5-membered heteroaryl, wherein said 5-membered heteroaryl of $R^{C1}$ and $R^{C2}$ are each optionally substituted with 1, 2, 3, or 4 substituents independently selected from halo, $C_{1-6}$ alkyl, $C_{1-6}$ alkyl substituted with R', $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each R' is independently selected from halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^{D1}$ and $R^{D2}$ are H;

$R^{11}$ is H, CN, $CH_3$, $CH_2OH$, $CHF_2$, or $CH_2F$;

$R^{12}$ is H;

$R^{13}$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, or $S(O)_2NR^{c3}R^{d3}$, wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^{13}$ is optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$, wherein when A is a group of formula:

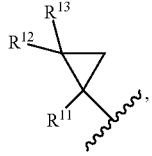

then R$^{13}$ is other than H, CH$_3$, and CN;

or R$^{12}$ and R$^{13}$, together with the C atom to which they are attached, form a C$_3$ cycloalkyl or 3-membered heterocycloalkyl group comprising one heteroatom selected from N and O, optionally substituted with 1, 2, or 3 substituents independently selected from halo, C$_{1-4}$ alkyl, C$_{1-4}$haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

each Cy$^1$ is 5-10 membered heteroaryl or 4-10 membered heterocycloalkyl, each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

each R$^a$, R$^b$, R$^e$, R$^d$, R$^{a1}$, R$^{b1}$, R$^{c1}$, R$^{d1}$, R$^{a2}$, R$^{b2}$, R$^{c2}$, R$^{d2}$, R$^{a3}$, R$^{b3}$, R$^{c3}$, and R$^{d3}$ is independently selected from H and C$_{1-6}$ alkyl;

each R$^e$, R$^{e1}$, R$^{e2}$, R$^{e3}$, and R$^{e4}$ is independently selected from H and C$_{1-4}$ alkyl.

In some embodiments, provided herein is a compound of Formula (I), or a pharmaceutically acceptable salt thereof, wherein:

A is a group having the formula:

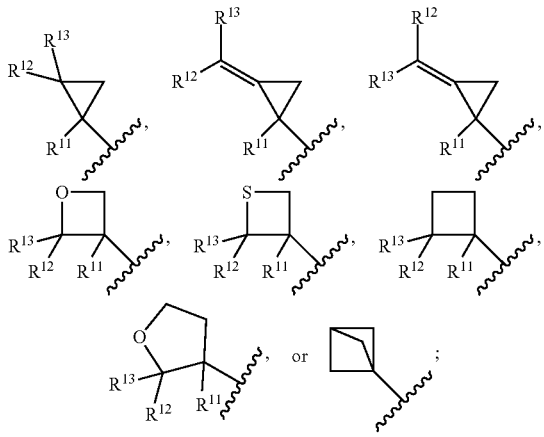

B is a group of formula (a), formula (b), or formula (c):

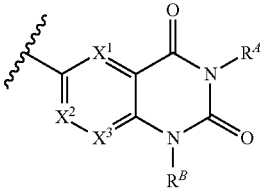
(a)

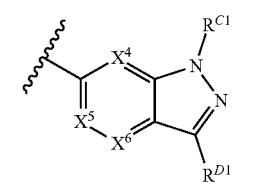
(b)

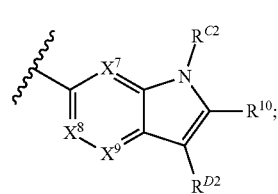
(c)

X$^1$ is CR$^1$;
X$^2$ is CR$^2$;
X$^3$ is CR$^3$;
X$^4$ is CR$^4$;
X$^5$ is CR$^5$;
X$^6$ is CR$^6$;
X$^7$ is CR$^7$;
X$^8$ is CR$^8$;
X$^9$ is CR$^9$;
R$^1$, R$^2$, R$^4$, R$^5$, R$^7$, and R$^8$ are each independently selected from H, halo, and C$_{1-4}$ alkyl;
R$^3$, R$^6$, and R$^9$ are each independently selected from H, C$_{6-10}$ aryl, C$_{3-7}$ cycloalkyl, 5-10 membered heteroaryl, and 4-10 membered heterocycloalkyl, wherein said C$_{6-10}$ aryl, C$_{3-7}$ cycloalkyl, 5-10 membered heteroaryl, and 4-10 membered heterocycloalkyl of R$^3$, R$^6$, and R$^9$ are each optionally substituted with 1, 2, 3, or 4 substituents independently selected from halo, C$_{1-6}$ alkyl, C$_{2-6}$ alkenyl, C$_{2-6}$ alkynyl, C$_{1-6}$ haloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

R$^{10}$ is H;

R$^A$ and R$^B$ are each independently selected from H, C$_{1-4}$ alkyl, and C$_{2-6}$ alkenyl, wherein said C$_{1-4}$ alkyl and C$_{2-6}$ alkenyl of R$^A$ and R$^B$ are each optionally substituted with 1, 2, or 3 substituents independently selected from Cy$^1$, halo, C$_{1-4}$ alkyl, C$_{2-6}$ alkenyl, C$_{2-6}$ alkynyl, C$_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$ NR$^{c1}$R$^{d1}$;

wherein at least one of $R^A$ and $R^B$ is other than H;

$R^{C1}$ and $R^{C2}$ are 5-membered heteroaryl, wherein said 5-membered heteroaryl of $R^{C1}$ and $R^{C2}$ are each optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^{D1}$ and $R^{D2}$ are H;

$R^{11}$ is CN, $CH_3$, $CHF_2$, or $CH_2F$;

$R^{12}$ is H;

$R^{13}$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{e3}R^{d3}$, $S(O)R^{b3}$, $S(O)NR^{c3}R^{d3}$, $S(O)_2R^{b3}$, or $S(O)_2NR^{c3}R^{d3}$, wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^{13}$ is optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein when A is a group of formula:

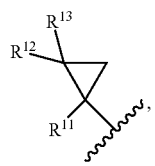

then $R^{13}$ is other than H, $CH_3$, and CN;

or $R^{12}$ and $R^{13}$, together with the C atom to which they are attached, form a $C_3$ cycloalkyl or 3-membered heterocycloalkyl group comprising one heteroatom selected from N and O, optionally substituted with 1, 2, or 3 substituents independently selected from halo, $C_{1-4}$ alkyl, $C_{1-4}$haloalkyl, CN, $OR^{a3}$, $SR^{a3}$, $C(O)R^{b3}$, $C(O)$ $NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $Cy^1$ is 5-10 membered heteroaryl or 4-10 membered heterocycloalkyl, each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^cC(O)OR^{a1}$, $NR^{c1}C(O)NR^{c1}R^{d1}$, $NR^cS(O)R^{b1}$, $NR^cS(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

each $R^a$, $R^b$, $R^e$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is independently selected from H and $C_{1-6}$ alkyl;

each $R^e$, $R^{e1}$, $R^{e2}$, $R^{e3}$, and $R^{e4}$ is independently selected from H and $C_{1-4}$ alkyl.

In some embodiments, provided herein is a compound of Formula (I), or a pharmaceutically acceptable salt thereof, wherein:

A is a group having the formula:

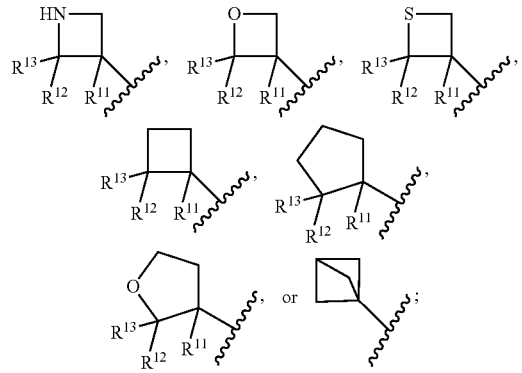

B is a group of formula (a) or formula (b):

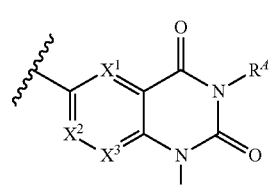

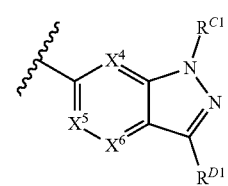

$X^1$ is $CR^1$;

$X^2$ is $CR^2$;

$X^3$ is $CR^3$;
$X^4$ is $CR^4$;
$X^5$ is $CR^5$;
$X^6$ is $CR^6$;
$R^1$, $R^2$, $R^4$, and $R^5$ are each H;
$R^3$ and $R^6$ are each independently selected from H, halo, $NR^cR^d$, $OR^a$, and 4-10 membered heterocycloalkyl, wherein said 4-10 membered heterocycloalkyl of $R^3$ and $R^6$ are each optionally substituted with $C(O)R^b$;
$R^A$ and $R^B$ are each independently selected from H, $C_{1-4}$ alkyl, and $C_{2-6}$ alkenyl, wherein said $C_{1-4}$ alkyl and $C_{2-6}$ alkenyl of $R^A$ and $R^B$ are each optionally substituted with 1, 2, or 3 substituents independently selected from $Cy^1$ and $C(O)NR^{c1}R^{d1}$, $C(O)OR^{a1}$;
wherein at least one of $R^A$ and $R^B$ is other than H;
$R^{C1}$ is $C_{1-6}$ alkyl or 5-membered heteroaryl, wherein the 5-membered heteroaryl is optionally substituted with $C_{1-6}$ alkyl, $C_{1-6}$ alkyl substituted with R', $C_{2-6}$ alkenyl, $C_{3-7}$ cycloalkyl, or $C_{1-6}$ haloalkyl;
each R' is $S(O)_2R^{b2}$;
$R^{D1}$ is H;
$R^{11}$ is CN, $CH_3$, or $CH_2F$;
$R^{12}$ is H;
$R^{13}$ is H or $C_{1-6}$ alkyl, wherein said $C_{1-6}$ alkyl is optionally substituted with 1, 2, 3, or 4 substituents independently selected from CN and $OR^{a3}$;
each $Cy^1$ is 5-10 membered heteroaryl or 4-10 membered heterocycloalkyl, optionally substituted with $C_{1-6}$ alkyl;
each $R^b$, $R^{a1}$, $R^c$, and $R^{d1}$ is independently selected from H and $C_{1-6}$ alkyl.

In some embodiments, provided herein is a compound of Formula (I), or a pharmaceutically acceptable salt thereof, wherein:
A is a group having the formula:

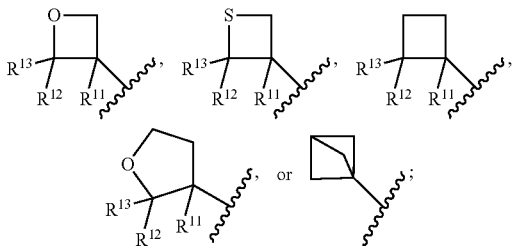

B is a group of formula (a) or formula (b):

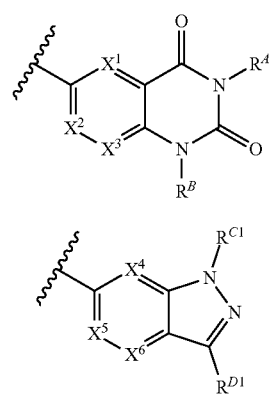

$X^1$ is $CR^1$;
$X^2$ is $CR^2$;
$X^3$ is $CR^3$;
$X^4$ is $CR^4$;
$X^5$ is $CR^5$;
$X^6$ is $CR^6$;
$R^1$, $R^2$, $R^4$, and $R^5$ are each H;
$R^3$ and $R^6$ are each independently selected from H and 4-10 membered heterocycloalkyl, wherein said 4-10 membered heterocycloalkyl of $R^3$ and $R^6$ are each optionally substituted with $C(O)R^b$;
$R^A$ and $R^B$ are each independently selected from H, $C_{1-4}$ alkyl, and $C_{2-6}$ alkenyl, wherein said $C_{1-4}$ alkyl and $C_{2-6}$ alkenyl of $R^A$ and $R^B$ are each optionally substituted with 1, 2, or 3 substituents independently selected from $Cy^1$ and $C(O)NR^{c1}R^{d1}$, $C(O)OR^{a1}$;
wherein at least one of $R^A$ and $R^B$ is other than H;
$R^{C1}$ is 5-membered heteroaryl, optionally substituted with $C_{1-6}$ haloalkyl;
$R^{D1}$ is H;
$R^{11}$ is CN, $CH_3$, or $CH_2F$;
$R^{12}$ is H;
$R^{13}$ is H or $C_{1-6}$ alkyl, wherein said $C_{1-6}$ alkyl is optionally substituted with 1, 2, 3, or 4 substituents independently selected from CN and $OR^{a3}$;
each $Cy^1$ is 5-10 membered heteroaryl or 4-10 membered heterocycloalkyl, optionally substituted with $C_{1-6}$ alkyl;
each $R^b$, $R^{a1}$, $R^{c1}$, and $R^{d1}$ is independently selected from H and $C_{1-6}$ alkyl.

In some embodiments, provided herein is a compound of Formula (I), or a pharmaceutically acceptable salt thereof, selected from:
ethyl (2E)-4-[6-({bicyclo[1.1.1]pentan-1-yl}sulfamoyl)-2,4-dioxo-1H-quinazolin-3-yl]but-2-enoate;
(2E)-4-[6-({bicyclo[1.1.1]pentan-1-yl}sulfamoyl)-2,4-dioxo-1H-quinazolin-3-yl]but-2-enoic acid;
(2E)-4-[6-({bicyclo[1.1.1]pentan-1-yl}sulfamoyl)-2,4-dioxo-1H-quinazolin-3-yl]but-2-enamide;
1,3-diethyl-N-(3-methyloxetan-3-yl)-2,4-dioxoquinazoline-6-sulfonamide;
1,3-diethyl-N-(3-methylthietan-3-yl)-2,4-dioxoquinazoline-6-sulfonamide;
1-[5-(difluoromethyl)-1,3,4-thiadiazol-2-yl]-N-(3-methyloxetan-3-yl)-4-[4-(2-methylpropanoyl)piperazin-1-yl]indazole-6-sulfonamide;
1,3-diethyl-N-(1-methylcyclobutyl)-2,4-dioxoquinazoline-6-sulfonamide;
1,3-diethyl-N-(3-methyloxolan-3-yl)-2,4-dioxoquinazoline-6-sulfonamide;
methyl (2E)-4-{6-[(3-methyloxetan-3-yl)sulfamoyl]-2,4-dioxo-1H-quinazolin-3-yl}but-2-enoate;
N-(3-cyanooxetan-3-yl)-1,3-diethyl-2,4-dioxoquinazoline-6-sulfonamide;
methyl (2E)-4-{6-[(3-methyloxetan-3-yl)sulfamoyl]-1-(oxetan-3-ylmethyl)-2,4-dioxoquinazolin-3-yl}but-2-enoate;
methyl (E)-5-(6-(N-(3-methyloxetan-3-yl)sulfamoyl)-2,4-dioxo-1,4-dihydroquinazolin-3(2H)-yl)pent-2-enoate;
1,3-diethyl-N-((1S,2R)-2-ethyl-1-methylcyclopropyl)-2,4-dioxo-1,2,3,4-tetrahydroquinazoline-6-sulfonamide;
1-((2,4-dimethylthiazol-5-yl)methyl)-N-(3-methyloxetan-3-yl)-3-((2-methylthiazol-5-yl)methyl)-2,4-dioxo-1,2,3,4-tetrahydroquinazoline-6-sulfonamide;
1,3-diethyl-N-((1S,2S)-2-(2-hydroxyethyl)-1-methylcyclopropyl)-2,4-dioxo-1,2,3,4-tetrahydroquinazoline-6-sulfonamide;

N-((1S,2S)-2-(cyanomethyl)-1-methylcyclopropyl)-1,3-diethyl-2,4-dioxo-1,2,3,4-tetrahydroquinazoline-6-sulfonamide;
N-((2S,3S)-2,3-dimethyloxetan-3-yl)-1,3-diethyl-2,4-dioxo-1,2,3,4-tetrahydroquinazoline-6-sulfonamide;
N-(3-(difluoromethyl)oxetan-3-yl)-1,3-diethyl-2,4-dioxo-1,2,3,4-tetrahydroquinazoline-6-sulfonamide;
(E)-N-methyl-4-(6-(N-(3-methyloxetan-3-yl)sulfamoyl)-2,4-dioxo-1,4-dihydroquinazolin-3(2H)-yl)but-2-enamide;
1,3-diethyl-N-(3-(fluoromethyl)oxetan-3-yl)-2,4-dioxo-1,2,3,4-tetrahydroquinazoline-6-sulfonamide;
1,3-diethyl-N-((1S,2S)-2-ethyl-1-methylcyclopropyl)-2,4-dioxo-1,2,3,4-tetrahydroquinazoline-6-sulfonamide;
1,3-diethyl-N-((1R,2R)-2-ethyl-1-methylcyclopropyl)-2,4-dioxo-1,2,3,4-tetrahydroquinazoline-6-sulfonamide;
1,3-diethyl-N-((1R,2S)-2-ethyl-1-methylcyclopropyl)-2,4-dioxo-1,2,3,4-tetrahydroquinazoline-6-sulfonamide;
1,3-diethyl-N-((1R,2R)-2-(2-hydroxyethyl)-1-methylcyclopropyl)-2,4-dioxo-1,2,3,4-tetrahydroquinazoline-6-sulfonamide;
N-((2S,3S)-2,3-dimethyloxetan-3-yl)-1,3-diethyl-2,4-dioxo-1,2,3,4-tetrahydroquinazoline-6-sulfonamide;
N-((2R,3R)-2,3-dimethyloxetan-3-yl)-1,3-diethyl-2,4-dioxo-1,2,3,4-tetrahydroquinazoline-6-sulfonamide;
N-((2R,3S)-2,3-dimethyloxetan-3-yl)-1,3-diethyl-2,4-dioxo-1,2,3,4-tetrahydroquinazoline-6-sulfonamide;
1-(5-(difluoromethyl)-1,3,4-thiadiazol-2-yl)-4-(4-isobutyrylpiperazin-1-yl)-N-(1-methylcyclobutyl)-1H-indazole-6-sulfonamide;
1-(5-(difluoromethyl)-1,3,4-thiadiazol-2-yl)-N-(3-(fluoromethyl)oxetan-3-yl)-4-(4-isobutyrylpiperazin-1-yl)-1H-indazole-6-sulfonamide;
1-(5-(difluoromethyl)-1,3,4-thiadiazol-2-yl)-N-(3-methyloxetan-3-yl)-1H-indazole-6-sulfonamide;
4-chloro-N-(3-cyanooxetan-3-yl)-1-(5-(difluoromethyl)-1,3,4-thiadiazol-2-yl)-1H-indazole-6-sulfonamide;
N-(3-cyanooxetan-3-yl)-1-((2,4-dimethylthiazol-5-yl)methyl)-3-((2-methylthiazol-5-yl)methyl)-2,4-dioxo-1,2,3,4-tetrahydroquinazoline-6-sulfonamide;
N-(3-cyanooxetan-3-yl)-3-((2-methylthiazol-5-yl)methyl)-2,4-dioxo-1,2,3,4-tetrahydroquinazoline-6-sulfonamide;
1-(5-(difluoromethyl)-1,3,4-thiadiazol-2-yl)-4-(dimethylamino)-N-(3-methyloxetan-3-yl)-1H-indazole-6-sulfonamide;
1-(5-(difluoromethyl)-1,3,4-thiadiazol-2-yl)-N-((2S,3S)-2,3-dimethyloxetan-3-yl)-4-(4-isobutyrylpiperazin-1-yl)-1H-indazole-6-sulfonamide;
N-(3-(fluoromethyl)oxetan-3-yl)-3-((2-methylthiazol-5-yl)methyl)-2,4-dioxo-1,2,3,4-tetrahydroquinazoline-6-sulfonamide;
1-((2,4-dimethylthiazol-5-yl)methyl)-N-(3-(fluoromethyl)oxetan-3-yl)-3-((2-methylthiazol-5-yl)methyl)-2,4-dioxo-1,2,3,4-tetrahydroquinazoline-6-sulfonamide;
1-(5-(difluoromethyl)-1,3,4-thiadiazol-2-yl)-4-(4-isobutyrylpiperazin-1-yl)-N-(oxetan-3-yl)-1H-indazole-6-sulfonamide;
N-(3-cyanooxetan-3-yl)-1-(5-(difluoromethyl)-1,3,4-thiadiazol-2-yl)-4-(4-isobutyrylpiperazin-1-yl)-1H-indazole-6-sulfonamide;
4-(4-isobutyrylpiperazin-1-yl)-N-(3-methyloxetan-3-yl)-1-(5-((methylsulfonyl)methyl)-1,3,4-thiadiazol-2-yl)-1H-indazole-6-sulfonamide;
N-(3-cyano-2-methyloxetan-3-yl)-1-(5-(difluoromethyl)-1,3,4-thiadiazol-2-yl)-4-(4-isobutyrylpiperazin-1-yl)-1H-indazole-6-sulfonamide;
1-(5-(difluoromethyl)-1,3,4-thiadiazol-2-yl)-4-(4-(isopropylsulfonyl)piperazin-1-yl)-N-(3-methyloxetan-3-yl)-1H-indazole-6-sulfonamide;
4-(4-(cyclopentanecarbonyl)piperazin-1-yl)-1-(5-(difluoromethyl)-1,3,4-thiadiazol-2-yl)-N-(3-(fluoromethyl)oxetan-3-yl)-1H-indazole-6-sulfonamide;
1-(5-(difluoromethyl)-1,3,4-thiadiazol-2-yl)-N-(3-methyloxetan-3-yl)-4-(4-(pyrrolidine-1-carbonyl)piperazin-1-yl)-1H-indazole-6-sulfonamide;
1-(5-(difluoromethyl)-1,3,4-thiadiazol-2-yl)-N-(3-(fluoromethyl)oxetan-3-yl)-4-(4-(pyrrolidine-1-carbonyl)piperazin-1-yl)-1H-indazole-6-sulfonamide;
N-(2,2-difluoroethyl)-4-(1-(5-(difluoromethyl)-1,3,4-thiadiazol-2-yl)-6-(N-(3-methyloxetan-3-yl)sulfamoyl)-1H-indazol-4-yl)-N-methylpiperazine-1-carboxamide;
N-(3-cyanooxetan-3-yl)-1-(5-(difluoromethyl)-1,3,4-thiadiazol-2-yl)-4-(4-(pyrrolidine-1-carbonyl)piperazin-1-yl)-1H-indazole-6-sulfonamide;
N-(3-cyanooxetan-3-yl)-4-(4-(cyclopropanecarbonyl)piperazin-1-yl)-1-(5-(difluoromethyl)-1,3,4-thiadiazol-2-yl)-1H-indazole-6-sulfonamide;
N-(3-cyanooxetan-3-yl)-4-(4-(cyclopentanecarbonyl)piperazin-1-yl)-1-(5-(difluoromethyl)-1,3,4-thiadiazol-2-yl)-1H-indazole-6-sulfonamide;
4-(6-(N-(3-cyanooxetan-3-yl)sulfamoyl)-1-(5-(difluoromethyl)-1,3,4-thiadiazol-2-yl)-1H-indazol-4-yl)-N-(2,2-difluoroethyl)-N-methylpiperazine-1-carboxamide;
N-(3-(fluoromethyl)oxetan-3-yl)-4-(4-isobutyrylpiperazin-1-yl)-1-(5-methyl-1,3,4-thiadiazol-2-yl)-1H-indazole-6-sulfonamide;
1-(5-cyclopropyl-1,3,4-thiadiazol-2-yl)-N-(3-(fluoromethyl)oxetan-3-yl)-4-(4-isobutyrylpiperazin-1-yl)-1H-indazole-6-sulfonamide;
N-(3-(fluoromethyl)oxetan-3-yl)-4-(4-isobutyrylpiperazin-1-yl)-1-(1,3,4-thiadiazol-2-yl)-1H-indazole-6-sulfonamide;
4-(4-isobutyrylpiperazin-1-yl)-1-(5-methyl-1,3,4-thiadiazol-2-yl)-N-(3-methyloxetan-3-yl)-1H-indazole-6-sulfonamide;
4-(4-isobutyrylpiperazin-1-yl)-N-(3-methyloxetan-3-yl)-1-(1,3,4-thiadiazol-2-yl)-1H-indazole-6-sulfonamide;
N-(3-(fluoromethyl)oxetan-3-yl)-4-(4-isobutyrylpiperazin-1-yl)-1-(5-vinyl-1,3,4-thiadiazol-2-yl)-1H-indazole-6-sulfonamide;
1-(5-(difluoromethyl)-1,3,4-thiadiazol-2-yl)-N-(3-methyloxetan-3-yl)-4-(4-methylpiperazin-1-yl)-1H-indazole-6-sulfonamide;
1,3-diethyl-N-(3-methylazetidin-3-yl)-2,4-dioxo-1,2,3,4-tetrahydroquinazoline-6-sulfonamide;
1,3-diethyl-N-(1-methylcyclopentyl)-2,4-dioxo-1,2,3,4-tetrahydroquinazoline-6-sulfonamide;
N-((1S,2S)-1-cyano-2-vinylcyclopropyl)-1,3-diethyl-2,4-dioxo-1,2,3,4-tetrahydroquinazoline-6-sulfonamide;
N-((1R,2S)-1-cyano-2-vinylcyclopropyl)-1,3-diethyl-2,4-dioxo-1,2,3,4-tetrahydroquinazoline-6-sulfonamide;
N-((1S,2R)-1-cyano-2-ethylcyclopropyl)-1,3-diethyl-2,4-dioxo-1,2,3,4-tetrahydroquinazoline-6-sulfonamide;
N-((1R,2S)-1-cyano-2-ethylcyclopropyl)-1,3-diethyl-2,4-dioxo-1,2,3,4-tetrahydroquinazoline-6-sulfonamide;
1,3-diethyl-N-((1S,2S)-1-methyl-2-vinylcyclopropyl)-2,4-dioxo-1,2,3,4-tetrahydroquinazoline-6-sulfonamide;
N-(1-cyano-2-(2-hydroxyethyl)cyclopropyl)-1,3-diethyl-2,4-dioxo-1,2,3,4-tetrahydroquinazoline-6-sulfonamide;
N-((1S,2S)-1-cyano-2-(2-methoxyethyl)cyclopropyl)-1,3-diethyl-2,4-dioxo-1,2,3,4-tetrahydroquinazoline-6-sulfonamide;

N-((1R,2R)-1-cyano-2-(2-methoxyethyl)cyclopropyl)-1,3-diethyl-2,4-dioxo-1,2,3,4-tetrahydroquinazoline-6-sulfonamide;

1-(5-(difluoromethyl)-1,3,4-thiadiazol-2-yl)-N-(3-methyloxetan-3-yl)-1H-indazole-6-sulfonamide;

N-((2R,3S)-3-cyano-2-methyloxetan-3-yl)-1,3-diethyl-2,4-dioxo-1,2,3,4-tetrahydroquinazoline-6-sulfonamide;

N-((2S,3R)-3-cyano-2-methyloxetan-3-yl)-1,3-diethyl-2,4-dioxo-1,2,3,4-tetrahydroquinazoline-6-sulfonamide;

N-((2S,3S)-3-cyano-2-methyloxetan-3-yl)-1,3-diethyl-2,4-dioxo-1,2,3,4-tetrahydroquinazoline-6-sulfonamide;

4-chloro-N-(3-cyanooxetan-3-yl)-1-(5-(difluoromethyl)-1,3,4-thiadiazol-2-yl)-1H-indazole-6-sulfonamide;

4-chloro-N-(1-cyano-2-(2-hydroxyethyl)cyclopropyl)-1-(5-(difluoromethyl)-1,3,4-thiadiazol-2-yl)-1H-indazole-6-sulfonamide;

4-chloro-1-(5-(difluoromethyl)-1,3,4-thiadiazol-2-yl)-N-(2-(2-hydroxyethyl)-1-methylcyclopropyl)-1H-indazole-6-sulfonamide;

1,3-diethyl-N-((1R,2S)-1-(hydroxymethyl)-2-vinylcyclopropyl)-2,4-dioxo-1,2,3,4-tetrahydroquinazoline-6-sulfonamide;

N-((1S,2S)-1-cyano-2-(2-hydroxyethyl)cyclopropyl)-1-(5-(difluoromethyl)-1,3,4-thiadiazol-2-yl)-4-(4-isobutyrylpiperazin-1-yl)-1H-indazole-6-sulfonamide;

N-((1R,2R)-1-cyano-2-(2-hydroxyethyl)cyclopropyl)-1-(5-(difluoromethyl)-1,3,4-thiadiazol-2-yl)-4-(4-isobutyrylpiperazin-1-yl)-1H-indazole-6-sulfonamide;

1-(5-(difluoromethyl)-1,3,4-thiadiazol-2-yl)-N-((1S,2S)-2-(2-hydroxyethyl)-1-methylcyclopropyl)-4-(4-isobutyrylpiperazin-1-yl)-1H-indazole-6-sulfonamide;

1-(5-(difluoromethyl)-1,3,4-thiadiazol-2-yl)-N-((1R,2R)-2-(2-hydroxyethyl)-1-methylcyclopropyl)-4-(4-isobutyrylpiperazin-1-yl)-1H-indazole-6-sulfonamide;

4-chloro-1-(5-(difluoromethyl)-1,3,4-thiadiazol-2-yl)-N-(2,3-dimethyloxetan-3-yl)-1H-indazole-6-sulfonamide;

1-methyl-N-(3-methyloxetan-3-yl)-1H-indazole-6-sulfonamide;

1-(5-(difluoromethyl)-1,3,4-thiadiazol-2-yl)-4-methoxy-N-(3-methyloxetan-3-yl)-1H-indazole-6-sulfonamide;

1,3-diethyl-N-((1R,2R)-2-(hydroxymethyl)cyclobutyl)-2,4-dioxo-1,2,3,4-tetrahydroquinazoline-6-sulfonamide;

1,3-diethyl-N-((1S,2S)-2-(hydroxymethyl)cyclobutyl)-2,4-dioxo-1,2,3,4-tetrahydroquinazoline-6-sulfonamide;

4-(4-(cyclopentanecarbonyl)piperazin-1-yl)-1-(5-(difluoromethyl)-1,3,4-thiadiazol-2-yl)-N-(3-methyloxetan-3-yl)-1H-indazole-6-sulfonamide;

N-(2,2-difluoroethyl)-4-(1-(5-(difluoromethyl)-1,3,4-thiadiazol-2-yl)-6-(N-(3-(fluoromethyl)oxetan-3-yl)sulfamoyl)-1H-indazol-4-yl)-N-methylpiperazine-1-carboxamide;

N-((1S,2S)-1-cyano-2-(hydroxymethyl)cyclopropyl)-1,3-diethyl-2,4-dioxo-1,2,3,4-tetrahydroquinazoline-6-sulfonamide;

(S)-1-(5-(difluoromethyl)-1,3,4-thiadiazol-2-yl)-4-(4-isobutyryl-3-methylpiperazin-1-yl)-N-(3-methyloxetan-3-yl)-1H-indazole-6-sulfonamide;

4-(4-isobutyrylpiperazin-1-yl)-N-(3-methyloxetan-3-yl)-1-(5-vinyl-1,3,4-thiadiazol-2-yl)-1H-indazole-6-sulfonamide; and 1-(5-bromo-1,3,4-thiadiazol-2-yl)-4-(4-isobutyrylpiperazin-1-yl)-N-(3-methyloxetan-3-yl)-1H-indazole-6-sulfonamide.

In some embodiments, provided herein is a compound of Formula (I), or a pharmaceutically acceptable salt thereof, selected from:

ethyl (2E)-4-[6-({bicyclo[1.1.1]pentan-1-yl}sulfamoyl)-2,4-dioxo-1H-quinazolin-3-yl]but-2-enoate;

(2E)-4-[6-({bicyclo[1.1.1]pentan-1-yl}sulfamoyl)-2,4-dioxo-1H-quinazolin-3-yl]but-2-enoic acid;

(2E)-4-[6-({bicyclo[1.1.1]pentan-1-yl}sulfamoyl)-2,4-dioxo-1H-quinazolin-3-yl]but-2-enamide;

1,3-diethyl-N-(3-methyloxetan-3-yl)-2,4-dioxoquinazoline-6-sulfonamide;

1,3-diethyl-N-(3-methylthietan-3-yl)-2,4-dioxoquinazoline-6-sulfonamide;

1-[5-(difluoromethyl)-1,3,4-thiadiazol-2-yl]-N-(3-methyloxetan-3-yl)-4-[4-(2-methylpropanoyl)piperazin-1-yl]indazole-6-sulfonamide;

1,3-diethyl-N-(1-methylcyclobutyl)-2,4-dioxoquinazoline-6-sulfonamide;

1,3-diethyl-N-(3-methyloxolan-3-yl)-2,4-dioxoquinazoline-6-sulfonamide;

methyl (2E)-4-{6-[(3-methyloxetan-3-yl)sulfamoyl]-2,4-dioxo-1H-quinazolin-3-yl}but-2-enoate;

N-(3-cyanooxetan-3-yl)-1,3-diethyl-2,4-dioxoquinazoline-6-sulfonamide;

methyl (2E)-4-{6-[(3-methyloxetan-3-yl)sulfamoyl]-1-(oxetan-3-ylmethyl)-2,4-dioxoquinazolin-3-yl}but-2-enoate;

methyl (E)-5-(6-(N-(3-methyloxetan-3-yl)sulfamoyl)-2,4-dioxo-1,4-dihydroquinazolin-3(2H)-yl)pent-2-enoate;

1,3-diethyl-N-((1S,2R)-2-ethyl-1-methylcyclopropyl)-2,4-dioxo-1,2,3,4-tetrahydroquinazoline-6-sulfonamide;

1-((2,4-dimethylthiazol-5-yl)methyl)-N-(3-methyloxetan-3-yl)-3-((2-methylthiazol-5-yl)methyl)-2,4-dioxo-1,2,3,4-tetrahydroquinazoline-6-sulfonamide;

1,3-diethyl-N-((1S,2S)-2-(2-hydroxyethyl)-1-methylcyclopropyl)-2,4-dioxo-1,2,3,4-tetrahydroquinazoline-6-sulfonamide;

N-((1S,2S)-2-(cyanomethyl)-1-methylcyclopropyl)-1,3-diethyl-2,4-dioxo-1,2,3,4-tetrahydroquinazoline-6-sulfonamide;

N-((2S,3S)-2,3-dimethyloxetan-3-yl)-1,3-diethyl-2,4-dioxo-1,2,3,4-tetrahydroquinazoline-6-sulfonamide;

N-(3-(difluoromethyl)oxetan-3-yl)-1,3-diethyl-2,4-dioxo-1,2,3,4-tetrahydroquinazoline-6-sulfonamide;

(E)-N-methyl-4-(6-(N-(3-methyloxetan-3-yl)sulfamoyl)-2,4-dioxo-1,4-dihydroquinazolin-3(2H)-yl)but-2-enamide; and 1,3-diethyl-N-(3-(fluoromethyl)oxetan-3-yl)-2,4-dioxo-1,2,3,4-tetrahydroquinazoline-6-sulfonamide.

In some embodiments, provided herein is a compound of Formula (I), or a pharmaceutically acceptable salt thereof, selected from:

1,3-diethyl-N-((1S,2S)-2-ethyl-1-methylcyclopropyl)-2,4-dioxo-1,2,3,4-tetrahydroquinazoline-6-sulfonamide;

1,3-diethyl-N-((1R,2R)-2-ethyl-1-methylcyclopropyl)-2,4-dioxo-1,2,3,4-tetrahydroquinazoline-6-sulfonamide;

1,3-diethyl-N-((1R,2S)-2-ethyl-1-methylcyclopropyl)-2,4-dioxo-1,2,3,4-tetrahydroquinazoline-6-sulfonamide;

1,3-diethyl-N-((1R,2R)-2-(2-hydroxyethyl)-1-methylcyclopropyl)-2,4-dioxo-1,2,3,4-tetrahydroquinazoline-6-sulfonamide;

N-((2S,3S)-2,3-dimethyloxetan-3-yl)-1,3-diethyl-2,4-dioxo-1,2,3,4-tetrahydroquinazoline-6-sulfonamide;

N-((2R,3R)-2,3-dimethyloxetan-3-yl)-1,3-diethyl-2,4-dioxo-1,2,3,4-tetrahydroquinazoline-6-sulfonamide;

N-((2R,3S)-2,3-dimethyloxetan-3-yl)-1,3-diethyl-2,4-dioxo-1,2,3,4-tetrahydroquinazoline-6-sulfonamide;

1-(5-(difluoromethyl)-1,3,4-thiadiazol-2-yl)-4-(4-isobutyrylpiperazin-1-yl)-N-(1-methylcyclobutyl)-1H-indazole-6-sulfonamide;

1-(5-(difluoromethyl)-1,3,4-thiadiazol-2-yl)-N-(3-(fluoromethyl)oxetan-3-yl)-4-(4-isobutyrylpiperazin-1-yl)-1H-indazole-6-sulfonamide;

1-(5-(difluoromethyl)-1,3,4-thiadiazol-2-yl)-N-(3-methyloxetan-3-yl)-1H-indazole-6-sulfonamide;

4-chloro-N-(3-cyanooxetan-3-yl)-1-(5-(difluoromethyl)-1,3,4-thiadiazol-2-yl)-1H-indazole-6-sulfonamide;

N-(3-cyanooxetan-3-yl)-1-((2,4-dimethylthiazol-5-yl)methyl)-3-((2-methylthiazol-5-yl)methyl)-2,4-dioxo-1,2,3,4-tetrahydroquinazoline-6-sulfonamide;

N-(3-cyanooxetan-3-yl)-3-((2-methylthiazol-5-yl)methyl)-2,4-dioxo-1,2,3,4-tetrahydroquinazoline-6-sulfonamide;

1-(5-(difluoromethyl)-1,3,4-thiadiazol-2-yl)-4-(dimethylamino)-N-(3-methyloxetan-3-yl)-1H-indazole-6-sulfonamide;

1-(5-(difluoromethyl)-1,3,4-thiadiazol-2-yl)-N-((2S,3S)-2,3-dimethyloxetan-3-yl)-4-(4-isobutyrylpiperazin-1-yl)-1H-indazole-6-sulfonamide;

N-(3-(fluoromethyl)oxetan-3-yl)-3-((2-methylthiazol-5-yl)methyl)-2,4-dioxo-1,2,3,4-tetrahydroquinazoline-6-sulfonamide;

1-((2,4-dimethylthiazol-5-yl)methyl)-N-(3-(fluoromethyl)oxetan-3-yl)-3-((2-methylthiazol-5-yl)methyl)-2,4-dioxo-1,2,3,4-tetrahydroquinazoline-6-sulfonamide;

1-(5-(difluoromethyl)-1,3,4-thiadiazol-2-yl)-4-(4-isobutyrylpiperazin-1-yl)-N-(oxetan-3-yl)-1H-indazole-6-sulfonamide;

N-(3-cyanooxetan-3-yl)-1-(5-(difluoromethyl)-1,3,4-thiadiazol-2-yl)-4-(4-isobutyrylpiperazin-1-yl)-1H-indazole-6-sulfonamide;

4-(4-isobutyrylpiperazin-1-yl)-N-(3-methyloxetan-3-yl)-1-(5-((methylsulfonyl)methyl)-1,3,4-thiadiazol-2-yl)-1H-indazole-6-sulfonamide;

N-(3-cyano-2-methyloxetan-3-yl)-1-(5-(difluoromethyl)-1,3,4-thiadiazol-2-yl)-4-(4-isobutyrylpiperazin-1-yl)-1H-indazole-6-sulfonamide;

1-(5-(difluoromethyl)-1,3,4-thiadiazol-2-yl)-4-(4-(isopropylsulfonyl)piperazin-1-yl)-N-(3-methyloxetan-3-yl)-1H-indazole-6-sulfonamide;

4-(4-(cyclopentanecarbonyl)piperazin-1-yl)-1-(5-(difluoromethyl)-1,3,4-thiadiazol-2-yl)-N-(3-(fluoromethyl)oxetan-3-yl)-1H-indazole-6-sulfonamide;

1-(5-(difluoromethyl)-1,3,4-thiadiazol-2-yl)-N-(3-methyloxetan-3-yl)-4-(4-(pyrrolidine-1-carbonyl)piperazin-1-yl)-1H-indazole-6-sulfonamide;

1-(5-(difluoromethyl)-1,3,4-thiadiazol-2-yl)-N-(3-(fluoromethyl)oxetan-3-yl)-4-(4-(pyrrolidine-1-carbonyl)piperazin-1-yl)-1H-indazole-6-sulfonamide;

N-(2,2-difluoroethyl)-4-(1-(5-(difluoromethyl)-1,3,4-thiadiazol-2-yl)-6-(N-(3-methyloxetan-3-yl)sulfamoyl)-1H-indazol-4-yl)-N-methylpiperazine-1-carboxamide;

N-(3-cyanooxetan-3-yl)-1-(5-(difluoromethyl)-1,3,4-thiadiazol-2-yl)-4-(4-(pyrrolidine-1-carbonyl)piperazin-1-yl)-1H-indazole-6-sulfonamide;

N-(3-cyanooxetan-3-yl)-4-(4-(cyclopropanecarbonyl)piperazin-1-yl)-1-(5-(difluoromethyl)-1,3,4-thiadiazol-2-yl)-1H-indazole-6-sulfonamide;

N-(3-cyanooxetan-3-yl)-4-(4-(cyclopentanecarbonyl)piperazin-1-yl)-1-(5-(difluoromethyl)-1,3,4-thiadiazol-2-yl)-1H-indazole-6-sulfonamide;

4-(6-(N-(3-cyanooxetan-3-yl)sulfamoyl)-1-(5-(difluoromethyl)-1,3,4-thiadiazol-2-yl)-1H-indazol-4-yl)-N-(2,2-difluoroethyl)-N-methylpiperazine-1-carboxamide;

N-(3-(fluoromethyl)oxetan-3-yl)-4-(4-isobutyrylpiperazin-1-yl)-1-(5-methyl-1,3,4-thiadiazol-2-yl)-1H-indazole-6-sulfonamide;

1-(5-cyclopropyl-1,3,4-thiadiazol-2-yl)-N-(3-(fluoromethyl)oxetan-3-yl)-4-(4-isobutyrylpiperazin-1-yl)-1H-indazole-6-sulfonamide;

N-(3-(fluoromethyl)oxetan-3-yl)-4-(4-isobutyrylpiperazin-1-yl)-1-(1,3,4-thiadiazol-2-yl)-1H-indazole-6-sulfonamide;

4-(4-isobutyrylpiperazin-1-yl)-1-(5-methyl-1,3,4-thiadiazol-2-yl)-N-(3-methyloxetan-3-yl)-1H-indazole-6-sulfonamide;

4-(4-isobutyrylpiperazin-1-yl)-N-(3-methyloxetan-3-yl)-1-(1,3,4-thiadiazol-2-yl)-1H-indazole-6-sulfonamide;

N-(3-(fluoromethyl)oxetan-3-yl)-4-(4-isobutyrylpiperazin-1-yl)-1-(5-vinyl-1,3,4-thiadiazol-2-yl)-1H-indazole-6-sulfonamide;

1-(5-(difluoromethyl)-1,3,4-thiadiazol-2-yl)-N-(3-methyloxetan-3-yl)-4-(4-methylpiperazin-1-yl)-1H-indazole-6-sulfonamide;

1,3-diethyl-N-(3-methylazetidin-3-yl)-2,4-dioxo-1,2,3,4-tetrahydroquinazoline-6-sulfonamide;

1,3-diethyl-N-(1-methylcyclopentyl)-2,4-dioxo-1,2,3,4-tetrahydroquinazoline-6-sulfonamide;

N-((1S,2S)-1-cyano-2-vinylcyclopropyl)-1,3-diethyl-2,4-dioxo-1,2,3,4-tetrahydroquinazoline-6-sulfonamide;

N-((1R,2S)-1-cyano-2-vinylcyclopropyl)-1,3-diethyl-2,4-dioxo-1,2,3,4-tetrahydroquinazoline-6-sulfonamide;

N-((1S,2R)-1-cyano-2-ethylcyclopropyl)-1,3-diethyl-2,4-dioxo-1,2,3,4-tetrahydroquinazoline-6-sulfonamide;

N-((1R,2S)-1-cyano-2-ethylcyclopropyl)-1,3-diethyl-2,4-dioxo-1,2,3,4-tetrahydroquinazoline-6-sulfonamide;

1,3-diethyl-N-((1S,2S)-1-methyl-2-vinylcyclopropyl)-2,4-dioxo-1,2,3,4-tetrahydroquinazoline-6-sulfonamide;

N-(1-cyano-2-(2-hydroxyethyl)cyclopropyl)-1,3-diethyl-2,4-dioxo-1,2,3,4-tetrahydroquinazoline-6-sulfonamide;

N-((1S,2S)-1-cyano-2-(2-methoxyethyl)cyclopropyl)-1,3-diethyl-2,4-dioxo-1,2,3,4-tetrahydroquinazoline-6-sulfonamide;

N-((1R,2R)-1-cyano-2-(2-methoxyethyl)cyclopropyl)-1,3-diethyl-2,4-dioxo-1,2,3,4-tetrahydroquinazoline-6-sulfonamide;

1-(5-(difluoromethyl)-1,3,4-thiadiazol-2-yl)-N-(3-methyloxetan-3-yl)-1H-indazole-6-sulfonamide;

N-((2R,3S)-3-cyano-2-methyloxetan-3-yl)-1,3-diethyl-2,4-dioxo-1,2,3,4-tetrahydroquinazoline-6-sulfonamide;

N-((2S,3R)-3-cyano-2-methyloxetan-3-yl)-1,3-diethyl-2,4-dioxo-1,2,3,4-tetrahydroquinazoline-6-sulfonamide;

N-((2S,3S)-3-cyano-2-methyloxetan-3-yl)-1,3-diethyl-2,4-dioxo-1,2,3,4-tetrahydroquinazoline-6-sulfonamide;

4-chloro-N-(3-cyanooxetan-3-yl)-1-(5-(difluoromethyl)-1,3,4-thiadiazol-2-yl)-1H-indazole-6-sulfonamide;

4-chloro-N-(1-cyano-2-(2-hydroxyethyl)cyclopropyl)-1-(5-(difluoromethyl)-1,3,4-thiadiazol-2-yl)-1H-indazole-6-sulfonamide;

4-chloro-1-(5-(difluoromethyl)-1,3,4-thiadiazol-2-yl)-N-(2-(2-hydroxyethyl)-1-methylcyclopropyl)-1H-indazole-6-sulfonamide;

1,3-diethyl-N-((1R,2S)-1-(hydroxymethyl)-2-vinylcyclopropyl)-2,4-dioxo-1,2,3,4-tetrahydroquinazoline-6-sulfonamide;

N-((1S,2S)-1-cyano-2-(2-hydroxyethyl)cyclopropyl)-1-(5-(difluoromethyl)-1,3,4-thiadiazol-2-yl)-4-(4-isobutyrylpiperazin-1-yl)-1H-indazole-6-sulfonamide;

N-((1R,2R)-1-cyano-2-(2-hydroxyethyl)cyclopropyl)-1-(5-(difluoromethyl)-1,3,4-thiadiazol-2-yl)-4-(4-isobutyrylpiperazin-1-yl)-1H-indazole-6-sulfonamide;

1-(5-(difluoromethyl)-1,3,4-thiadiazol-2-yl)-N-((1S,2S)-2-(2-hydroxyethyl)-1-methylcyclopropyl)-4-(4-isobutyrylpiperazin-1-yl)-1H-indazole-6-sulfonamide;

1-(5-(difluoromethyl)-1,3,4-thiadiazol-2-yl)-N-((1R,2R)-2-(2-hydroxyethyl)-1-methylcyclopropyl)-4-(4-isobutyrylpiperazin-1-yl)-1H-indazole-6-sulfonamide;

4-chloro-1-(5-(difluoromethyl)-1,3,4-thiadiazol-2-yl)-N-(2,3-dimethyloxetan-3-yl)-1H-indazole-6-sulfonamide;

1-methyl-N-(3-methyloxetan-3-yl)-1H-indazole-6-sulfonamide;

1-(5-(difluoromethyl)-1,3,4-thiadiazol-2-yl)-4-methoxy-N-(3-methyloxetan-3-yl)-1H-indazole-6-sulfonamide;

1,3-diethyl-N-((1R,2R)-2-(hydroxymethyl)cyclobutyl)-2,4-dioxo-1,2,3,4-tetrahydroquinazoline-6-sulfonamide;

1,3-diethyl-N-((1S,2S)-2-(hydroxymethyl)cyclobutyl)-2,4-dioxo-1,2,3,4-tetrahydroquinazoline-6-sulfonamide;

4-(4-(cyclopentanecarbonyl)piperazin-1-yl)-1-(5-(difluoromethyl)-1,3,4-thiadiazol-2-yl)-N-(3-methyloxetan-3-yl)-1H-indazole-6-sulfonamide;

N-(2,2-difluoroethyl)-4-(1-(5-(difluoromethyl)-1,3,4-thiadiazol-2-yl)-6-(N-(3-(fluoromethyl)oxetan-3-yl)sulfamoyl)-1H-indazol-4-yl)-N-methylpiperazine-1-carboxamide;

N-((1S,2S)-1-cyano-2-(hydroxymethyl)cyclopropyl)-1,3-diethyl-2,4-dioxo-1,2,3,4-tetrahydroquinazoline-6-sulfonamide;

(S)-1-(5-(difluoromethyl)-1,3,4-thiadiazol-2-yl)-4-(4-isobutyryl-3-methylpiperazin-1-yl)-N-(3-methyloxetan-3-yl)-1H-indazole-6-sulfonamide;

4-(4-isobutyrylpiperazin-1-yl)-N-(3-methyloxetan-3-yl)-1-(5-vinyl-1,3,4-thiadiazol-2-yl)-1H-indazole-6-sulfonamide; and 1-(5-bromo-1,3,4-thiadiazol-2-yl)-4-(4-isobutyrylpiperazin-1-yl)-N-(3-methyloxetan-3-yl)-1H-indazole-6-sulfonamide.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "pyridinyl," "pyridyl," or "a pyridine ring" may refer to a pyridin-2-yl, pyridin-3-yl, or pyridin-4-yl ring.

The term "n-membered," where "n" is an integer, typically describes the number of ring-forming atoms in a moiety where the number of ring-forming atoms is "n". For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen group. It is to be understood that substitution at a given atom is limited by valency.

As used herein, the term "$C_{i-j}$," where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. In some embodiments, the alkyl group contains 1 to 7, 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, n-heptyl, and the like. In some embodiments, the alkyl group is methyl, ethyl, or propyl.

As used herein, "alkenyl," employed alone or in combination with other terms, refers to an alkyl group having one or more carbon-carbon double bonds. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl," employed alone or in combination with other terms, refers to an alkyl group having one or more carbon-carbon triple bonds. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, "halo" or "halogen", employed alone or in combination with other terms, includes fluoro, chloro, bromo, and iodo. In some embodiments, halo is F or Cl.

As used herein, the term "haloalkyl," employed alone or in combination with other terms, refers to an alkyl group having up to the full valency of halogen atom substituents, which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like.

As used herein, the term "alkoxy," employed alone or in combination with other terms, refers to a group of formula —O-alkyl. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "haloalkoxy," employed alone or in combination with other terms, refers to a group of formula —O-(haloalkyl). In some embodiments, the alkyl group has 1 to 6 or 1 to 4 carbon atoms. An example haloalkoxy group is —$OCF_3$.

As used herein, "amino," employed alone or in combination with other terms, refers to $NH_2$.

As used herein, the term "cycloalkyl," employed alone or in combination with other terms, refers to a non-aromatic cyclic hydrocarbon including cyclized alkyl and alkenyl groups. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5]octane and the like). In some embodiments, the cycloalkyl group has 3 to 10 ring members, or 3 to 7 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "heterocycloalkyl," employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-aza-spiro[4.5]decan-N-yl] and the like). In some embodiments, the heterocycloalkyl group has 3 to 10 ring-forming atoms, 4 to 10 ring-forming atoms, or about 3 to 8 ring forming atoms. In some embodiments, the heterocycloalkyl group has 2 to 20 carbon atoms, 2 to 15 carbon atoms, 2 to 10 carbon atoms, or about 2 to 8 carbon atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, tetrahydropyran ring, tetrahyropyridine, azetidine ring, or tetrahydrofuran ring.

As used herein, the term "aryl," employed alone or in combination with other terms, refers to a monocyclic or polycyclic (e.g., a fused ring system) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl.

As used herein, the term "heteroaryl," employed alone or in combination with other terms, refers to a monocyclic or polycyclic (e.g., a fused ring system) aromatic hydrocarbon moiety, having one or more heteroatom ring members independently selected from nitrogen, sulfur and oxygen. In some embodiments, the heteroaryl group is a monocyclic or a bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In some embodiments, the heteroaryl group has from 3 to 10 carbon atoms, from 3 to 8 carbon atoms, from 3 to 5 carbon atoms, from 1 to 5 carbon atoms, or from 5 to 10 carbon atoms. In some embodiments, the heteroaryl group contains 3 to 14, 4 to 12, 4 to 8, 9 to 10, or 5 to 6 ring-forming atoms. In some embodiments, the heteroaryl group has 1 to 4, 1 to 3, or 1 to 2 heteroatoms.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Geometric isomers of olefins, C=N double bonds, and the like can also be present in the compounds described herein, and all such stable isomers are contemplated in the present invention. Cis and trans geometric isomers of the compounds of the present invention may be isolated as a mixture of isomers or as separated isomeric forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution. An example of tautomeric forms, pyridazin-3(2H)-one and pyridazin-3-ol, is depicted below:

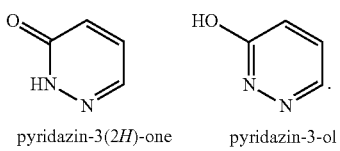 [SMILES: O=c1cccn[nH]1 ; Oc1cccnn1]

pyridazin-3(2H)-one       pyridazin-3-ol

Compounds of the invention also include all isotopes of atoms occurring in the intermediates or final compounds. Isotopes include those atoms having the same atomic number but different mass numbers. For example, isotopes of hydrogen include tritium and deuterium. In some embodiments, the compounds of the invention include at least one deuterium atom.

The term, "compound," as used herein is meant to include all stereoisomers, geometric iosomers, tautomers, and isotopes of the structures depicted, unless otherwise specified.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

As used herein, and unless otherwise specified, the term "about", when used in connection with a numeric value or range of values which is provided to describe a particular solid form (e.g., a specific temperature or temperature range, such as describing a melting, dehydration, or glass transition; a mass change, such as a mass change as a function of temperature or humidity; a solvent or water content, in terms of, for example, mass or a percentage; or a peak position, such as in analysis by, for example, $^{13}C$ NMR, DSC, TGA and XRPD), indicate that the value or range of values may deviate to an extent deemed reasonable to one of ordinary skill in the art while still describing the particular solid form.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "RT", as used herein, are understood in the art, and refer generally to a temperature, e.g. a reaction temperature, that is about the temperature of the room in which the reaction is carried out, for example, a temperature from about 20° C. to about 30° C.

Compounds of Formula I can be prepared according to numerous preparatory routes known in the literature. Example synthetic methods for preparing compounds of the invention are provided in the Schemes below. Unless noted otherwise, all substituents are as defined herein.

In the process depicted in Scheme 1, an appropriately substituted, sulfonic acid chloride containing compound of Formula (1-1) is substituted with amine compound (1-2) in the presence of a base (e.g., DIEA) to form the sulfonamide compound of Formula (1-3). The compound of Formula (1-3) is substituted with a compound of Formula (1-4) in the presence of base (e.g., potassium carbonate) to form the ester compound of Formula (1-5). The ester compound of Formula (1-5) is hydrolyzed in the presence of lithium hydroxide to form the carboxylic acid compound of Formula (1-6). The carboxylic acid compound of Formula (1-6) is aminated in the presence of thionyl chloride and ammonia to form the amide compound of Formula (1-7).

Scheme 1

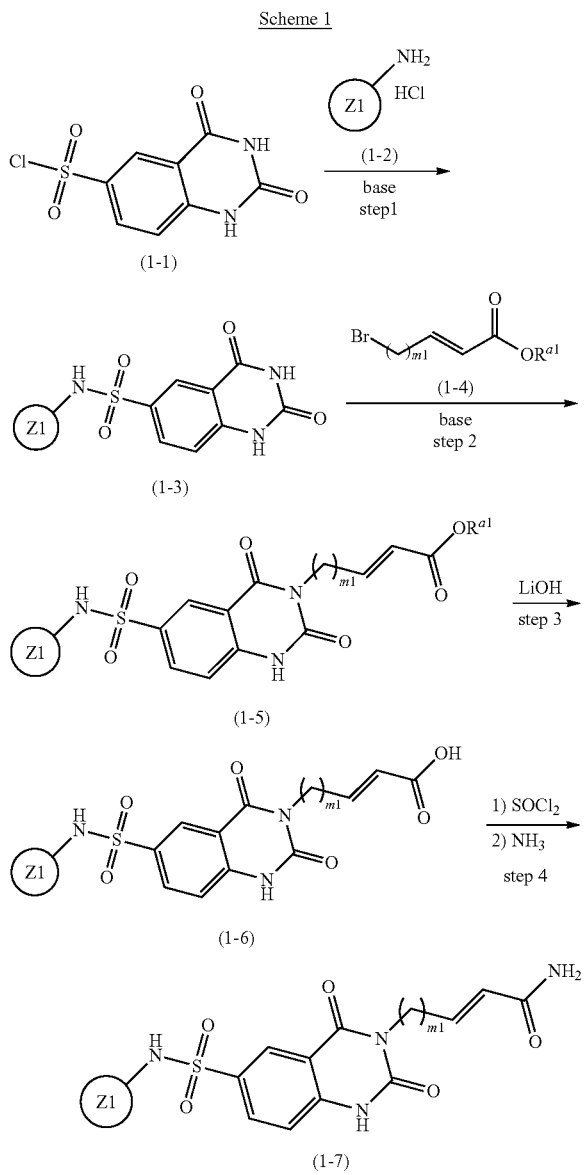

wherein Z1 is a group having the formula:

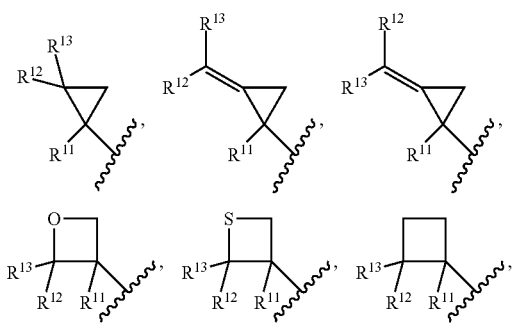

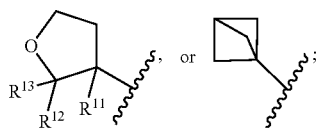

and m1 is an integer selected from 1, 2, 3, and 4.

In the process depicted in Scheme 1', an appropriately substituted, sulfonic acid chloride containing compound of Formula (1-1) is substituted with amine compound (1-2) in the presence of a base (e.g., DIEA) to form the sulfonamide compound of Formula (1-3). The compound of Formula (1-3) is substituted with a compound of Formula (1-4) in the presence of base (e.g., potassium carbonate) to form the ester compound of Formula (1-5). The ester compound of Formula (1-5) is hydrolyzed in the presence of lithium hydroxide to form the carboxylic acid compound of Formula (1-6). The carboxylic acid compound of Formula (1-6) is aminated in the presence of thionyl chloride and ammonia to form the amide compound of Formula (1-7).

Scheme 1'

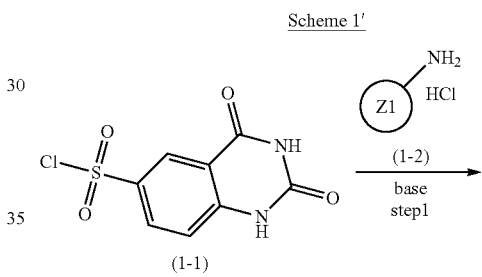

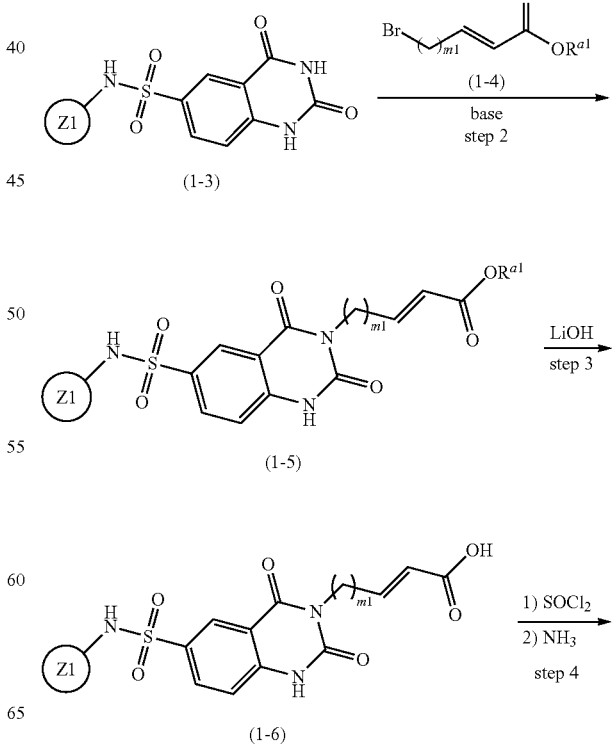

-continued

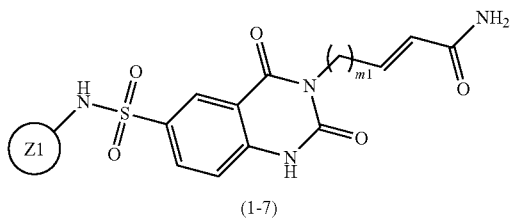

(1-7)

wherein Z1 is a group having the formula:

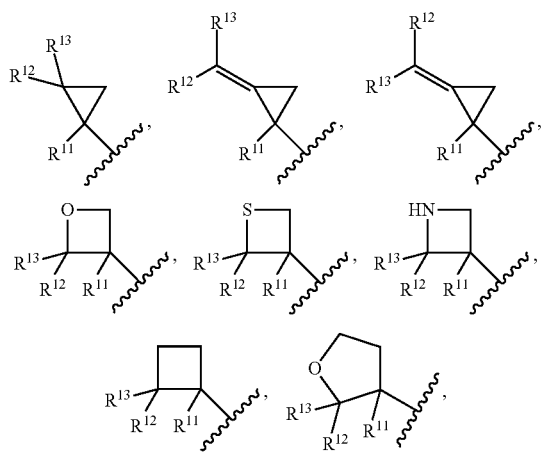

and m1 is an integer selected from 1, 2, 3, and 4.

In the process depicted in Scheme 2, a compound of Formula (2-1) is substituted with a compound of Formula (2-2) in the presence of base (e.g., potassium carbonate) to form a compound of Formula (2-3). The compound of Formula (2-3) is sulfonated in the presence of sulfurochloridic acid (2-4) to form the sulfonic acid compound of Formula (2-5). The sulfonic acid compound of Formula (2-5) is substituted with amine compound (2-6) in the presence of a base (e.g., triethylamine) to form the sulfonamide compound of Formula (2-7).

Scheme 2

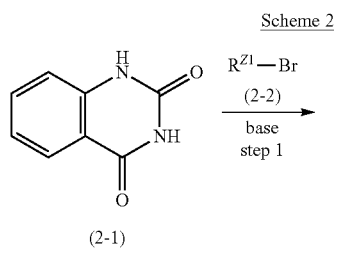

-continued

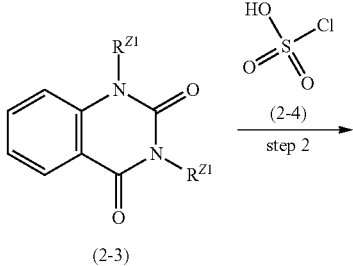

(2-3)

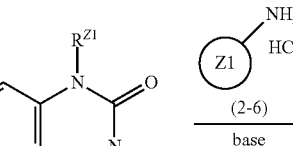

(2-4)
step 2

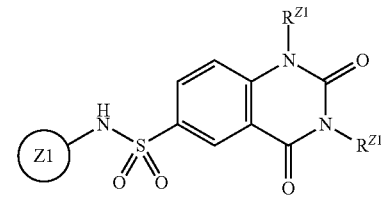

(2-5)

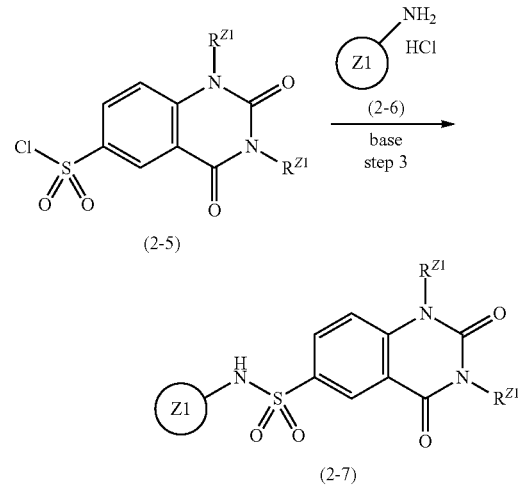

(2-7)

wherein Z1 is a group having the formula:

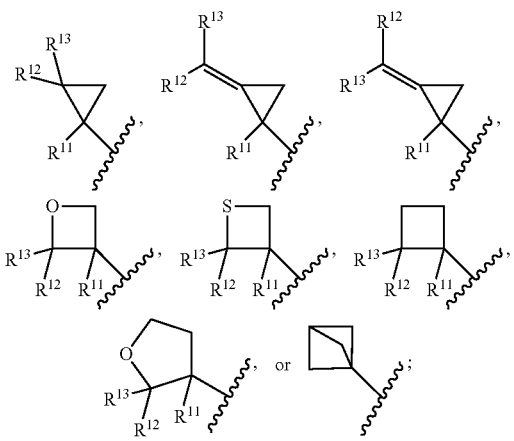

and $R^{Z1}$ is selected from selected from H, $C_{1-4}$ alkyl, and $C_{2-6}$ alkenyl, wherein said $C_{1-4}$ alkyl and $C_{2-6}$ alkenyl are each optionally substituted with 1, 2, or 3 substituents independently selected from $Cy^1$, halo, $C_{1-4}$ alkyl, $C_{2-6}$ alkenyl, $C_{2-6}$ alkynyl, $C_{1-6}$ haloalkyl, CN, $NO_2$, $OR^a$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In the process depicted in Scheme 2', a compound of Formula (2-1) is substituted with a compound of Formula (2-2) in the presence of base (e.g., potassium carbonate) to form a compound of Formula (2-3). The compound of Formula (2-3) is sulfonated in the presence of sulfurochloridic acid (2-4) to form the sulfonic acid compound of Formula (2-5). The sulfonic acid compound of Formula (2-5) is substituted with amine compound (2-6) in the presence of a base (e.g., triethylamine) to form the sulfonamide compound of Formula (2-7).

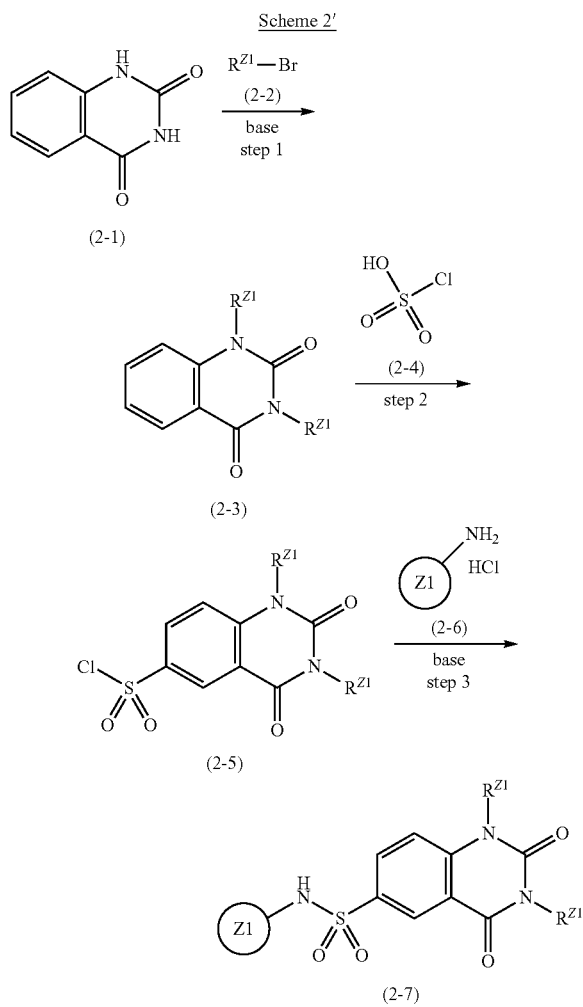

wherein Z1 is a group having the formula:

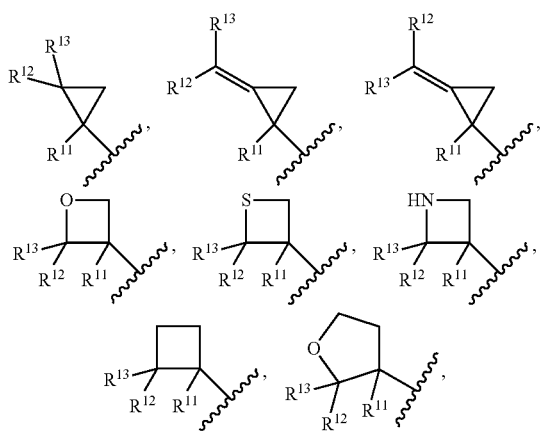

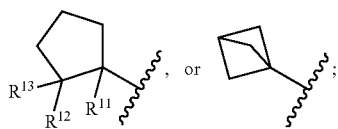

and $R^{Z1}$ is selected from selected from H, $C_{1-4}$ alkyl, and $C_{2-6}$ alkenyl, wherein said $C_{1-4}$ alkyl and $C_{2-6}$ alkenyl are each optionally substituted with 1, 2, or 3 substituents independently selected from $Cy^1$, halo, $C_{1-4}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In the process depicted in Scheme 3, an appropriately substituted bromide compound of Formula (3-1) is substituted with a thiol compound of Formula (3-2) in the presence of XantPhos, $Pd_2(dba)_3$-$CHCl_3$, and a base (e.g., DIEA) to form a compound of Formula (3-3). The compound of Formula (3-3) is substituted with compound (3-4) in the presence of base (e.g., cesium carbonate) to form a compound of Formula (3-5). The thiol compound of Formula (3-5) is reacted with 1,3-dichloro-5,5-dimethylimidazolidine-2,4-dione in the presence of acid (e.g., acetic acid) to form the sulfonic acid compound of Formula (3-6). The sulfonic acid compound of Formula (3-6) is substituted with the amine compound of Formula (3-7) in the presence of a base (e.g., pyridine) to form the sulfonamide compound of Formula (3-8). The sulfonamide compound of Formula (3-8) is substituted with the amine compound of Formula (3-9) in the presence of RuPhos, RuPhos Pd G3, and a base (e.g., cesium carbonate) to form the compound of Formula (3-10).

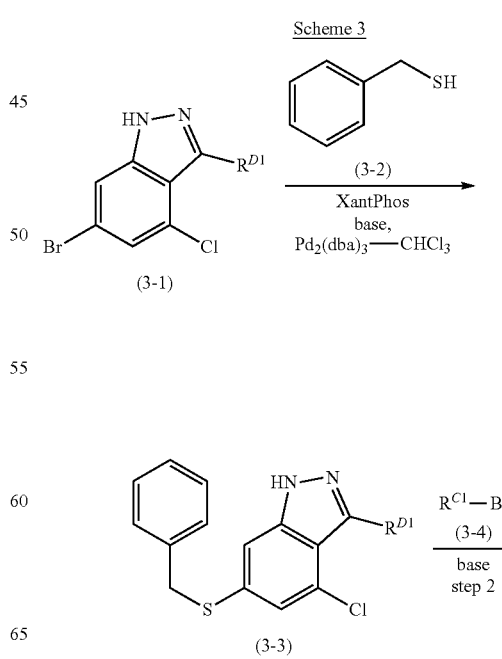

-continued

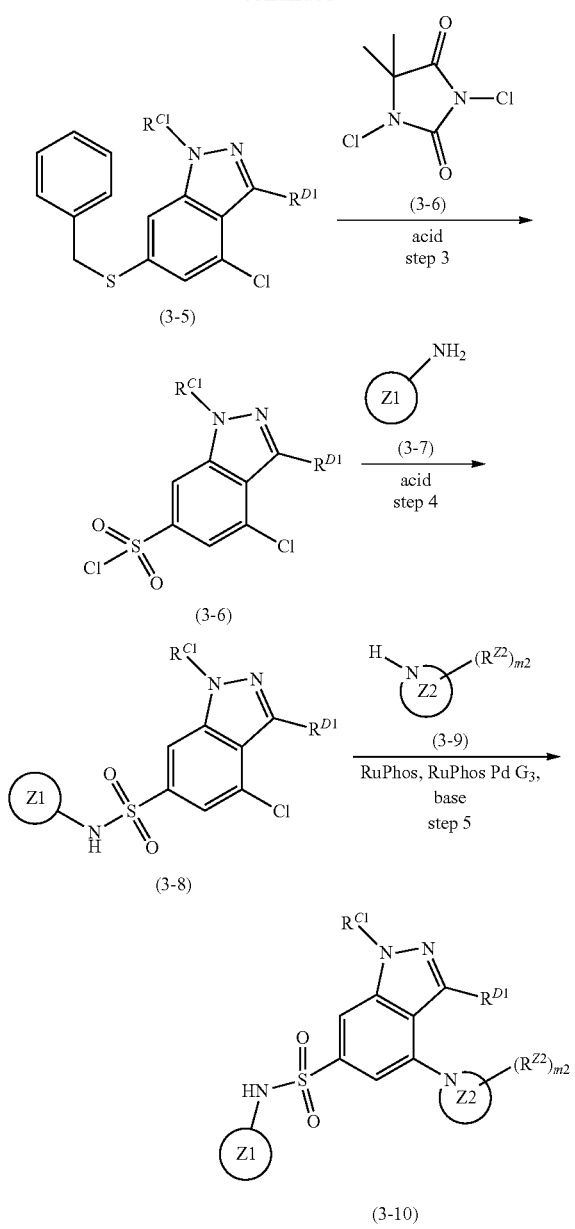

wherein Z1 is a group having the formula:

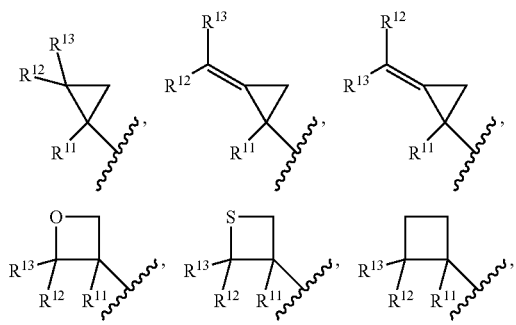

-continued

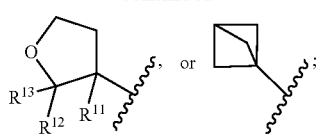

and

Z2 is a heterocycloalkyl, comprising 3-9 ring members in addition to the N atom;

$R^{Z2}$ is selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; and m2 is an integer selected from 1, 2, 3, and 4.

In the process depicted in Scheme 3', an appropriately substituted bromide compound of Formula (3-1) is substituted with a thiol compound of Formula (3-2) in the presence of XantPhos, $Pd_2(dba)_3$-$CHCl_3$, and a base (e.g., DIEA) to form a compound of Formula (3-3). The compound of Formula (3-3) is substituted with compound (3-4) in the presence of base (e.g., cesium carbonate) to form a compound of Formula (3-5). The thiol compound of Formula (3-5) is reacted with 1,3-dichloro-5,5-dimethylimidazolidine-2,4-dione in the presence of acid (e.g., acetic acid) to form the sulfonic acid compound of Formula (3-6). The sulfonic acid compound of Formula (3-6) is substituted with the amine compound of Formula (3-7) in the presence of a base (e.g., pyridine) to form the sulfonamide compound of Formula (3-8). The sulfonamide compound of Formula (3-8) is substituted with the amine compound of Formula (3-9) in the presence of RuPhos, RuPhos Pd G3, and a base (e.g., cesium carbonate) to form the compound of Formula (3-10).

Scheme 3'

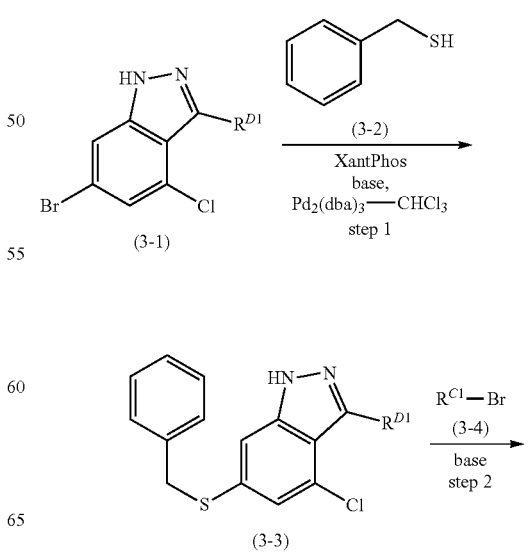

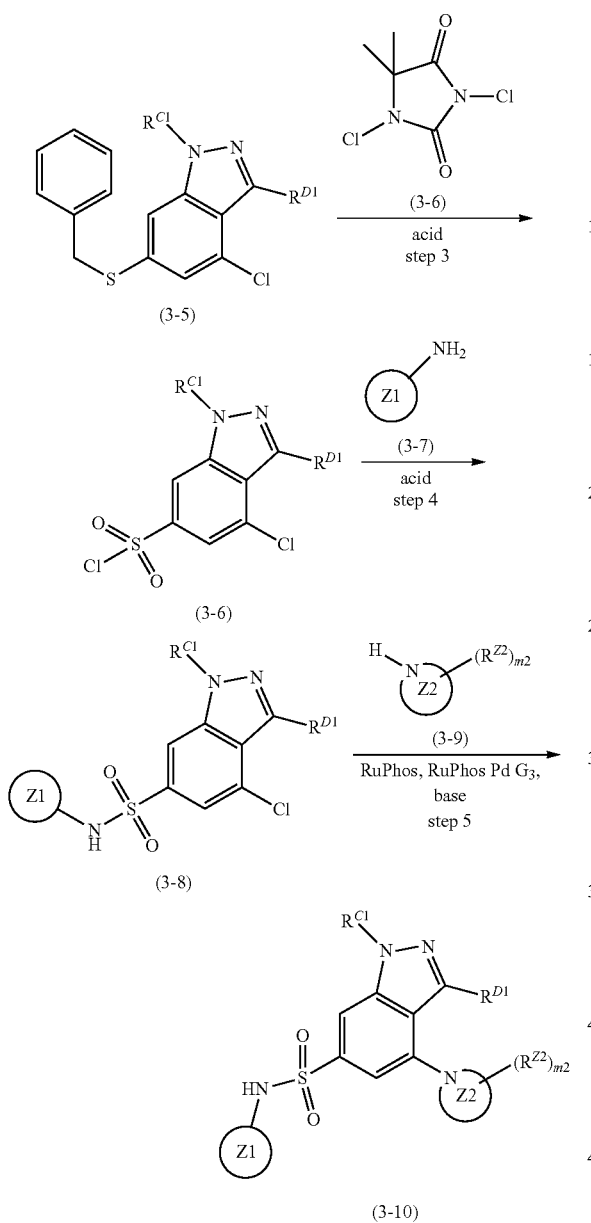

(3-5)

(3-6)

(3-7)

(3-8)

(3-9)

(3-10)

wherein Z1 is a group having the formula:

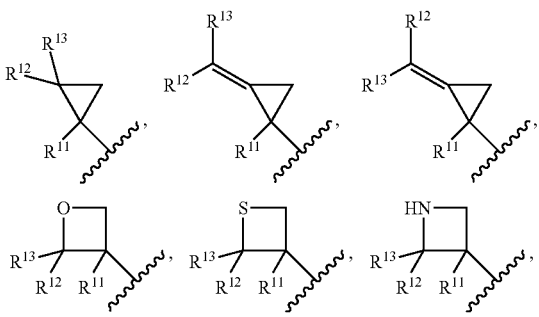

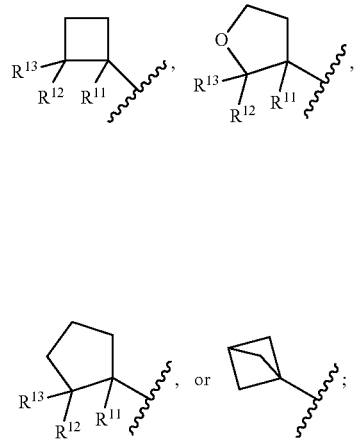

and

Z2 is a heterocycloalkyl, comprising 3-9 ring members in addition to the N atom;

$R^{Z2}$ is selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; and m2 is an integer selected from 1, 2, 3, and 4.

In the process depicted in Scheme 4, an appropriately substituted, aldehyde fluoride-containing compound of Formula (4-1) is substituted with amine compound (4-2) in the presence of a base to form the aldehyde compound of Formula (4-3). The compound of Formula (4-3) is reacted with a hydrazine compound of Formula (4-4) to form the indazole compound of Formula (4-5). The indazole compound of Formula (4-5) is substituted with thiadiazole-bromide compound of Formula (4-6) in the presence of a base to form a 1-indazole compound of Formula (4-7). The indazole compound of Formula (4-7) is substituted with an amine compound of Formula (4-8) in the presence of potassium metabisulfite and a base to form a sulfonamide compound of Formula (4-9).

Scheme 4

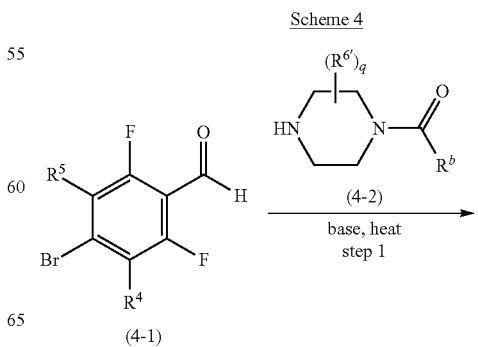

(4-1)

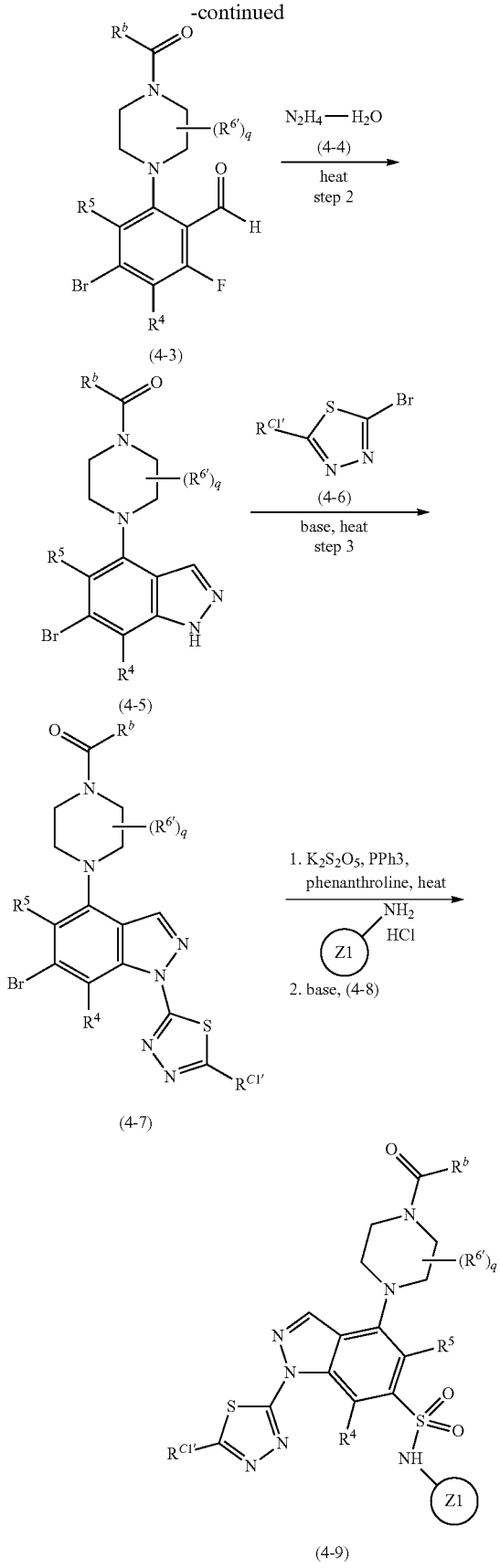

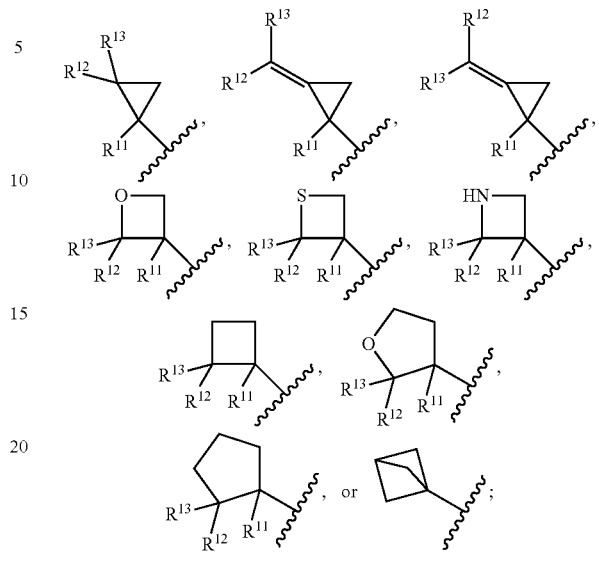

wherein Z1 is a group having the formula:

each $R^{6'}$ is independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; and q is an integer selected from 0, 1, 2, and 3.

Methods of Use

Compounds of the invention can inhibit the activity of PARG. For example, the compounds of the invention can be used to inhibit activity of PARG in a cell or in an individual or patient in need of inhibition of the enzyme by administering an inhibiting amount of a compound of the invention to the cell, individual, or patient. In some embodiments, the PARG is PARG1.

As PARG inhibitors, the compounds of the invention are useful in the treatment of various diseases or disorders associated with abnormal expression or activity of PARG. For example, the compounds of the invention are useful in the treatment of cancer.

In some embodiments, the cancer is a stress-dependent cancer.

In some embodiments, the cancer is selected from lung cancer, colon cancer, breast cancer, ovarian cancer, prostate cancer, liver cancer, pancreatic cancer, brain cancer, skin cancer, bladder cancer, esophageal cancer, head and neck cancer, kidney cancer, rectal cancer, stomach cancer, thyroid cancer, uterine cancer, mantle cell lymphoma, and renal cell carcinoma.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" PARG or "contacting" a cell with a compound of the invention includes the administration of a compound of the present invention to an individual or patient, such as a human, having PARG, as well as, for example, introducing a compound of the invention into a sample containing a cellular or purified preparation containing PARG.

As used herein, the term "individual" or "patient," used interchangeably, refers to mammals, and particularly humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease in an individual who is experiencing or displaying the pathology or symptomatology of the disease (i.e., arresting further development of the pathology and/or symptomatology), or 2) ameliorating the disease in an individual who is experiencing or displaying the pathology or symptomatology of the disease (i.e., reversing the pathology and/or symptomatology).

As used herein the term "preventing" or "prevention" refers to preventing the disease in an individual who may be predisposed to the disease but does not yet experience or display the pathology or symptomatology of the disease.

Combination Therapy

One or more additional pharmaceutical agents or treatment methods such as, for example, chemotherapeutics or other anti-cancer agents, immune enhancers, immunosuppressants, immunotherapies, radiation, anti-tumor and anti-viral vaccines, cytokine therapy (e.g., IL2, GM-CSF, etc.), and/or kinase (tyrosine or serine/threonine), epigenetic or signal transduction inhibitors can be used in combination with the compounds of the present invention. The agents can be combined with the present compounds in a single dosage form, or the agents can be administered simultaneously or sequentially as separate dosage forms.

Suitable agents for use in combination with the compounds of the present invention for the treatment of cancer include chemotherapeutic agents, targeted cancer therapies, immunotherapies or radiation therapy. Compounds of this invention may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present invention. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Angiogenesis inhibitors may be efficacious in some tumors in combination with the compounds of the present invention. These include antibodies against VEGF or VEGFR, or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Suitable chemotherapeutic or other anti-cancer agents for use in combination with the compounds of the present invention include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethio-phosphoramine, busulfan, carmustine, lomustine, streptozocin, dacarbazine, and temozolomide.

Other anti-cancer agent(s) for use in combination with the compounds of the present invention include antibody therapeutics to checkpoint or costimulatory molecules such as CTLA-4, PD-1, PD-L1 or 4-1BB, respectively, or antibodies to cytokines (IL-10, TGF-β, etc.). Exemplary cancer immunotherapy antibodies include pembrolizumab, ipilimumab, nivolumab, atezolizumab and durvalumab. Additional anti-cancer agent(s) for use in combination with the compounds of the present invention include antibody therapeutics directed to surface molecules of hematological cancers such as ofatumumab, rituximab, and alemtuzumab.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions. A pharmaceutical composition refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be oral, topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, or parenteral.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The compositions can be formulated in a unit dosage form. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, anti-cancer agents, vaccines, antibodies, immune enhancers, immune suppressants, anti-inflammatory agents and the like.

EXAMPLES

Definitions: ACN (acetonitrile); AcOH (acetic acid); BPO (benzoyl peroxide); $CH_3CN$ (acetonitrile); $CDCl_3$ (deuterated chloroform); $CD_3OD$ (deuterated methanol); $CH_2Cl_2$ (dichloromethane); $Cs_2CO_3$ (cesium carbonate); DCM (dichloromethane); DEA (diethylamine); DEAD (diethyl azodicarboxylate); DIEA (N,N-diisopropylethylamine); DMF (N,N-dimethylformamide); DMAP (4-dimethyl aminopyridine); DMSO (dimethylsulfoxide); DMSO-$d_6$ (deuterated dimethylsulfoxide); EA (ethyl acetate); ESI (electrospray ionization); EtOAc (ethyl acetate); EtOH (ethanol); g (gram); h (hour); $^1H$ NMR (proton nuclear magnetic resonance); HCl (hydrochloric acid); Hz (hertz); IPA (iso-propyl alcohol); $K_2CO_3$ (potassium carbonate); L (liter); LiCl (lithium chloride); LiOH (lithium hydroxide); LCMS (liquid chromatography-mass spectrometry); M (molar); MeMgBr (methyl magnesium bromide); MeOH (methanol); mg (milligrams); MHz (megahertz); min (minutes); mL (milliliters), mmol (millimoles); MTBE (methyl tert-butyl ether); m/z (mass per charge); $N_2$ (nitrogen); NaCl (sodium chloride); $NH_4Cl$ (ammonium chloride); $NaN_3$ (sodium azide); $NH_3$ (ammonia); $NH_4HCO_3$ (ammonium bicarbonate); nm (nanometers); PE (petroleum ether); $PPh_3$ (triphenylphosphine); prep-HPLC (preparative high-performance liquid chromatography); ppm (parts per million); RT (room temperature); RuPhos (2-Dicyclohexylphosphino-2',6'-diisopropoxybiphenyl); RuPhos-G3-Palladacycle ((2-Dicyclohexylphosphino-2,6-diisopropoxy-1,1-biphenyl)[2-(2-amino-1,1-biphenyl)]palladium(II) methanesulfonate); TEA (triethylamine); TEMPO ((2,2,6,6-tetramethylpiperidin-1-yl)oxyl); THF (tetrahydrofuran); TsCl (tosyl chloride); Rt (retention time); TLC (thin layer chromatography); TMSCN (trimethylsilyl cyanide); UV (ultraviolet); v/v (volume/volume); Xantphos ((9,9-dimethyl-9H-xanthene-4,5-diyl)bis(diphenylphosphane).

Example 1: ethyl (2E)-4-[6-({bicyclo[1.1.1]pentan-1-yl}sulfamoyl)-2,4-dioxo-1H-quinazolin-3-yl]but-2-enoate

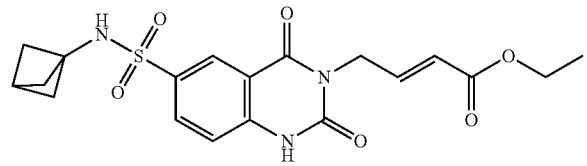 [SMILES: CCOC(=O)/C=C/Cn1c(=O)[nH]c2ccc(S(=O)(=O)NC34CC(C3)C4)cc2c1=O]

Step 1: Synthesis of N-{bicyclo[1.1.1]pentan-1-yl}-2,4-dioxo-1,3-dihydroquinazoline-6-sulfonamide Bicyclo[1.1.1]pentan-1-amine hydrochloride (917.63 mg, 7.673 mmol, 1.0 equiv) and 2,4-dioxo-1,3-dihydroquinazoline-6-sulfonyl chloride (2 g, 7.673 mmol, 1 equiv) were dissolved in THF (20 mL). DIEA (2479.32 mg, 19.183 mmol, 2.5 equiv) was added. The mixture was stirred for overnight at room temperature. The mixture was analyzed by TLC (DCM/MeOH 1:1). The mixture was poured into water and the precipitated solids were collected by filtration and washed with water (2×10 mL). This resulted in N-{bicyclo[1.1.1]pentan-1-yl}-2,4-dioxo-1,3-dihydroquinazoline-6-sulfonamide (2 g, 76.33%) as a white solid. $^1$H NMR (300 MHz, DMSO-$d_6$) δ 11.56 (s, 2H), 8.66 (s, 1H), 8.28 (s, 1H), 7.99 (d, J=8.6 Hz, 1H), 7.31 (d, J=8.6 Hz, 1H), 2.28 (s, 1H), 1.71 (s, 6H).

Step 2: Synthesis of ethyl (2E)-4-[6-({bicyclo[1.1.1]pentan-1-yl}sulfamoyl)-2,4-dioxo-1H-quinazolin-3-yl]but-2-enoate A mixture of N-{bicyclo[1.1.1]pentan-1-yl}-2,4-dioxo-1,3-dihydroquinazoline-6-sulfonamide (1.2 g, 3.905 mmol, 1 equiv) and ethyl (2E)-4-bromobut-2-enoate (0.75 g, 3.905 mmol, 1.0 equiv) in DMF (12 mL), $K_2CO_3$ (589.68 mg, 4.267 mmol, 1.05 equiv) was added and stirred for overnight at room temperature. Desired product could be detected by LCMS. The mixture was diluted with EA (50 mL) and washed with water (3×20 mL). The resulting mixture was dried over $Na_2SO_4$ and concentrated under pressure. The crude product (1.5 g) was purified by reverse flash chromatography with the following conditions: column, C18 gel; mobile phase, MeCN in water, 10% to 80% gradient in 40 min; detector, UV 254 nm. The desired compound was collected and concentrated under vacuum for Prep-HPLC with the following conditions (XBridge Shield RP 18OBD column 30*150 mm, 5 um; Mobile Phase A: Water-$NH_4HCO_3$, Mobile B: ACN; flow rate 60 mL/min; Gradient 25% B to 51% B in 7 min; 254/220 nm; Rt 6.32 minutes (detected by LCMS and collectEd)) to afford ethyl (2E)-4-[6-({bicyclo[1.1.1]pentan-1-yl}sulfamoyl)-2,4-dioxo-1H-quinazolin-3-yl]but-2-enoate (222.9 mg) as a white solid. LCMS (ESI, m/z): 420.05 [M+H]$^+$; $^1$H NMR (400 MHz, DMSO-d6) δ 11.86 (s, 1H), 8.71 (s, 1H), 8.32 (d, J=2.2 Hz, 1H), 8.03 (dd, J=8.6, 2.2 Hz, 1H), 7.34 (d, J=8.5 Hz, 1H), 6.92 (dt, J=15.9, 4.7 Hz, 1H), 5.94 (dt, J=15.7, 1.8 Hz, 1H), 4.82-4.60 (m, 2H), 4.10 (q, J=7.1 Hz, 2H), 2.28 (s, 1H), 1.72 (s, 7H), 1.19 (t, J=7.1 Hz, 3H).

Example 2: (2E)-4-[6-({bicyclo[1.1.1]pentan-1-yl}sulfamoyl)-2,4-dioxo-1H-quinazolin-3-yl]but-2-enoic acid

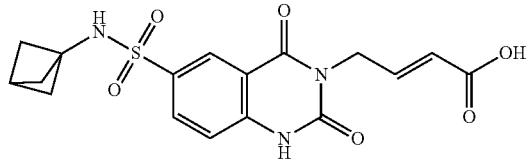 [SMILES: O=C(O)/C=C/Cn1c(=O)[nH]c2ccc(S(=O)(=O)NC34CC(C3)C4)cc2c1=O]

Step 1: Synthesis of (2E)-4-[6-({bicyclo[1.1.1]pentan-1-yl}sulfamoyl)-2,4-dioxo-1H-quinazolin-3-yl]but-2-enoic acid Ethyl (2E)-4-[6-({bicyclo[1.1.1]pentan-1-yl}sulfamoyl)-2,4-dioxo-1H-quinazolin-3-yl]but-2-enoate (220 mg, 0.524 mmol, 1 equiv) in THF (3 mL), LiOH—$H_2O$ (220.08 mg, 5.240 mmol, 10 equiv) in $H_2O$ (3 mL) was added. The mixture was stirred overnight at room temperature. The mixture was acidified to pH 1-2 with HCl (1M). The aqueous layer was extracted with EA (2×10 mL). The layer was washed with water (1×10 mL), dried over $Na_2SO_4$ and concentrated under vacuum. The resulting was lyophilized directly to give desired product (2E)-4-[6-({bicyclo[1.1.1]pentan-1-yl}sulfamoyl)-2,4-dioxo-1H-quinazolin-3-yl]but-2-enoic acid (200 mg, 87.68%) as a white solid. LCMS (ESI, m/z): 392 [M+H]$^+$; $^1$H NMR (400 MHz, DMSO-$d_6$) δ 11.95 (s, 2H), 8.74 (s, 1H), 8.33 (d, J=2.2 Hz, 1H), 8.03 (dd, J=8.7, 2.2 Hz, 1H), 7.35 (d, J=8.7 Hz, 1H), 6.82 (dt, J=15.8, 4.9 Hz, 1H), 5.83 (dt, J=15.8, 1.8 Hz, 1H), 4.65 (dd, J=4.9, 1.9 Hz, 2H), 2.29 (s, 1H), 1.72 (s, 6H).

Example 3: (2E)-4-[6-({bicyclo[1.1.1]pentan-1-yl}sulfamoyl)-2,4-dioxo-1H-quinazolin-3-yl]but-2-enamide

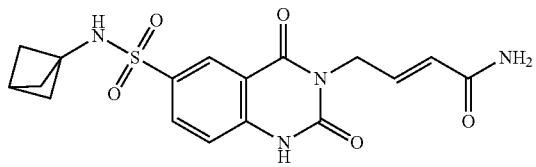 [SMILES: NC(=O)/C=C/Cn1c(=O)[nH]c2ccc(S(=O)(=O)NC34CC(C3)C4)cc2c1=O]

Step 1: Synthesis of (2E)-4-[6-({bicyclo[1.1.1]pentan-1-yl}sulfamoyl)-2,4-dioxo-1H-quinazolin-3-yl]but-2-enamide A mixture of (2E)-4-[6-({bicyclo[1.1.1]pentan-1-yl}sulfamoyl)-2,4-dioxo-1H-quinazolin-3-yl]but-2-enoic acid (120 mg, 0.307 mmol, 1 equiv) in $SOCl_2$ (1 mL, 13.786 mmol, 44.97 equiv) was stirred for 2 hours at 60° C. The resulting mixture was concentrated under reduced pressure. $NH_3$(g) in dioxane (0.5M, 3 mL) was added. The mixture was stirred for 10 minutes at room temperature. The resulting mixture was concentrated under reduced pressure. The mixture was diluted with DMF (2 mL) for Pre-HPLC. (Column: YMC-Actus Triart C18, 30×150 nm, 5 um; mobile phase A: Water (10 mmol/L NH$_4$HCO$_3$, mobile B: ACN; flow rate: 60 ml/min); Gradient: 20% B to 42% B in 7 minutes, wave length: 254 nm; RT 4.98). This resulted in (2E)-4-[6-({bicyclo[1.1.1]pentan-1-yl}sulfamoyl)-2,4-di-oxo-1H-quinazolin-3-yl]but-2-enamide (23.9 mg, 19.87%) as a white solid. LCMS (ESI, m/z): 391 [M+H]$^+$; $^1$H NMR (300 MHz, methanol-d4) δ 8.50 (d, J=2.2 Hz, 1H), 8.05 (dd, J=8.6, 2.2 Hz, 1H), 7.31 (d, J=8.7 Hz, 1H), 6.80 (dt, J=15.6, 5.2 Hz, 1H), 6.05 (dt, J=15.6, 1.7 Hz, 1H), 4.77 (dd, J=5.3, 1.8 Hz, 2H), 2.28 (s, 1H), 1.81 (s, 6H).

Example 4: 1,3-diethyl-N-(3-methyloxetan-3-yl)-2,4-dioxoquinazoline-6-sulfonamide

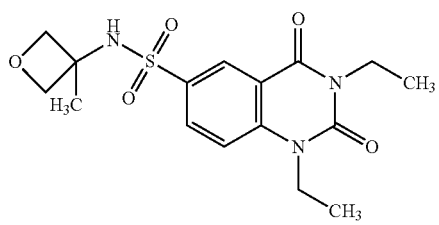

Step 1: Synthesis of 1,3-diethyl-N-(3-methyloxetan-3-yl)-2,4-dioxoquinazoline-6-sulfonamide To a solution of 3-methyloxetan-3-amine (27.50 mg, 0.316 mmol, 1 equiv) in pyridine (2 mL) was added 1,3-diethyl-2,4-dioxoquinazoline-6-sulfonyl chloride (100 mg, 0.316 mmol, 1 equiv). The mixture was stirred for 16 h at rt. The resulting mixture was concentrated under reduced pressure. The solid was purified by Prep-HPLC with the following conditions (Column: XBridge Prep OBD C18 Column, 30×150 mm, 5 μm; Mobile Phase A: Water (10 mmol/L NH$_4$HCO$_3$+0.1% NH$_3$—H$_2$O), Mobile Phase B: ACN; Flow rate: 60 mL/min; Gradient: 20% B to 40% B in 7 min, 40% B; Wave Length: 254 nm; RT1(min): 6.43) to afford 1,3-diethyl-N-(3-methyloxetan-3-yl)-2,4-dioxoquinazoline-6-sulfonamide (36.9 mg, 31.75%) as a white solid. LCMS (ES. m/z): 368 [M+H]$^+$; $^1$H NMR (300 MHz, DMSO-d$_6$) δ 8.44 (d, J=2.3 Hz, 1H), 8.31 (s, 1H), 8.09 (dd, J=8.9, 2.4 Hz, 1H), 7.70 (d, J=9.0 Hz, 1H), 4.55 (d, J=6.1 Hz, 2H), 4.16 (m, 4H), 3.99 (q, J=7.0 Hz, 2H), 1.42 (s, 3H), 1.21 (dt, J=17.0, 7.0 Hz, 6H).

Example 5: 1,3-diethyl-N-(3-methylthietan-3-yl)-2,4-dioxoquinazoline-6-sulfonamide

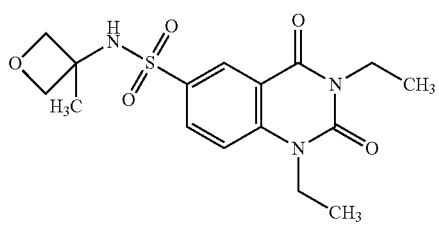 [SMILES: CCn1c(=O)c2cc(S(=O)(=O)NC3(C)COC3)ccc2n(CC)c1=O]

Step 1: Synthesis of 1,3-diethyl-N-(3-methylthietan-3-yl)-2,4-dioxoquinazoline-6-sulfonamide To a solution of 3-methylthietan-3-amine hydrochloride (44.08 mg, 0.316 mmol, 1 equiv) in pyridine (2 mL) was added 1,3-diethyl-2,4-dioxoquinazoline-6-sulfonyl chloride (100 mg, 0.316 mmol, 1 equiv). The mixture was stirred for 16 h at rt. The resulting mixture was concentrated under reduced pressure. The residue was purified by Prep-TLC (PE/EA 1:1). The crude product was purified by Prep-HPLC with the following conditions (Column: XBridge Prep OBD C18 Column, 30×150 mm, 5 μm; Mobile Phase A: Water (10 mmol/L NH$_4$HCO$_3$+0.1% NH$_3$—H$_2$O), Mobile Phase B: ACN; Flow rate: 60 mL/min; Gradient: 33% B to 63% B in 7 min, 63% B; Wave Length: 254 nm; RT1(min): 6) to afford 1,3-diethyl-N-(3-methylthietan-3-yl)-2,4-dioxoquinazoline-6-sulfonamide (8.1 mg, 6.62%) as a white solid. LCMS (ES. m/z): 384 [M+H]$^+$; $^1$H NMR (300 MHz, DMSO-d$_6$) δ 8.45 (d, J=2.4 Hz, 1H), 8.10 (dd, J=8.9, 2.4 Hz, 1H), 7.70 (d, J=8.9 Hz, 1H), 4.17 (q, J=7.0 Hz, 2H), 3.99 (q, J=7.0 Hz, 2H), 3.53 (d, J=9.2 Hz, 2H), 2.74-2.64 (m, 2H), 1.57 (s, 3H), 1.21 (dt, J=16.4, 7.0 Hz, 6H).

Example 6: Synthesis of 1-[5-(difluoromethyl)-1,3,4-thiadiazol-2-yl]-N-(3-methyloxetan-3-yl)-4-[4-(2-methylpropanoyl)piperazin-1-yl]indazole-6-sulfonamide

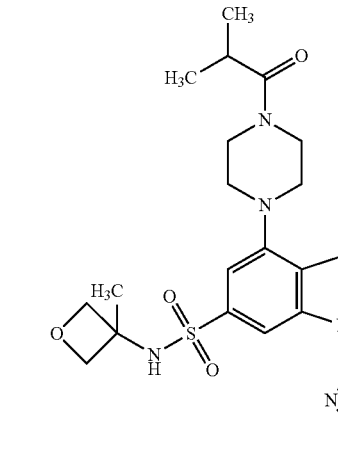

Step 1: Synthesis of 6-(benzylsulfanyl)-4-chloro-1H-indazole

To a stirred solution of 6-bromo-4-chloro-1H-indazole (5 g, 21.600 mmol, 1 equiv) and benzyl mercaptan (5.37 g, 43.200 mmol, 2 equiv) in 1,4-dioxane (50 ml) were added Xantphos (2.50 g, 4.320 mmol, 0.2 equiv) and Pd$_2$(dba)$_3$CHCl$_3$ (2.24 g, 2.160 mmol, 0.1 equiv) in portions at room temperature under N$_2$ atmosphere. To the above mixture was added DIEA (8.38 g, 64.800 mmol, 3 equiv) dropwise over 2 min at room temperature. The resulting mixture was stirred for additional 3 h at 100° C. The resulting mixture was concentrated under reduced pressure. The residue was purified by silica gel column chromatography, eluted with PE/EA (6:1) to afford 6-(benzylsulfanyl)-4-chloro-1H-indazole (5.6 g, 93.41%) as a yellow solid. LCMS (ESI, m/z): 275 [M+H]$^+$.

Step 2: Synthesis of 6-(benzylsulfanyl)-4-chloro-1-[5-(difluoromethyl)-1,3,4-thiadiazol-2-yl]indazole To a stirred solution of 6-(benzylsulfanyl)-4-chloro-1H-indazole (2.6 g, 9.368 mmol, 1 equiv, 99%) and 2-bromo-5-(difluoromethyl)-1,3,4-thiadiazole (2.01 g, 9.368 mmol, 1 equiv) in DMF (25 mL) was added Cs₂CO₃ (3.05 g, 9.368 mmol, 1 equiv) in portions at room temperature under nitrogen atmosphere. The resulting mixture was stirred for 3 h at 100° C. under nitrogen atmosphere. The resulting mixture was diluted with ethyl acetate (100 mL).

The resulting mixture was washed with of water (2×100 mL). The resulting mixture was concentrated under reduced pressure. The residue was purified by silica gel column chromatography, eluted with CH₂Cl₂/MeOH (12:1) to afford 6-(benzylsulfanyl)-4-chloro-1-[5-(difluoromethyl)-1,3,4-thiadiazol-2-yl]indazole (3 g, 72.06%) as a yellow solid. LCMS (ESI, m/z): 409 [M+H]⁺.

Step 3: Synthesis of 4-chloro-1-[5-(difluoromethyl)-1,3,4-thiadiazol-2-yl]indazole-6-sulfonyl chloride To a stirred solution of 6-(benzylsulfanyl)-4-chloro-1-[5-(difluoromethyl)-1,3,4-thiadiazol-2-yl]indazole (2.8 g, 6.300 mmol, 1 equiv, 92%) and AcOH (0.5 mL) in acetonitrile (50 mL) was added H₂O (50 mL) dropwise at room temperature under air atmosphere. To the above mixture was added 1,3-dichloro-5,5-dimethylimidazolidine-2,4-dione (1.86 g, 9.450 mmol, 1.5 equiv) in portions over 5 min at 0° C. The resulting mixture was stirred for additional 2 h at 0° C. The resulting mixture was concentrated under reduced pressure. The residue was purified by silica gel column chromatography, eluted with CH₂Cl₂/MeOH (9:1) to afford 4-chloro-1-[5-(difluoromethyl)-1,3,4-thiadiazol-2-yl]indazole-6-sulfonyl chloride (2.5 g, 97.87%) as a yellow solid. LCMS (ESI, m/z): 365 [M−H]⁻.

Step 4: Synthesis of 4-chloro-1-[5-(difluoromethyl)-1,3,4-thiadiazol-2-yl]-N-(3-methyloxetan-3-yl)indazole-6-sulfonamide To a stirred solution of 3-methyloxetan-3-amine (54.28 mg, 0.623 mmol, 1.2 equiv) in pyridine (2 mL) was added 4-chloro-1-[5-(difluoromethyl)-1,3,4-thiadiazol-2-yl]indazole-6-sulfonyl chloride (200 mg, 0.519 mmol, 1 equiv) in portions at room temperature under air atmosphere. The resulting mixture was stirred for additional overnight at room temperature. The resulting mixture was concentrated under reduced pressure. The residue was purified by silica gel column chromatography, eluted with CH₂Cl₂/MeOH (12:1) to afford 4-chloro-1-[5-(difluoromethyl)-1,3,4-thiadiazol-2-yl]-N-(3-methyloxetan-3-yl)indazole-6-sulfonamide (220 mg, 92.35%) as off-white solid. LCMS: (ES, m/z): [M+H]⁺=436.

Step 5: Synthesis of 1-[5-(difluoromethyl)-1,3,4-thiadiazol-2-yl]-N-(3-methyloxetan-3-yl)-4-[4-(2-methylpropanoyl)piperazin-1-yl]indazole-6-sulfonamide To a stirred solution of 4-chloro-1-[5-(difluoromethyl)-1,3,4-thiadiazol-2-yl]-N-(3-methyloxetan-3-yl)indazole-6-sulfonamide (160 mg, 0.367 mmol, 1 equiv) and 2-methyl-1-(piperazin-1-yl)propan-1-one (86.03 mg, 0.550 mmol, 1.5 equiv) in 1,4-dioxane (2 mL) were added RuPhos (68.52 mg, 0.147 mmol, 0.4 equiv) and RuPhos Palladacycle Gen.3 (61.41 mg, 0.073 mmol, 0.2 equiv) dropwise at room temperature under nitrogen atmosphere. To the above mixture was added Cs₂CO₃ (239.22 mg, 0.734 mmol, 2 equiv) dropwise at room temperature. The resulting mixture was stirred for additional 16 h at 100° C. The resulting mixture was concentrated under reduced pressure. The crude product was purified by reverse phase flash with the following conditions (Column: XBridge Prep OBD C18 Column, 19*250 mm, 5 μm; Mobile Phase A: Water (10 mmol/L NH₄HCO₃), Mobile Phase B: ACN; Flow rate: 25 mL/min; Gradient: 47% B to 67% B in 7 min, 67% B; Wave Length: 254 nm; RT1(min): 5.38) to afford 1-[5-(difluoromethyl)-1,3,4-thiadiazol-2-yl]-N-(3-methyloxetan-3-yl)-4-[4-(2-methylpropanoyl)piperazin-1-yl]indazole-6-sulfonamide (65 mg, 31.84%) as a white solid. LCMS (ESI, m/z): 556 [M+H]⁺; ¹H NMR (300 MHz, DMSO-d₆) δ 8.95 (s, 1H), 8.63 (s, 1H), 8.45 (s, 1H), 7.60 (t, J=53.0 Hz, 1H), 7.15 (d, J=1.4 Hz, 1H), 4.57 (d, J=6.1 Hz, 2H), 4.17-4.09 (d, J=6.1 Hz, 2H), 3.83-3.72 (m, 4H), 3.47 (m, 4H), 2.95 (p, J=6.8 Hz, 1H), 1.44 (s, 3H), 1.05 (d, J=6.7 Hz, 6H).

Example 7: 1,3-diethyl-N-(1-methylcyclobutyl)-2,4-dioxoquinazoline-6-sulfonamide

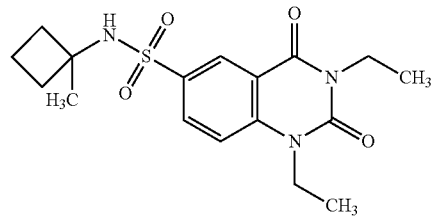 [SMILES: CCn1c(=O)c2cc(S(=O)(=O)NC3(C)CCC3)ccc2n(CC)c1=O]

Step 1: 1,3-diethylquinazoline-2,4-dione

A solution of 1,3-dihydroquinazoline-2,4-dione (6 g, 37.003 mmol, 1 equiv), bromoethane (12.10 g, 111.009 mmol, 3 equiv), K₂CO₃ (15.34 g, 111.009 mmol, 3 equiv) in DMF (100 mL) was stirred for 16 h at room temperature. The resulting mixture was extracted with EA (3×100 mL). The combined organic layers were washed with brine, dried over anhydrous Na₂SO₄. After filtration, the filtrate was concentrated under reduced pressure. The residue was purified by silica gel column chromatography, eluted with PE/EA (1:1) to afford 1,3-diethylquinazoline-2,4-dione (8 g, 89.15%) as a white solid. LCMS (ES. m/z): 219 [M+H]⁺.

Step 2: 1,3-diethyl-2,4-dioxoquinazoline-6-sulfonyl chloride

A solution of 1,3-diethylquinazoline-2,4-dione (3 g, 13.745 mmol, 1 equiv) in chlorosulfonic acid (10 mL) was stirred for 5 h at 60° C. The mixture was allowed to cool down to room temperature. The reaction mixture was dropwise poured into crushed ice and the isolated solid was collected. The solid was washed with diethyl ether. The precipitated solid was collected by filtration. This resulted in 1,3-diethyl-2,4-dioxoquinazoline-6-sulfonyl chloride (4 g, 78.09%) as a light brown solid. LCMS (ESI, m/z): 317 [M+H]⁺.

Step 3: 1,3-diethyl-N-(1-methylcyclobutyl)-2,4-dioxoquinazoline-6-sulfonamide To a solution of 1-methylcyclobutan-1-amine hydrochloride (42.23 mg, 0.348 mmol, 1.1 equiv), TEA (95.84 mg, 0.948 mmol, 3 equiv) in DCM (3 mL) was added 1,3-diethyl-2,4-dioxoquinazoline-6-sulfonyl chloride (100 mg, 0.316 mmol, 1 equiv). The mixture was stirred for 16 h at rt. The resulting mixture was concentrated under reduced pressure. The residue was purified by silica gel column chromatography, eluted with CH$_2$Cl$_2$/EA (3:1). The resulting mixture was concentrated under reduced pressure. The crude product was purified by Prep-HPLC with the following conditions (Column: XBridge Shield RP18 OBD Column, 30×150 mm, 5 μm; Mobile Phase A: Water (10 mmol/L NH$_4$HCO$_3$+0.1% NH$_3$—H$_2$O), Mobile Phase B: ACN; Flow rate: 60 mL/min; Gradient: 35% B to 55% B in 7 min, 55% B; Wave Length: 254 nm; RT1(min): 5.45) to afford 1,3-diethyl-N-(1-methylcyclobutyl)-2,4-dioxoquinazoline-6-sulfonamide (55.2 mg, 47.80%) as a white solid. LCMS (ES. m/z): 366 [M+H]$^+$; $^1$H NMR (300 MHz, DMSO-d$_6$) δ 8.44 (d, J=2.3 Hz, 1H), 8.09 (dd, J=8.9, 2.3 Hz, 1H), 8.00 (s, 1H), 7.69 (d, J=8.9 Hz, 1H), 4.17 (q, J=7.0 Hz, 2H), 3.99 (q, J=7.0 Hz, 2H), 2.19-2.02 (m, 2H), 1.74-1.51 (m, 4H), 1.31-1.17 (m, 9H).

Example 8: 1,3-diethyl-N-(3-methyloxolan-3-yl)-2,4-dioxoquinazoline-6-sulfonamide

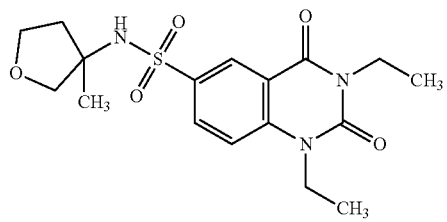 [SMILES: CCn1c(=O)c2cc(S(=O)(=O)NC3(C)CCOC3)ccc2n(CC)c1=O]

Step 1: Synthesis of 1,3-diethyl-N-(3-methyloxolan-3-yl)-2,4-dioxoquinazoline-6-sulfonamide To a solution of 3-methyloxolan-3-amine hydrochloride (65.16 mg, 0.474 mmol, 1 equiv), TEA (143.76 mg, 1.422 mmol, 3 equiv) in DCM (3 mL) was added 1,3-diethyl-2,4-dioxoquinazoline-6-sulfonyl chloride (150 mg, 0.474 mmol, 1 equiv). The mixture was stirred for 16 h at rt. The resulting mixture was concentrated under reduced pressure. The residue was purified by Prep-TLC (CH$_2$Cl$_2$/EA 1:1). The resulting mixture was concentrated under reduced pressure. The crude product was purified by Prep-HPLC with the following conditions (Column: XBridge Shield RP18 OBD Column, 30×150 mm, 5 μm; Mobile Phase A: Water (10 mmol/L NH$_4$HCO$_3$), Mobile Phase B: ACN; Flow rate: 60 mL/min; Gradient: 25% B to 45% B in 7 min, 45% B; Wave Length: 254 nm; RT1(min): 5.18) to afford 1,3-diethyl-N-(3-methyloxolan-3-yl)-2,4-dioxoquinazoline-6-sulfonamide (56.1 mg, 31.03%) as a white solid. LCMS (ES. m/z): 382 [M+H]$^+$; $^1$H NMR (300 MHz, DMSO-d$_6$) δ 8.46 (d, J=2.3 Hz, 1H), 8.11 (dd, J=8.9, 2.4 Hz, 1H), 8.08 (s, 1H), 7.69 (d, J=8.9 Hz, 1H), 4.17 (q, J=7.0 Hz, 2H), 3.99 (q, J=7.0 Hz, 2H), 3.70 (dt, J=8.3, 6.3 Hz, 3H), 3.34 (d, J=8.8 Hz, 1H), 2.13 (dt, J=13.3, 6.8 Hz, 1H), 1.72 (dt, J=12.7, 7.6 Hz, 1H), 1.29-1.12 (m, 9H).

Example 9: methyl (2E)-4-{6-[(3-methyloxetan-3-yl)sulfamoyl]-2,4-dioxo-1H-quinazolin-3-yl}but-2-enoate

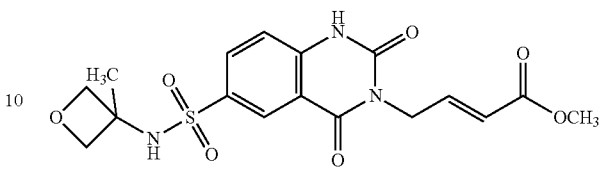

Step 1: Synthesis of N-(3-methyloxetan-3-yl)-2,4-dioxo-1,3-dihydroquinazoline-6-sulfonamide A mixture of 3-methyloxetan-3-amine (0.33 g, 3.837 mmol, 1.0 equiv) and DIEA (1.49 g, 11.511 mmol, 3.0 equiv) in THF (15 mL), 2,4-dioxo-1,3-dihydroquinazoline-6-sulfonyl chloride (1 g, 3.837 mmol, 1 equiv) was added in portion at 0° C. The mixture was stirred for overnight at room temperature. Desired product could be detected by LCMS. The mixture pours into water. The precipitated solids were collected by filtration and washed with H$_2$O. The resulting mixture was concentrated under reduced pressure. This resulted in N-(3-methyloxetan-3-yl)-2,4-dioxo-1,3-dihydroquinazoline-6-sulfonamide (1 g, 75.35%) as a white solid. LCMS (ESI, m/z): 312[M+H]$^+$.

Step 2: Synthesis of methyl (2E)-4-{6-[(3-methyloxetan-3-yl)sulfamoyl]-2,4-dioxo-1H-quinazolin-3-yl}but-2-enoate A mixture of N-(3-methyloxetan-3-yl)-2,4-dioxo-1,3-dihydroquinazoline-6-sulfonamide (1 g, 3.212 mmol, 1 equiv) and methyl (2E)-4-bromobut-2-enoate (0.52 g, 2.891 mmol, 0.9 equiv), K$_2$CO$_3$ (0.47 g, 3.373 mmol, 1.05 equiv) in DMF (12 mL) was stirred for overnight at room temperature. The resulting mixture was diluted with EA (30 mL). The resulting mixture was washed with H$_2$O (5×15 mL). The resulting was dried Na$_2$SO$_4$. The resulting mixture was concentrated under reduced pressure. The residue was purified by silica gel column chromatography, eluted with DCM/MeOH (100:0 to 95:5) to afford methyl (2E)-4-{6-[(3-methyloxetan-3-yl)sulfamoyl]-2,4-dioxo-1H-quinazolin-3-yl}but-2-enoate (400 mg, pure 90%). The mixture was diluted with DMF (2 mL) for Pre-HPLC. (Column: XBridge Prep OBD column, 19*250 nm, 5 um; mobile phase A: Water (10 mmol/L NH$_4$HCO$_3$, mobile B: ACN; flow rate: 25 mL/min); Gradient: 24% B to 52% B in 7 minutes, wave length: 254 nm; RT 5.25.) The resulting was lyophilized directly to give desired product methyl (2E)-4-{6-[(3-methyloxetan-3-yl)sulfamoyl]-2,4-dioxo-1H-quinazolin-3-yl}but-2-enoate (300 mg, 22.47%) as a white solid. LCMS (ESI, m/z): 410 [M+H]$^+$; $^1$H NMR (400 MHz, DMSO-d6) δ 11.91 (s, 1H), 8.45 (s, 1H), 8.32 (d, J=2.2 Hz, 1H), 8.04 (dd, J=8.6, 2.3 Hz, 1H), 7.35 (d, J=8.7 Hz, 1H), 6.93 (dt, J=15.9, 4.8 Hz, 1H), 5.97 (dt, J=15.9, 1.8 Hz, 1H), 4.67 (dd, J=4.9, 1.9 Hz, 2H), 4.53 (d, J=6.1 Hz, 2H), 4.13-4.11 (m, 2H), 3.64 (s, 3H), 1.42 (s, 3H).

Example 10: N-(3-cyanooxetan-3-yl)-1,3-diethyl-2, 4-dioxoquinazoline-6-sulfonamide

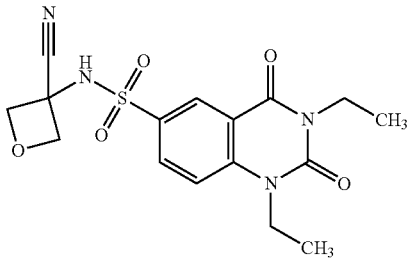 [SMILES: CCn1c(=O)c2cc(S(=O)(=O)NC3(C#N)COC3)ccc2n(CC)c1=O]

Step 1: Synthesis of N-(3-cyanooxetan-3-yl)-1,3-diethyl-2,4-dioxoquinazoline-6-sulfonamide To a solution of 3-aminooxetane-3-carbonitrile hydrochloride (63.72 mg, 0.474 mmol, 1 equiv) in pyridine (3 mL) was added 1,3-diethyl-2,4-dioxoquinazoline-6-sulfonyl chloride (150 mg, 0.474 mmol, 1 equiv). The mixture was stirred for 16 h at rt. The resulting mixture was concentrated under reduced pressure. The residue was purified by Prep-TLC ($CH_2Cl_2$/EA, 1:1). The resulting mixture was concentrated under reduced pressure. The crude product was purified by Prep-HPLC with the following conditions (Column: XBridge Shield RP18 OBD Column, 30×150 mm, 5 μm; Mobile Phase A: Water (10 mmol/L $NH_4HCO_3$), Mobile Phase B: ACN; Flow rate: 60 mL/min; Gradient: 5% B to 25% B in 7 min, 25% B; Wave Length: 254 nm; RT1(min): 6.1) to afford N-(3-cyanooxetan-3-yl)-1,3-diethyl-2,4-dioxoquinazoline-6-sulfonamide (37.7 mg, 20.77%) as a white solid. LCMS (ESI, m/z): 379 [M+H]$^+$; $^1$H NMR (400 MHz, DMSO-$d_6$) δ 8.45 (d, J=2.3 Hz, 1H), 8.09 (dd, J=8.9, 2.4 Hz, 1H), 7.72 (d, J=9.0 Hz, 1H), 4.87-4.80 (m, 2H), 4.73-4.67 (m, 2H), 4.18 (q, J=7.0 Hz, 2H), 3.99 (q, J=7.0 Hz, 2H), 1.20 (dt, J=19.7, 7.0 Hz, 6H).

Example 11: methyl (2E)-4-{6-[(3-methyloxetan-3-yl)sulfamoyl]-1-(oxetan-3-ylmethyl)-2,4-dioxoquinazolin-3-yl}but-2-enoate

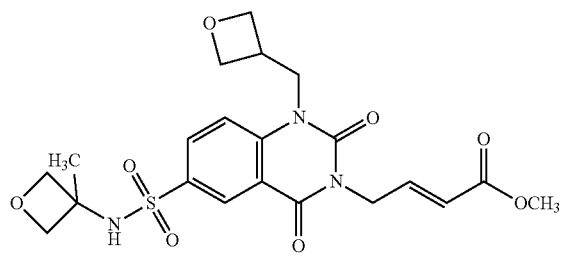 [SMILES: COC(=O)/C=C/Cn1c(=O)c2cc(S(=O)(=O)NC3(C)COC3)ccc2n(CC2COC2)c1=O]

Step 1: Synthesis of methyl (2E)-4-{6-[(3-methyloxetan-3-yl)sulfamoyl]-1-(oxetan-3-ylmethyl)-2,4-dioxoquinazolin-3-yl}but-2-enoate To a solution of methyl (2E)-4-{6-[(3-methyloxetan-3-yl)sulfamoyl]-2,4-dioxo-1H-quinazolin-3-yl}but-2-enoate (100 mg, 0.244 mmol, 1 equiv) and oxetan-3-ylmethanol (21.52 mg, 0.244 mmol, 1 equiv) in THF were added $Ph_3P$ (96.10 mg, 0.366 mmol, 1.5 equiv) and DEAD (63.81 mg, 0.366 mmol, 1.5 equiv). After stirring for 16 hours at room temperature under a nitrogen atmosphere, the resulting mixture was concentrated under reduced pressure.

The residue was purified by flash chromatography with the following conditions: column, silica gel; mobile phase, EA in PE, 0% to 50% gradient in 40 min; detector, UV 254 nm. The residue was purified by Prep-HPLC (Column: XSelect CSH Prep C18 OBD Column, 19*150 mm, 5 μm; Mobile Phase A: Water (10 mmol/L $NH_4HCO_3$+0.1% $NH_3$—$H_2O$), Mobile Phase B: ACN; Flow rate: 25 mL/min; Gradient: 24% B to 54% B in 7 min, 54% B; Wave Length: 254 nm; RT1(min): 5) to afford methyl (2E)-4-{6-[(3-methyloxetan-3-yl)sulfamoyl]-1-(oxetan-3-ylmethyl)-2,4-dioxoquinazolin-3-yl}but-2-enoate (34.4 mg, 29.34%) as a white solid. LCMS (ESI, m/z): 478[M−H]$^-$; $^1$H NMR (300 MHz, DMSO-$d_6$) δ 8.54 (m, 1H), 8.41 (d, J=2.1 Hz, 1H), 8.07 (dd, J=8.9, 2.4 Hz, 1H), 7.73 (d, J=9.0 Hz, 1H), 6.93 (dt, J=15.9, 4.6 Hz, 1H), 6.00 (dt, J=15.8, 1.8 Hz, 1H), 4.71 (dd, J=4.6, 2.0 Hz, 2H), 4.61 (dd, J=7.8, 6.1 Hz, 2H), 4.54 (d, J=6.1 Hz, 2H), 4.49-4.43 (m, 4H), 4.14 (d, J=6.0 Hz, 2H), 3.64 (s, 3H), 3.40 (d, J=7.2 Hz, 1H), 1.42 (s, 3H).

Example 12: methyl (E)-5-(6-(N-(3-methyloxetan-3-yl)sulfamoyl)-2,4-dioxo-1,4-dihydroquinazolin-3 (2H)-yl)pent-2-enoate

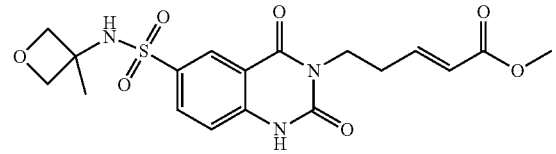 [SMILES: COC(=O)/C=C/CCn1c(=O)[nH]c2ccc(S(=O)(=O)NC3(C)COC3)cc2c1=O]

Step 1: Synthesis of 3-allyl-N-(3-methyloxetan-3-yl)-2,4-dioxo-1, 2, 3,4-tetrahydroquinazoline-6-sulfonamide A mixture of N-(3-methyloxetan-3-yl)-2,4-dioxo-1,3-dihydroquinazoline-6-sulfonamide (1 g, 3.212 mmol, 1 equiv) and 4-bromo-1-butene (0.41 g, 3.051 mmol, 0.95 equiv), $K_2CO_3$ (0.47 g, 3.373 mmol, 1.05 equiv) in DMF (15 mL) was stirred overnight at room temperature. Desired product could be detected by LCMS. The resulting mixture was diluted with EA (50 mL). The resulting mixture was washed with $H_2O$ (3×20 mL). The resulting solution was dried over $Na_2SO_4$ and concentrated. The residue was purified by silica gel column chromatography, eluted with EA/PE (0:100 to 55:45) to afford 3-(but-3-en-1-yl)-N-(3-methyloxetan-3-yl)-2,4-dioxo-1H-quinazoline-6-sulfonamide (400 mg crude). The mixture was purified by HPLC with following condition: Column: YMC-Actus Triart C18. 30*150 nm, 5 μm; mobile phase a: water (10 mmol/L $NH_4HCO_3$), Mobile b: ACN; flow rate: 65 mL/min; Gradient: 22% b to 42% in 7 min, wave length 254 nm; RT: 4.87/6.18. This resulted in 3-(but-3-en-1-yl)-N-(3-methyloxetan-3-yl)-2,4-dioxo-1H-quinazoline-6-sulfonamide (170 mg, 13.76%) as a white solid. LCMS (ESI, m/z): 352[M+H]$^+$

Step 2: Synthesis of methyl (E)-5-(6-(N-(3-methyloxetan-3-yl)sulfamoyl)-2,4-dioxo-1,4-dihydroquinazolin-3(2H)-yl)pent-2-enoate A mixture of 3-(but-3-en-1-yl)-N-(3-methyloxetan-3-yl)-2,4-dioxo-1H-quinazoline-6-sulfonamide (130 mg, 0.356 mmol, 1 equiv) and methyl acrylate (30.63 mg, 0.356 mmol, 1.0 equiv), Grubbs 2nd (90.61 mg, 0.107 mmol, 0.3 equiv) in DCM (35 mL) was stirred overnight at room temperature. Desired product could be detected by LCMS (LCMS about 20%). The resulting mixture was concentrated under reduced pressure. The residue was purified by silica gel column chromatography, eluted with DCM/MeOH (100:0 to 90:10) to afford methyl (2E)-5-{6-[(3-methyloxetan-3-yl)sulfamoyl]-2,4-dioxo-1H-quinazolin-3-yl}pent-2-enoate (35 mg crude). The crude product was purified by Prep-HPLC with the following conditions (Column: XBridge Shield rp18 OBD column, 19*250 nm, 10 μm; mobile phase A: Water (10 mmol/L NH$_4$HCO$_3$, mobile B: ACN; flow rate: 25 mL/min); Gradient: 10% B to 25% B in 10 minutes, wave length: 254 nm; RT 8.3) to afford methyl (2E)-5-{6-[(3-methyloxetan-3-yl)sulfamoyl]-2,4-dioxo-1H-quinazolin-3-yl}pent-2-enoate (25.1 mg, 16.58%) as a white solid. LCMS (ESI, m/z): 424[M+H]$^+$; $^1$H NMR (400 MHz, Methanol-d4) δ 8.51 (d, J=2 Hz, 1H), 8.09-8.07 (m, 1H), 7.32 (d, J=8.4 Hz, 1H), 7.02-6.99 (m, 1H), 5.90 (d, J=15.6 Hz, 1H), 4.72 (d, J=6 Hz, 2H), 4.26 (d, J=6.4 Hz, 2H), 4.27-4.17 (m, 2H), 3.71 (s, 3H), 2.67-2.62 (m, 2H), 1.55 (s, 3H).

Example 13A: 1,3-diethyl-N-((1S,2R)-2-ethyl-1-methylcyclopropyl)-2,4-dioxo-1,2,3,4-tetrahydroquinazoline-6-sulfonamide (Stereochemistry Assumed)

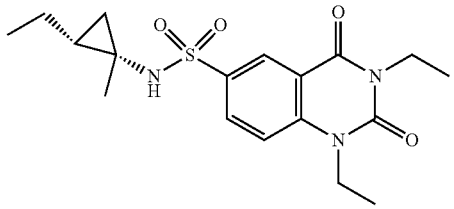 [SMILES: CC[C@@H]1C[C@]1(C)NS(=O)(=O)c1ccc2c(c1)c(=O)n(CC)c(=O)n2CC]

Step 1: Synthesis of 2-ethyl-1-methylcyclopropan-1-amine

To a solution of titanium isopropoxide (4.15 g, 14.615 mmol, 0.60 equiv), CH$_3$CN (1.00 g, 24.359 mmol, 1.00 equiv) in THF (15 mL) was added butyl(chloro)magnesium (12.06 mL, 24.115 mmol, 0.99 equiv) at 0° C. The mixture was stirred for 1 h at 0° C. BF$_3$-Et$_2$O (6.57 mL, 24.367 mmol, 1.00 equiv, 47%) was added and stirred for 1 h at 0° C. The resulting mixture was extracted with EtOEt (2×50 mL), dried over anhydrous Na$_2$SO$_4$. After filtration, the filtrate was concentrated under reduced pressure. The crude product was used in the next step directly without further purification. LCMS (ES. m/z): 100 [M+H]$^+$.

Step 2: Synthesis of 1,3-diethyl-N—((S,2R)-2-ethyl-1-methylcyclopropyl)-2,4-dioxo-1, 2, 3,4-tetrahydroquinazoline-6-sulfonamide (Assumed)

To a solution of 2-ethyl-1-methylcyclopropan-1-amine (313.1 mg, 3.155 mmol, 5 equiv), TEA (191.68 mg, 1.893 mmol, 3 equiv) in DCM (8 mL) was added 1,3-diethyl-2,4-dioxoquinazoline-6-sulfonyl chloride (200 mg, 0.631 mmol, 1.00 equiv). The mixture was stirred for 16 h at rt. The resulting mixture was concentrated under reduced pressure. The residue was purified by Prep-TLC (CH$_2$Cl$_2$/EA 10:1). The resulting mixture was concentrated under reduced pressure. The crude product was purified by Prep-HPLC with the following conditions (Column: XBridge Prep OBD C18 Column, 30×150 mm, 5 μm; Mobile Phase A: Water (10 mmol/L NH$_4$HCO$_3$+0.1% NH$_3$—H$_2$O), Mobile Phase B: ACN; Flow rate: 60 mL/min; Gradient: 42% B to 62% B in 7 min, 62% B; Wave Length: 254 nm; RT1(min): 5.72). The resulting mixture was concentrated under reduced pressure. The product was purified by Prep-Chiral-HPLC with the following conditions (Column: CHIRALPAK IE, 2×25 cm, 5 μm; Mobile Phase A: Hex:DCM=3:1(0.5% 2M NH$_3$-MeOH)-HPLC, Mobile Phase B: EtOH-HPLC; Flow rate: 20 mL/min; Gradient: 20% B to 20% B in 20 min; Wave Length: 220/254 nm; RT1(min): 11.997; RT2 (min): 13.686; Sample Solvent: EtOH-HPLC; Injection Volume: 0.6 mL; Number Of Runs: 10. //Column: CHIRALPAK IF, 2×25 cm, 5 μm; Mobile Phase A: EtOH-HPLC, Mobile Phase B: Hex (0.5% 2M NH$_3$-MeOH)-HPLC; Flow rate: 18 mL/min; Gradient: 60% B to 60% B in 30 min; Wave Length: 220/254 nm; RT1(min): 18.07; RT2(min): 22.72; Sample Solvent: EtOH:DCM=1:1; Injection Volume: 0.5 mL; Number Of Runs: 4) to afford rel-1,3-diethyl-N-((1S,2S)-2-ethyl-1-methylcyclopropyl)-2,4-dioxo-1,2,3,4-tetrahydroquinazoline-6-sulfonamide (5.4 mg, 2.24%), rel-1,3-diethyl-N-((1R,2R)-2-ethyl-1-methylcyclopropyl)-2,4-dioxo-1,2,3,4-tetrahydroquinazoline-6-sulfonamide (34.1 mg, 14.19%), rel-1,3-diethyl-N-((1S,2R)-2-ethyl-1-methylcyclopropyl)-2,4-dioxo-1,2,3,4-tetrahydroquinazoline-6-sulfonamide (5.6 mg, 2.32%), rel-1,3-diethyl-N-((1R,2S)-2-ethyl-1-methylcyclopropyl)-2,4-dioxo-1,2,3,4-tetrahydroquinazoline-6-sulfonamide (30.1 mg, 12.51%) as an off-white solid.

Example 13A: 1,3-diethyl-N-((1S,2R)-2-ethyl-1-methylcyclopropyl)-2,4-dioxo-1,2,3,4-tetrahydroquinazoline-6-sulfonamide (stereochemistry assumed): $^1$H NMR (300 MHz, DMSO-d$_6$) δ 8.46 (d, J=2.3 Hz, 1H), 8.14-8.04 (m, 2H), 7.71 (d, J=8.9 Hz, 1H), 4.17 (q, J=7.0 Hz, 2H), 3.99 (q, J=7.0 Hz, 2H), 1.45-1.36 (m, 1H), 1.25-1.09 (m, 7H), 0.94-0.89 (m, 6H), 0.61 (d, J=10.7 Hz, 1H), 0.53 (s, 2H).

Example 13B: 1,3-diethyl-N-((1S,2S)-2-ethyl-1-methylcyclopropyl)-2,4-dioxo-1,2,3,4-tetrahydroquinazoline-6-sulfonamide (stereochemistry assumed): $^1$H NMR (300 MHz, DMSO-d6) δ 8.46 (d, J=2.3 Hz, 1H), 8.14-8.05 (m, 2H), 7.72 (d, J=8.9 Hz, 1H), 4.17 (q, J=7.0 Hz, 2H), 3.99 (q, J=7.0 Hz, 2H), 1.45-1.34 (m, 1H), 1.25-1.09 (m, 7H), 0.98-0.87 (m, 6H), 0.63 (s, 1H), 0.53 (s, 2H).

Example 13C: 1,3-diethyl-N-((1R,2R)-2-ethyl-1-methylcyclopropyl)-2,4-dioxo-1,2,3,4-tetrahydroquinazoline-6-sulfonamide (stereochemistry assumed): $^1$H NMR (300 MHz, DMSO-d$_6$) δ 8.43 (d, J=2.3 Hz, 1H), 8.15 (s, 1H), 8.05 (dd, J=8.9, 2.3 Hz, 1H), 7.71 (d, J=8.9 Hz, 1H), 4.18 (q, J=7.0 Hz, 2H), 3.99 (q, J=7.0 Hz, 2H), 1.20-1.04 (m, 11H), 0.83-0.73 (m, 5H), 0.10-0.02 (m, 1H).

Example 13D: 1,3-diethyl-N-((1R,2S)-2-ethyl-1-methylcyclopropyl)-2,4-dioxo-1,2,3,4-tetrahydroquinazoline-6-sulfonamide (stereochemistry assumed): $^1$H NMR (300 MHz, DMSO-d$_6$) δ 8.43 (d, J=2.3 Hz, 1H), 8.14 (s, 1H), 8.05 (dd, J=8.9, 2.3 Hz, 1H), 7.70 (d, J=8.9 Hz, 1H), 4.17 (q, J=7.0 Hz, 2H), 3.99 (q, J=7.0 Hz, 2H), 1.25-1.04 (m, 11H), 0.83-0.69 (m, 5H), 0.1-0.02 (m, 1H).

Example 14: 1-((2,4-dimethylthiazol-5-yl)methyl)-N-(3-methyloxetan-3-yl)-3-((2-methylthiazol-5-yl)methyl)-2,4-dioxo-1,2,3,4-tetrahydroquinazoline-6-sulfonamide

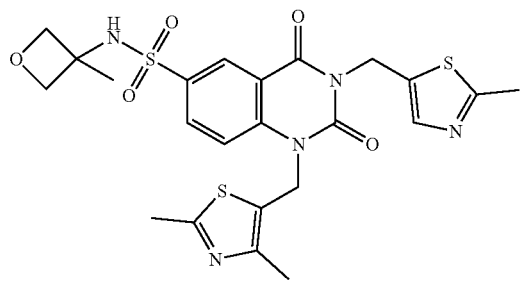 [SMILES: Cc1ncc(Cn2c(=O)c3cc(S(=O)(=O)NC4(C)COC4)ccc3n(Cc3sc(C)nc3C)c2=O)s1]

Step 1: Synthesis of 5-(bromomethyl)-2-methyl-1,3-thiazole

A solution of 2,5-dimethyl-1,3-thiazole (2.4 g, 21.205 mmol, 1 equiv), NBS (4.53 g, 25.446 mmol, 1.2 equiv) and BPO (6.52 g, 25.446 mmol, 1.2 equiv) in benzene (50 mL) was stirred for 2 h at 120° C. under $N_2$ atmosphere. The resulting mixture was stirred for 16 h at room temperature. The residue was purified with the following conditions: column, silica gel; mobile phase, EA in PE, 0% to 50% gradient in 40 min; detector, UV 254 nm. This resulted in 5-(bromomethyl)-2-methyl-1,3-thiazole (300 mg, 7.37%) as an off-white solid. LCMS (ESI, m/z): 193.95 [M+H]$^+$.

Step 2: Synthesis of 3-[(2-methyl-1,3-thiazol-5-yl)methyl]-N-(3-methyloxetan-3-yl)-2,4-dioxo-1H-quinazoline-6-sulfonamide A solution of N-(3-methyloxetan-3-yl)-2,4-dioxo-1,3-dihydroquinazoline-6-sulfonamide (500 mg, 1.606 mmol, 1.00 equiv), $Cs_2CO_3$ (784.95 mg, 2.409 mmol, 1.5 equiv) and 5-(bromomethyl)-2-methyl-1,3-thiazole (246.79 mg, 1.285 mmol, 0.8 equiv) in DMF (10 mL, 129.215 mmol) was stirred for 3 h at room temperature. The aqueous layer was extracted with EA (3×50 mL). The residue was purified with the following conditions: column, silica gel; mobile phase, EA in PE, 0% to 50% gradient in 40 min; detector, UV 254 nm. This resulted in 3-[(2-methyl-1,3-thiazol-5-yl)methyl]-N-(3-methyloxetan-3-yl)-2,4-dioxo-H-quinazoline-6-sulfonamide (100 mg, 14.74%) as a white solid. LCMS (ESI, m/z): 422.95[M+H]$^+$.

Step 3: Synthesis of 1-((2,4-dimethylthiazol-5-yl)methyl)-N-(3-methyloxetan-3-yl)-3-((2-methylthiazol-5-yl)methyl)-2,4-dioxo-1,2,3,4-tetrahydroquinazoline-6-sulfonamide To a solution of 3-[(2-methyl-1,3-thiazol-5-yl)methyl]-N-(3-methyloxetan-3-yl)-2,4-dioxo-TH-quinazoline-6-sulfonamide (80 mg, 0.189 mmol, 1 equiv) and (2,4-dimethyl-1,3-thiazol-5-yl)methanol (27.12 mg, 0.189 mmol, 1 equiv) in THF (2 mL, 24.686 mmol) were added DIAD (49.47 mg, 0.283 mmol, 1.5 equiv) and $PPh_3$ (74.50 mg, 0.283 mmol, 1.5 equiv). After stirring for 16 h at room temperature under a nitrogen atmosphere, the residue was purified by silica gel column chromatography, eluted with DCM:MeOH (10:1). The residue was purified by reverse flash chromatography with the following conditions: column, C18 silica gel; mobile phase, ACN in $H_2O$, 10% to 50% gradient in 40 min; detector, UV 254 nm. This resulted in 1-[(2,4-dimethyl-1,3-thiazol-5-yl)methyl]-3-[(2-methyl-1,3-thiazol-5-yl)methyl]-N-(3-methyloxetan-3-yl)-2,4-dioxoquinazoline-6-sulfonamide (42.5 mg, 37.74%) as an off-white solid. LCMS (ESI, m/z): 548.05[M+H]$^+$; $^1$H NMR (300 MHz, DMSO-$d_6$) δ 8.56 (s, 1H), 8.45 (d, J=2.1 Hz, 1H), 8.18-8.14 (m, 1H), 7.66 (d, J=8.7 Hz, 2H), 5.46 (s, 2H), 5.27 (s, 2H), 4.53 (d, J=6.0 Hz, 2H), 4.14 (d, J=6.3 Hz, 2H), 2.58 (s, 3H), 2.51-2.47 (m, 6H), 1.40 (s, 3H).

Example 15A: 1,3-diethyl-N-((1S,2S)-2-(2-hydroxyethyl)-1-methylcyclopropyl)-2,4-dioxo-1,2,3,4-tetrahydroquinazoline-6-sulfonamide (Stereochemistry Assumed)

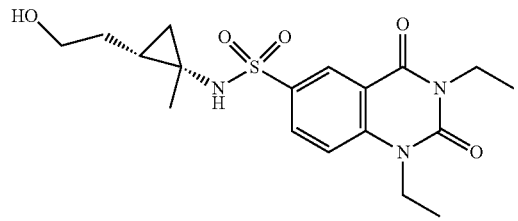 [SMILES: CCn1c(=O)c2cc(S(=O)(=O)N[C@@]3(C)C[C@H]3CCO)ccc2n(CC)c1=O]

Step 1: Synthesis of 2-(2-amino-2-methylcyclopropyl)ethanol

A solution of 3-buten-1-ol (4 g, 55.473 mmol, 1.2 equiv), ACN (1.90 g, 46.227 mmol, 1 equiv) and titanium isopropylate (15.77 g, 55.473 mmol, 1.2 equiv) in THF (464 mL, 5727.045 mmol) was stirred for 30 minutes at room temperature under $N_2$ atmosphere. To the stirred mixture was added bromo(cyclohexyl)magnesium (110.95 mL, 110.946 mmol, 2.4 equiv) in portions at room temperature under $N_2$ atmosphere, and stirred for 3 hours. The reaction was quenched with $H_2O$ at room temperature. The resulting mixture was filtered, the filter cake was washed with EA (100 mL). The filtrate was concentrated under reduced pressure. The resulting mixture was extracted with EA (3×150 mL). The combined organic layers were dried over anhydrous $Na_2SO_4$. After filtration, the filtrate was concentrated under reduced pressure. The resulting mixture was used in the next step directly without further purification. LCMS (ESI, m/z): 116 [M+H]$^+$.

Step 2: Synthesis of 1,3-diethyl-N—((S,2S)-2-(2-hydroxyethyl)-1-methylcyclopropyl)-2,4-dioxo-1,2,3,4-tetrahydroquinazoline-6-sulfonamide To a stirred solution of 2-[(1R,2R)-2-amino-2-methylcyclopropyl]ethanol (2 g, 5 equiv, crude) and 1,3-diethyl-2,4-dioxoquinazoline-6-sulfonyl chloride (1 g, 3.157 mmol, 1 equiv.) in DCM (20 mL, 314.612 mmol) was added TEA (1.1 g, 10.870 mmol) dropwise at room temperature, and stirred for 16 h. The residue was purified with the following conditions: column, silica gel; mobile phase, EA in PE, 0% to 80% gradient in 60 min; detector, UV 254 nm. The resulting mixture was purified by Chiral_HPLC with the following conditions (Column: CHIRALPAK IE-3, 4.6*50 mm 3 um; Mobile Phase A: (Hex:DCM=3:1)(0.1% DEA): EtOH=50:50; Flow rate: 1 mL/min; Gradient: 0% B to 0%

B; Injection Volume: 5 ul mL) to afford 1,3-diethyl-N-[(1R,2R)-2-(2-hydroxyethyl)-1-methylcyclopropyl]-2,4-dioxoquinazoline-6-sulfonamide (23.4 mg) as a white solid, and 1,3-diethyl-N-[(1S,2S)-2-(2-hydroxyethyl)-1-methylcyclopropyl]-2,4-dioxoquinazoline-6-sulfonamide (22.5 mg) as a white solid.

Example 15A: 1,3-diethyl-N-((1S,2S)-2-(2-hydroxyethyl)-1-methylcyclopropyl)-2,4-dioxo-1,2,3,4-tetrahydroquinazoline-6-sulfonamide (stereochemistry assumed): LCMS (ESI, m/z): 396.15[M+H]+; 1H NMR (300 MHz, DMSO-d6) δ 8.45 (d, J=2.1 Hz, 1H), 8.11-8.07 (m, 1H), 7.71 (d, J=9.0 Hz, 1H), 5.10 (brs, 1H), 4.18 (q, J=7.0 Hz, 2H), 3.99 (q, J=7.0 Hz, 2H), 3.44 (t, J=6.7 Hz, 2H), 1.61-1.54 (m, 1H), 1.35-1.20 (m, 7H), 0.93 (s, 3H), 0.70-0.52 (m, 3H).

Example 15B: 1,3-diethyl-N-((1R,2R)-2-(2-hydroxyethyl)-1-methylcyclopropyl)-2,4-dioxo-1,2,3,4-tetrahydroquinazoline-6-sulfonamide (stereochemistry assumed): LCMS (ESI, m/z): 396.10[M+H]+; 1H NMR (300 MHz, DMSO-d6) δ 8.45 (d, J=2.4 Hz, 1H), 8.11-8.04 (m, 2H), 7.71 (d, J=9.0 Hz, 1H), 4.49 (s, 1H), 4.18 (q, J=7.0 Hz, 2H), 3.99 (q, J=7.0 Hz, 2H), 3.44 (q, J=6.4 Hz, 2H), 1.60-1.52 (m, 1H), 1.37-1.28 (m, 1H), 1.26-1.16 (m, 6H), 0.93 (s, 3H), 0.67-0.52 (m, 3H).

Example 16: N-((1SR,2SR)-2-(cyanomethyl)-1-methylcyclopropyl)-1,3-diethyl-2,4-dioxo-1,2,3,4-tetrahydroquinazoline-6-sulfonamide (Stereochemistry Assumed)

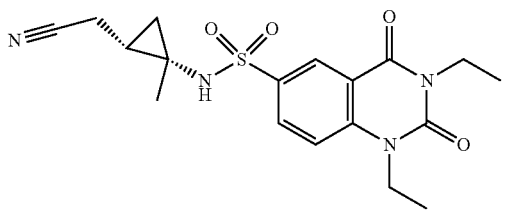 [SMILES: CCn1c(=O)c2cc(S(=O)(=O)N[C@@]3(C)C[C@H]3CC#N)ccc2n(CC)c1=O]

To a stirred solution of 1,3-diethyl-N-[2-(2-hydroxyethyl)-1-methylcyclopropyl]-2,4-dioxoquinazoline-6-sulfonamide (70 mg, 0.177 mmol, 1 equiv) and NH4OAc (54.58 mg, 0.708 mmol, 4 equiv) in ACN (4.5 mL, 85.609 mmol) and H2O (0.5 mL, 27.755 mmol) were added (acetyloxy)(phenyl)-lambda3-iodanyl acetate (125.43 mg, 0.389 mmol, 2.2 equiv) and TEMPO (14.11 mg, 0.090 mmol, 0.51 equiv) in portions at room temperature, and stirred for 16 h. The resulting mixture was quenched, extracted, dried and concentrated under reduced pressure. The residue was purified with the following conditions: column, silica gel; mobile phase, EA in PE, 0% to 50% gradient in 40 min; detector, UV 254 nm. The residue was purified by Prep-TLC (Column: XBridge Prep OBD C18 Column, 30*150 mm, 5 μm; Mobile Phase A: Water (10 mmol/L NH4HCO3+0.1% NH3—H2O), Mobile Phase B: ACN; Flow rate: 60 mL/min; Gradient: 33% B to 57% B in 8 min, 57% B; Wave Length: 254 nm; RT1(min): 7) to afford N-((1SR,2SR)-2-(cyanomethyl)-1-methylcyclopropyl)-1,3-diethyl-2,4-dioxo-1,2,3,4-tetrahydroquinazoline-6-sulfonamide (23.7 mg, 34.19%) as a white solid. LCMS (ESI, m/z): 391.05[M+H]+; 1H NMR (400 MHz, DMSO-d6) δ 8.47 (d, J=1.2 Hz, 1H), 8.34 (s, 1H), 8.13-8.11 (m, 1H), 7.72 (d, J=8.8 Hz, 1H), 4.18 (q, J=6.9 Hz, 2H), 3.99 (q, J=7.0 Hz, 2H), 2.65-2.59 (m, 1H), 2.45-2.39 (m, 1H), 1.24-1.17 (m, 6H), 1.10-1.00 (m, 1H), 0.90 (s, 4H), 0.79-0.75 (m, 1H).

Example 17A: N-((2S,3S)-2,3-dimethyloxetan-3-yl)-1,3-diethyl-2,4-dioxo-1,2,3,4-tetrahydroquinazoline-6-sulfonamide (Stereochemistry Assumed)

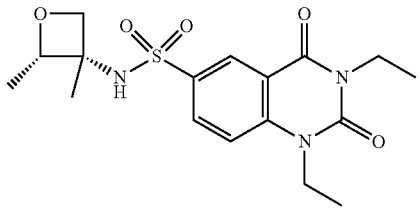 [SMILES: CCn1c(=O)c2cc(S(=O)(=O)N[C@@]3(C)CO[C@H]3C)ccc2n(CC)c1=O]

Step 1: Synthesis of 3-(dibenzylamino)-2-methyloxetane-3-carbonitrile

A solution of 2-methyloxetan-3-one (250 mg, 2.904 mmol, 1 equiv) in DCE was treated with AcOH (261.58 mg, 4.356 mmol, 1.5 equiv) for 2 min at room temperature under nitrogen atmosphere followed by the addition of dibenzyl amine (859.34 mg, 4.356 mmol, 1.5 equiv) dropwise at room temperature. The resulting mixture was stirred for 10 min at room temperature under nitrogen atmosphere. To the above mixture was added TMSCN (432.14 mg, 4.356 mmol, 1.5 equiv) dropwise over 3 min at room temperature. The resulting mixture was stirred for additional 18 h at 60° C. Desired product could be detected by LCMS. The resulting mixture was concentrated under reduced pressure. The residue was purified by silica gel column chromatography, eluted with PE/EA (10:1) to afford 3-(dibenzylamino)-2-methyloxetane-3-carbonitrile (250 mg, 23.70%) as an off-white oil. LCMS (ES. m/z): 293 [M+H]+.

Step 2: Synthesis of dibenzyl-2,3-dimethyloxetan-3-amine

To a stirred mixture of 3-(dibenzylamino)-2-methyloxetane-3-carbonitrile (250 mg, 0.855 mmol, 1 equiv) in THF was added MeMgBr (509.80 mg, 4.275 mmol, 5 equiv) dropwise at room temperature under nitrogen atmosphere. The resulting mixture was stirred for 5 h at 60° C. under nitrogen atmosphere. Desired product could be detected by LCMS. The reaction was quenched by the addition of water (20 mL) at room temperature. The resulting mixture was extracted with CH2Cl2 (3×20 mL). The combined organic layers were washed with water (3×10 mL), dried over anhydrous Na2SO4. After filtration, the filtrate was concentrated under reduced pressure. The residue was purified by silica gel column chromatography, eluted with PE/EA (10:1) to afford N,N-dibenzyl-2,3-dimethyloxetan-3-amine (120 mg, 45.48%) as an off-white oil. LCMS (ES. m/z): 282 [M+H]+.

Step 3: Synthesis of 2,3-dimethyloxetan-3-amine

A mixture of Pd(OH)2/C (299.43 mg, 2.130 mmol, 5 equiv) and N,N-dibenzyl-2,3-dimethyloxetan-3-amine (120 mg, 0.426 mmol, 1 equiv) in MeOH was stirred overnight at room temperature under hydrogen atmosphere. Desired product could be detected by LCMS. The resulting mixture was filtered, the filter cake was washed with CH₂Cl₂ (5×10 mL). The filtrate was concentrated under reduced pressure. The crude product was used in the next step directly without further purification. LCMS (ES. m/z): 102 [M+H]⁺.

Step 4: Synthesis of N-((2S,3S)-2,3-dimethyl-oxetan-3-yl)-1,3-diethyl-2,4-dioxo-1,2,3,4-tetrahydroquinazoline-6-sulfonamide To a stirred mixture of 2,3-dimethyloxetan-3-amine (20 mg, 0.198 mmol, 1 equiv) and pyridine (5 mL, 0.063 mmol, 0.32 equiv) in DCM was added 1,3-diethyl-2,4-dioxoquinazoline-6-sulfonyl chloride (62.63 mg, 0.198 mmol, 1 equiv) dropwise at room temperature under air atmosphere. The resulting mixture was stirred for 2 h at rt under air atmosphere. Desired product could be detected by LCMS. The residue was purified by silica gel column chromatography, eluted with PE/EA (7:1) to afford N-(2,3-dimethyloxetan-3-yl)-1,3-diethyl-2,4-dioxoquinazoline-6-sulfonamide as an off-white solid. The crude product as purified by chiral HPLC with the following conditions (Column: CHIRALPAK IC-3, 4.6*50 mm, 3 μm; Mobile Phase A: MTBE (0.1% DEA):IPA=60:40; Flow rate: 1 mL/min; Gradient: 0% B to 0% B; Injection Volume: 5 μl mL) to afford rel-N-[(2S,3S)-2,3-dimethyloxetan-3-yl]-1,3-diethyl-2,4-dioxoquinazoline-6-sulfonamide (7.5 mg, 9.70%), rel-N-[(2R,3R)-2,3-dimethyloxetan-3-yl]-1,3-diethyl-2,4-dioxoquinazoline-6-sulfonamide (7.1 mg, 9.20%), rel-N-[(2R,3S)-2,3-dimethyloxetan-3-yl]-1,3-diethyl-2,4-dioxoquinazoline-6-sulfonamide (10.1 mg, 13.08%), rel-N-[(2R,3S)-2,3-dimethyloxetan-3-yl]-1,3-diethyl-2,4-dioxoquinazoline-6-sulfonamide (11.8 mg, 15.50%) as an off-white solid.

Example 17A: N-((2S,3S)-2,3-dimethyloxetan-3-yl)-1,3-diethyl-2,4-dioxo-1,2,3,4-tetrahydroquinazoline-6-sulfonamide (stereochemistry assumed): ¹H NMR (400 MHz, Chloroform-d) δ 8.76 (s, 1H), 8.17-8.14 (m, 1H), 7.46-7.29 (m, 2H), 5.67 (s, 1H), 4.61-4.58 (m, 2H), 4.32-4.15 (m, 5H), 1.48-1.15 (m, 11H).

Example 17B: N-((2R,3R)-2,3-dimethyloxetan-3-yl)-1,3-diethyl-2,4-dioxo-1,2,3,4-tetrahydroquinazoline-6-sulfonamide (stereochemistry assumed): ¹H NMR (400 MHz, Chloroform-d) δ 8.76-8.74 (m, 1H), 8.17-8.15 (m, 1H), 7.35-7.26 (m, 2H), 5.67 (s, 1H), 4.61-4.56 (m, 2H), 4.32-4.14 (m, 5H), 1.65-1.31 (m, 11H).

Example 17C: N-((2R,3S)-2,3-dimethyloxetan-3-yl)-1,3-diethyl-2,4-dioxo-1,2,3,4-tetrahydroquinazoline-6-sulfonamide (stereochemistry assumed): ¹H NMR (400 MHz, Chloroform-d) δ 8.74 (d, J=8.2 Hz, 1H), 8.15 (d, J=9.2 Hz, 1H), 7.47-7.27 (m, 1H), 5.95 (d, J=8.7 Hz, 1H), 4.92-4.88 (m, 1H), 4.60-4.58 (m, 1H), 4.26-4.01 (m, 5H), 1.43-1.25 (m, 14H).

Example 17D: N-((2S,3R)-2,3-dimethyloxetan-3-yl)-1,3-diethyl-2,4-dioxo-1,2,3,4-tetrahydroquinazoline-6-sulfonamide (stereochemistry assumed): ¹H NMR (400 MHz, Chloroform-d) δ 8.74 (s, 1H), 8.17-8.14 (m, 1H), 7.35-7.26 (m, 1H), 6.03 (d, J=6.6 Hz, 1H), 4.93-4.89 (m, 1H), 4.60-4.57 (m, 1H), 4.28-4.08 (m, 5H), 1.43-1.28 (m, 14H).

Example 18: N-(3-(difluoromethyl)oxetan-3-yl)-1,3-diethyl-2,4-dioxo-1,2,3,4-tetrahydroquinazoline-6-sulfonamide

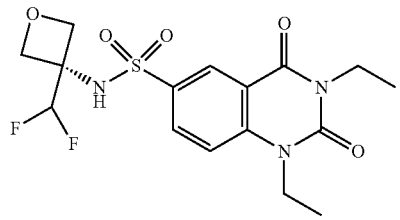

To a solution of 3-(difluoromethyl)oxetan-3-amine (58.29 mg, 0.474 mmol, 1 equiv), TEA (143.76 mg, 1.422 mmol, 3 equiv) in DCM (3 mL) was added 1,3-diethyl-2,4-dioxoquinazoline-6-sulfonyl chloride (150 mg, 0.474 mmol, 1 equiv). The mixture was stirred for 16 h at rt. The resulting mixture was concentrated under reduced pressure. The residue was purified by Prep-TLC (CH₂Cl₂/EA 1:1). The resulting mixture was concentrated under reduced pressure. The crude product was purified by Prep-HPLC with the following conditions (Column: XBridge Prep OBD C18 Column, 30×150 mm, 5 μm; Mobile Phase A: water (10 mmol/L NH₄HCO₃), Mobile Phase B: ACN; Flow rate: 60 mL/min; Gradient: 22% B to 47% B in 7 min, 47% B; Wave Length: 254 nm; RT1(min): 6.03) to afford N-[3-(difluoromethyl)oxetan-3-yl]-1,3-diethyl-2,4-dioxoquinazoline-6-sulfonamide (29.0 mg, 15.14%) as a white solid. ¹H NMR (300 MHz, DMSO-d₆) δ 9.11 (s, 1H), 8.46 (d, J=2.3 Hz, 1H), 8.13 (dd, J=8.9, 2.4 Hz, 1H), 7.73 (d, J=9.0 Hz, 1H), 6.31 (t, J=55.2 Hz, 1H), 4.55 (s, 4H), 4.18 (q, J=7.0 Hz, 2H), 3.99 (q, J=7.0 Hz, 2H), 1.21 (t*2, J=7.0 Hz, 6H). LCMS (ES. m/z): 404 [M+H]⁺.

Example 19: (E)-N-methyl-4-(6-(N-(3-methyl-oxetan-3-yl)sulfamoyl)-2,4-dioxo-1,4-dihydroquinazolin-3(2H)-yl)but-2-enamide

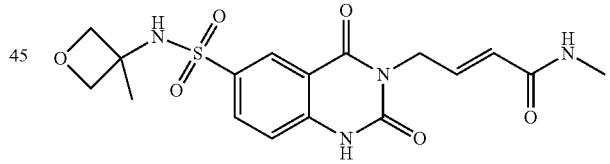

Step 1: Synthesis of (2E)-4-{6-[(3-methyloxetan-3-yl)sulfamoyl]-2,4-dioxo-1H-quinazolin-3-yl}but-2-enoic acid A mixture of methyl (2E)-4-{6-[(3-methyloxetan-3-yl)sulfamoyl]-2,4-dioxo-1H-quinazolin-3-yl}but-2-enoate (150 mg, 0.366 mmol, 1 equiv) in THF (2 mL) and LiOH—H₂O (76.87 mg, 1.830 mmol, 5.0 equiv) in H₂O (2 mL) was stirred for overnight at room temperature. Desired product could be detected by LCMS. The mixture was acidified to pH 1-2 with HCl (2 M). The aqueous layer was extracted with EA (2×5 mL), dried over Na₂SO₄. After filtrate was concentrated under reduced pressure to give desired product (2E)-4-{6-[(3-methyloxetan-3-yl)sulfamoyl]-2,4-dioxo-1H-quinazolin-3-yl}but-2-enoic acid (130 mg, 80.77%) as a white solid. LCMS (ESI, m/z): 396[M+H]⁺

Step 2: Synthesis of (E)-N-methyl-4-(6-(N-(3-methyloxetan-3-yl)sulfamoyl)-2,4-dioxo-1,4-dihydroquinazolin-3(2H)-yl)but-2-enamide A mixture of (2E)-4-{6-[(3-methyloxetan-3-yl)sulfamoyl]-2,4-dioxo-1H-quinazolin-3-yl}but-2-enoic acid (40 mg, 0.101 mmol, 1 equiv) and methylamine (3.14 mg, 0.101 mmol, 1.0 equiv), EDCI (23.27 mg, 0.121 mmol, 1.2 equiv), HOBT (16.40 mg, 0.121 mmol, 1.2 equiv), DIEA (32.69 mg, 0.253 mmol, 2.5 equiv) in THF (4 mL) was stirred for overnight at room temperature. Desired product could be detected by LCMS. The resulting mixture was diluted with EA (25 mL) and washed with H$_2$O (3×10 mL). The resulting was dried Na$_2$SO$_4$ and concentrated under vacuum. The mixture was diluted with DMF (2 mL) for Pre-HPLC. (Column: XBridge Shield rp18 OBD column, 19*250 nm, 10 um; mobile phase A: Water (10 mmol/L NH$_4$HCO$_3$, mobile B: ACN; flow rate: 25 mL/min); Gradient: 10% B to 25% B in 10 minutes, wave length: 254 nm; RT 8.3. This resulted in (2E)-N-methyl-4-{6-[(3-methyloxetan-3-yl)sulfamoyl]-2,4-dioxo-1H-quinazolin-3-yl}but-2-enamide (14.1 mg, 34.09%) as a white solid. LCMS (ESI, m/z): 409 [M+H]$^+$; $^1$H NMR (300 MHz, Methanol-d4) δ 8.51 (d, J=2.2 Hz, 1H), 8.08 (dd, J=8.7, 2.2 Hz, 1H), 7.34 (d, J=8.6 Hz, 1H), 6.79 (dt, J=15.5, 5.3 Hz, 1H), 6.16-5.80 (m, 1H), 4.84-4.60 (m, 4H), 4.41-4.18 (m, 2H), 2.77 (s, 3H), 1.55 (s, 3H).

Example 20: 1,3-diethyl-N-(3-(fluoromethyl)oxetan-3-yl)-2,4-dioxo-1,2,3,4-tetrahydroquinazoline-6-sulfonamide

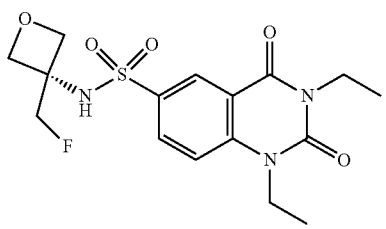

Intermediate 1: 4-{6-bromo-1-[5-(difluoromethyl)-1,3,4-thiadiazol-2-yl]indazol-4-yl}piperazine-1-carboxylate

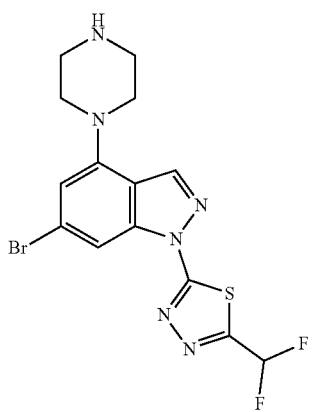 [SMILES: FC(F)c1nnc(-n2ncc3c(N4CCNCC4)cc(Br)cc32)s1]

Step 1: Synthesis of tert-butyl 4-(5-bromo-3-fluoro-2-formylphenyl)piperazine-1-carboxylate A mixture of 4-bromo-2,6-difluorobenzaldehyde (5 g, 22.624 mmol, 1 equiv), tert-butyl piperazine-1-carboxylate (5.06 g, 27.149 mmol, 1.2 equiv) and K$_2$CO$_3$ (6.25 g, 45.248 mmol, 2 equiv) in DMF (50 mL) was stirred for 12 h at 80° C. The reaction was monitored by LCMS. The mixture was allowed to cool down to room temperature. Then water (150 mL) was added. The mixture was extracted with EA (3×100 mL). The combined organic layers were washed with brine (150 mL), dried over anhydrous Na$_2$SO$_4$ and concentrated. The residue was purified by silica gel column chromatography (eluting with 1:1 EA/PE) to afford tert-butyl 4-(5-bromo-3-fluoro-2-formylphenyl)piperazine-1-carboxylate (5 g, 51.36%) as a yellow solid. LCMS (ESI, m/z): 387, 389 [M+H]$^+$.

Step 2: Synthesis of tert-butyl 4-(6-bromo-1H-indazol-4-yl)piperazine-1-carboxylate A mixture of tert-butyl 4-(5-bromo-3-fluoro-2-formylphenyl)piperazine-1-carboxylate (5 g, 12.912 mmol, 1 equiv) and hydrazine hydrate (80%, 2.59 g, 51.648 mmol, 4 equiv) in DMSO (40 mL) was stirred for 30 h at 100° C. The reaction was monitored by LCMS. The mixture was allowed to cool down to room temperature. Then water (150 mL) was added. The mixture was extracted with EA (3×100 mL), the combined organic layers were washed with brine (150 mL), dried over anhydrous Na$_2$SO$_4$ and concentrated. The residue was purified by silica gel column chromatography (eluting with 1:1 EA/PE) to afford tert-butyl 4-(6-bromo-1H-indazol-4-yl)piperazine-1-carboxylate (4 g, 73.13%) as a yellow solid. LCMS (ESI, m/z): 381, 383[M+H]$^+$.

Step 3: Synthesis of tert-butyl 4-{6-bromo-1-[5-(difluoromethyl)-1,3,4-thiadiazol-2-yl]indazol-4-yl}piperazine-1-carboxylate A mixture of tert-butyl 4-(6-bromo-1H-indazol-4-yl)piperazine-1-carboxylate (4 g, 10.491 mmol, 1 equiv), 2-bromo-5-(difluoromethyl)-1,3,4-thiadiazole (2.71 g, 12.589 mmol, 1.2 equiv) and Cs$_2$CO$_3$ (6.84 g, 20.982 mmol, 2 equiv) in DMF (40 mL) was stirred for 2 h at 70° C. The reaction was monitored by LCMS. The mixture was allowed to cool down to room temperature. Then water (100 mL) was added. The mixture was extracted with EA (3×80 mL), the combined organic layers were washed with brine (100 mL), dried over anhydrous Na$_2$SO$_4$ and concentrated. The residue was purified by silica gel column chromatography (eluting with 1:1 EA/PE) to afford tert-butyl 4-{6-bromo-1-[5-(difluoromethyl)-1,3,4-thiadiazol-2-yl]indazol-4-yl}piperazine-1-carboxylate (3.0 g, 55%) as a yellow solid and tert-butyl 4-{6-bromo-2-[5-(difluoromethyl)-1,3,4-thiadiazol-2-yl]indazol-4-yl}piperazine-1-carboxylate (0.5 g, 9.2%) as a yellow solid. LCMS (ESI, m/z): 515, 517 [M+H]$^+$.

Step 4: Synthesis of 6-bromo-1-[5-(difluoromethyl)-1,3,4-thiadiazol-2-yl]-4-(piperazin-1-yl)indazole To a stirred solution of tert-butyl 4-{6-bromo-1-[5-(difluoromethyl)-1,3,4-thiadiazol-2-yl]indazol-4-yl}piperazine-1-carboxylate (2.5 g, 4.851 mmol, 1 equiv) in 1,4-dioxane (20 mL) was added HCl (4M in 1,4-dioxane, 5 mL) dropwise. The resulting mixture was stirred for 1 h at rt. The reaction was monitored by LCMS. The mixture was concentrated. The residue was purified by silica gel column chromatography (eluting with 3:1 EA/PE) to afford 6-bromo-1-[5-(difluoromethyl)-1,3,4-thiadiazol-2-yl]-4-(piperazin-1-yl)indazole (1.8 g, 80.42%) as a yellow solid. LCMS (ESI, m/z): 415, 417 [M+H]⁺.

Example 21: 1-(5-(difluoromethyl)-1,3,4-thiadiazol-2-yl)-4-(4-isobutyrylpiperazin-1-yl)-N-(1-methylcyclobutyl)-1H-indazole-6-sulfonamide

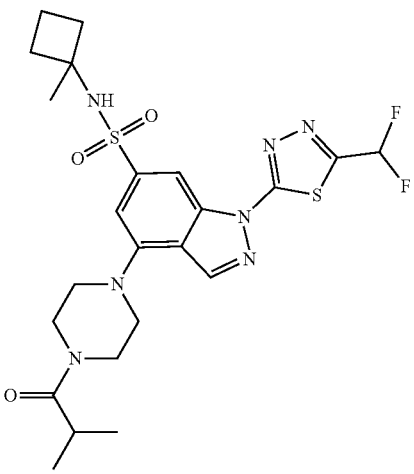 [SMILES: CC(C)C(=O)N1CCN(c2cc(S(=O)(=O)NC3(C)CCC3)cc3c2cnn3-c2nnc(C(F)F)s2)CC1]

Step 1: Synthesis of 4-chloro-1-[5-(difluoromethyl)-1,3,4-thiadiazol-2-yl]-N-(1-methylcyclobutyl)indazole-6-sulfonamide To a stirred solution of 1-methylcyclobutan-1-amine hydrochloride (189.43 mg, 1.558 mmol, 2 equiv) in DMF was added DIEA (301.99 mg, 2.337 mmol, 3 equiv) in portions at 0° C. The resulting mixture was stirred for 2 h at room temperature. The reaction was monitored by LCMS. Then water (20 mL) was added. The resulting mixture was extracted with EA (3×20 mL). The combined organic layers were washed with brine (50 mL), dried over anhydrous Na₂SO₄. After filtration, the filtrate was concentrated under reduced pressure to afford 4-chloro-1-[5-(difluoromethyl)-1,3,4-thiadiazol-2-yl]-N-(1-methylcyclobutyl)indazole-6-sulfonamide (60 mg, crude) as a yellow oil. LCMS (ESI, m/z): 434, 436[M+H]⁺.

Step 2: Synthesis of 1-(5-(difluoromethyl)-1,3,4-thiadiazol-2-yl)-4-(4-isobutyrylpiperazin-1-yl)-N-(1-methylcyclobutyl)-1H-indazole-6-sulfonamide To a stirred mixture of 4-chloro-1-[5-(difluoromethyl)-1,3,4-thiadiazol-2-yl]-N-(1-methylcyclobutyl)indazole-6-sulfonamide (60 mg, 0.138 mmol, 1 equiv) and 2-methyl-1-(piperazin-1-yl)propan-1-one (25.93 mg, 0.166 mmol, 1.2 equiv) in 1,4-dioxane (2 mL) were added RuPhos Palladacycle Gen.3 (11.57 mg, 0.014 mmol, 0.1 equiv), RuPhos (12.91 mg, 0.028 mmol, 0.2 equiv) and Cs₂CO₃ (135.17 mg, 0.414 mmol, 3 equiv). The mixture was stirred at 70° C. for 4 h under nitrogen atmosphere. The resulting mixture was filtered, the filter cake was washed with DCM (3×5 mL). The filtrate was concentrated under reduced pressure. The crude product was purified by Prep-HPLC with the following conditions (Column: XBridge Prep OBD C18 Column, 30*150 mm, 5 μm; Mobile Phase A: Water (10 mmol/L NH₄HCO₃+0.1% NH₃·H₂O), Mobile Phase B: ACN; Flow rate: 60 mL/min; Gradient: 45% B to 75% B in 7 min, 75% B; Wave Length: 254 nm; RT1(min): 6; Number Of Runs: 0) to afford 1-(5-(difluoromethyl)-1,3,4-thiadiazol-2-yl)-4-(4-isobutyrylpiperazin-1-yl)-N-(1-methylcyclobutyl)-1H-indazole-6-sulfonamide (21.3 mg, 27.74%) as a white solid. LCMS (ESI, m/z): 554.15 [M+H]⁺. ¹H NMR (400 MHz, Chloroform-d) δ=8.77 (s, 1H), 8.31 (s, 1H), 7.26 (s, 1H), 7.15-6.87 (m, 1H), 4.83 (s, 1H), 3.95-3.78 (m, 4H), 3.48-3.39 (m, 4H), 2.92-2.81 (m, 1H), 2.34-2.22 (m, 2H), 1.98-1.87 (m, 2H), 1.83-1.66 (m, 2H), 1.45 (s, 3H), 1.19 (d, J=6.8 Hz, 6H).

Example 22: 1-(5-(difluoromethyl)-1,3,4-thiadiazol-2-yl)-N-(3-(fluoromethyl)oxetan-3-yl)-4-(4-isobutyrylpiperazin-1-yl)-1H-indazole-6-sulfonamide

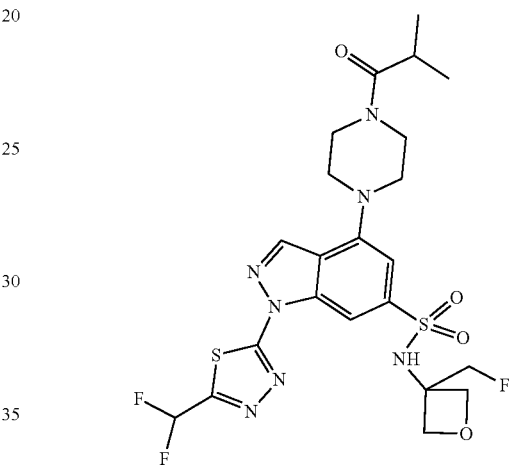

A mixture of 1-(4-{6-bromo-1-[5-(difluoromethyl)-1,3,4-thiadiazol-2-yl]indazol-4-yl}piperazin-1-yl)-2-methylpropan-1-one (1 g, 2.060 mmol, 1 equiv), dipotassium sulfinosulfonate (0.92 g, 4.120 mmol, 2 equiv), triphenylphosphane (0.16 g, 0.618 mmol, 0.3 equiv), tetraethylazanium bromide (0.48 g, 2.266 mmol, 1.1 equiv), sodium formate (0.42 g, 6.180 mmol, 3 equiv), Pd(AcO)₂ (0.05 g, 0.206 mmol, 0.1 equiv) and 1,10-phenanthroline (0.11 g, 0.618 mmol, 0.3 equiv) in DMSO (10 mL) was stirred for 4 h at 70° C. under nitrogen atmosphere. The mixture was allowed to cool down to room temperature. To the above mixture was added 3-(fluoromethyl)oxetan-3-amine hydrochloride (0.88 g, 6.180 mmol, 3 equiv) in DIEA (5 mL) at 0° C. Then NCS (1.38 g, 10.335 mmol, 5.02 equiv) in THF (10 mL) was added at 0° C. The resulting mixture was stirred for additional 1 h at room temperature. The resulting mixture was diluted with water (100 mL). The resulting mixture was extracted with EtOAc (3×100 mL). The combined organic layers were washed with brine (3×100 mL), dried over anhydrous Na₂SO₄. After filtration, the filtrate was concentrated under reduced pressure. The residue was purified by reversed-phase flash chromatography with the following conditions: column, C18 silica gel; mobile phase, MeCN in Water (10 mmol/L NH4HCO3), 30% to 70% gradient in 10 min; detector, UV 254 nm. This resulted in 1-(5-(difluoromethyl)-1,3,4-thiadiazol-2-yl)-N-(3-(fluoromethyl)oxetan-3-yl)-4-(4-isobutyrylpiperazin-1-yl)-1H-indazole-6-sulfonamide (155.2 mg, 13.03%) as an off-white solid. LCMS (ESI, m/z): 574[M+H]⁺. ¹H NMR (400 MHz, Chloroform-d)

δ=8.77 (s, 1H), 8.33 (s, 1H), 7.19 (s, 1H), 7.17-6.87 (m, 1H), 5.80 (s, 1H), 4.88-4.78 (m, 3H), 4.71 (s, 1H), 4.46 (d, J=7.2 Hz, 2H), 3.99-3.76 (m, 4H), 3.55-3.39 (m, 4H), 2.96-2.81 (m, 1H), 1.19 (d, J=6.4 Hz, 6H)

Example 23: 1-(5-(difluoromethyl)-1,3,4-thiadiazol-2-yl)-N-(3-methyloxetan-3-yl)-1H-indazole-6-sulfonamide

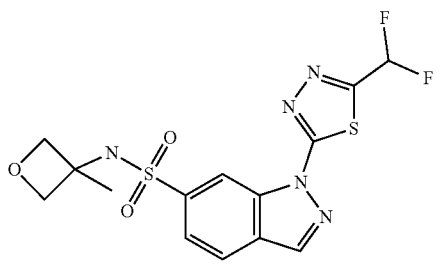 [SMILES: CC1(NS(=O)(=O)c2ccc3cnn(-c4nnc(C(F)F)s4)c3c2)COC1]

Step 1: Synthesis of 6-(benzylsulfanyl)-1H-indazole

A mixture of 6-bromo-1H-indazole (1 g, 5.075 mmol, 1 equiv), benzyl mercaptan (1.26 g, 10.150 mmol, 2 equiv), DIEA (1.97 g, 15.225 mmol, 3 equiv), Pd$_2$(dba)$_3$ (464.75 mg, 0.508 mmol, 0.1 equiv) and XantPhos (587.34 mg, 1.015 mmol, 0.2 equiv) in 1,4-dioxane (12 mL) was stirred for 3 h at 100° C. under N$_2$ atmosphere. The reaction was monitored by LCMS. The mixture was allowed to cool down to room temperature. Then water (100 mL) was added. The mixture was extracted with EA (3×100 mL). The combined organic layers were washed with brine (100 mL), dried over anhydrous Na$_2$SO$_4$ and concentrated. The residue was purified by silica gel column chromatography (eluting with 1:1 EA/PE) to afford 6-(benzylsulfanyl)-1H-indazole (800 mg, 59.03%) as a yellow solid. LCMS (ESI, m/z): 241 [M+H]$^+$.

Step 2: Synthesis of 6-(benzylsulfanyl)-1-[5-(difluoromethyl)-1,3,4-thiadiazol-2-yl]indazole and 2-(6-(benzylthio)-2H-indazol-2-yl)-5-(difluoromethyl)-1,3,4-thiadiazole A mixture of 6-(benzylsulfanyl)-1H-indazole (800 mg, 3.329 mmol, 1 equiv), 2-bromo-5-(difluoromethyl)-1,3,4-thiadiazole (1.07 g, 4.994 mmol, 1.5 equiv) and Cs$_2$CO$_3$ (2.17 g, 6.658 mmol, 2 equiv) in DMF (10 mL) was stirred for 3 h at 100° C. The reaction was monitored by LCMS. The mixture was allowed to cool down to room temperature. Then water (100 mL) was added. The mixture was extracted with EA (3×100 mL). The combined organic layers were washed with brine (100 mL), dried over anhydrous Na$_2$SO$_4$ and concentrated. The residue was purified by silica gel column chromatography (eluting with 1:1 EA/PE) to afford the mixture of 6-(benzylsulfanyl)-1-[5-(difluoromethyl)-1,3,4-thiadiazol-2-yl]indazole and 2-(6-(benzylthio)-2H-indazol-2-yl)-5-(difluoromethyl)-1,3,4-thiadiazole (800 mg, 58%) as a yellow solid. LCMS (ESI, m/z): 375 [M+H]$^+$.

Step 3: Synthesis of J-[5-(difluoromethyl)-1,3,4-thiadiazol-2-yl]indazole-6-sulfonyl chloride To a stirred solution of 6-(benzylsulfanyl)-1-[5-(difluoromethyl)-1,3,4-thiadiazol-2-yl]indazole and 2-(6-(benzylthio)-2H-indazol-2-yl)-5-(difluoromethyl)-1,3,4-thiadiazole (200 mg, 0.534 mmol, 1 equiv) in DCM (4 mL), AcOH (0.3 mL, 5.235 mmol, 9.80 equiv) and H$_2$O (0.6 mL, 33.306 mmol, 62.35 equiv) was added 1,3-dichloro-5,5-dimethyl-imidazolidine-2,4-dione (315.71 mg, 1.602 mmol, 3 equiv) dropwise at 0° C. The resulting mixture was stirred for 12 h at room temperature. The reaction was monitored by LCMS. The reaction was quenched by the addition of water (50 mL). The resulting mixture was extracted with EA (3×50 mL). The combined organic layers were dried over anhydrous Na$_2$SO4. After filtration, the filtrate was concentrated under reduced pressure to afford the mixture of 1-[5-(difluoromethyl)-1,3,4-thiadiazol-2-yl]indazole-6-sulfonyl chloride and 2-[5-(difluoromethyl)-1,3,4-thiadiazol-2-yl]indazole-6-sulfonyl chloride (100 mg, crude) as a white solid. LCMS (ESI, m/z): 351, 353 [M+H]$^+$.

Step 4: Synthesis of 1-(5-(difluoromethyl)-1,3,4-thiadiazol-2-yl)-N-(3-methyloxetan-3-yl)-1H-indazole-6-sulfonamide To a stirred solution of the mixture of 1-[5-(difluoromethyl)-1,3,4-thiadiazol-2-yl]indazole-6-sulfonyl chloride in DCM (3 mL) and TEA (57.70 mg, 0.570 mmol, 2 equiv) was added 3-methyloxetan-3-amine (37.26 mg, 0.427 mmol, 1.5 equiv) in DCM dropwise at 0° C. The resulting mixture was stirred for 2 h at room temperature. The reaction was monitored by LCMS. The resulting mixture was concentrated. The residue was purified by reverse phase chromatography (Column: C18; Mobile phase, A: water (containing 10 mmol/L NH$_4$HCO$_3$) and B: ACN (5% to 60% over 30 min); Detector, UV 254 nm) to afford 1-(5-(difluoromethyl)-1,3,4-thiadiazol-2-yl)-N-(3-methyloxetan-3-yl)-1H-indazole-6-sulfonamide (18.8 mg, 32.42%) as a white solid LCMS (ESI, m/z): 401.95 [M+H]$^+$, $^1$H NMR (400 MHz, DMSO-d$_6$) δ=8.97 (s, 1H), 8.85 (s, 1H), 8.78 (s, 1H), 8.24 (d, J=8.4 Hz, 1H), 7.89 (d, J=8.4 Hz, 1H), 7.76-7.50 (m, 1H), 4.57 (d, J=6.0 Hz, 2H), 4.15 (d, J=6.8 Hz, 2H), 1.44 (s, 3H).

Example 24 Synthesis of 4-chloro-N-(3-cyanooxetan-3-yl)-1-(5-(difluoromethyl)-1,3,4-thiadiazol-2-yl)-1H-indazole-6-sulfonamide

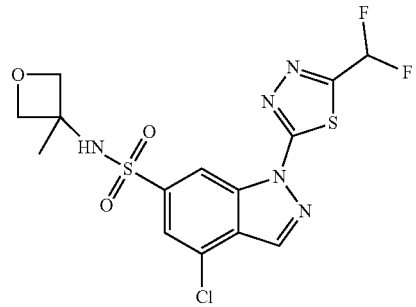 [SMILES: CC1(NS(=O)(=O)c2cc(Cl)c3cnn(-c4nnc(C(F)F)s4)c3c2)COC1]

To a stirred solution of 3-methyloxetan-3-amine (67.86 mg, 0.778 mmol, 2 equiv) in DCM (2 mL) was added TEA (157.63 mg, 1.556 mmol, 4 equiv) and 4-chloro-1-[5-(difluoromethyl)-1,3,4-thiadiazol-2-yl]indazole-6-sulfonyl chloride (150 mg, 0.389 mmol, 1 equiv) at 0° C. The resulting mixture was stirred for 2 h at 25° C. The reaction was monitored by LCMS. The mixture was concentrated under reduced pressure. The residue was purified by silica gel column chromatography, eluted with PE/EA (1:1). The crude product was purified by Prep-HPLC with the following conditions (Column: X Bridge Shield RP18 OBD Column, 30*150 mm, 5 μm; Mobile Phase A: Water (10 mmol/L NH$_4$HCO$_3$), Mobile Phase B: ACN; Flow rate: 60 mL/min; Gradient: 34% B to 64% B in 7 min, 64% B; Wave Length: 254 nm; RT1(min): 6.2; Number Of Runs: 0) to afford 4-chloro-N-(3-cyanooxetan-3-yl)-1-(5-(difluoromethyl)-1,3,4-thiadiazol-2-yl)-1H-indazole-6-sulfonamide (10.6 mg, 6.20%) as a white solid. LCMS (ESI, m/z): 436.00 [M+H]$^+$. $^1$H NMR (300 MHz, Chloroform-d) δ=9.10 (s, 1H), 8.46 (s, 1H), 7.89 (s, 1H), 7.19-6.84 (m, 1H), 5.37 (s, 1H), 4.76 (d, J=6.6 Hz, 2H), 4.38 (d, J=6.9 Hz, 2H), 1.65 (s, 3H).

Example 25A: N-(3-cyanooxetan-3-yl)-3-((2-methylthiazol-5-yl)methyl)-2,4-dioxo-1,2,3,4-tetrahydroquinazoline-6-sulfonamide

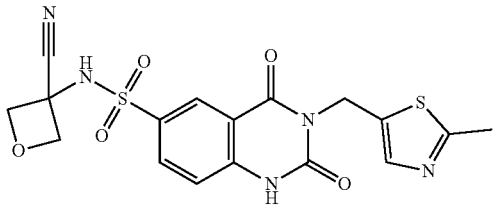 [SMILES: Cc1ncc(Cn2c(=O)[nH]c3ccc(S(=O)(=O)NC4(C#N)COC4)cc3c2=O)s1]

Step 1: Synthesis of 3-[(2-methyl-1,3-thiazol-5-yl)methyl]-2,4-dioxo-1H-quinazoline-6-sulfonyl chloride A mixture of 3-[(2-methyl-1,3-thiazol-5-yl)methyl]-1H-quinazoline-2,4-dione (400 mg, 1.464 mmol, 1 equiv) in ClSO$_3$H (1 mL) dropwise at 0° C., The resulting mixture was stirred for 3 h at 60° C. The reaction was monitored by LCMS. The mixture was allowed to cool down to room temperature. The reaction was quenched by the addition of water (50 mL) at 0° C. The mixture was extracted with EA (3×50 mL). The combined organic layers were washed with brine (50 mL), dried over anhydrous Na$_2$SO$_4$ and concentrated to afford 3-[(2-methyl-1,3-thiazol-5-yl)methyl]-2,4-dioxo-1H-quinazoline-6-sulfonyl chloride (400 mg, crude) as a yellow solid. LCMS (ESI, m/z): 372, 374[M+H]$^+$ Step 2: Synthesis of N-(3-cyanooxetan-3-yl)-3-((2-methylthiazol-5-yl)methyl)-2,4-dioxo-1,2,3,4-tetrahydroquinazoline-6-sulfonamide A mixture of 3-[(2-methyl-1,3-thiazol-5-yl)methyl]-2,4-dioxo-1H-quinazoline-6-sulfonyl chloride (100 mg, 0.269 mmol, 1 equiv) and 3-aminooxetane-3-carbonitrile (31.66 mg, 0.323 mmol, 1.2 equiv) in pyridine (2 mL, 0.025 mmol, 0.09 equiv) was stirred for 2 h at room temperature. The reaction was monitored with LCMS. The reaction was diluted with ethyl acetate (20 mL). The resulting mixture was washed with brine (3×20 mL), dried over anhydrous Na$_2$SO$_4$. After filtration, the filtrate was concentrated under reduced pressure. The residue was purified by Prep-HPLC with the following conditions (Column: XBridge Prep OBD C18 Column, 30*150 mm, 5 μm; Mobile Phase A: Water (10 mmol/L NH4HCO3+0.1% NH3·H2O), Mobile Phase B: ACN; Flow rate: 60 mL/min; Gradient: 5% B to 25% B in 7 min, 25% B; Wave Length: 254 nm; RT1(min): 6; Number Of Runs: 0) to afford N-(3-cyanooxetan-3-yl)-3-((2-methylthiazol-5-yl)methyl)-2,4-dioxo-1,2,3,4-tetrahydroquinazoline-6-sulfonamide (19.3 mg, 16.43%) as a white solid. LCMS (ESI, m/z): 434.05 [M+H]$^+$ $^1$H NMR (400 MHz, Chloroform-d) δ=11.96 (br, 1H), 8.34 (s, 1H), 8.03 (d, J=8.7 Hz, 1H), 7.61 (s, 1H), 7.33 (d, J=8.7 Hz, 1H), 5.20 (s, 2H), 4.81 (d, J=7.5 Hz, 2H), 4.69 (d, J=7.2 Hz, 2H), 2.67 (s, 3H).

Example 25B: N-(3-cyanooxetan-3-yl)-1-((2,4-dimethylthiazol-5-yl)methyl)-3-((2-methylthiazol-5-yl)methyl)-2,4-dioxo-1,2,3,4-tetrahydroquinazoline-6-sulfonamide

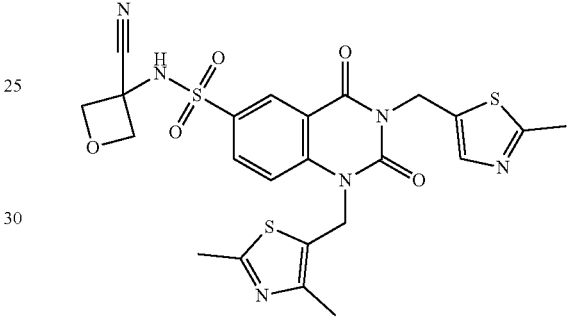

To a mixture of N-(3-cyanooxetan-3-yl)-3-[(2-methyl-1,3-thiazol-5-yl)methyl]-2,4-dioxo-1H-quinazoline-6-sulfonamide (100 mg, 0.231 mmol, 1 equiv), (2,4-dimethyl-1,3-thiazol-5-yl)methanol (49.55 mg, 0.347 mmol, 1.5 equiv) and PPh3 (121.02 mg, 0.462 mmol, 2 equiv) in THF (2 mL) was added (E)-N-[[(propan-2-yloxy)carbonyl]imino](propan-2-yloxy)formamide (93.30 mg, 0.462 mmol, 2 equiv) dropwise at 0° C. The resulting mixture was stirred for 16 h at room temperature. The reaction was monitored with LCMS. The resulting mixture was diluted with ethyl acetate (20 mL). The resulting mixture was washed with brine (3×20 mL), dried over anhydrous Na$_2$SO$_4$. After filtration, the filtrate was concentrated under reduced pressure. The residue was purified by Prep-HPLC with the following conditions (Column: XBridge Prep OBD C18 Column, 19*250 mm, 5 μm; Mobile Phase A: Water (10 mmol/L NH$_4$HCO$_3$), Mobile Phase B: ACN; Flow rate: 25 mL/min; Gradient: 23% B to 53% B in 7 min, 53% B; Wave Length: 254 nm; RT1(min): 6.88; Number Of Runs: 0) to afford N-(3-cyanooxetan-3-yl)-1-((2,4-dimethylthiazol-5-yl)methyl)-3-((2-methylthiazol-5-yl)methyl)-2,4-dioxo-1,2,3,4-tetrahydroquinazoline-6-sulfonamide (7.9 mg, 6.08%) as a white solid. LCMS (ESI, m/z): 559.05[M+H]$^+$ $^1$H NMR (400 MHz, Chloroform-d) δ=12.03 (br, 1H), 8.18 (s, 1H), 8.12 (d, J=8.7 Hz, 1H), 7.64 (s, 1H), 7.33 (d, J=8.7 Hz, 1H), 5.26 (s, 2H), 4.91 (d, J=7.5 Hz, 2H), 4.75 (d, J=7.8 Hz, 2H), 4.50 (s, 2H), 2.63 (s, 3H), 2.40 (s, 3H), 2.18 (s, 3H).

Example 26: 1-(5-(difluoromethyl)-1,3,4-thiadiazol-2-yl)-4-(dimethylamino)-N-(3-methyloxetan-3-yl)-1H-indazole-6-sulfonamide

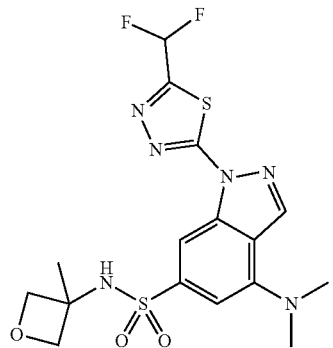 [SMILES: CN(C)c1cc(S(=O)(=O)NC2(C)COC2)cc2c1cnn2-c1nnc(C(F)F)s1]

Step 1: Synthesis of 4-bromo-2-(dimethylamino)-6-fluorobenzaldehyde

A mixture of 4-bromo-2,6-difluorobenzaldehyde (500 mg, 2.262 mmol, 1 equiv), dimethylamine (102.00 mg, 2.262 mmol, 1 equiv) and $K_2CO_3$ (625.36 mg, 4.524 mmol, 2 equiv) in DMF (10 mL) was stirred for 16 h at 80° C. The reaction was monitored by LCMS. The mixture was allowed to cool down to room temperature. The resulting mixture was diluted with EA (40 mL). The resulting mixture was washed with 4×10 mL of water, dried over anhydrous $Na_2SO_4$. After filtration, the filtrate was concentrated under reduced pressure. The residue was purified by silica gel column chromatography, eluted with PE/EA (3:1) to afford 4-bromo-2-(dimethylamino)-6-fluorobenzaldehyde (500 mg, 90%) as a yellow solid. LCMS (ESI, m/z): 246, 248 $[M+H]^+$.

Step 2: Synthesis of 6-bromo-N,N-dimethyl-1H-indazol-4-amine

Into a stirred solution 4-bromo-2-(dimethylamino)-6-fluorobenzaldehyde (1 g, 4.064 mmol, 1 equiv) in DMSO (10 mL) was hydrazine hydrate (797.35 mg, 16.256 mmol, 4 equiv). The mixture was stirred for 16 h at 100° C. The reaction was monitored by LCMS. The mixture was allowed to cool down to room temperature. The reaction was diluted with EA (100 mL). The resulting mixture was washed with brine (3×80 mL), dried over anhydrous $Na_2SO_4$. After filtration, the filtrate was concentrated under reduced pressure. The residue was purified by silica gel column chromatography, eluted with PE/EA (3:1) to afford 6-bromo-N,N-dimethyl-1H-indazol-4-amine (800 mg, 81.99%) as a yellow solid. LCMS (ESI, m/z): 240, 242$[M+H]^+$

Step 3: Synthesis of 6-bromo-1-[5-(difluoromethyl)-1,3,4-thiadiazol-2-yl]-N,N-dimethylindazol-4-amine To a stirred mixture of 6-bromo-N,N-dimethyl-1H-indazol-4-amine (800 mg, 3.332 mmol, 1 equiv), and $Cs_2CO_3$ (2.17 g, 6.664 mmol, 2 equiv) in DMF (10 mL) was added 2-bromo-5-(difluoromethyl)-1,3,4-thiadiazole (859.71 mg, 3.998 mmol, 1.2 equiv). The mixture was stirred for 2 h at 70° C. The reaction was monitored by LCMS. The mixture was allowed to cool down to room temperature. Then water (60 mL) was added. The mixture was washed with EA (3×80 mL), dried over anhydrous $Na_2SO_4$. After filtration, the filtrate was concentrated under reduced pressure. The residue was purified by silica gel column chromatography (eluting with 3:1 EA/PE) to afford 6-bromo-1-[5-(difluoromethyl)-1,3,4-thiadiazol-2-yl]-N,N-dimethylindazol-4-amine (750 mg, 60.15%) as a white solid. LCMS (ESI, m/z): 374, 376$[M+H]^+$.

Step 4: Synthesis of 1-(5-(difluoromethyl)-1,3,4-thiadiazol-2-yl)-4-(dimethylamino)-N-(3-methyloxetan-3-yl)-1H-indazole-6-sulfonamide A mixture of 6-bromo-1-[5-(difluoromethyl)-1,3,4-thiadiazol-2-yl]-N,N-dimethylindazol-4-amine (200 mg, 0.534 mmol, 1 equiv), potassium metabisulfite (237.65 mg, 1.068 mmol, 2 equiv), TEAB (151.23 mg, 1.043 mmol, 1.1 equiv), sodium formate (72.70 mg, 1.068 mmol, 2 equiv), $PPh_3$ (42.06 mg, 0.160 mmol, 0.3 equiv), phen (28.89 mg, 0.160 mmol, 0.3 equiv) and palladium acetate (12.00 mg, 0.053 mmol, 0.1 equiv) in DMSO (3 mL) was stirred for 4 h at 70° C. under nitrogen atmosphere. Then the reaction was cooled to room temperature. A solution of 3-methyloxetan-3-amine (93.13 mg, 1.068 mmol, 2 equiv) in THF (3 mL) and a solution of NBS (285.38 mg, 1.602 mmol, 3 equiv) in THF (2 mL) were added. The resulting mixture was stirred for 1 h at room temperature. The reaction was monitored with LCMS. Then water (50 mL) was added. The mixture was washed with EA (3×50 mL), dried over anhydrous $Na_2SO_4$. After filtration, the filtrate was concentrated under reduced pressure. The residue was purified by Prep-HPLC with the following conditions (Column: XBridge Prep OBD C18 Column, 30*150 mm, 5 μm; Mobile Phase A: Water (10 mmol/L NH4HCO3+0.1% NH3·H2O), Mobile Phase B: ACN; Flow rate: 60 mL/min; Gradient: 15% B to 45% B in 7 min, 45% B; Wave Length: 254 nm; RT1(min): 6; Number Of Runs: 0) to afford 1-(5-(difluoromethyl)-1,3,4-thiadiazol-2-yl)-4-(dimethylamino)-N-(3-methyloxetan-3-yl)-1H-indazole-6-sulfonamide (22.5 mg, 9.45%) as a white solid. LCMS (ESI, m/z): 445.05 $[M+H]^+$. $^1H$ NMR (400 MHz, Chloroform-d) δ=8.91 (s, 1H), 8.55 (s, 1H), 8.22 (s, 1H), 7.76-7.41 (m, 1H), 6.87 (s, 1H), 4.58 (d, J=6.0 Hz, 2H), 4.13 (d, J=6.6 Hz, 2H), 3.31 (s, 6H), 1.58 (s, 3H)

Example 27: 1-(5-(difluoromethyl)-1,3,4-thiadiazol-2-yl)-N-((2S,3S)-2,3-dimethyloxetan-3-yl)-4-(4-isobutyrylpiperazin-1-yl)-1H-indazole-6-sulfonamide (Stereochemistry Assumed)

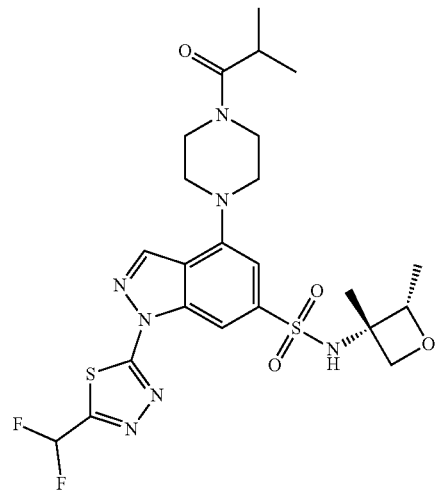 [SMILES: CC(C)C(=O)N1CCN(c2cc(S(=O)(=O)N[C@@]3(C)CO[C@H]3C)cc3c2cnn3-c2nnc(C(F)F)s2)CC1]

Step 1: Synthesis of 3-(dibenzylamino)-2-methyloxetane-3-carbonitrile

A solution of 2-methyloxetan-3-one (700 mg, 8.131 mmol, 1 equiv) and dibenzyl amine (3208.19 mg, 16.262 mmol, 2 equiv) in AcOH (8 mL) was treated with TMSCN (1613.33 mg, 16.262 mmol, 2 equiv) at 0° C. The resulting mixture was stirred for 14 h at 25° C. under nitrogen atmosphere. Desired product could be detected by LCMS. The reaction was quenched with water (50 mL). The resulting mixture was washed with EA (3×50 mL). The combined organic layers dried over anhydrous Na$_2$SO$_4$. After filtration, the filtrate was concentrated under reduced pressure to afford 3-(dibenzylamino)-2-methyloxetane-3-carbonitrile (500 mg, crude). LCMS (ESI, m/z): 293[M+H]$^+$

Step 2: Synthesis of N,N-dibenzyl-2,3-dimethyloxetan-3-amine

A solution of 3-(dibenzylamino)-2-methyloxetane-3-carbonitrile (500 mg, 1.710 mmol, 1 equiv) in THF (10 mL) was added MeMgBr (1019.59 mg, 8.550 mmol, 5 equiv) dropwise at 0° C. The resulting mixture was stirred for 5 h at 60° C. under nitrogen atmosphere. Desired product could be detected by LCMS. The reaction was quenched with saturated NH$_4$Cl (50 mL). The resulting mixture was washed with EA (3×50 mL). The combined organic layers dried over anhydrous Na$_2$SO$_4$. After filtration, the filtrate was concentrated under reduced pressure to afford N,N-dibenzyl-2,3-dimethyloxetan-3-amine (300 mg, crude).
LCMS (ESI, m/z): 282[M+H]$^+$

Step 3: Synthesis of 2,3-dimethyloxetan-3-amine

To a stirred solution of N,N-dibenzyl-2,3-dimethyloxetan-3-amine (300 mg, 1.066 mmol, 1 equiv) in MeOH (8 mL) was added Pd(OH)$_2$/C (149.71 mg, 1.066 mmol, 1 equiv) in portions at 25° C. under N$_2$ atmosphere. The resulting mixture was stirred for 14 h at 25° C. under H$_2$ atmosphere. Desired product could be detected by LCMS. The resulting mixture was filtered, the filter cake was washed with MeOH (3×5 mL). The filtrate was concentrated under reduced pressure to afford 2,3-dimethyloxetan-3-amine (80 mg, crude). LCMS (ESI, m/z): 102[M+H]$^+$

Step 4: Synthesis of 4-chloro-1-[5-(difluoromethyl)-1,3,4-thiadiazol-2-yl]-N-(2,3-dimethyloxetan-3-yl)indazole-6-sulfonamide A solution of 2,3-dimethyloxetan-3-amine (13.13 mg, 0.130 mmol, 1 equiv) and pyridine (102.68 mg, 1.300 mmol, 10 equiv) in DCM (2 mL) was added 4-chloro-1-[5-(difluoromethyl)-1,3,4-thiadiazol-2-yl] indazole-6-sulfonyl chloride (50 mg, 0.130 mmol, 1 equiv) at 0° C. The resulting mixture was stirred for 2 h at room temperature. Desired product could be detected by LCMS. The solids were filtered out and were washed with DCM (3×5 mL). The filtration was concentrated under reduced pressure. The residue was purified by Prep-HPLC with the following condition: (Column: XBridge Prep OBD C18 Column, 19*250 mm, 5 μm; Mobile Phase A: Water (10 mmol/L NH4HCO3), Mobile Phase B: ACN; Flow rate: 25 mL/min; Gradient: 41% B to 71% B in 10 min, 71% B; Wave Length: 254 nm; RT1(min): 8.7; Number Of Runs: 0) to afford 4-chloro-1-[5-(difluoromethyl)-1,3,4-thiadiazol-2-yl]-N-(2,3-dimethyloxetan-3-yl)indazole-6-sulfonamide (4.6 mg, 7.61%) as a white solid. LCMS (ESI, m/z): 450, 452[M+H]$^+$. $^1$H NMR (400 MHz, DMSO-d6) δ 9.12 (s, 1H), 9.10 (s, 1H), 8.44 (s, 1H), 7.88 (s, 1H), 7.15-6.88 (m, 1H), 5.30-5.20 (m, 1H), 4.65-4.61 (m, 1H), 4.36-4.14 (m, 1H), 1.55 (s, 3H), 1.31-1.25 (m, 3H).

Step 5: Synthesis of 1-(5-(difluoromethyl)-1,3,4-thiadiazol-2-yl)-N-((2S,3S)-2,3-dimethyloxetan-3-yl)-4-(4-isobutyrylpiperazin-1-yl)-1H-indazole-6-sulfonamide To a stirred mixture of 4-chloro-1-[5-(difluoromethyl)-1,3,4-thiadiazol-2-yl]-N-(2,3-dimethyloxetan-3-yl)indazole-6-sulfonamide (15 mg, 0.033 mmol, 1 equiv), RuPhos Pd G3 (5.58 mg, 0.007 mmol, 0.2 equiv), RuPhos (6.30 mg, 0.013 mmol, 0.4 equiv) and cesium carbonate (32.59 mg, 0.099 mmol, 3 equiv) in dioxane) was added 2-methyl-1-(piperazin-1-yl)propan-1-one (6.25 mg, 0.040 mmol, 1.2 equiv) in portions at room temperature. The resulting mixture was stirred for 24 h at 100° C. under N$_2$ atmosphere. Desired product could be detected by LCMS. The solids out and were washed with EA (3×5 mL). The filtration was concentrated under reduced pressure. The residue was purified by Prep-HPLC with the following condition: (Column: XBridge Prep OBD C18 Column, 30*150 mm, 5 μm; Mobile Phase A: Water (10 mmol/L NH4HCO3+0.1% NH3·H2O), Mobile Phase B: ACN; Flow rate: 60 mL/min; Gradient: 33% B to 63% B in 7 min, 63% B; Wave Length: 254 nm; RT1(min): 6; Number Of Runs: 0) to afford 1-(5-(difluoromethyl)-1,3,4-thiadiazol-2-yl)-N-((2S,3S)-2,3-dimethyloxetan-3-yl)-4-(4-isobutyrylpiperazin-1-yl)-1H-indazole-6-sulfonamide (stereochemistry assumed) (4.1 mg, 21.56%) as a white solid. LCMS (ESI, m/z): 570.10[M+H]$^+$, $^1$H NMR (300 MHz, DMSO-d6) δ 8.93 (s, 1H), 8.51-8.44 (m, 2H), 7.77-7.42 (m, 1H), 7.15 (s, 1H), 4.78-4.71 (m, 1H), 4.42 (d, J=5.7 Hz, 1H), 3.87 (d, J=5.7 Hz, 1H), 3.78-3.74 (m, 4H), 3.44-3.32 (m, 4H), 2.99-2.90 (m, 1H), 1.25 (s, 3H), 1.06-1.02 (m, 9H).

Example 28A: N-(3-(fluoromethyl)oxetan-3-yl)-3-((2-methylthiazol-5-yl)methyl)-2,4-dioxo-1,2,3,4-tetrahydroquinazoline-6-sulfonamide

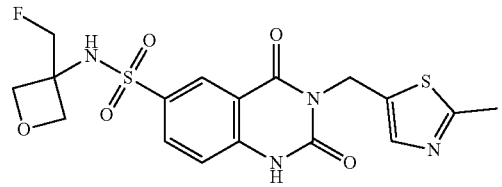 [SMILES: Cc1ncc(Cn2c(=O)[nH]c3ccc(S(=O)(=O)NC4(CF)COC4)cc3c2=O)s1]

Step 1: Synthesis of 3-[(2-methyl-1,3-thiazol-5-yl)methyl]-2,4-dioxo-1H-quinazoline-6-sulfonyl chloride A solution of 3-[(2-methyl-1,3-thiazol-5-yl)methyl]-1H-quinazoline-2,4-dione (200.00 mg, 0.73 mmol, 1.00 equiv) in chlorosulfonic acid (0.50 mL) was stirred for 1.5 h at 60° C. After reaction, the reaction mixture was poured into EA (5 mL) and then added to ice water (5 mL). The resulting mixture was extracted with EtOAc (3×10 mL). The combined organic layers were washed with brine (1×5 mL), dried over anhydrous Na$_2$SO$_4$. After filtration, the filtrate was concentrated under reduced pressure. This resulted in 3-[(2-methyl-1,3-thiazol-5-yl)methyl]-2,4-dioxo-1H-quinazoline-6-sulfonyl chloride (200.00 mg, crude) as a light yellow solid. The crude product was used for the next step directly without further purification. LCMS (ESI, m/z): 372, 374 [M+H]$^+$

Step 2: Synthesis of N-(3-(fluoromethyl)oxetan-3-yl)-3-((2-methylthiazol-5-yl)methyl)-2,4-dioxo-1,2,3,4-tetrahydroquinazoline-6-sulfonamide To a stirred solution of 3-[(2-methyl-1,3-thiazol-5-yl)methyl]-2,4-dioxo-1H-quinazoline-6-sulfonyl chloride (165.07 mg, 0.44 mmol, 1.00 equiv) in pyridine (3.00 mL) was added 3-(fluoromethyl)oxetan-3-amine (70.00 mg, 0.67 mmol, 1.50 equiv) in portions at 0° C. The resulting mixture was stirred for 1.0 h at room temperature. The resulting mixture was extracted with CH$_2$Cl$_2$ (3×10 mL). The combined organic layers, dried over anhydrous Na$_2$SO$_4$. The residue was purified by silica gel column chromatography, eluted with PE/EA (1:1) to afford N-[3-(fluoromethyl)oxetan-3-yl]-3-[(2-methyl-1,3-thiazol-5-yl)methyl]-2,4-dioxo-1H-quinazoline-6-sulfonamide (80.00 mg, 40.88%) as a light yellow solid. The crude product (20 mg) was purified by Prep-HPLC with the following conditions (Column: Xselect CSH C18 OBD Column 30*150 mm 5 µm, n; Mobile Phase A: Water (0.1% FA), Mobile Phase B: ACN; Flow rate: 60 mL/min; Gradient: 16% B to 46% B in 7 min, 46% B; Wave Length: 254 nm; RT1(min): 6.00 (detected by lcms and collected). This resulted in N-(3-(fluoromethyl)oxetan-3-yl)-3-((2-methylthiazol-5-yl)methyl)-2,4-dioxo-1,2,3,4-tetrahydroquinazoline-6-sulfonamide; formic acid (13.0 mg, 65.00%) as a white solid. LCMS (ESI, m/z): 441.00 [M+H]$^+$, $^1$H NMR (300 MHz, DMSO-d6) δ=12.01 (s, 1H), 8.80 (s, 1H), 8.34 (s, 1H), 8.05 (d, J=8.7 Hz, 1H), 7.61 (s, 1H), 7.33 (d, J=8.7 Hz, 1H), 5.19 (s, 2H), 4.68 (s, 1H), 4.52-4.50 (m, 3H), 4.32 (d, J=6.6 Hz, 2H), 2.57 (s, 3H).

Example 28B: 1-((2,4-dimethylthiazol-5-yl)methyl)-N-(3-(fluoromethyl)oxetan-3-yl)-3-((2-methylthiazol-5-yl)methyl)-2,4-dioxo-1,2,3,4-tetrahydroquinazoline-6-sulfonamide

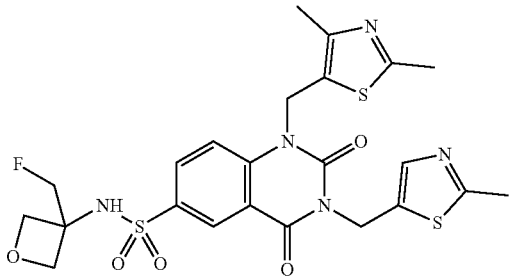 [SMILES: Cc1ncc(Cn2c(=O)c3cc(S(=O)(=O)NC4(CF)COC4)ccc3n(Cc3sc(C)nc3C)c2=O)s1]

To a stirred solution of N-[3-(fluoromethyl)oxetan-3-yl]-3-[(2-methyl-1,3-thiazol-5-yl)methyl]-2,4-dioxo-1H-quinazoline-6-sulfonamide (55.00 mg, 0.13 mmol, 1.00 equiv) and (2,4-dimethyl-1,3-thiazol-5-yl)methanol (17.88 mg, 0.13 mmol, 1.00 equiv) in THF (8.00 mL) was added PPh$_3$ (65.50 mg, 0.25 mmol, 2.00 equiv) in portions at 0° C. under nitrogen atmosphere. The resulting mixture was stirred for 30 min at 0° C. Then DIEA (32.28 mg, 0.25 mmol, 2.00 equiv) was added at 0° C. The resulting mixture was stirred for additional 1.5 h at 0° C. The reaction was quenched with H$_2$O (10 mL) at 0° C. The resulting mixture was extracted with EA (3×10 mL), dried over anhydrous Na$_2$SO$_4$. After filtration, the filtrate was concentrated under reduced pressure. The crude product was purified by Prep-HPLC with the following conditions (Column: XBridge Prep OBD C18 Column, 30*150 mm, 5 µm; Mobile Phase A: Water (10 mmol/L NH$_4$HCO$_3$+0.1% NH$_3$·H$_2$O), Mobile Phase B: ACN; Flow rate: 60 mL/min; Gradient: 23% B to 53% B in 7 min, 53% B; Wave Length: 254 nm; RT1(min): 6 (detected by lcms and collected). This resulted in 1-((2,4-dimethylthiazol-5-yl)methyl)-N-(3-(fluoromethyl)oxetan-3-yl)-3-((2-methylthiazol-5-yl)methyl)-2,4-dioxo-1,2,3,4-tetrahydroquinazoline-6-sulfonamide (8.2 mg, 11.38%) as a white solid. LCMS (ESI, m/z): 566.05 [M+H]$^+$, $^1$H NMR (300 MHz, DMSO-d6) δ=8.47 (s, 1H), 8.17 (d, J=9.0 Hz, 1H), 7.67-7.63 (m, 2H), 5.46 (s, 2H), 5.26 (s, 2H), 4.69 (s, 1H), 4.53-4.51 (m, 3H), 4.34 (d, J=6.9 Hz, 2H), 2.58 (s, 3H), 2.49 (s, 3H), 2.47 (s, 3H).

Example 29: 1-(5-(difluoromethyl)-1,3,4-thiadiazol-2-yl)-4-(4-isobutyrylpiperazin-1-yl)-N-(oxetan-3-yl)-1H-indazole-6-sulfonamide

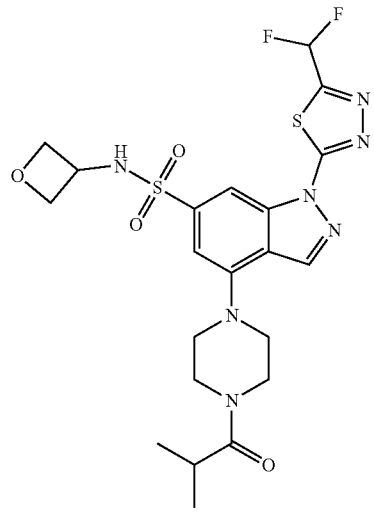 [SMILES: CC(C)C(=O)N1CCN(c2cc(S(=O)(=O)NC3COC3)cc3c2cnn3-c2nnc(C(F)F)s2)CC1]

To a stirred mixture of 1-(4-{6-bromo-1-[5-(difluoromethyl)-1,3,4-thiadiazol-2-yl]indazol-4-yl}piperazin-1-yl)-2-methylpropan-1-one (100 mg, 0.206 mmol, 1 equiv), potassium metabisulfite (91.61 mg, 0.412 mmol, 2 equiv), sodium formate (42.06 mg, 0.618 mmol, 3 equiv), PPh$_3$ (59.45 mg, 0.227 mmol, 1.1 equiv), phen (9.28 mg, 0.051 mmol, 0.25 equiv) and Pd(OAc)$_2$ (4.63 mg, 0.021 mmol, 0.1 equiv) in DMSO (3 mL) was added tetraethylazanium boranuide (32.88 mg, 0.227 mmol, 1.1 equiv). The mixture was stirred for 4 h at 70° C. under N$_2$ atmosphere. To the above was added oxetan-3-amine (30.12 mg, 0.412 mmol, 2 equiv) and NBS (110.01 mg, 0.618 mmol, 3 equiv) in THF (1 mL) dropwise. The mixture was stirred for at 25° C. for other 1 h. Desired product could be detected by LCMS. The solids were filtered out and were washed with (3×5 mL). The filtration was concentrated under reduced pressure. The residue was purified by Prep-HPLC with the following condition: (Column: XBridge Shield RP18 OBD Column, 30*150 mm, 5 µm; Mobile Phase A: Water (10 mmol/L NH4HCO3+0.1% NH3·H2O), Mobile Phase B: ACN; Flow rate: 60 m/min; Gradient: 30% B to 60% B in 7 min; Wave Length: 254 nm; RT1(min): 6) to afford 1-(5-(difluoromethyl)-1,3,4-thiadiazol-2-yl)-4-(4-isobutyrylpiperazin-1-yl)-N-(oxetan-3-yl)-1H-indazole-6-sulfonamide (17.8 mg, 14.97%) as a yellow solid. LCMS (ESI, m/z): 542.10[M+H]+, 1H NMR (300 MHz, DMSO-d6) δ=8.94 (s, 1H), 8.79 (br, 1H), 8.39 (s, 1H), 7.78-7.43 (m, 1H), 7.08 (s, 1H), 4.52-4.40 (m, 3H), 4.35-4.26 (m, 2H), 3.78-3.75 (m, 4H), 3.47-3.35 (m, 4H), 2.99-2.90 (m, 1H), 1.06 (d, J=6.9 Hz, 6H).

Example 30: N-(3-cyanooxetan-3-yl)-1-(5-(difluoromethyl)-1,3,4-thiadiazol-2-yl)-4-(4-isobutyrylpiperazin-1-yl)-1H-indazole-6-sulfonamide

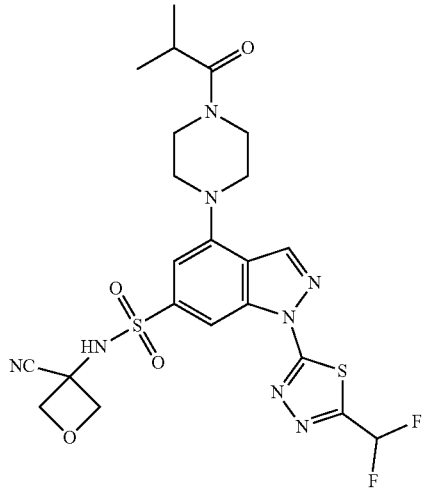 [SMILES: CC(C)C(=O)N1CCN(c2cc(S(=O)(=O)NC3(C#N)COC3)cc3c2cnn3-c2nnc(C(F)F)s2)CC1]

Step 1: Synthesis of 1-[5-(difluoromethyl)-1,3,4-thiadiazol-2-yl]-4-[4-(2-methylpropanoyl)piperazin-1-yl]indazole-6-sulfonamide A solution of 1-(4-{6-bromo-1-[5-(difluoromethyl)-1,3,4-thiadiazol-2-yl]indazol-4-yl}piperazin-1-yl)-2-methylpropan-1-one (500 mg, 1.030 mmol, 1 equiv) in DMSO (5 mL) was added dipotassium sulfinosulfonate (458.07 mg, 2.060 mmol, 2 equiv), tetraethylazanium boranuide (164.42 mg, 1.133 mmol, 1.1 equiv), sodium formate (210.18 mg, 3.090 mmol, 3 equiv), triphenylphosphine (81.06 mg, 0.309 mmol, 0.3 equiv), phen (55.69 mg, 0.309 mmol, 0.3 equiv) and Pd(OAc)$_2$ (23.13 mg, 0.103 mmol, 0.1 equiv). The mixture was stirred for 4 h at 70° C. under nitrogen atmosphere. To the above was added ammonium hydroxide (108.31 mg, 3.090 mmol, 3 equiv) in THF (1 mL) and NBS (550.07 mg, 3.090 mmol, 3 equiv) in THF (3 mL) dropwise at 0° C. under nitrogen atmosphere. The resulting mixture was stirred for 1 h at 25° C. under nitrogen atmosphere. Desired product could be detected by LCMS. The resulting mixture was diluted with brine (30 mL). The aqueous layer was extracted with EA (3×30 mL). The resulting mixture was concentrated under reduced pressure. The residue was purified by silica gel column chromatography, eluted with PE/EA (2:3) to afford 1-[5-(difluoromethyl)-1,3,4-thiadiazol-2-yl]-4-[4-(2-methylpropanoyl)piperazin-1-yl]indazole-6-sulfonamide (340 mg, 54.38%) as a yellow solid. LCMS (ESI, m/z): 486[M+H]+, Rt 0.769 min.

Step 2: Synthesis of 1-[5-(difluoromethyl)-1,3,4-thiadiazol-2-yl]-4-[4-(2-methylpropanoyl)piperazin-1-yl]-N-(oxetan-3-ylidene)indazole-6-sulfonamide To a stirred mixture of 1-[5-(difluoromethyl)-1,3,4-thiadiazol-2-yl]-4-[4-(2-methylpropanoyl) piperazin-1-yl]indazole-6-sulfonamide (800 mg, 1.648 mmol, 1 equiv) in THF (12 mL) was added titanium isopropylate (2.34 g, 8.240 mmol, 5 equiv) and 3-oxetanone (1.19 g, 16.480 mmol, 10 equiv) dropwise at room temperature. The mixture was stirred for 2 h at 60° C. To above mixture was added another batch of titanium isopropylate (2.34 g, 8.240 mmol, 5 equiv) and 3-oxetanone (1.19 g, 16.480 mmol, 10 equiv) dropwise at room temperature. The resulting mixture was stirred for another 2 h at 60° C. The resulting mixture was concentrated to afford 1-[5-(difluoromethyl)-1,3,4-thiadiazol-2-yl]-4-[4-(2-methylpropanoyl)piperazin-1-yl]-N-(oxetan-3-ylidene)indazole-6-sulfonamide (crude), which was used in the next step directly without further purification. LCMS (ES, m/z): 540[M+H]+, Rt 1.096 min.

Step 3: Synthesis of N-(3-cyanooxetan-3-yl)-1-(5-(difluoromethyl)-1,3,4-thiadiazol-2-yl)-4-(4-isobutyrylpiperazin-1-yl)-1H-indazole-6-sulfonamide To a stirred mixture of 1-[5-(difluoromethyl)-1,3,4-thiadiazol-2-yl]-4-[4-(2-methylpropanoyl) piperazin-1-yl]-N-(oxetan-3-ylidene)indazole-6-sulfonamide (2.3 g, 4.263 mmol, 1 equiv) in THF (10 mL) was added trimethylsilanecarbonitrile (2.11 g, 21.315 mmol, 5 equiv) in DCM (3 mL). The resulting mixture was stirred for 1 h at room temperature. The reaction was quenched with brine (50 mL). After filtration, the filtrate was extracted with EA (3×50 mL). The combined organic layers were washed with brine, dried over anhydrous Na$_2$SO$_4$. After filtration, the filtrate was concentrated under reduced pressure. The residue was purified by reverse phase flash chromatography with the following conditions: (column, C18 silica gel; Mobile Phase A: Water (10 MMOL/L NH$_4$HCO$_3$+0.1% NH$_3$·H$_2$O), Mobile Phase B: ACN (30% to 30% in 20 min); Flow rate: 100 mL/min; UV 254 nm) to afford N-(3-cyanooxetan-3-yl)-1-(5-(difluoromethyl)-1,3,4-thiadiazol-2-yl)-4-(4-isobutyrylpiperazin-1-yl)-1H-indazole-6-sulfonamide (152.6 mg, 6.14%) as a yellow solid. 1H NMR (300 MHz, DMSO-d6) δ=9.67 (br, 1H), 8.95 (s, 1H), 8.45 (s, 1H), 7.78-7.43 (m, 1H), 7.14 (s, 1H), 4.81 (d, J=6.9 Hz, 2H), 4.70 (d, J=7.2 Hz, 2H), 3.82-3.74 (m, 4H), 3.47-3.42 (m, 4H), 2.99-2.90 (m, 1H), 1.05 (d, J=6.9 Hz, 6H). LCMS (ES, m/z): 567[M+H]+, Rt 0.910 min.

Example 31: 4-(4-isobutyrylpiperazin-1-yl)-N-(3-methyloxetan-3-yl)-1-(5-((methylsulfonyl)methyl)-1,3,4-thiadiazol-2-yl)-1H-indazole-6-sulfonamide

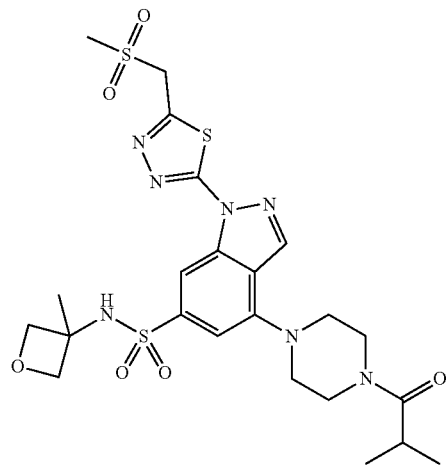 [SMILES: CC(C)C(=O)N1CCN(c2cc(S(=O)(=O)NC3(C)COC3)cc3c2cnn3-c2nnc(CS(C)(=O)=O)s2)CC1]

Step 1: Synthesis of 2-bromo-5-(methanesulfonylmethyl)-1,3,4-thiadiazole

A mixture of 2-bromo-5-[(methylsulfanyl)methyl]-1,3,4-thiadiazole (300 mg, 0.044 mmol, 1 equiv) and m-CPBA (15.33 mg, 0.088 mmol, 2 equiv) in DCM (5 mL) was stirred for 2 h at room temperature. The reaction was monitored by LCMS. The resulting mixture was quenched with water (30 mL). The aqueous layer was extracted with DCM (3×30 mL). The combined organic layers were dried over anhydrous $Na_2SO_4$. After filtration, the filtrate was concentrated under reduced pressure to afford 2-bromo-5-(methanesulfonylmethyl)-1,3,4-thiadiazole (150 mg, crude) as a yellow oil. LCMS (ESI, m/z): 257, 259 [M+H]$^+$.

Step 2: Synthesis of 1-(4-{6-bromo-1-[5-(methanesulfonylmethyl)-1,3,4-thiadiazol-2-yl]indazol-4-yl}piperazin-1-yl)-2-methylpropan-1-one A mixture of 1-[4-(6-bromo-1H-indazol-4-yl)piperazin-1-yl]-2-methylpropan-1-one (300 mg, 0.854 mmol, 1 equiv), 2-bromo-5-(methanesulfonylmethyl)-1,3,4-thiadiazole (329.41 mg, 1.281 mmol, 1.5 equiv) and $Cs_2CO_3$ (695.70 mg, 2.135 mmol, 2.5 equiv) in DMF (3 mL) was stirred for 2 h at 70° C. The reaction was monitored by LCMS. The mixture was allowed to cool down to room temperature. The resulting mixture was quenched with water (50 mL). The aqueous layer was extracted with EA (3×50 mL). The combined organic layers were washed by brine (50 mL), dried over anhydrous $Na_2SO_4$. After filtration, the filtrate was concentrated under reduced pressure. The residue was purified by silica gel column chromatography, eluted with PE/EA (1:1) to afford 1-(4-{6-bromo-1-[5-(methanesulfonylmethyl)-1,3,4-thiadiazol-2-yl]indazol-4-yl} piperazin-1-yl)-2-methylpropan-1-one (87 mg, 19.31%) as a yellow solid. LCMS (ESI, m/z): 527, 529 [M+H]$^+$.

Step 3: Synthesis of 4-(4-isobutyrylpiperazin-1-yl)-N-(3-methyloxetan-3-yl)-1-(5-((methylsulfonyl)methyl)-1,3,4-thiadiazol-2-yl)-1H-indazole-6-sulfonamide A mixture of 1-(4-{6-bromo-1-[5-(methanesulfonylmethyl)-1,3,4-thiadiazol-2-yl]indazol-4-yl}piperazin-1-yl)-2-methylpropan-1-one (87 mg, 0.165 mmol, 1 equiv), potassium metabisulfite (73.34 mg, 0.330 mmol, 2 equiv), TEAB (27.44 mg, 0.182 mmol, 1.1 equiv), sodium formate (33.65 mg, 0.495 mmol, 3 equiv), PPh3 (12.98 mg, 0.050 mmol, 0.3 equiv), phen (8.92 mg, 0.050 mmol, 0.3 equiv) and Pd(OAc)$_2$ (3.70 mg, 0.017 mmol, 0.1 equiv) in DMSO (1 mL) was stirred for 4 h at 70° C. under nitrogen atmosphere. Then the reaction was cooled to room temperature. A solution of 3-methyloxetan-3-amine (28.74 mg, 0.330 mmol, 2 equiv) in THF (1 mL) and a solution of NBS (88.07 mg, 0.495 mmol, 3 equiv) in DMF (1 mL) was stirred for 1 h at room temperature. The reaction was monitored with LCMS. The resulting mixture was quenched with water (30 mL). The aqueous layer was extracted with EA (3×30 mL). The combined organic layers were washed by brine (50 mL), dried over anhydrous $Na_2SO_4$. After filtration, the filtrate was concentrated under reduced pressure. The residue was purified by Prep-HPLC with the following conditions (Column: XBridge Prep OBD C18 Column, 30*150 mm, 5 μm; Mobile Phase A: Water (10 mmol/L NH4HCO3+0.1% NH3·H2O), Mobile Phase B: ACN; Flow rate: 60 mL/min; Gradient: 20% B to 50% B in 7 min, 50% B; Wave Length: 254 nm; RT1(min): 5.87; Number Of Runs: 0) to afford 4-(4-isobutyrylpiperazin-1-yl)-N-(3-methyloxetan-3-yl)-1-(5-((methylsulfonyl)methyl)-1,3,4-thiadiazol-2-yl)-1H-indazole-6-sulfonamide (11.2 mg, 11.01%) as a yellow solid. LCMS (ESI, m/z): 598.10[M+H]$^+$. $^1$HNMR (300 MHz, DMSO-d6) δ=8.95 (s, 1H), 8.71 (br, 1H), 8.57 (s, 1H), 7.13 (s, 1H), 5.27 (s, 2H), 4.57 (d, J=6.0 Hz, 2H), 4.12 (d, J=6.0 Hz, 2H), 4.83-4.67 (m, 4H), 3.54-3.33 (m, 4H), 3.18 (s, 3H), 3.02-2.91 (m, 1H), 1.43 (s, 3H), 1.05 (d, J=6.6 Hz, 6H).

Example 32: N-(3-cyano-2-methyloxetan-3-yl)-1-(5-(difluoromethyl)-1,3,4-thiadiazol-2-yl)-4-(4-isobutyrylpiperazin-1-yl)-1H-indazole-6-sulfonamide

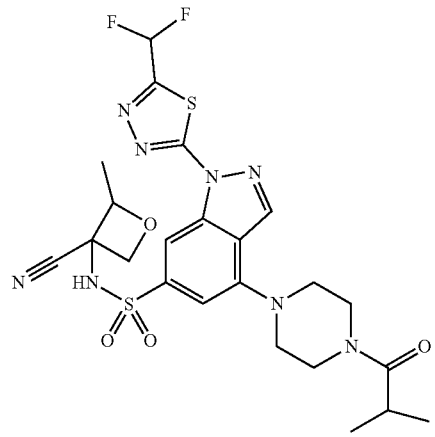 [SMILES: CC(C)C(=O)N1CCN(c2cc(S(=O)(=O)NC3(C#N)COC3C)cc3c2cnn3-c2nnc(C(F)F)s2)CC1]

Step 1: Synthesis of 1-[5-(difluoromethyl)-1,3,4-thiadiazol-2-yl]-4-[4-(2-methylpropanoyl)piperazin-1-yl]indazole-6-sulfonamide Into a 20 mL vial were added 1-(4-{6-bromo-1-[5-(difluoromethyl)-1,3,4-thiadiazol-2-yl]indazol-4-yl}piperazin-1-yl)-2-methylpropan-1-one (300.00 mg, 0.62 mmol, 1.00 equiv), dipotassium sulfinosulfonate (274.44 mg, 1.24 mmol, 2.00 equiv), tetraethylazanium boranuide (98.65 mg, 0.68 mmol, 1.10 equiv), Sodium formate (92.47 mg, 1.36 mmol, 2.20 equiv), PPh$_3$ (48.64 mg, 0.19 mmol, 0.30 equiv), phen (33.42 mg, 0.19 mmol, 0.30 equiv), Pd(OAc)$_2$ (13.88 mg, 0.06 mmol, 0.10 equiv) and DMSO (5.00 mL) at room temperature under nitrogen atmosphere. The resulting mixture was stirred for 4.0 h at 70° C. under nitrogen atmosphere. Then the reaction mixture was cooled down to 0° C. and added NH$_3$·H$_2$O (216.62 mg, 6.18 mmol, 10.00 equiv) in THF (1 mL) and NBS (220.03 mg, 1.24 mmol, 2.00 equiv) in THF (1.00 mL) dropwise at 0° C. The resulting mixture was stirred for 1.0 h at room temperature under nitrogen atmosphere. After reaction, Desired product could be detected by LCMS. The reaction was poured into 10 mL ice/water. The precipitated solids were collected by filtration and washed with water (3×5 mL). The obtained solid was purified by TLC-plate (CH$_2$Cl$_2$/MeOH=15:1) to afford 1-[5-(difluoromethyl)-1,3,4-thiadiazol-2-yl]-4-[4-(2-methylpropanoyl)piperazin-1-yl]indazole-6-sulfonamide (90.00 mg, 29.99%) as a brow yellow solid. LCMS (ESI, m/z): 485.95 [M+H]$^+$.

Step 2: Synthesis of N-(3-cyano-2-methyloxetan-3-yl)-1-[5-(difluoromethyl)-1,3,4-thiadiazol-2-yl]-4-[4-(2-methylpropanoyl) piperazin-1-yl]indazole-6-sulfonamide To a stirred solution of 1-[5-(difluoromethyl)-1,3,4-thiadiazol-2-yl]-4-[4-(2-methylpropanoyl) piperazin-1-yl]indazole-6-sulfonamide (50.00 mg, 0.10 mmol, 1.00 equiv) in THF (2.00 mL) was added Ti(Oi-Pr)$_4$ (292.69 mg, 1.03 mmol, 10.00 equiv) and 2-methyloxetan-3-one (88.66 mg, 1.03 mmol, 10.00 equiv) dropwise room temperature. The resulting mixture was stirred for 17.0 h at 70° C. To the above mixture was added trimethylsilyl cyanide (102.16 mg, 1.03 mmol, 10.00 equiv) dropwise at 0° C. The resulting mixture was stirred for additional 1.0 h at room temperature. Desired product was detected by LCMS. The reaction was quenched with water (10 mL) at 0° C. The resulting mixture was filtered, the filter cake was washed with EtOAc (3×5 mL). The filtrate was extracted with EtOAc (3×10 mL). The combined organic layers were washed with brine (1×15 mL), dried over anhydrous Na$_2$SO$_4$. After filtration, the filtrate was concentrated under reduced pressure. The residue was purified by TLC (100% EA) to afford N-(3-cyano-2-methyloxetan-3-yl)-1-[5-(difluoromethyl)-1,3,4-thiadiazol-2-yl]-4-[4-(2-methylpropanoyl) piperazin-1-yl]indazole-6-sulfonamide (20 mg). The crude product (20 mg) was purified by Prep-HPLC with the following conditions (Column: XBridge Prep OBD C18 Column, 30*150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 20% B to 50% B in 7 min, 50% B; Wave Length: 254 nm; RT1(min): 5.87 (detected by lcms and collected); to afford N-(3-cyano-2-methyloxetan-3-yl)-1-(5-(difluoromethyl)-1,3,4-thiadiazol-2-yl)-4-(4-isobutyrylpiperazin-1-yl)-1H-indazole-6-sulfonamide (3.00 mg, 4.81%) as a light yellow solid. LCMS (ESI, m/z): 581.15 [M+H]$^+$. NMR: $^1$H NMR (400 MHz, DMSO-d$_6$) δ=8.90 (s, 1H), 8.44 (s, 1H), 7.56 (t, J=56.0 Hz, 1H), 7.15 (s, 1H), 5.05-4.82 (m, 1H), 4.67-4.52 (m, 2H) 3.82-3.76 (m, 4H), 3.50-3.40 (m, 4H), 2.97-2.90 (m, 1H), 1.42-1.35 (m, 3H), 1.03 (d, J=6.8 Hz, 6H). $^{19}$F NMR (376 MHz, DMSO-d6) δ −109.76.

Example 33: 1-(5-(difluoromethyl)-1,3,4-thiadiazol-2-yl)-4-(4-(isopropylsulfonyl)piperazin-1-yl)-N-(3-methyloxetan-3-yl)-1H-indazole-6-sulfonamide

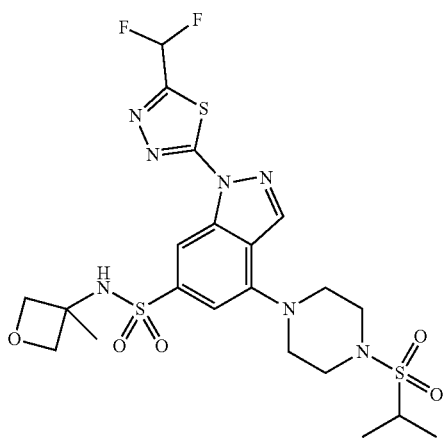 [SMILES: CC(C)S(=O)(=O)N1CCN(c2cc(S(=O)(=O)NC3(C)COC3)cc3c2cnn3-c2nnc(C(F)F)s2)CC1]

Step 1: Synthesis of 4-chloro-N-(3-methyloxetan-3-yl)-1H-indazole-6-sulfonamide

To the mixture of 6-bromo-4-chloro-1H-indazole (500 mg, 2.160 mmol, 1 equiv), tetraethylazanium bromide (499.33 mg, 2.376 mmol, 1.1 equiv), sodium formate (323.14 mg, 4.752 mmol, 2.2 equiv), PPh3 (169.97 mg, 0.648 mmol, 0.3 equiv), phen (116.78 mg, 0.648 mmol, 0.3 equiv) and dipotassium sulfinosulfonate (960.45 mg, 4.320 mmol, 2 equiv) in DMSO (8 mL) was added Pd(OAc)$_2$ (48.49 mg, 0.216 mmol, 0.1 equiv). The mixture was degassed by bubbling N$_2$ stirring for 10 min. The mixture was stirred for 4 h. To the mixture was added 3-methyloxetan-3-amine (376.37 mg, 4.320 mmol, 2 equiv) in THF (5.00 mL) at room temperature, the solution of NBS (768.90 mg, 4.320 mmol, 2 equiv) in THF (5.00 mL) was added at 0° C. followed by. The mixture was stirred at rt for 30 min. Desired product could be detected by LCMS. The mixture was added with brine (10 mL) and H2O (10 mL), and extracted by EtOAc (10 mL×3). The organic layer was combined, dried over Na$_2$SO$_4$, filtered and concentrated. The residue was purified by reversed-phase flash chromatography with the following conditions: column, C18 silica gel; mobile phase, MeCN in Water (0.05% TFA), 10% to 50% gradient in 20 min; detector, UV 254 nm to afford 4-chloro-N-(3-methyloxetan-3-yl)-1H-indazole-6-sulfonamide (80 mg, 12.27%) as yellow oil. LCMS (ESI, m/z): 302.00 [M+H]$^+$.

Step 2: Synthesis of 4-chloro-1-[5-(difluoromethyl)-1,3,4-thiadiazol-2-yl]-N-(3-methyloxetan-3-yl)indazole-6-sulfonamide To the mixture of 4-chloro-N-(3-methyloxetan-3-yl)-1H-indazole-6-sulfonamide (80 mg, 0.265 mmol, 1 equiv) and 2-bromo-5-(difluoromethyl)-1,3,4-thiadiazole (68.41 mg, 0.318 mmol, 1.2 equiv) in DMF (2 mL) was added Cs2CO3 (215.95 mg, 0.663 mmol, 2.5 equiv). The mixture was stirred at rt for 16 h. Desired product could be detected by LCMS. The mixture was purified by reversed-phase flash chromatography with the following conditions: column, C18 silica gel; mobile phase, MeCN in Water (0.05% TFA), 20% to 80% gradient in 30 min; detector, UV 254 nm to afford 4-chloro-1-[5-(difluoromethyl)-1,3,4-thiadiazol-2-yl]-N-(3-methyloxetan-3-yl)indazole-6-sulfonamide (30 mg, 25.96%) as yellow oil. LCMS (ESI, m/z): 435.95[M+H]$^+$ Step 3: Synthesis of 1-[5-(difluoromethyl)-1,3,4-thiadiazol-2-yl]-N-(3-methyloxetan-3-yl)-4-[4-(propane-2-sulfonyl)piperazin-1-yl]indazole-6-sulfonamide To the mixture of 4-chloro-1-[5-(difluoromethyl)-1,3,4-thiadiazol-2-yl]-N-(3-methyloxetan-3-yl)indazole-6-sulfonamide (60 mg, 0.138 mmol, 1 equiv) and piperazine (13.04 mg, 0.152 mmol, 1.1 equiv) in dioxane (3 mL) was added Ruphos (6.42 mg, 0.014 mmol, 0.1 equiv) and Cs$_2$CO$_3$ (7.48 mg, 0.022 mmol, 2 equiv). The mixture was stirred at 100° C. for 16 h under N2 atmosphere. Desired product could be detected by LCMS. The mixture was filtered. The filtrate was concentrated under reduced pressure. The residue was purified by reversed-phase flash chromatography with the following conditions: column, C18 silica gel; mobile phase, MeCN in Water (0.05% TFA), 30% to 100% gradient in 20 min; detector, UV 254 nm to afford 1-[5-(difluoromethyl)-1,3,4-thiadiazol-2-yl]-N-(3-methyloxetan-3-yl)-4-[4-(propane-2-sulfonyl)piperazin-1-yl]indazole-6-sulfonamide (30 mg, 36.83%) as yellow oil. LCMS (ESI, m/z): 486.05[M+H]$^+$ Step 4: Synthesis of 1-(5-(difluoromethyl)-1,3,4-thiadiazol-2-yl)-4-(4-(isopropylsulfonyl)piperazin-1-yl)-N-(3-methyloxetan-3-yl)-1H-indazole-6-sulfonamide To the mixture of 1-[5-(difluoromethyl)-1,3,4-thiadiazol-2-yl]-N-(3-methyloxetan-3-yl)-4-(piperazin-1-yl)indazole- 6-sulfonamide (20 mg, 0.041 mmol, 1 equiv) in DCM (2 mL) was added propane-2-sulfonyl chloride (7.05 mg, 0.049 mmol, 1.2 equiv) and TEA (8.34 mg, 0.082 mmol, 2 equiv) at −78° C. The mixture was stirred at −78° C. for 30 min and 0° C. for 2 h. Desired product could be detected by LCMS. The mixture was concentrated under reduced pressure. The residue was purified by Prep-HPLC with the following conditions (Column: XBridge Prep C18 OBD Column, 19*150 mm, 5 μm; Mobile Phase A: Water (10 mmol/L NH4HCO3), Mobile Phase B: ACN; Flow rate: 25 mL/min; Gradient: 45% B to 65% B in 7 min, 65% B; Wave Length: 254 nm; RT1(min): 6.23; Number Of Runs: 0) to afford 1-(5-(difluoromethyl)-1,3,4-thiadiazol-2-yl)-4-(4-(isopropylsulfonyl)piperazin-1-yl)-N-(3-methyloxetan-3-yl)-1H-indazole-6-sulfonamide (2.3 mg, 9.43%) as an off-white solid. $^1$H NMR (300 MHz, DMSO-d6) δ 8.94 (d, J=1.0 Hz, 1H), 8.62 (s, 1H), 8.49 (s, 1H), 7.42-7.80 (m, 1H), 7.20 (d, J=3.0 Hz, 1H), 4.58 (d, J=6.0 Hz, 2H), 4.18-4.10 (m, 2H), 3.59-3.41 (m, 9H), 1.44 (s, 3H), 1.29 (d, J=6.0 Hz, 6H). $^{19}$F NMR (282 MHz, DMSO-d6) δ −109.83. LCMS (ESI, m/z): 592.15[M+H]$^+$.

Example 34: 4-(4-(cyclopentanecarbonyl)piperazin-1-yl)-1-(5-(difluoromethyl)-1,3,4-thiadiazol-2-yl)-N-(3-(fluoromethyl)oxetan-3-yl)-1H-indazole-6-sulfonamide

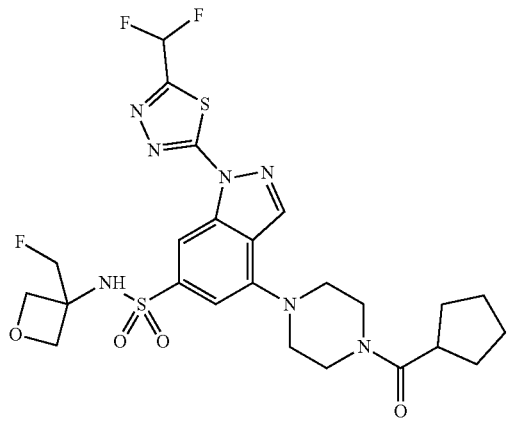 [SMILES: O=C(C1CCCC1)N1CCN(c2cc(S(=O)(=O)NC3(CF)COC3)cc3c2cnn3-c2nnc(C(F)F)s2)CC1]

Step 1: Synthesis of 4-(4-(cyclopentanecarbonyl)piperazin-1-yl)-1-(5-(difluoromethyl)-1,3,4-thiadiazol-2-yl)-N-(3-(fluoromethyl)oxetan-3-yl)-1H-indazole-6-sulfonamide A mixture of 6-bromo-4-(4-cyclopentanecarbonylpiperazin-1-yl)-1-[5-(difluoromethyl)-1,3,4-thiadiazol-2-yl]indazole (150 mg, 0.293 mmol, 1 equiv), potassium metabisulfite (130.42 mg, 0.586 mmol, 2 equiv), tetraethylazanium boranuide (46.81 mg, 0.322 mmol, 1.1 equiv), sodium formate (59.84 mg, 0.879 mmol, 3 equiv), PPh3 (23.08 mg, 0.088 mmol, 0.3 equiv), phen (15.86 mg, 0.088 mmol, 0.3 equiv) and Pd(OAc)2 (6.59 mg, 0.029 mmol, 0.1 equiv) in DMSO (2 mL) was stirred for 4 h at 70° C. under nitrogen atmosphere. Then the reaction was cooled to room temperature. A solution of 3-(fluoromethyl)oxetan-3-amine (61.66 mg, 0.586 mmol, 2 equiv) in Pyridine (2 mL) and a solution of NBS (208.82 mg, 1.172 mmol, 4 equiv) in THF (2 mL) were stirred for 1 h at room temperature. The reaction was monitored with LCMS. The resulting mixture was quenched with water (30 mL). The aqueous layer was extracted with EA (3×30 mL). The combined organic layers were washed by brine (50 mL), dried over anhydrous Na2SO4. After filtration, the filtrate was concentrated under reduced pressure. The residue was purified by Prep-HPLC with the following conditions (Column: XBridge Prep OBD C18 Column, 30*150 mm, 5 μm; Mobile Phase A: Water (10 mmol/L NH4HCO3), Mobile Phase B: ACN; Flow rate: 60 mL/min; Gradient: 35% B to 65% B in 7 min, 65% B; Wave Length: 254 nm; RT1(min): 6.73; Number Of Runs: 0) to afford 4-(4-(cyclopentanecarbonyl)piperazin-1-yl)-1-(5-(difluoromethyl)-1,3,4-thiadiazol-2-yl)-N-(3-(fluoromethyl)oxetan-3-yl)-1H-indazole-6-sulfonamide (9.3 mg, 5.28%) as a white solid. LCMS (ESI, m/z): 600.05[M+H]$^+$, $^1$HNMR (300 MHz, DMSO-d6) δ=9.03 (br, 1H), 8.95 (s, 1H), 8.46 (s, 1H), 7.78-7.43 (m, 1H), 7.18 (s, 1H), 4.68 (s, 1H), 4.59-4.52 (m, 3H), 4.34 (d, J=6.6 Hz, 2H), 3.85-3.71 (m, 4H), 3.52-3.41 (m, 4H), 3.11-3.00 (m, 1H), 1.88-1.51 (m, 8H).

Example 35: 1-(5-(difluoromethyl)-1,3,4-thiadiazol-2-yl)-N-(3-methyloxetan-3-yl)-4-(4-(pyrrolidine-1-carbonyl)piperazin-1-yl)-1H-indazole-6-sulfonamide

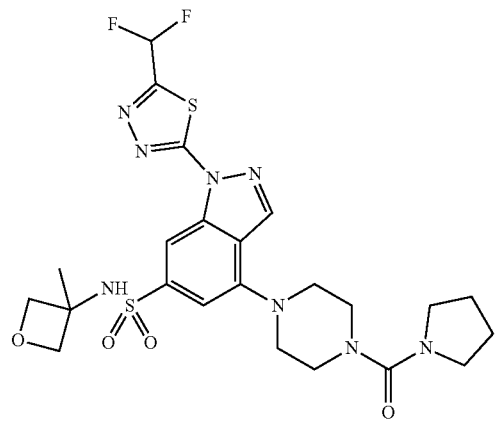

Step 1: Synthesis of (4-(6-bromo-1-(5-(difluoromethyl)-1,3,4-thiadiazol-2-yl)-1H-indazol-4-yl)piperazin-1-yl)(pyrrolidin-1-yl)methanone To a stirred mixture of 6-bromo-1-[5-(difluoromethyl)-1,3,4-thiadiazol-2-yl]-4-(piperazin-1-yl)indazole (1 g, 2.408 mmol, 1 equiv) and TEA (970 mg, 7.224 mmol, 3 equiv) in DCM (10 mL) was added pyrrolidine-1-carbonyl chloride (390 mg, 2.890 mmol, 1.2 equiv) in portions at 0° C. The resulting mixture was stirred for 4 h at 25° C. The reaction was monitored by LCMS. The resulting mixture was concentrated under vacuum. The residue was purified by silica gel column chromatography, eluted with EA/PE (1:2) to afford (4-(6-bromo-1-(5-(difluoromethyl)-1,3,4-thiadiazol-2-yl)-1H-indazol-4-yl)piperazin-1-yl)(pyrrolidin-1-yl)methanone (400 mg, 32.42%) as a yellow solid. LCMS (ES, m/z): 512, 514 [M+H]*.

Step 2: Synthesis of 1-(5-(difluoromethyl)-1,3,4-thiadiazol-2-yl)-N-(3-methyloxetan-3-yl)-4-(4-(pyrrolidine-1-carbonyl)piperazin-1-yl)-1H-indazole-6-sulfonamide To a stirred mixture of (4-(6-bromo-1-(5-(difluoromethyl)-1,3,4-thiadiazol-2-yl)-1H-indazol-4-yl)piperazin-1- yl)(pyrrolidin-1-yl)methanone (100 mg, 0.195 mmol, 1 equiv) in DMSO (2 mL) was added potassium metabisulfite (87 mg, 0.390 mmol, 2 equiv), PPh$_3$ (15 mg, 0.058 mmol, 0.3 equiv), sodium formate (40 mg, 0.585 mmol, 3 equiv), phen (11 mg, 0.058 mmol, 0.3 equiv), palladium acetate (4 mg, 0.020 mmol, 0.1 equiv) and TEAB (31 mg, 0.215 mmol, 1.1 equiv). The resulting mixture was stirred for 4 h at 70° C. under N$_2$ atmosphere. Then NBS (122 mg, 0.682 mmol, 3.5 equiv) and 3-methyloxetan-3-amine (34 mg, 0.390 mmol, 2 equiv) in THF (2 mL) was dropwise at 0° C. The resulting mixture was stirred for other 1 h at room temperature. Desired product could be detected by LCMS. The reaction was quenched with water (20 mL). The mixture was washed with EA (3×15 mL), dried over anhydrous Na$_2$SO$_4$. After filtration, the filtrate was concentrated under reduced pressure. The residue was purified by Prep-HPLC with the following condition: (Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 310% B to 610% B in 7 min, 610% B; Wave Length: 254 nm; RT1(min): 6.35; Number Of Runs: 0) to afford 1-(5-(difluoromethyl)-1,3,4-thiadiazol-2-yl)-N-(3-methyloxetan-3-yl)-4-(4-(pyrrolidine-1-carbonyl)piperazin-1-yl)-1H-indazole-6-sulfonamide (13.1 mg, 11.47%) as a yellow solid. LCMS (ES, m/z): 583.20 [M+H]$^+$, $^1$H NMR (300 MHz, Chloroform-d) δ=8.71 (s, 1H), 8.32 (s, 1H), 7.20 (s, 1H), 7.18-6.82 (m, 1H), 5.42 (s, 1H), 4.76 (d, J=6.6 Hz, 2H), 4.35 (d, J=6.9 Hz, 2H), 3.58-3.53 (m, 4H), 3.49-3.41 (m, 8H), 1.90-1.85 (m, 4H), 1.66 (s, 3H).

Example 36: 1-(5-(difluoromethyl)-1,3,4-thiadiazol-2-yl)-N-(3-(fluoromethyl)oxetan-3-yl)-4-(4-(pyrrolidine-1-carbonyl)piperazin-1-yl)-1H-indazole-6-sulfonamide

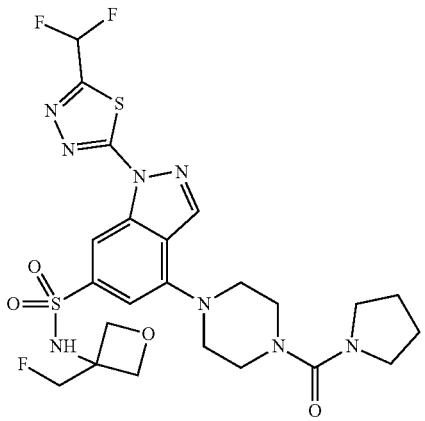 [SMILES: O=C(N1CCCC1)N1CCN(c2cc(S(=O)(=O)NC3(CF)COC3)cc3c2cnn3-c2nnc(C(F)F)s2)CC1]

Step 1: Synthesis of 1-(5-(difluoromethyl)-1,3,4-thiadiazol-2-yl)-N-(3-(fluoromethyl)oxetan-3-yl)-4-(4-(pyrrolidine-1-carbonyl)piperazin-1-yl)-1H-indazole-6-sulfonamide To a stirred mixture of 6-bromo-1-[5-(difluoromethyl)-1,3,4-thiadiazol-2-yl]-4-[4-(pyrrolidine-1-carbonyl)piperazin-1-yl]indazole (200 mg, 0.390 mmol, 1 equiv) in DMSO (2 mL) was added potassium metabisulfite (174 mg, 0.780 mmol, 2 equiv), PPh$_3$ (31 mg, 0.117 mmol, 0.3 equiv), sodium formate (80 mg, 1.170 mmol, 3 equiv), palladium acetate (9 mg, 0.039 mmol, 0.1 equiv) and phen (21 mg, 0.117 mmol, 0.3 equiv). The resulting mixture was stirred for 4 h at 70° C. under N$_2$ atmosphere. Then 3-(fluoromethyl) oxetan-3-amine (82 mg, 0.780 mmol, 2 equiv), DIEA (1 mL) and NCS (182 mg, 1.365 mmol, 3.5 equiv) in THF (2 mL) were added dropwise. The mixture was stirred at 0° C. for other 1 h. Desired product could be detected by LCMS. The reaction was quenched with water (20 mL). The mixture was washed with EA (3×15 mL), dried over anhydrous Na$_2$SO$_4$. After filtration, the filtrate was concentrated under reduced pressure. The residue was purified by Prep-HPLC with the following condition: (Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 30% B to 60% B in 7 min, 60% B; Wave Length: 254 nm; RT1(min): 6.8; Number Of Runs: 0) to afford 1-(5-(difluoromethyl)-1,3,4-thiadiazol-2-yl)-N-(3-(fluoromethyl)oxetan-3-yl)-4-(4-(pyrrolidine-1-carbonyl)piperazin-1-yl)-1H-indazole-6-sulfonamide (16.6 mg, 6.84%) as a yellow solid. LCMS (ESI, m/z): 601.15 [M+H], $^1$H NMR (300 MHz, DMSO-d6) δ=9.03-8.94 (m, 2H), 8.45 (s, 1H), 7.77-7.42 (m, 1H), 7.18 (s, 1H), 4.69 (s, 1H), 4.58-4.54 (m, 3H), 4.35 (d, J=6.6 Hz, 2H), 3.52-3.46 (m, 5H), 3.45-3.33 (m, 7H), 1.82-1.78 (m, 4H).

Example 37: N-(2,2-difluoroethyl)-4-(1-(5-(difluoromethyl)-1,3,4-thiadiazol-2-yl)-6-(N-(3-methyloxetan-3-yl)sulfamoyl)-1H-indazol-4-yl)-N-methylpiperazine-1-carboxamide

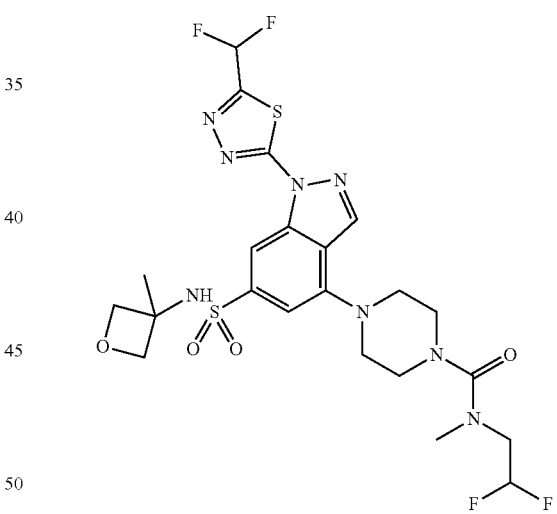

Step 1: Synthesis of 4-{6-bromo-1-[5-(difluoromethyl)-1,3,4-thiadiazol-2-yl]indazol-4-yl}piperazine-1-carbonyl chloride A solution of 6-bromo-1-[5-(difluoromethyl)-1,3,4-thiadiazol-2-yl]-4-(piperazin-1-yl)indazole (500 mg, 1.204 mmol, 1 equiv), TEA (365.53 mg, 3.612 mmol, 3 equiv) in DCM (3 mL) was treated with triphosgene (117.90 mg, 0.397 mmol, 0.33 equiv) at 0° C. under nitrogen atmosphere. The resulting mixture was stirred for 1.5 h at 70° C. The reaction was monitored by LCMS. The mixture was allowed to cool down to room temperature. The resulting mixture was concentrated under reduced pressure to afford 4-{6-bromo-1-[5-(difluoromethyl)-1,3,4-thiadiazol-2-yl]indazol- 4-yl}piperazine-1-carbonyl chloride (600 mg, crude) as a yellow solid. LCMS (ESI, m/z): 477, 479 [M+H]+

Step 2: Synthesis of 4-{6-bromo-1-[5-(difluoromethyl)-1,3,4-thiadiazol-2-yl]indazol-4-yl}-N-(2,2-difluoroethyl)-N-methylpiperazine-1-carboxamide A solution of (2,2-difluoroethyl)(methyl)amine (358.31 mg, 3.768 mmol, 3 equiv) in THF (5 mL) was treated with TEA (381.29 mg, 3.768 mmol, 3 equiv) for 10 min at 10° C. followed by the addition of 4-{6-bromo-1-[5-(difluoromethyl)-1,3,4-thiadiazol-2-yl]indazol-4-yl}piperazine-1-carbonyl chloride (600 mg, 1.256 mmol, 1 equiv) dropwise at 0° C. The resulting mixture was stirred for 16 h at room temperature. The reaction was monitored by LCMS. The resulting mixture was diluted with water (50 mL). The aqueous layer was extracted with DCM (3×30 mL), dried over anhydrous Na$_2$SO$_4$. After filtration, the filtrate was concentrated under reduced pressure. The residue was purified by silica gel column chromatography, eluted with PE:EA (3:1) to afford 4-{6-bromo-1-[5-(difluoromethyl)-1,3,4-thiadiazol-2-yl]indazol-4-yl}-N-(2,2-difluoroethyl)-N-methylpiperazine-1-carboxamide (300 mg, 44.53%) as a white solid. LCMS (ESI, m/z): 536, 538 [M+H]+

Step 3: Synthesis of N-(2,2-difluoroethyl)-4-(1-(5-(difluoromethyl)-1,3,4-thiadiazol-2-yl)-6-(N-(3-methyloxetan-3-yl)sulfamoyl)-1H-indazol-4-yl)-N-methylpiperazine-1-carboxamide A mixture of 4-{6-bromo-1-[5-(difluoromethyl)-1,3,4-thiadiazol-2-yl]indazol-4-yl}-N-(2,2-difluoroethyl)-N-methylpiperazine-1-carboxamide (70 mg, 0.131 mmol, 1 equiv), potassium metabisulfite (58.03 mg, 0.261 mmol, 2.00 equiv), TEAB (20.83 mg, 0.144 mmol, 1.1 equiv), sodium formate (26.63 mg, 0.393 mmol, 3 equiv), PPh$_3$ (10.27 mg, 0.039 mmol, 0.3 equiv), phen (7.06 mg, 0.039 mmol, 0.3 equiv) and Pd(OAc)$_2$ (2.93 mg, 0.013 mmol, 0.1 equiv) in DMSO (2 mL) was stirred for 4 h at 70° C. under nitrogen atmosphere. Then the mixture was cooled to room temperature. A solution of 3-methyloxetan-3-amine (22.74 mg, 0.262 mmol, 2 equiv) in THF (2 mL) and a solution of NBS (92.92 mg, 0.524 mmol, 4 equiv) in THF (2 mL) were added dropwise. The mixture was stirred for 1 h at room temperature. The reaction was monitored with LCMS. The resulting mixture was diluted with ethyl acetate (30 mL). The resulting mixture was washed with brine (4×20 mL), dried over anhydrous Na$_2$SO$_4$. After filtration, the filtrate was concentrated under reduced pressure. The residue was purified by Prep-HPLC with the following conditions (Column: XBridge Prep OBD C18 Column, 30*150 mm, 5 μm; Mobile Phase A: Water (10 mmol/L NH4HCO3), Mobile Phase B: ACN; Flow rate: 60 mL/min; Gradient: 33% B to 63% B in 7 min, 63% B; Wave Length: 254 nm; RT1(min): 6.45; Number Of Runs: 0) to afford N-(2,2-difluoroethyl)-4-(1-(5-(difluoromethyl)-1,3,4-thiadiazol-2-yl)-6-(N-(3-methyloxetan-3-yl)sulfamoyl)-1H-indazol-4-yl)-N-methylpiperazine-1-carboxamide (20.3 mg, 25.51%) as a yellow solid. LCMS (ESI, m/z): 607.05[M+H]+. $^1$H NMR (300 MHz, DMSO-d6) δ=8.94 (s, 1H), 8.61 (br, 1H), 8.46 (s, 1H), 7.78-7.43 (m, 1H), 7.17 (s, 1H), 6.41-6.01 (m, 1H), 4.57 (d, J=6.0 Hz, 2H), 4.13 (d, J=6.3 Hz, 2H), 3.69-3.61 (m, 2H), 3.58-3.49 (m, 8H), 2.99 (s, 3H), 1.43 (s, 3H).

Example 38: N-(3-cyanooxetan-3-yl)-1-(5-(difluoromethyl)-1,3,4-thiadiazol-2-yl)-4-(4-(pyrrolidine-1-carbonyl)piperazin-1-yl)-1H-indazole-6-sulfonamide

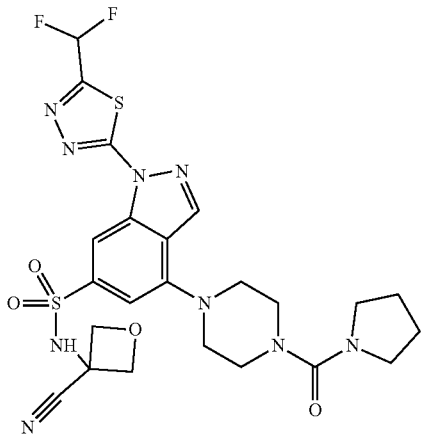 [SMILES: N#CC1(NS(=O)(=O)c2cc(N3CCN(C(=O)N4CCCC4)CC3)c3cnn(-c4nnc(C(F)F)s4)c3c2)COC1]

Step 1: Synthesis of 1-[5-(difluoromethyl)-1,3,4-thiadiazol-2-yl]-4-[4-(pyrrolidine-1-carbonyl)piperazin-1-yl]indazole-6-sulfonamide To a stirred mixture of 6-bromo-1-[5-(difluoromethyl)-1,3,4-thiadiazol-2-yl]-4-[4-(pyrrolidine-1-carbonyl)piperazin-1-yl]indazole (150 mg, 0.293 mmol, 1 equiv), potassium metabisulfite (130 mg, 0.586 mmol, 2 equiv), PPh$_3$ (23 mg, 0.088 mmol, 0.3 equiv), sodium formate (60 mg, 0.879 mmol, 3 equiv), palladium acetate (7 mg, 0.029 mmol, 0.1 equiv) and TEAB (47 mg, 0.322 mmol, 1.1 equiv) in DMSO (3 mL) was stirred for 4 h at 70° C. under N$_2$ atmosphere. To the above was added ammonium hydroxide (103 mg, 2.930 mmol, 10 equiv) and NBS (182 mg, 1.025 mmol, 3.5 equiv) in THF (1 mL) dropwise. The mixture was stirred for at 0° C. for other 1 h. Desired product could be detected by LCMS. The reaction was quenched with water (20 mL). The mixture was washed with EA (2×20 mL), dried over anhydrous Na$_2$SO$_4$. After filtration, the filtrate was concentrated under reduced pressure. The residue was purified by Prep-TLC (PE/EA 1:1) to afford 1-[5-(difluoromethyl)-1,3,4-thiadiazol-2-yl]-4-[4-(pyrrolidine-1-carbonyl)piperazin-1-yl]indazole-6-sulfonamide (80 mg, 53.33%) as a yellow solid. LCMS (ES, m/z): 513[M+H]+, Step 2: Synthesis of 1-(5-(difluoromethyl)-1,3,4-thiadiazol-2-yl)-N-(oxetan-3-ylidene)-4-(4-(pyrrolidine-1-carbonyl)piperazin-1-yl)-1H-indazole-6-sulfonamide To a stirred mixture of 1-[5-(difluoromethyl)-1,3,4-thiadiazol-2-yl]-4-[4-(2-methylpropanoyl) piperazin-1-yl]indazole-6-sulfonamide (80 mg, 0.165 mmol, 1 equiv) in tetrahydrofuran (6 mL) was added titanium isopropylate (230 mg, 0.825 mmol, 5 equiv) and 3-oxetanone (120 mg, 1.650 mmol, 10 equiv) dropwise. The resulting mixture was stirred for 12 h at 60° C. To above mixture was added another batch of titanium isopropylate (230 mg, 0.825 mmol, 5 equiv) and 3-oxetanone (120 mg, 1.650 mmol, 10 equiv) dropwise. The resulting mixture was stirred for another 5 h at 60° C. The resulting mixture was concentrated to afford 1-(5-(difluoromethyl)-1,3,4-thiadiazol-2-yl)-N-(oxetan-3-ylidene)-4-(4-

(pyrrolidine-1-carbonyl)piperazin-1-yl)-1H-indazole-6-sulfonamide (150 mg, crude). LCMS (ES, m/z): 567[M+H]+.

Step 3: Synthesis of N-(3-cyanooxetan-3-yl)-1-(5-(difluoromethyl)-1,3,4-thiadiazol-2-yl)-4-(4-(pyrrolidine-1-carbonyl)piperazin-1-yl)-1H-indazole-6-sulfonamide A solution of 1-[5-(difluoromethyl)-1,3,4-thiadiazol-2-yl]-N-(oxetan-3-ylidene)-4-[4-(pyrrolidine-1-carbonyl)piperazin-1-yl]indazole-6-sulfonamide (100 mg, 0.176 mmol, 1 equiv) in THF (2 mL) was treated with TMSCN (87.55 mg, 0.880 mmol, 5 equiv) dropwise. The resulting mixture was stirred for 1 h at room temperature. The resulting mixture was filtered, the filter cake was washed with EA (3×10 mL). The solids were filtered out and were washed with (3×5 mL). The filtration was concentrated under reduced pressure. The residue was purified by Prep-HPLC with the following condition: (Column: XBridge Shield RP18 OBD Column, 30*150 mm, 5 μm; Mobile Phase A: Water (10 mmol/L NH4HCO3+0.1% NH3·H2O), Mobile Phase B: ACN; Flow rate: 60 mL/min; Gradient: 19% B to 49% B in 7 min; Wave Length: 254 nm; RT1 (min): 6) to afford N-(3-cyanooxetan-3-yl)-1-(5-(difluoromethyl)-1,3,4-thiadiazol-2-yl)-4-(4-(pyrrolidine-1-carbonyl)piperazin-1-yl)-1H-indazole-6-sulfonamide (4.8 mg, 4.43%) as a yellow solid. LCMS (ESI, m/z): 594.05[M+H]+, 1H NMR (400 MHz, DMSO-d6) δ=9.61 (br, 1H), 8.95 (s, 1H), 8.45 (s, 1H), 7.73-7.47 (m, 1H), 7.14 (s, 1H), 4.82 (d, J=7.2 Hz, 2H), 4.71 (d, J=7.2 Hz, 2H), 3.52-3.45 (m, 8H), 3.33-3.31 (m, 4H), 1.79-1.76 (m, 4H).

Example 39: N-(3-cyanooxetan-3-yl)-4-(4-(cyclopropanecarbonyl)piperazin-1-yl)-1-(5-(difluoromethyl)-1,3,4-thiadiazol-2-yl)-1H-indazole-6-sulfonamide

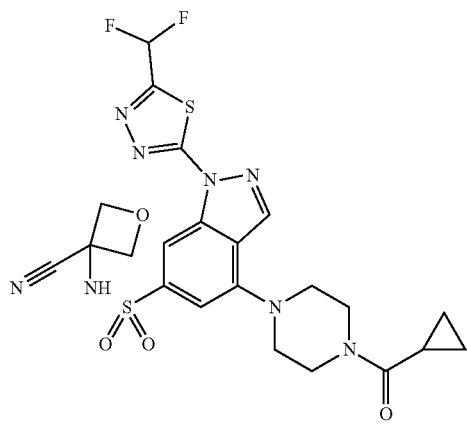

Step 1: Synthesis of 6-bromo-4-(4-cyclopropanecarbonylpiperazin-1-yl)-1-[5-(difluoromethyl)-1,3,4-thiadiazol-2-yl]indazole To a stirred solution of 6-bromo-1-[5-(difluoromethyl)-1,3,4-thiadiazol-2-yl]-4-(piperazin-1-yl)indazole (380 mg, 0.915 mmol, 1 equiv) and cyclopropanecarboxylic acid (94 mg, 1.098 mmol, 1.2 equiv) in DMF (5 mL) was added DIEA (591.36 mg, 4.575 mmol, 5 equiv) and HATU (695.90 mg, 1.830 mmol, 2 equiv) in portions at 0° C. The resulting mixture was stirred for 1 h at room temperature. The reaction was monitored by LCMS. Then water (50 mL) was added. The mixture was extracted with EA (3×50 mL). The combined organic layers were washed with brine (2×50 mL), dried over anhydrous Na2SO4 and concentrated. The residue was purified by silica gel column chromatography (eluting with 1:1 EA/PE) to afford 6-bromo-4-(4-cyclopropanecarbonylpiperazin-1-yl)-1-[5-(difluoromethyl)-1,3,4-thiadiazol-2-yl]indazole (300 mg, 64%) as a yellow solid. LCMS (ES, m/z): 483, 485[M+H]+.

Step 2: Synthesis of 4-(4-cyclopropanecarbonylpiperazin-1-yl)-1-[5-(difluoromethyl)-1,3,4-thiadiazol-2-yl]indazole-6-sulfonamide A mixture of 6-bromo-4-(4-cyclopropanecarbonylpiperazin-1-yl)-1-[5-(difluoromethyl)-1,3,4-thiadiazol-2-yl]indazole (100 mg, 0.207 mmol, 1 equiv), dipotassium sulfinosulfonate (91.99 mg, 0.414 mmol, 2 equiv), triphenylphosphine (16.28 mg, 0.062 mmol, 0.3 equiv), sodium formate (42.21 mg, 0.621 mmol, 3 equiv), TEAB (33.02 mg, 0.228 mmol, 1.1 equiv), phen (11.19 mg, 0.062 mmol, 0.3 equiv) and Pd(OAC)2 (4.64 mg, 0.021 mmol, 0.1 equiv) in DMSO (2 mL) was stirred for 4 h at 70° C. under nitrogen atmosphere. The mixture was allowed to cool down to room temperature. To above mixture was added ammonium hydroxide (21.75 mg, 0.621 mmol, 3 equiv) and NBS (110.47 mg, 0.621 mmol, 3 equiv) in THF (1 mL) at 0° C. The resulting mixture was stirred for 1 h at room temperature under nitrogen atmosphere. The reaction was monitored by LCMS. The resulting mixture was diluted with water (30 mL). The resulting mixture was extracted with EA (3×30 mL). The combined organic layers were washed with brine (2×50 mL), dried over anhydrous Na2SO4. After filtration, the filtrate was concentrated under reduced pressure. The residue was purified by silica gel column chromatography, eluted with PE/EA (1:2) to afford 4-(4-cyclopropanecarbonylpiperazin-1-yl)-1-[5-(difluoromethyl)-1,3,4-thiadiazol-2-yl]indazole-6-sulfonamide (60 mg, 53.98%) as a yellow solid. LCMS (ES, m/z): 484[M+H]+.

Step 3: Synthesis of 4-(4-cyclopropanecarbonylpiperazin-1-yl)-1-[5-(difluoromethyl)-1,3,4-thiadiazol-2-yl]-N-(oxetan-3-ylidene)indazole-6-sulfonamide To a stirred mixture of 4-(4-cyclopropanecarbonylpiperazin-1-yl)-1-[5-(difluoromethyl)-1,3,4-thiadiazol-2-yl]indazole-6-sulfonamide (50 mg, 0.103 mmol, 1 equiv) in tetrahydrofuran (3 mL) was added titanium isopropylate (146.96 mg, 0.515 mmol, 5 equiv) and 3-oxetanone (74.52 mg, 1.030 mmol, 10 equiv) dropwise at room temperature. The resulting mixture was stirred for 16 h at 60° C. The resulting mixture was concentrated to afford 4-(4-cyclopropanecarbonylpiperazin-1-yl)-1-[5-(difluoromethyl)-1,3,4-thiadiazol-2-yl]-N-(oxetan-3-ylidene)indazole-6-sulfonamide (100 mg, crude). LCMS (ES, m/z): 538[M+H]+.

Step 4: Synthesis of N-(3-cyanooxetan-3-yl)-4-(4-(cyclopropanecarbonyl)piperazin-1-yl)-1-(5-(difluoromethyl)-1,3,4-thiadiazol-2-yl)-1H-indazole-6-sulfonamide To a stirred mixture of 4-(4-cyclopropanecarbonylpiperazin-1-yl)-1-[5-(difluoromethyl)-1,3,4-thiadiazol-2-yl]-N-(oxetan-3-ylidene)indazole-6-sulfonamide (50 mg, 0.093 mmol, 1 equiv) in DCM (2 mL) was added trimethylsilanecarbonitrile (46.14 mg, 0.465 mmol, 5 equiv) dropwide. The resulting mixture was stirred for 2 h at room temperature. The reaction was quenched with water (20 mL). The mixture was washed with EA (3×15 mL), dried over anhydrous $Na_2SO_4$. After filtration, the filtrate was concentrated under reduced pressure. The residue was purified by Prep-HPLC with the following conditions: (Column: XBridge Prep Phenyl OBD Column, 19*100 mm, 5 μm; Mobile Phase A: Water (10 mmol/L NH4HCO3+0.1% NH3·H2O), Mobile Phase B: ACN; Flow rate: 60 mL/min; Gradient: 30% B to 60% B in 7 min, 60% B; Wave Length: 254 nm; RT1(min): 6; Number Of Runs: 0) to afford N-(3-cyanooxetan-3-yl)-4-(4-(cyclopropanecarbonyl)piperazin-1-yl)-1-(5-(difluoromethyl)-1,3,4-thiadiazol-2-yl)-1H-indazole-6-sulfonamide (2.0 mg, 3.77%) as an off-white solid. 1H NMR (300 MHz, DMSO-d6) δ=9.59 (br, 1H), 8.96 (s, 1H), 8.45 (s, 1H), 7.77-7.42 (m, 1H), 7.14 (s, 1H), 4.82 (d, J=6.9 Hz, 2H), 4.71 (d, J=6.9 Hz, 2H), 4.02-3.95 (m, 2H), 3.81-3.66 (m, 2H), 3.55-3.42 (m, 4H), 2.09-2.01 (m, 1H), 0.79-0.72 (m, 4H). LCMS (ES, m/z): 565 [M+H]⁺.

Example 40: N-(3-cyanooxetan-3-yl)-4-(4-(cyclopentanecarbonyl)piperazin-1-yl)-1-(5-(difluoromethyl)-1,3,4-thiadiazol-2-yl)-1H-indazole-6-sulfonamide

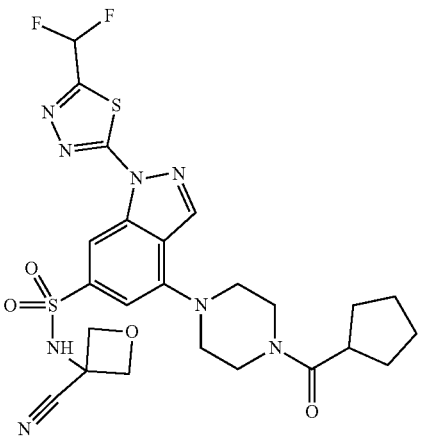 [SMILES: N#CC1(NS(=O)(=O)c2cc(N3CCN(C(=O)C4CCCC4)CC3)c3cnn(-c4nnc(C(F)F)s4)c3c2)COC1]

Step 1: Synthesis of 6-bromo-4-(4-(cyclopentanecarbonyl)piperazin-1-yl)-1-[5-(difluoromethyl)-1,3,4-thiadiazol-2-yl]indazole To a mixture of 6-bromo-1-[5-(difluoromethyl)-1,3,4-thiadiazol-2-yl]-4-(piperazin-1-yl)indazole hydrochloride (500 mg, 1.107 mmol, 1 equiv), cyclopentanecarboxylic acid (252.69 mg, 2.214 mmol, 2 equiv) and DIEA (715.30 mg, 5.535 mmol, 5 equiv) in DMF (20 mL) was added HATU (841.75 mg, 2.214 mmol, 2 equiv) in portions at 0° C. The resulting mixture was stirred for 2 h at room temperature. The reaction was monitored by LCMS. The resulting mixture was quenched with water (100 mL). The aqueous layer was extracted with EA (3×100 mL). The combined organic layers were washed by brine (100 mL), dried over anhydrous $Na_2SO_4$. After filtration, the filtrate was concentrated under reduced pressure. The residue was purified by silica gel column chromatography, eluted with PE/EA (2:1) to afford 6-bromo-4-(4-cyclopentanecarbonylpiperazin-1-yl)-1-[5-(difluoromethyl)-1,3,4-thiadiazol-2-yl]indazole (400 mg, 70.67%) as a yellow solid. LCMS (ESI, m/z): 511, 513 [M+H]⁺.

Step 2: Synthesis of 4-(4-cyclopentanecarbonylpiperazin-1-yl)-1-[5-(difluoromethyl)-1,3,4-thiadiazol-2-yl]indazole-6-sulfonamide A mixture of 6-bromo-4-(4-cyclopentanecarbonylpiperazin-1-yl)-1-[5-(difluoromethyl)-1,3,4-thiadiazol-2-yl]indazole (140 mg, 0.274 mmol, 1 equiv), potassium metabisulfite (121.73 mg, 0.548 mmol, 2 equiv), tetraethylazanium bromide (58.63 mg, 0.279 mmol, 1.1 equiv), tetraethylazanium bromide (63.29 mg, 0.301 mmol, 1.1 equiv), $PPh_3$ (21.54 mg, 0.082 mmol, 0.3 equiv), phen (14.80 mg, 0.082 mmol, 0.3 equiv) and $Pd(OAc)_2$ (6.15 mg, 0.027 mmol, 0.1 equiv) in DMSO (2 mL) was stirred for 4 h at 70° C. under nitrogen atmosphere. Then the reaction was cooled to room temperature. A solution of $NH_3·H_2O$ (19.19 mg, 0.548 mmol, 2 equiv) in THF (1 mL) and a solution of NBS (146.18 mg, 0.822 mmol, 3 equiv) in THF (1 mL) were stirred for 1 h at room temperature. The reaction was monitored by LCMS. The resulting mixture was quenched with water (30 mL). The aqueous layer was extracted with EA (3×30 mL). The combined organic layers were washed by brine (50 mL), dried over anhydrous $Na_2SO_4$. After filtration, the filtrate was concentrated under reduced pressure. The residue was purified by silica gel column chromatography, eluted with PE/EA (1:1) to afford 4-(4-cyclopentanecarbonylpiperazin-1-yl)-1-[5-(difluoromethyl)-1,3,4-thiadiazol-2-yl]indazole-6-sulfonamide (80 mg, 57.12%) as a yellow solid. LCMS (ESI, m/z): 512 [M+H]⁺.

Step 3: Synthesis of 4-(4-cyclopentanecarbonylpiperazin-1-yl)-1-[5-(difluoromethyl)-1,3,4-thiadiazol-2-yl]-N-(oxetan-3-ylidene)indazole-6-sulfonamide To a stirred mixture of 4-(4-cyclopentanecarbonylpiperazin-1-yl)-1-[5-(difluoromethyl)-1,3,4-thiadiazol-2-yl]indazole-6-sulfonamide (80 mg, 0.156 mmol, 1 equiv) in THF (2 mL) was added Ti(Oi-Pr)₄ (177.79 mg, 0.624 mmol, 4 equiv) and 3-oxetanone (112.69 mg, 1.560 mmol, 10 equiv) dropwise at room temperature. The resulting mixture was stirred for 16 h at 60° C. The reaction was monitored by LCMS. The resulting mixture was concentrated to afford 4-(4-cyclopentanecarbonylpiperazin-1-yl)-1-[5-(difluoromethyl)-1,3,4-thiadiazol-2-yl]-N-(oxetan-3-ylidene)indazole-6-sulfonamide (100 mg, crude). LCMS (ESI, m/z): 566 [M+H]⁺.

Step 4: Synthesis of N-(3-cyanooxetan-3-yl)-4-(4-(cyclopentanecarbonyl)piperazin-1-yl)-1-(5-(difluoromethyl)-1,3,4-thiadiazol-2-yl)-1H-indazole-6-sulfonamide A mixture of 4-(4-cyclopentanecarbonylpiperazin-1-yl)-1-[5-(difluoromethyl)-1,3,4-thiadiazol-2-yl]-N-(oxetan-3-ylidene)indazole-6-sulfonamide (80 mg, 0.141 mmol, 1 equiv) and trimethylsilyl cyanide (70.16 mg, 0.705 mmol, 5 equiv) in THF (2 mL) was stirred for 1 h at room temperature. The reaction was monitored with LCMS. The resulting mixture was concentrated under reduced pressure. The residue was purified by Prep-HPLC with the following conditions (Column: XBridge Prep OBD C18 Column, 30*150 mm, 5 μm; Mobile Phase A: Water (10 mmol/L NH4HCO3), Mobile Phase B: ACN; Flow rate: 60 mL/min; Gradient: 23% B to 53% B in 7 min, 53% B; Wave Length: 254 nm; RT1(min): 6.8; Number Of Runs: 0) to afford N-(3-cyanooxetan-3-yl)-4-(4-(cyclopentanecarbonyl)piperazin-1-yl)-1-(5-(difluoromethyl)-1,3,4-thiadiazol-2-yl)-1H-indazole-6-sulfonamide (10.4 mg, 11.18%) as a yellow solid. LCMS (ESI, m/z): 593.10 [M+H]+. 1H NMR (300 MHz, DMSO-d6) δ=9.65 (br, 1H), 8.96 (s, 1H), 8.46 (s, 1H), 7.78-7.43 (m, 1H), 7.14 (s, 1H), 4.83 (d, J=7.2 Hz, 2H), 4.71 (d, J=7.2 Hz, 2H), 3.75-3.46 (m, 4H), 3.46-3.33 (m, 4H), 3.09-3.01 (m, 1H), 1.82-1.72 (m, 4H), 1.71-1.59 (m, 4H).

Example 41: 4-(6-(N-(3-cyanooxetan-3-yl)sulfamoyl)-1-(5-(difluoromethyl)-1,3,4-thiadiazol-2-yl)-1H-indazol-4-yl)-N-(2,2-difluoroethyl)-N-methylpiperazine-1-carboxamide

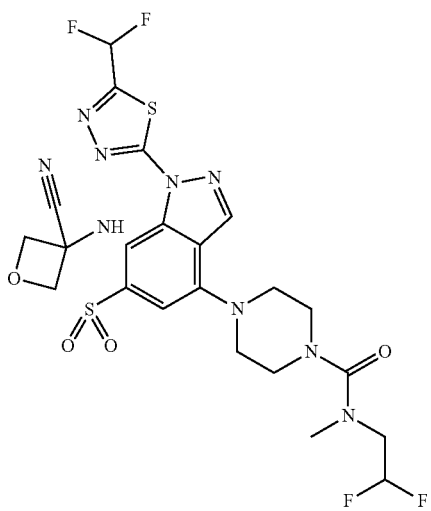

Step 1: Synthesis of N-(2,2-difluoroethyl)-4-{1-[5-(difluoromethyl)-1,3,4-thiadiazol-2-yl]-6-sulfamoylindazol-4-yl}-N-methylpiperazine-1-carboxamide A mixture of 4-{6-bromo-1-[5-(difluoromethyl)-1,3,4-thiadiazol-2-yl]indazol-4-yl}-N-methyl-N-(2-methylpropyl)piperazine-1-carboxamide (150 mg, 0.284 mmol, 1 equiv), potassium metabisulfite (126.22 mg, 0.568 mmol, 2 equiv), tetraethylazanium bromide (65.62 mg, 0.312 mmol, 1.1 equiv), sodium formate (57.91 mg, 0.852 mmol, 3.00 equiv), phen (15.35 mg, 0.085 mmol, 0.3 equiv), PPh3 (22.34 mg, 0.085 mmol, 0.3 equiv) and Pd(OAc)2 (6.37 mg, 0.028 mmol, 0.1 equiv) in DMSO (2 mL) was stirred for 4 h at 70° C. under nitrogen atmosphere. To the above mixture was added NH3·H2O (19.90 mg, 0.568 mmol, 2 equiv) and NBS (50.52 mg, 0.285 mmol, 3 equiv) in THF (1 mL) dropwise at 0° C. The resulting mixture was stirred for additional 1 h at room temperature. The reaction was monitored with LCMS. The resulting mixture was quenched with water (30 mL). The aqueous layer was extracted with EA (3×20 mL). The combined organic layers were washed by brine (50 mL), dried over anhydrous Na2SO4. After filtration, the filtrate was concentrated under reduced pressure. The residue was purified by silica gel column chromatography, eluted with PE/EA (1:1) to afford N-(2,2-difluoroethyl)-4-{1-[5-(difluoromethyl)-1,3,4-thiadiazol-2-yl]-6-sulfamoylindazol-4-yl}-N-methylpiperazine-1-carboxamide (100 mg, 65.66%) as a yellow solid. LCMS (ESI, m/z): 537[M+H]+

Step 2: Synthesis of N-(2,2-difluoroethyl)-4-{1-[5-(difluoromethyl)-1,3,4-thiadiazol-2-yl]-6-[(oxetan-3-ylidene)sulfamoyl]indazol-4-yl}-N-methylpiperazine-1-carboxamide To a stirred mixture of 4-{1-[5-(difluoromethyl)-1,3,4-thiadiazol-2-yl]-6-sulfamoylindazol-4-yl}-N-(2-fluoroethyl)-N-methylpiperazine-1-carboxamide (100 mg, 0.193 mmol, 1 equiv) in THF (3 mL) was added Ti(Oi-Pr)4 (219.25 mg, 0.772 mmol, 4 equiv) and 3-oxetanone (138.98 mg, 1.930 mmol, 10 equiv) dropwise at room temperature. The resulting mixture was stirred for 16 h at 60° C. The reaction was monitored by LCMS. The resulting mixture concentrated to afford N-(2,2-difluoroethyl)-4-{1-[5-(difluoromethyl)-1,3,4-thiadiazol-2-yl]-6-[(oxetan-3-ylidene)sulfamoyl]indazol-4-yl}-N-methylpiperazine-1-carboxamide (120 mg, crude). LCMS (ESI, m/z): 591[M+H]+.

Step 3: Synthesis of 4-(6-(N-(3-cyanooxetan-3-yl)sulfamoyl)-1-(5-(difluoromethyl)-1,3,4-thiadiazol-2-yl)-1H-indazol-4-yl)-N-(2,2-difluoroethyl)-N-methylpiperazine-1-carboxamide A mixture of N-(2,2-difluoroethyl)-4-{1-[5-(difluoromethyl)-1,3,4-thiadiazol-2-yl]-6-[(oxetan-3-ylidene)sulfamoyl]indazol-4-yl}-N-methylpiperazine-1-carboxamide (100 mg, 0.169 mmol, 1 equiv) in THF (3 mL) was added trimethylsilyl cyanide (83.99 mg, 0.845 mmol, 5 equiv) dropwise. The resulting mixture was stirred for 1 h at room temperature. The reaction was monitored with LCMS. The resulting mixture was concentrated under reduced pressure. The residue was purified by Prep-HPLC with the following conditions (Column: XBridge Prep Phenyl OBD Column, 19*100 mm, 5 μm; Mobile Phase A: Water (10 mmol/L NH4HCO3+0.1% NH3·H2O), Mobile Phase B: ACN; Flow rate: 60 mL/min; Gradient: 19% B to 49% B in 7 min, 49% B; Wave Length: 254 nm; RT1(min): 6; Number Of Runs: 0) to afford 4-(6-(N-(3-cyanooxetan-3-yl)sulfamoyl)-1-(5-(difluoromethyl)-1,3,4-thiadiazol-2-yl)-1H-indazol-4-yl)-N-(2,2-difluoroethyl)-N-methylpiperazine-1-carboxamide (6.1 mg, 5.73%) as a yellow solid. LCMS (ESI, m/z): 618.05 [M+H]+. 1H NMR (300 MHz, DMSO-d6) δ=9.63 (br, 1H), 8.95 (s, 1H), 8.46 (s, 1H), 7.96-7.34 (m, 1H), 7.16 (s, 1H), 6.57-5.91 (m, 1H), 4.83 (d, J=7.2 Hz, 2H), 4.70 (d, J=7.2 Hz, 2H), 3.68-3.61 (m, 2H), 3.45-3.33 (m, 8H), 2.99 (s, 3H).

Example 42: N-(3-(fluoromethyl)oxetan-3-yl)-4-(4-isobutyrylpiperazin-1-yl)-1-(5-methyl-1,3,4-thiadiazol-2-yl)-1H-indazole-6-sulfonamide

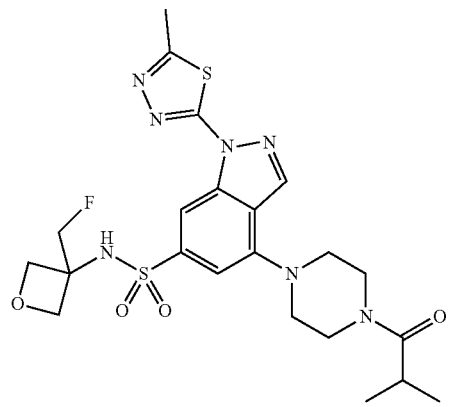 [SMILES: Cc1nnc(-n2ncc3c(N4CCN(C(=O)C(C)C)CC4)cc(S(=O)(=O)NC4(CF)COC4)cc32)s1]

Step 1: Synthesis of 1-(4-(6-bromo-1-(5-methyl-1,3, 4-thiadiazol-2-yl)-1H-indazol-4-yl) piperazin-1-yl)-2-methylpropan-1-one Into a solution of 1-[4-(6-bromo-1H-indazol-4-yl) piperazin-1-yl]-2-methylpropan-1-one (1 g, 2.847 mmol, 1 equiv) and Cs$_2$CO$_3$ (2.78 g, 8.541 mmol, 3 equiv) in DMF (10 mL) was added 2-bromo-5-methyl-1,3,4-thiadiazole (1.02 g, 5.694 mmol, 2 equiv) in portions. The resulting mixture was stirred for 2 h at 70° C. Desired product could be detected by LCMS. The reaction was with quenched with brine (100 mL). The resulting mixture extracted with EA (3×100 mL). The combined organic layers were washed with brine (2×100 mL), dried over anhydrous Na$_2$SO$_4$. After filtration, the filtrate was concentrated under reduced pressure. The residue was purified by silica gel column chromatography, eluted with EA/PE (1:1) to afford 1-(4-(6-bromo-1-(5-methyl-1,3,4-thiadiazol-2-yl)-1H-indazol-4-yl) piperazin-1-yl)-2-methylpropan-1-one (400 mg, 31.27%) as a yellow solid. LCMS (ES, m/z): 449, 451[M+H]$^+$, Step 2: Synthesis of N-(3-(fluoromethyl)oxetan-3-yl)-4-(4-isobutyrylpiperazin-1-yl)-1-(5-methyl-1,3,4-thiadiazol-2-yl)-1H-indazole-6-sulfonamide To a stirred mixture of 1-{4-[6-bromo-1-(5-methyl-1,3,4-thiadiazol-2-yl)indazol-4-yl]piperazin-1-yl}-2-methylpropan-1-one (200 mg, 0.445 mmol, 1 equiv) in DMSO (3 mL) was added dipotassium sulfinosulfonate (198 mg, 0.890 mmol, 2 equiv), PPh$_3$ (35 mg, 0.134 mmol, 0.3 equiv), sodium formate (91 mg, 1.335 mmol, 3 equiv), Pd(OAc)$_2$ (10 mg, 0.045 mmol, 0.1 equiv), TEAB (71.03 mg, 0.490 mmol, 1.1 equiv) and phen (24 mg, 0.134 mmol, 0.3 equiv). The resulting mixture was stirred for 4 h at 70° C. under N$_2$ atmosphere. Then 3-(fluoromethyl)oxetan-3-amine hydrochloride (189 mg, 1.335 mmol, 3 equiv) in pyridine (1.5 mL) and NBS (316 mg, 1.780 mmol, 4 equiv) in THF (2 mL) were added dropwise at 0° C. The resulting mixture was stirred for another 1 h at room temperature. Desired product could be detected by LCMS. The reaction was quenched with water (20 mL). The mixture was washed with EA (3×15 mL). After filtration, the filtrate was concentrated under reduced pressure. The residue was purified by Prep-HPLC with the following condition: (Column: XBridge Prep OBD C18 Column, 30*150 mm, 5 μm; Mobile Phase A: Water (10 mmol/L NH4HCO3), Mobile Phase B: ACN; Flow rate: 60 mL/min; Gradient: 26% B to 56% B in 7 min, 56% B; Wave Length: 254 nm; RT1(min): 5.55; Injection Volume: 1.7 mL; Number Of Runs: 1) to afford N-(3-(fluoromethyl)oxetan-3-yl)-4-(4-isobutyrylpiperazin-1-yl)-1-(5-methyl-1,3,4-thiadiazol-2-yl)-1H-indazole-6-sulfonamide (10.2 mg, 4.24%) as a white solid. LCMS (ES, m/z): 538.05 [M+H]$^+$, $^1$H NMR (300 MHz, DMSO-d6) δ=8.85-8.84 (m, 2H), 8.46 (s, 1H), 7.12 (s, 1H), 4.69 (s, 1H), 4.57-4.53 (m, 3H), 4.34 (d, J=6.9 Hz, 2H), 3.81-3.74 (m, 4H), 3.50-3.40 (m, 4H), 3.02-2.91 (m, 1H), 2.74 (s, 3H), 1.05 (d, J=6.6 Hz, 6H).

Example 43:1-(5-cyclopropyl-1,3,4-thiadiazol-2-yl)-N-(3-(fluoromethyl)oxetan-3-yl)-4-(4-isobutyrylpiperazin-1-yl)-1H-indazole-6-sulfonamide

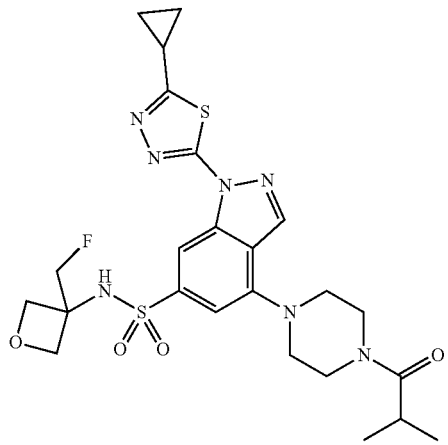 [SMILES: CC(C)C(=O)N1CCN(c2cc(S(=O)(=O)NC3(CF)COC3)cc3c2cnn3-c2nnc(C3CC3)s2)CC1]

Step 1: Synthesis of 2-bromo-5-cyclopropyl-1,3,4-thiadiazole

A mixture of 2-methyl-2-propylnitrit (1.68 g, 16.291 mmol, 2.3 equiv) and CuBr$_2$ (3.64 g, 16.291 mmol, 2.3 equiv) in ACN (20 mL) was stirred for 10 min at room temperature. To the above mixture was added 5-cyclopropyl-1,3,4-thiadiazol-2-amine (1 g, 7.083 mmol, 1 equiv) in portions. The mixture was stirred for additional 3 h at room temperature. The reaction was monitored by LCMS. The resulting mixture was concentrated under reduced pressure. The residue was purified by silica gel column chromatography, eluted with PE/EA (1:1) to afford 2-bromo-5-cyclopropyl-1,3,4-thiadiazole (700 mg, 48.19%) as a yellow oil. LCMS (ESI, m/z): 205, 207[M+H]$^+$ Step 2: Synthesis of 1-{4-[6-bromo-1-(5-cyclopropyl-1,3,4-thiadiazol-2-yl)indazol-4-yl]piperazin-1-yl}-2-methylpropan-1-one and 1-{4-[6-bromo-2-(5-cyclopropyl-1,3,4-thiadiazol-2-yl)indazol-4-yl]piperazin-1-yl}-2-methylpropan-1-one A mixture of 1-[4-(6-bromo-1H-indazol-4-yl)piperazin-1-yl]-2-methylpropan-1-one (1 g, 2.85 mmol, 1 equiv), 2-bromo-5-cyclopropyl-1,3,4-thiadiazole (701 mg, 3.42 mmol, 1.2 equiv) and Cs$_2$CO$_3$ (2.31 g, 7.12 mmol, 2.5 equiv) in DMF (10 mL) was stirred for 3 h at 70° C. The reaction was monitored by LCMS. The resulting mixture was quenched with water (100 mL). The aqueous layer was extracted with EA (3×100 mL). The combined organic layers were washed by brine (100 mL), dried over anhydrous Na$_2$SO$_4$. After filtration, the filtrate was concentrated under reduced pressure. The residue was purified by silica gel column chromatography, eluted with PE/EA (1:1) to afford the mixture of 1-{4-[6-bromo-1-(5-cyclopropyl-1,3,4-thiadiazol-2-yl)indazol-4-yl]piperazin-1-yl}-2-methylpropan-1-one and 1-{4-[6-bromo-2-(5-cyclopropyl-1,3,4-thiadiazol-2-yl)indazol-4-yl]piperazin-1-yl}-2-methylpropan-1-one (600 mg, 44%) as a yellow solid. LCMS (ESI, m/z): 475, 477[M+H]$^+$

Step 3: synthesis of 1-(5-cyclopropyl-1,3,4-thiadiazol-2-yl)-N-(3-(fluoromethyl)oxetan-3-yl)-4-(4-isobutyrylpiperazin-1-yl)-1H-indazole-6-sulfonamide A mixture of 1-{4-[6-bromo-1-(5-cyclopropyl-1,3,4-thiadiazol-2-yl)indazol-4-yl]piperazin-1-yl}-2-methylpropan-1-one and 1-{4-[6-bromo-2-(5-cyclopropyl-1,3,4-thiadiazol-2-yl)indazol-4-yl]piperazin-1-yl}-2-methylpropan-1-one (300 mg, 0.631 mmol, 1 equiv), potassium metabisulfite (280.59 mg, 1.262 mmol, 2 equiv), tetraethylazanium bromide (145.88 mg, 0.694 mmol, 1.1 equiv), sodium formate (128.74 mg, 1.893 mmol, 3 equiv), PPh3 (49.65 mg, 0.189 mmol, 0.3 equiv), phen (34.12 mg, 0.189 mmol, 0.3 equiv) and Pd(AcO)$_2$ (14.17 mg, 0.063 mmol, 0.1 equiv) in DMSO (2 mL) was stirred for 4 h at 70° C. under nitrogen atmosphere. To the above mixture was added 3-(fluoromethyl)oxetan-3-amine (265.32 mg, 2.524 mmol, 4 equiv), pyridine (0.5 mL, 0.006 mmol, 0.01 equiv) and NBS (449.26 mg, 2.524 mmol, 4 equiv) in THF (2 mL) dropwise at 0° C. The resulting mixture was stirred for additional 1 h at room temperature. The reaction was monitored withe LCMS. The resulting mixture was quenched with water (50 mL). The aqueous layer was extracted with EA (3×50 mL). The combined organic layers were washed by brine (50 mL), dried over anhydrous Na$_2$SO$_4$. After filtration, the filtrate was concentrated under reduced pressure. The product was purified by Prep-HPLC with the following conditions (Column: XBridge Prep OBD C18 Column, 30*150 mm, 5 μm; Mobile Phase A: Water (10 mmol/L NH4HCO3), Mobile Phase B: ACN; Flow rate: 60 mL/min; Gradient: 30% B to 60% B in 7 min, 60% B; Wave Length: 254 nm; RT1(min): 6.17; Injection Volume: 0.8 mL; Number Of Runs: 2) to afford 1-(5-cyclopropyl-1,3,4-thiadiazol-2-yl)-N-(3-(fluoromethyl)oxetan-3-yl)-4-(4-isobutyrylpiperazin-1-yl)-1H-indazole-6-sulfonamide (24.6 mg, 6.85%) and 2-(5-cyclopropyl-1,3,4-thiadiazol-2-yl)-N-[3-(fluoromethyl)oxetan-3-yl]-4-[4-(2-methylpropanoyl) piperazin-1-yl]indazole-6-sulfonamide (13.6 mg, 3.79%) as a white solid. 1-(5-cyclopropyl-1,3,4-thiadiazol-2-yl)-N-(3-(fluoromethyl) oxetan-3-yl)-4-(4-isobutyrylpiperazin-1-yl)-1H-indazole-6-sulfonamide: LCMS (ESI, m/z): 564.25[M+H]$^+$. $^1$HNMR (300 MHz, DMSO-d6) δ=8.89 (br, 1H), 8.84 (s, 1H), 8.43 (s, 1H), 7.12 (s, 1H), 4.68 (s, 1H), 4.61-4.48 (m, 3H), 4.33 (d, J=6.9 Hz, 2H), 3.77-3.74 (m, 4H), 3.43-3.32 (m, 4H), 2.97-2.89 (m, 1H), 2.59-2.51 (m, 1H), 1.28-1.25 (m, 2H), 1.24-1.21 (m, 2H), 1.06 (d, J=6.6 Hz, 6H). 2-(5-cyclopropyl-1,3,4-thiadiazol-2-yl)-N-(3-(fluoromethyl)oxetan-3-yl)-4-(4-isobutyrylpiperazin-1-yl)-2H-indazole-6-sulfonamide $^1$H NMR (300 MHz, DMSO-d6) δ 9.52 (s, 1H), 8.69 (br, 1H), 7.65 (s, 1H), 6.72 (s, 1H), 4.68 (s, 1H), 4.59-4.50 (m, 3H), 4.33 (d, J=6.6 Hz, 2H), 3.76-3.71 (m, 4H), 3.38-3.29 (m, 4H), 2.99-2.90 (m, 1H), 2.73-2.50 (m, 1H), 1.35-1.28 (m, 2H), 1.21-1.11 (m, 2H), 1.06 (d, J=6.6 Hz, 6H).

Example 44: N-(3-(fluoromethyl)oxetan-3-yl)-4-(4-isobutyrylpiperazin-1-yl)-1-(1,3,4-thiadiazol-2-yl)-1H-indazole-6-sulfonamide

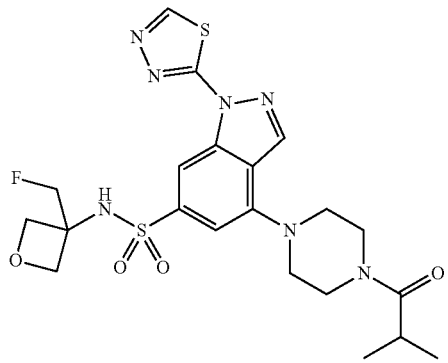 [SMILES: CC(C)C(=O)N1CCN(c2cc(S(=O)(=O)NC3(CF)COC3)cc3c2cnn3-c2nncs2)CC1]

A solution of 1-{4-[6-bromo-1-(1,3,4-thiadiazol-2-yl)indazol-4-yl]piperazin-1-yl}-2-methylpropan-1-one (200 mg, 0.459 mmol, 1.00 equiv) in DMSO (5 mL) was treated with potassium metabisulfite (204.28 mg, 0.918 mmol, 2.00 equiv), tetraethylazanium boranuide (106.20 mg, 0.505 mmol, 1.10 equiv), sodium formate (93.73 mg, 1.377 mmol, 3.00 equiv), triphenylphosphine (32.42 mg, 0.124 mmol, 0.30 equiv), PPh$_3$ (36.15 mg, 0.138 mmol, 0.30 equiv), 1,10-phenanthroline (24.84 g, 0.138 mmol, 0.30 equiv) and Palladium acetate (10.31 mg, 0.046 mmol, 0.10 equiv). The mixture was stirred for 4 h at 70° C. under nitrogen atmosphere. To the above was added 3-(fluoromethyl)oxetan-3-amine (144.87 mg, 1.377 mmol, 3.00 equiv) and pyridine (2 mL) in portions. Then NBS (245.30 mg, 1.377 mmol, 3.00 equiv) in THF (5 mL) was added dropwise at 0° C. The resulting mixture was stirred for 1 h at 25° C. under nitrogen atmosphere. The reaction was monitored by LCMS. The reaction mixture was diluted with water (30 mL). The resulting mixture was extracted with EA (3×30 mL). The combined organic layers were washed with brine (2×50 mL), dried over anhydrous Na$_2$SO$_4$. The resulting mixture was concentrated under reduced pressure. The crude product was purified by Prep-HPLC with the following conditions (Column: XBridge Prep OBD C18 Column, 30*150 mm, 5 μm; Mobile Phase A: Water (10 mmol/L NH$_4$HCO$_{3+0.1}$% NH$_3$·H$_2$O), Mobile Phase B: ACN; Flow rate: 60 mL/min; Gradient: 24% B to 54% B in 7 min, 54% B; Wave Length: 220 nm; RT1(min): 5.23; Injection Volume: 1 mL; Number Of Runs: 3) to afford N-(3-(fluoromethyl)oxetan-3-yl)-4-(4-isobutyrylpiperazin-1-yl)-1-(1,3,4-thiadiazol-2-yl)-1H-indazole-6-sulfonamide (22.1 g, 9.15%) as a white solid. LCMS (ESI, m/z): 524.05. $^1$HNMR (300 MHz, DMSO-d6) δ=9.45 (s, 1H), 8.94-8.88 (m, 2H), 8.53 (s, 1H), 7.15 (s, 1H), 4.70 (s, 1H), 4.58-4.54 (m, 3H), 4.35 (d, J=6.9 Hz, 2H), 3.85-3.76 (m, 4H), 3.48-3.41 (s, 4H), 2.97-2.93 (m, 1H), 1.05 (d, J=6.6 Hz, 6H).

Example 45: 4-(4-isobutyrylpiperazin-1-yl)-1-(5-methyl-1,3,4-thiadiazol-2-yl)-N-(3-methyloxetan-3-yl)-1H-indazole-6-sulfonamide

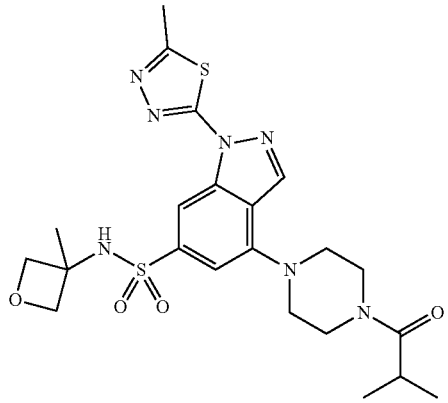 [SMILES: Cc1nnc(-n2ncc3c(N4CCN(C(=O)C(C)C)CC4)cc(S(=O)(=O)NC4(C)COC4)cc32)s1]

A mixture of 1-{4-[6-bromo-1-(5-methyl-1,3,4-thiadiazol-2-yl)indazol-4-yl]piperazin-1-yl}-2-methylpropan-1-one (120 mg, 0.267 mmol, 1 equiv), potassium metabisulfite (118.74 mg, 0.534 mmol, 2 equiv), tetraethylazanium bromide (61.73 mg, 0.294 mmol, 1.1 equiv), sodium formate (54.48 mg, 0.801 mmol, 3 equiv), PPh₃ (21.01 mg, 0.080 mmol, 0.3 equiv), phen (14.44 mg, 0.080 mmol, 0.3 equiv) and Pd(AcO)₂ (6.00 mg, 0.027 mmol, 0.1 equiv) in DMSO (2 mL) was stirred for 4 h at 70° C. under nitrogen atmosphere. To the above mixture was added 3-methyloxetan-3-amine (93.06 mg, 1.068 mmol, 4 equiv), pyridine (0.5 mL, 0.006 mmol, 0.01 equiv) and NBS (190.12 mg, 1.068 mmol, 4 equiv) in THF (1 mL) dropwise at 0° C. The resulting mixture was stirred for additional 1 h at room temperature. The reaction was monitored with LCMS. The resulting mixture was quenched with water (30 mL). The aqueous layer was extracted with EA (3×30 mL). The combined organic layers were washed by brine (50 mL), dried over anhydrous Na₂SO₄. After filtration, the filtrate was concentrated under reduced pressure. The product was purified by Prep-HPLC with the following conditions (Column: XBridge Shield RP18 OBD Column, 30*150 mm, 5 μm; Mobile Phase A: Water (10 mmol/L NH4HCO3+0.1% NH3·H2O), Mobile Phase B: ACN; Flow rate: 60 mL/min; Gradient: 26% B to 56% B in 7 min, 56% B; Wave Length: 254 nm; RT1(min): 6; Injection Volume: 1.1 mL; Number Of Runs: 2) to afford 4-(4-isobutyrylpiperazin-1-yl)-1-(5-methyl-1,3,4-thiadiazol-2-yl)-N-(3-methyloxetan-3-yl)-1H-indazole-6-sulfonamide (26.6 mg, 19.14%) as a white solid. LCMS (ESI, m/z): 520.15[M+H]⁺. 1H NMR (400 MHz, DMSO-d6) δ=8.84 (s, 1H), 8.60 (s, 1H), 8.45 (s, 1H), 7.11 (s, 1H), 4.57 (d, J=6.0 Hz, 2H), 4.12 (d, J=6.4 Hz, 2H), 3.79-3.75 (m, 4H), 3.51-3.33 (m, 4H), 2.98-2.90 (m, 1H), 2.75 (s, 3H), 1.44 (s, 3H), 1.06 (d, J=6.8 Hz, 6H).

Example 46: 4-(4-isobutyrylpiperazin-1-yl)-N-(3-methyloxetan-3-yl)-1-(1,3,4-thiadiazol-2-yl)-1H-indazole-6-sulfonamide

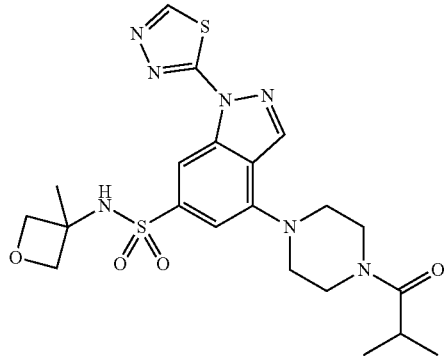 [SMILES: CC(C)C(=O)N1CCN(c2cc(S(=O)(=O)NC3(C)COC3)cc3c2cnn3-c2nncs2)CC1]

Step 1: Synthesis of 1-{4-[6-bromo-1-(1,3,4-thiadiazol-2-yl)indazol-4-yl]piperazin-1-yl}-2-methylpropan-1-one To a stirred solution of 1-[4-(6-bromo-1H-indazol-4-yl)piperazin-1-yl]-2-methylpropan-1-one (1 g, 2.847 mmol, 1.00 equiv) in DMF (5 mL) was added 2-bromo-1,3,4-thiadiazole (0.70 g, 4.271 mmol, 1.50 equiv) and Cs₂CO₃ (1.86 g, 5.694 mmol, 2.00 equiv) in portions. The resulting mixture was stirred for 2 h at 25° C. The reaction was monitored by LCMS. The reaction mixture was diluted with water (100 mL). The resulting mixture was extracted with EA (3×100 mL). The combined organic layers were washed with brine (2×100 mL), dried over anhydrous Na₂SO₄. The resulting mixture was concentrated under reduced pressure. The crude product was purified by silica gel column chromatography, eluted with PE/EA (3:1) to afford 1-{4-[6-bromo-1-(1,3,4-thiadiazol-2-yl)indazol-4-yl]piperazin-1-yl}-2-methylpropan-1-one (400 mg, 32%) and 1-(4-(6-bromo-2-(1,3,4-thiadiazol-2-yl)-2H-indazol-4-yl)piperazin-1-yl)-2-methylpropan-1-one (200 mg, 16.00%) as a white solid. LCMS (ESI, m/z): 435.34[M+H]⁺.

Step 2: Synthesis of 4-(4-isobutyrylpiperazin-1-yl)-N-(3-methyloxetan-3-yl)-1-(1,3,4-thiadiazol-2-yl)-1H-indazole-6-sulfonamide A solution of 1-{4-[6-bromo-1-(1,3,4-thiadiazol-2-yl)indazol-4-yl]piperazin-1-yl}-2-methylpropan-1-one (150 mg, 0.345 mmol, 1 equiv) in DMSO (5 mL) was treated with potassium metabisulfite (153.21 mg, 0.690 mmol, 2 equiv), tetraethylazanium bromide (79.65 mg, 0.380 mmol, 1.1 equiv), sodium formate (70.30 mg, 1.035 mmol, 3 equiv), PPh₃ (27.11 mg, 0.103 mmol, 0.3 equiv), 1,10-phenanthroline (18.63 mg, 0.103 mmol, 0.3 equiv) and palladium acetate (7.74 mg, 0.034 mmol, 0.1 equiv). The mixture was stirred for 4 h at 70° C. under nitrogen atmosphere. To the above was added 3-methyloxetan-3-amine (90.06 mg, 1.035 mmol, 3 equiv) in pyridine (2 mL) in portions under nitrogen atmosphere. Then 1-bromopyrrolidine-2,5-dione (183.98 mg, 1.035 mmol, 3 equiv) in THF (5 mL) was added dropwise at 0° C. under nitrogen atmosphere. The resulting mixture was stirred for 1 h at 25° C. under nitrogen atmosphere. The resulting mixture was concentrated under reduced pressure. The crude product was purified by Prep- HPLC with the following conditions (Column: XBridge Prep Phenyl OBD Column, 19*100 mm, 5 μm; Mobile Phase A: Water (10 mmol/L NH₄HCO₃), Mobile Phase B: ACN; Flow rate: 60 mL/min; Gradient: 22% B to 52% B in 7 min, 52% B; Wave Length: 254 nm; RT1(min): 5.88; Injection Volume: 2 mL; Number Of Runs: 1) to afford 4-(4-isobutyrylpiperazin-1-yl)-N-(3-methyloxetan-3-yl)-1-(1,3,4-thiadiazol-2-yl)-1H-indazole-6-sulfonamide (24.1 mg, 13.83%) as an off-white solid. LCMS (ESI, m/z): 506.10[M+H]⁺. ¹H NMR (400 MHz, DMSO-d6) δ 9.45 (s, 1H), 8.88 (s, 1H), 8.61 (s, 1H), 8.52 (s, 1H), 7.12 (s, 1H), 4.57 (d, J=6.0 Hz, 2H), 4.13 (d, J=6.4 Hz, 2H), 3.87-3.71 (m, 4H), 3.52-3.43 (m, 4H), 2.98-2.91 (m, 1H), 1.43 (s, 3H), 1.05 (d, J=6.8 Hz, 6H).

Example 47: N-(3-(fluoromethyl)oxetan-3-yl)-4-(4-isobutyrylpiperazin-1-yl)-1-(5-vinyl-1,3,4-thiadiazol-2-yl)-1H-indazole-6-sulfonamide

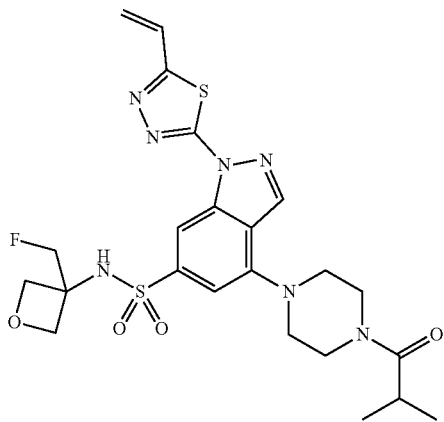 [SMILES: C=Cc1nnc(-n2ncc3c(N4CCN(C(=O)C(C)C)CC4)cc(S(=O)(=O)NC4(CF)COC4)cc32)s1]

Step 1: Synthesis of 1-[4-(6-bromo-{[2-(trimethylsilyl)ethoxy]methyl} indazol-4-yl)piperazin-1-yl]-2-methylpropan-1-one To a solution of 1-[4-(6-bromo-1H-indazol-4-yl)piperazin-1-yl]-2-methylpropan-1-one (1 g, 2.847 mmol, 1 equiv) and DIEA (1.10 g, 8.541 mmol, 3 equiv) was added [2-(chloromethoxy)ethyl]trimethylsilane dropwise at 0° C. The resulting mixture was stirred for 2 h at 25° C. The reaction was monitored by LCMS. Then the reaction was quenched with water (100 mL). The resulting mixture was extracted with EA (3×100 mL). The combined organic layers were washed with brine (100 mL), dried over anhydrous Na₂SO₄. After filtration, the filtrate was concentrated under reduced pressure. The residue was purified by silica gel column chromatography, eluted with PE/EA (1:1) to afford 1-[4-(6-bromo-1-{[2-(trimethylsilyl)ethoxy]methyl} indazol-4-yl)piperazin-1-yl]-2-methylpropan-1-one (950 mg, 69.30%) as a white solid. LCMS (ES, m/z): 481, 483 [M+H]⁺.

Step 2: Synthesis of 4-[4-(2-methylpropanoyl)piperazin-1-yl]-1-{[2-(trimethylsilyl)ethoxy]methyl}indazole-6-sulfonylfluoride A mixture of 1-[4-(6-bromo-1-{[2-(trimethylsilyl)ethoxy]methyl}indazol-4-yl)piperazin-1-yl]-2-methylpropan-1-one (880 mg, 1.828 mmol, 1.00 equiv), potassium metabisulfite (811.45 mg, 3.656 mmol, 2 equiv), TEAB (422.17 mg, 2.011 mmol, 1.1 equiv), sodium formate (372.83 mg, 5.484 mmol, 3 equiv), palladium acetate (40.94 mg, 0.183 mmol, 0.1 equiv) and o-phenanthroline (98.69 mg, 0.548 mmol, 0.3 equiv) in DMSO (10 mL) was stirred for 4 h at 70° C. under nitrogen atmosphere. Then to the above mixture was added N-(benzenesulfonyl)-N-fluorobenzenesulfonamide (576.29 mg, 1.828 mmol, 1.00 equiv) in THF (2 mL) dropwise over 2 min at 0° C. The resulting mixture was stirred for additional 25° C. at 2 h. The reaction was monitored by LCMS. Then, the reaction was quenched with water (40 mL). The resulting mixture was extracted with EA (3×50 mL). The combined organic layers were washed with brine (100 mL), dried over anhydrous Na₂SO₄. After filtration, the filtrate was concentrated under reduced pressure. The residue was purified by silica gel column chromatography, eluted with PE/EA (1:1) to afford 4-[4-(2-methylpropanoyl)piperazin-1-yl]-1-{[2-(trimethylsilyl)ethoxy]methyl}indazole-6-sulfonyl fluoride (770 mg, 86.87%) as an off-white solid. LCMS (ES, m/z): 485.30[M+H]⁺.

Step 3: Synthesis of N-[3-(fluoromethyl)oxetan-3-yl]-4-[4-(2-methylpropanoyl)piperazin-1-yl]-1-{[2-(trimethylsilyl)ethoxy]methyl}indazole-6-sulfonamide A solution of 4-[4-(2-methylpropanoyl)piperazin-1-yl]-1-{[2-(trimethylsilyl)ethoxy]methyl}indazole-6-sulfonyl fluoride (770 mg, 1.589 mmol, 1 equiv), HOBT (214.68 mg, 1.589 mmol, 1 equiv), DIEA (1437.38 mg, 11.123 mmol, 7 equiv) and 3-(fluoromethyl)oxetan-3-amine (333.99 mg, 3.178 mmol, 2 equiv) in DMSO (8 mL) was stirred for 2 h at 25° C. The reaction was monitored by LCMS. Then, the reaction was quenched with water (25 mL). The resulting mixture was extracted with EA (3×50 mL). The combined organic layers were washed with brine (50 mL), dried over anhydrous Na₂SO₄. After filtration, the filtrate was concentrated under reduced pressure. The residue was purified by silica gel column chromatography, eluted with PE/EA (1:3) to afford N-[3-(fluoromethyl)oxetan-3-yl]-4-[4-(2-methylpropanoyl)piperazin-1-yl]-1-{[2-(trimethylsilyl)ethoxy]methyl}indazole-6-sulfonamide (530 mg, 58.55%) as an off-white solid. LCMS (ES, m/z): 570.35 [M+H]⁺.

Step 4: Synthesis of N-[3-(fluoromethyl)oxetan-3-yl]-4-[4-(2-methylpropanoyl)piperazin-1-yl]-1H-indazole-6-sulfonamide A mixture of N-[3-(fluoromethyl)oxetan-3-yl]-4-[4-(2-methylpropanoyl)piperazin-1-yl]-1-{[2-(trimethylsilyl)ethoxy]methyl}indazole-6-sulfonamide (530 mg, 0.930 mmol, 1 equiv) and TFA (2 mL, 24.686 mmol, 26.54 equiv) in DCM (1 mL, 15.731 mmol, 16.91 equiv) was stirred at 0° C. for 2 h. The reaction was monitored by LCMS. The resulting mixture was concentrated under reduced pressure. This resulted in N-[3-(fluoromethyl)oxetan-3-yl]-4-[4-(2-methylpropanoyl)piperazin-1-yl]-1H-indazole-6-sulfonamide (400 mg, crude) as a white solid. LCMS (ES, m/z): 440.20 [M+H]⁺.

Step 5: Synthesis of 1-(5-bromo-1,3,4-thiadiazol-2-yl)-N-[3-(fluoromethyl)oxetan-3-yl]-4-[4-(2-methyl propanoyl)piperazin-1-yl]indazole-6-sulfonamide and 2-(5-bromo-1,3,4-thiadiazol-2-yl)-N-(3-(fluoromethyl) oxetan-3-yl)-4-(4-isobutyrylpiperazin-1-yl)-2H-indazole-6-sulfonamide Into a mixture of N-[3-(fluoromethyl)oxetan-3-yl]-4-[4-(2-methylpropanoyl)piperazin-1-yl]-1H-indazole-6-sulfonamide (230 mg, 0.523 mmol, 1 equiv) and K₂CO₃ (216.97 mg, 1.569 mmol, 3 equiv) in DMF (5 mL) was added dibromo-1,3,4-thiadiazole (153.16 mg, 0.628 mmol, 1.2 equiv). The resulting mixture was stirred for additional 16 h at 60° C. The reaction was monitored by LCMS. Then, the reaction was quenched with water (50 mL). The resulting mixture was extracted with EA (3×50 mL). The combined organic layers were washed with brine (2×50 mL), dried over anhydrous Na₂SO₄. After filtration, the filtrate was concentrated under reduced pressure. The residue was purified by silica gel column chromatography, eluted with PE/EA (1:1) to afford the mixture of 1-(5-bromo-1,3,4-thiadiazol-2-yl)-N-[3-(fluoromethyl)oxetan-3-yl]-4-[4-(2-methyl propanoyl)piperazin-1-yl]indazole-6-sulfonamide and 2-(5-bromo-1,3,4-thiadiazol-2-yl)-N-(3-(fluoromethyl)oxetan-3-yl)-4-(4-isobutyrylpiperazin-1-yl)-2H-indazole-6-sulfonamide (61 mg, 19.35%) as an off-white solid. LCMS (ES, m/z): 601, 603 [M+H]⁺.

Step 6: Synthesis of N-(3-(fluoromethyl)oxetan-3-yl)-4-(4-isobutyrylpiperazin-1-yl)-1-(5-vinyl-1,3,4-thiadiazol-2-yl)-1H-indazole-6-sulfonamide A mixture of 1-(5-bromo-1,3,4-thiadiazol-2-yl)-N-[3-(fluoromethyl)oxetan-3-yl]-4-[4-(2-methylpropanoyl)piperazin-1-yl]indazole-6-sulfonamide (30 mg, 0.050 mmol, 1 equiv) and 2-(5-bromo-1,3,4-thiadiazol-2-yl)-N-(3-(fluoromethyl)oxetan-3-yl)-4-(4-isobutyrylpiperazin-1-yl)-2H-indazole-6-sulfonamide (30 mg, 0.050 mmol, 1 equiv) and 2-ethenyl-4,4,5,5-tetramethyl-1,3,2-dioxaborolane (15.34 mg, 0.100 mmol, 2 equiv), Pd(dppf)Cl₂ (3.64 mg, 0.005 mmol, 0.1 equiv) and Na₂CO₃ (15.83 mg, 0.150 mmol, 3 equiv) in 1,4-dioxane (2 mL) and H₂O (0.5 mL) was stirred for 16 h at 90° C. under nitrogen atmosphere. The reaction was monitored by LCMS. Then, the reaction was quenched with water (20 mL). The resulting mixture was washed with EA (3×20 mL). The filtrate was concentrated under reduced pressure. The residue was purified by Prep-TLC, eluted with PE/EA (1:1). The crude product was purified by Prep-HPLC with the following conditions (Column: Agilent Poroshell HPH-C18; Mobile Phase A: Water (10 mmol/L NH₄HCO₃), Mobile Phase B: ACN; Flow rate: 25 mL/min; Gradient: 32% B to 58% B in 7 min; Wave Length: 254 nm/220 nm; RT1(min): 6.31) to afford N-(3-(fluoromethyl)oxetan-3-yl)-4-(4-isobutyrylpiperazin-1-yl)-1-(5-vinyl-1,3,4-thiadiazol-2-yl)-1H-indazole-6-sulfonamide (3.1 mg, 11.16%) as a white solid and 2-(5-ethenyl-1,3,4-thiadiazol-2-yl)-N-[3-(fluoromethyl)oxetan-3-yl]-4-[4-(2-methylpropanoyl)piperazin-1-yl]indazole-6-sulfonamide (1.6 mg, 8.62%) as a yellow solid. N-(3-(fluoromethyl)oxetan-3-yl)-4-(4-isobutyrylpiperazin-1-yl)-1-(5-vinyl-1,3,4-thiadiazol-2-yl)-1H-indazole-6-sulfonamide: LCMS (ES, m/z): 550.15 [M+H]⁺. Rt 0.886 min. ¹H NMR (400 MHz, Chloroform-d) δ=8.82 (s, 1H), 8.26 (s, 1H), 7.19 (s, 1H), 7.09-7.01 (m, 1H), 6.07-6.01 (m, 1H), 5.84 (d, J=8.8 Hz, 1H), 5.40 (s, 1H), 4.81-4.88 (m, 3H), 4.73 (s, 1H), 4.45 (d, J=7.2 Hz, 2H), 3.95-3.76 (m, 4H), 3.46-3.34 (m, 4H), 2.89-2.81 (m, 1H), 1.18 (d, J=6.8 Hz, 6H). 2-(5-ethenyl-1,3,4-thiadiazol-2-yl)-N-[3-(fluoromethyl)oxetan-3-yl]-4-[4-(2-methylpropanoyl) piperazin-1-yl]indazole-6-sulfonamide: LCMS (ES, m/z): 550.10 [M+H]⁺. Rt 0.865 min. ¹H NMR (400 MHz, Chloroform-d) δ=9.03 (s, 1H), 7.92 (s, 1H), 7.09-7.01 (m, 1H), 6.71 (s, 1H), 6.14-6.09 (m, 1H), 5.92-5.86 (m, 1H), 5.16 (s, 1H), 4.88-4.81 (m, 3H), 4.73 (s, 1H), 4.45 (d, J=6.8 Hz, 2H), 3.92-3.75 (m, 4H), 3.43-3.36 (m, 4H), 2.89-2.81 (m, 1H), 1.19 (d, J=6.8 Hz, 6H).

Example 48: 1-(5-(difluoromethyl)-1,3,4-thiadiazol-2-yl)-N-(3-methyloxetan-3-yl)-4-(4-methylpiperazin-1-yl)-1H-indazole-6-sulfonamide

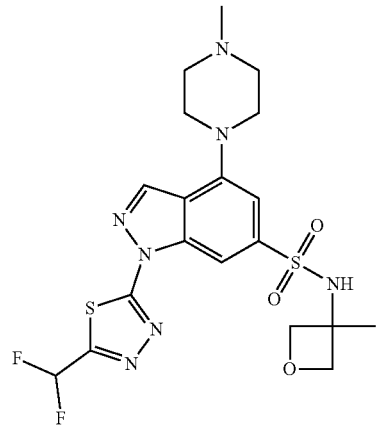 [SMILES: CN1CCN(c2cc(S(=O)(=O)NC3(C)COC3)cc3c2cnn3-c2nnc(C(F)F)s2)CC1]

Step 1: Synthesis of 4-bromo-2-fluoro-6-(4-methylpiperazin-1-yl) benzaldehyde

A mixture of 4-bromo-2,6-difluorobenzaldehyde (1 g, 4.525 mmol, 1 equiv), piperazine, 1-methyl-(0.45 g, 4.525 mmol, 1 equiv) and K₂CO₃ (1.56 g, 11.313 mmol, 2.5 equiv) in DMF (15 mL) was stirred at 80° C. for 2 h. The reaction was monitored by LCMS. The mixture was allowed to cool down to room temperature. The resulting mixture was diluted with H₂O (100 mL). The resulting mixture was extracted with EA (3×100 mL). The combined organic layers were washed with brine (2×100 mL), dried over anhydrous Na₂SO₄. After filtration, the filtrate was concentrated under reduced pressure to afford 4-bromo-2-fluoro-6-(4-methylpiperazin-1-yl) benzaldehyde (1.3 g, crude) as a white solid. LCMS (ESI, m/z): 301, 303[M+H]⁺

Step 2: Synthesis of 6-bromo-4-(4-methylpiperazin-1-yl)-1H-indazole

A mixture of 4-bromo-2-fluoro-6-(4-methylpiperazin-1-yl) benzaldehyde (1.3 g, 4.101 mmol, 1 equiv) and hydrazinium hydroxide solution (0.53 g, 16.404 mmol, 4 equiv) in DMSO (12 mL) was stirred at 100° C. for 16 h. The reaction was monitored by LCMS. The mixture was allowed to cool down to room temperature. The resulting mixture was diluted with H₂O (100 mL). The resulting mixture was extracted with EA (3×100 mL). The combined organic layers were washed with brine (2×100 mL), dried over anhydrous Na₂SO₄. After filtration, the filtrate was concentrated under reduced pressure to afford 6-bromo-4-(4-methylpiperazin-1-yl)-1H-indazole (1.3 g, crude) as a white solid. LCMS (ESI, m/z): 295, 297[M+H]⁺

Step 3: Synthesis of 6-bromo-1-[5-(difluoromethyl)-1,3,4-thiadiazol-2-yl]-4-(4-methylpiperazin-1-yl) indazole A mixture of 6-bromo-4-(4-methylpiperazin-1-yl)-1H-indazole (1.3 g, 4.404 mmol, 1 equiv), 2-bromo-5-(difluoromethyl)-1,3,4-thiadiazole (1.14 g, 5.285 mmol, 1.2 equiv) and Cs₂CO₃ (4.30 g, 13.212 mmol, 3 equiv) in DMF (15 mL) was stirred at 70° C. for 2 h. The reaction was monitored by LCMS. The mixture was allowed to cool down to room temperature. The resulting mixture was diluted with H₂O (100 mL). The resulting mixture was extracted with EA (3×100 mL). The combined organic layers were washed with brine (2×100 mL), dried over anhydrous Na₂SO₄. After filtration, the filtrate was concentrated under reduced pressure. The residue was purified by silica gel column chromatography, eluted with DCM/MeOH (10:1) to afford 6-bromo-1-[5-(difluoromethyl)-1,3,4-thiadiazol-2-yl]-4-(4-methylpiperazin-1-yl)indazole (708 mg, 28.84%) as a black solid LCMS (ESI, m/z): 429, 431[M+H]⁺.

Step 4: Synthesis of 1-[5-(difluoromethyl)-1,3,4-thiadiazol-2-yl]-N-(3-methyloxetan-3-yl)-4-(4-methylpiperazin-1-yl)indazole-6-sulfonamide To a stirred solution of 6-bromo-1-[5-(difluoromethyl)-1,3,4-thiadiazol-2-yl]-4-(4-methylpiperazin-1-yl)indazole (200 mg, 0.466 mmol, 1 equiv) in DMSO (3 mL) was added dipotassium 1-oxo-1lambda6-disulfene-1,1-bis(olate) (177.34 mg, 0.932 mmol, 2 equiv), tetraethylazanium boranuide (74.36 mg, 0.513 mmol, 1.1 equiv), sodium formate (95.05 mg, 1.398 mmol, 3 equiv), PPh₃ (36.66 mg, 0.140 mmol, 0.3 equiv), phen (25.19 mg, 0.140 mmol, 0.3 equiv) and Pd(AcO)₂ (10.46 mg, 0.047 mmol, 0.1 equiv) at room temperature under nitrogen atmosphere. The resulting mixture was stirred for 4 h at 70° C. under nitrogen atmosphere. The mixture was allowed to cool down to room temperature. To the above mixture was added the solution of 3-methyloxetan-3-amine (81.18 mg, 0.932 mmol, 2 equiv) and NBS (331.68 mg, 1.864 mmol, 4 equiv) in THF (2 mL) dropwise at room temperature. The resulting mixture was stirred for additional 1 h at room temperature. The reaction was monitored by LCMS. The resulting mixture was diluted with H₂O (30 mL). The resulting mixture was extracted with EtOAc (3×30 mL). The combined organic layers were washed with brine (2×50 mL), dried over anhydrous Na₂SO₄. After filtration, the filtrate was concentrated under reduced pressure. The residue was purified by silica gel column chromatography, eluted with DCM/MeOH (10:1). The crude product was purified by Prep-HPLC with the following conditions (Column: XBridge Shield RP 18 OBD Column, 30*150 mm, 5 μm; Mobile Phase A: Water (10 mmol/L NH4HCO3+0.1% NH3·H2O), Mobile Phase B: ACN; Flow rate: 60 mL/min mL/min; Gradient: 30% B to 60% B in 7 min; Wave Length: 254 nm nm; RT1(m): 6.32) to afford 1-[5-(difluoromethyl)-1,3,4-thiadiazol-2-yl]-N-(3-methyloxetan-3-yl)-4-(4-methylpiperazin-1-yl)indazole-6-sulfonamide (2.1 mg, 1.720) as a yellow solid. LCMS (ESI, m-z): 500 [M+H]⁺. ¹H NMR (300 MHz, Chloroform-d) δ=8.69 (s, 1H), 8.32 (s, 1H), 7.26 (s, 1H), 7.21-6.82 (m, 1H), 5.30 (s, 1H), 4.75 (d, J=6.3 Hz, 2H), 4.35 (d, J=6.0 Hz, 2H), 3.51-3.42 (m, 4H), 2.73-2.61 (m, 4H), 2.42 (s, 3H), 1.67 (s, 3H).

Examples 49-81 were prepared in the same manner as described for other compounds provided herein.

| Ex. No. | Compound Name | Compound Structure | Characterization Data |
|---|---|---|---|
| 49 | 1,3-diethyl-N-(3-methylazetidin-3-yl)-2,4-dioxo-1,2,3,4-tetrahydroquinazoline-6-sulfonamide | 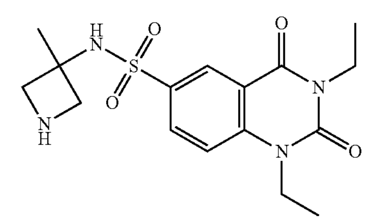 [SMILES: CCn1c(=O)c2cc(S(=O)(=O)NC3(C)CNC3)ccc2n(CC)c1=O] | LCMS (ES, m/z): 367.10[M + H]+. RT: 0.578 min. ¹H NMR (300 MHz, DMSO-d6) δ = 8.44 (d, J = 2.3 Hz, 1H), 8.08 (dd, J = 8.9, 2.4 Hz, 1H), 7.69 (d, J = 9.0 Hz, 1H), 4.17 (q, J = 7.0 Hz, 2H), 3.99 (q, J = 7.0 Hz, 2H), 3.52 (d, J = 7.6 Hz, 2H), 2.96 (d, J = 7.6 Hz, 2H), 1.38 (s, 3H), 1.28-1.13 (m, 6H). |
| 50 | 1,3-diethyl-N-(1-methylcyclopentyl)-2,4-dioxo-1,2,3,4-tetrahydroquinazoline-6-sulfonamide | 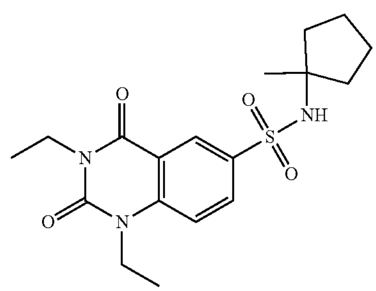 | LCMS (ES, m/z): 298.10[M + H]+. RT: 1.178 min. ¹H NMR (300 MHz, DMSO-d6) δ = 8.46 (d, J = 2.3 Hz, 1H), 8.11 (dd, J = 8.9, 2.4 Hz, 1H), 7.76-7.65 (m, 2H), 4.17 (q, J = 7.0 Hz, 2H), 3.99 (q, J = 7.0 Hz, 2H), 1.80 (dd, J = 12.4, 6.0 Hz, 2H), 1.54-1.38 (m, 4H), 1.42-1.29 (m, 2H), 1.24-1.10 (m, 9H). |

-continued

| Ex. No. | Compound Name | Compound Structure | Characterization Data |
|---|---|---|---|
| 51 | N-((1S,2S)-1-cyano-2-vinylcyclopropyl)-1,3-diethyl-2,4-dioxo-1,2,3,4-tetrahydroquinazoline-6-sulfonamide (stereochemistry assumed) | 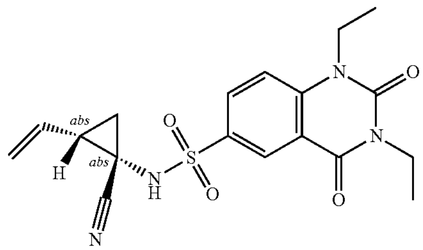 [SMILES: C=C[C@@H]1C[C@]1(C#N)NS(=O)(=O)c1ccc2c(c1)c(=O)n(CC)c(=O)n2CC] | LCMS (ESI, m/z): 389.15 [M + H]+, RT: 0.853 min $^1$H NMR (400 MHz, Chloroform-d) δ = 8.76 (s, 1H), 8.23-8.06 (m, 1H), 7.36 (d, J = 9.2 Hz, 1H), 5.81 (s, 1H), 5.61-5.45 (m, 1H), 5.45-5.05 (m, 2H), 4.38-4.19(m, 2H), 4.19-4.05 (m, 2H), 2.63-2.42 (m, 1H), 2.03-1.83 (m, 1H), 1.55-1.45 (m, 1H), 1.37 (t, J = 6.8 Hz, 3H), 1.30 (t, J = 7.2 Hz, 3H). |
| 52 | N-((1R,2S)-1-cyano-2-vinylcyclopropyl)-1,3-diethyl-2,4-dioxo-1,2,3,4-tetrahydroquinazoline-6-sulfonamide (stereochemistry assumed) | 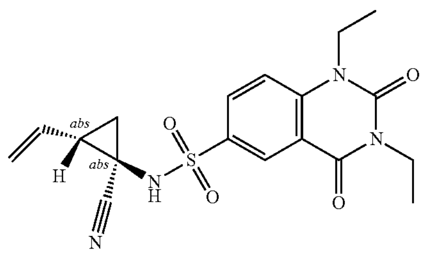 [SMILES: C=C[C@@H]1C[C@@]1(C#N)NS(=O)(=O)c1ccc2c(c1)c(=O)n(CC)c(=O)n2CC] | LCMS (ESI, m/z): 389.15 [M + H]+, RT: 0.855 min $^1$H NMR (400 MHz, Chloroform-d) δ = 8.77 (s, 1H), 8.21-8.05 (m, 1H), 7.36 (d, J = 8.8 Hz, 1H), 5.79 (s, 1H), 5.63-5.48 (m, 1H), 5.48-5.21 (m, 2H), 4.36-4.19(m, 2H), 4.19-3.98 (m, 2H), 2.63-2.41 (m, 1H), 1.98-1.81 (m, 1H), 1.52-1.43 (m, 1H), 1.37 (t, J = 7.2 Hz, 3H), 1.30(t, J = 7.2 Hz, 3H). |
| 53 | N-((1S,2R)-1-cyano-2-ethylcyclopropyl)-1,3-diethyl-2,4-dioxo-1,2,3,4-tetrahydroquinazoline-6-sulfonamide (stereochemistry assumed) | 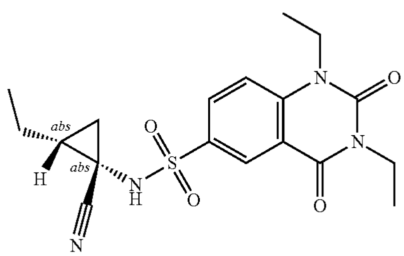 [SMILES: CC[C@@H]1C[C@]1(C#N)NS(=O)(=O)c1ccc2c(c1)c(=O)n(CC)c(=O)n2CC] | LCMS (ES, m/z): 391.15 [M + H]+, RT: 0.874 min. $^1$H NMR (400 MHz, Chloroform-d) δ = 8.77 (s, 1H), 8.26-8.18 (m, 1H), 7.37 (d, J = 8.8 Hz, 1H), 5.78 (s, 1H), 4.32-4.21 (m, 2H), 4.21-4.10 (m, 2H), 1.88-1.73 (m, 1H), 1.73-1.65 (m, 1H), 1.59-1.42 (m, 2H), 1.37 (t, J = 7.2 Hz, 3H), 1.30 (t, J = 7.2 Hz, 3H), 1.21-1.06 (m, 4H). |
| 54 | N-((1R,2S)-1-cyano-2-ethylcyclopropyl)-1,3-diethyl-2,4-dioxo-1,2,3,4-tetrahydroquinazoline-6-sulfonamide (stereochemistry assumed) | 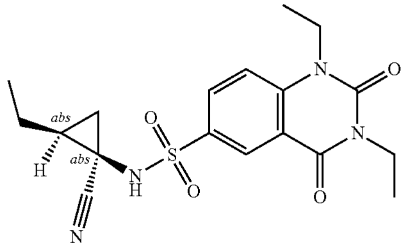 [SMILES: CC[C@H]1C[C@@]1(C#N)NS(=O)(=O)c1ccc2c(c1)c(=O)n(CC)c(=O)n2CC] | LCMS (ES, m/z): 391.15 [M + H]+, RT: 0.872 min. $^1$H NMR (400 MHz, Chloroform-d) δ = 8.77 (s, 1H), 8.23-8.16 (m, 1H), 7.37 (d, J = 8.8 Hz, 1H), 5.83 (s, 1H), 4.29-4.19 (m, 2H), 4.19-4.10 (m, 2H), 1.88-1.75 (m, 1H), 1.74-1.65 (m, 1H), 1.58-1.40 (m, 2H), 1.37 (t, J = 7.2 Hz, 3H), 1.29 (t, J = 7.2 Hz, 3H), 1.18-1.06 (m, 4H). |

-continued

| Ex. No. | Compound Name | Compound Structure | Characterization Data |
|---|---|---|---|
| 55 | 1,3-diethyl-N-((1S,2S)-1-methyl-2-vinylcyclopropyl)-2,4-dioxo-1,2,3,4-tetrahydroquinazoline-6-sulfonamide (stereochemistry assumed) | 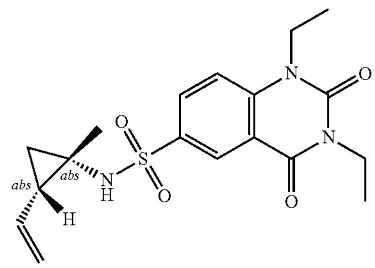 [SMILES: C=C[C@@H]1C[C@]1(C)NS(=O)(=O)c1ccc2c(c1)c(=O)n(CC)c(=O)n2CC] | LCMS (ES, m/z): 378.10 [M + H]+, RT: 1.141 min. $^1$H NMR (400 MHz, Chloroform-d) δ = 8.44 (s, 1H), 8.22-8.12 (m, 1H), 7.83 (d, J = 9.0 Hz, 1H), 4.38-4.25 (m, 2H), 4.23-4.15 (m, 2H), 3.59 (d, J = 9.3 Hz, 1H), 2.55-2.51 (m, 1H), 2.17-2.04 (m, 1H), 1.79-1.68 (m, 4H), 1.52-1.23 (m, 7H), 0.48-0.41 (m, 1H), 0.05-0.05 (m, 1H). |
| 56 | N-(1-cyano-2-(2-hydroxyethyl)cyclopropyl)-1,3-diethyl-2,4-dioxo-1,2,3,4-tetrahydroquinazoline-6-sulfonamide | 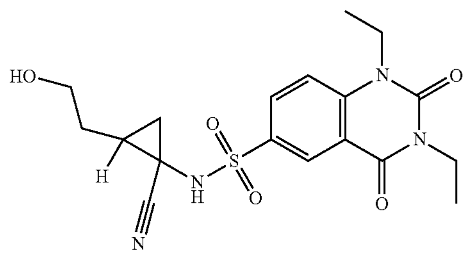 [SMILES: CCn1c(=O)c2cc(S(=O)(=O)NC3(C#N)CC3CCO)ccc2n(CC)c1=O] | LCMS (ESI, m/z): 407.15 [M + H]+, RT: 0.710 min $^1$H NMR (400 MHz, Chloroform-d) δ = 8.77 (s, 1H), 8.32-8.07 (m, 1H), 7.37 (d, J = 9.2 Hz, 1H), 6.10 (s, 1H), 4.35-3.99 (m, 4H), 3.89-3.78 (m, 2H), 2.42-2.31 (m, 1H), 2.08-1.89 (m, 2H), 1.78-1.65 (m, 1H), 1.55-1.45 (m, 1H), 1.37 (t, J = 7.2 Hz, 3H), 1.29 (t, J = 7.2 Hz, 3H), 1.21-1.13 (m, 1H). |
| 57 | N-((1S,2S)-1-cyano-2-(2-methoxyethyl)cyclopropyl)-1,3-diethyl-2,4-dioxo-1,2,3,4-tetrahydroquinazoline-6-sulfonamide (stereochemistry assumed) | 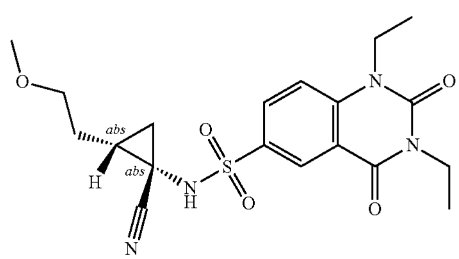 [SMILES: CCn1c(=O)c2cc(S(=O)(=O)N[C@@]3(C#N)C[C@H]3CCOC)ccc2n(CC)c1=O] | LCMS (ES, m/z): 421.10 [M + H]+; RT: 0.821 min. $^1$H NMR (300 MHz, DMSO-d6) δ = 8.47 (s, 1H), 8.10 (d, J = 8.7 Hz, 1H), 7.76 (d, J = 9.0 Hz, 1H), 4.26-4.13 (m, 2H), 4.06-3.93 (m, 2H), 3.47-3.33 (m, 2H), 3.25 (s, 3H), 1.67-1.44 (m, 3H), 1.43-1.33 (m, 1H), 1.31-1.13 (m, 7H). |
| 58 | N-((1R,2R)-1-cyano-2-(2-methoxyethyl)cyclopropyl)-1,3-diethyl-2,4-dioxo-1,2,3,4-tetrahydroquinazoline-6-sulfonamide (stereochemistry assumed) | 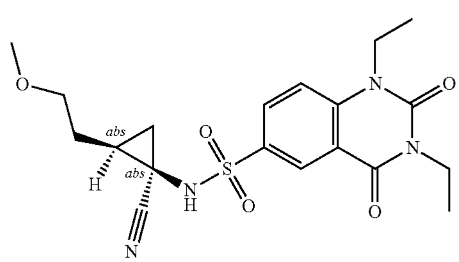 [SMILES: CCn1c(=O)c2cc(S(=O)(=O)N[C@]3(C#N)C[C@@H]3CCOC)ccc2n(CC)c1=O] | LCMS (ES, m/z): 421.10 [M + H]+; RT: 0.817 min. $^1$H NMR (300 MHz, DMSO-d6) δ = 8.48 (s, 1H), 8.10 (d, J = 9.0 Hz, 1H), 7.76 (d, J = 9.0 Hz, 1H), 4.25-4.13 (m, 2H), 4.06-3.92 (m, 2H), 3.47-3.33 (m, 2H), 3.25 (s, 3H), 1.67-1.44 (m, 3H), 1.44-1.33 (m, 1H), 1.31-1.13 (m, 7H). |

| Ex. No. | Compound Name | Compound Structure | Characterization Data |
|---|---|---|---|
| 59 | N-((2R,3S)-3-cyano-2-methyloxetan-3-yl)-1,3-diethyl-2,4-dioxo-1,2,3,4-tetrahydroquinazoline-6-sulfonamide (stereochemistry assumed) | 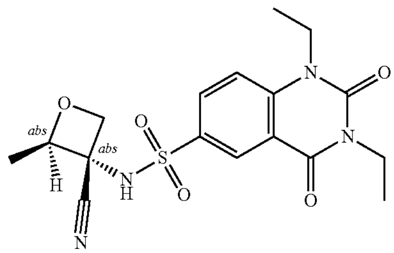 [SMILES: CCn1c(=O)c2cc(S(=O)(=O)N[C@@]3(C#N)CO[C@@H]3C)ccc2n(CC)c1=O] | LCMS (ES, m/z): 393.15 [M + H]+; RT: 0.800 min. $^1$H NMR (300 MHz, DMSO-d6) δ = 8.42 (s, 1H), 8.06 (d, J = 8.7 Hz, 1H), 7.70 (d, J = 9.0 Hz, 1H), 4.95-4.82 (m, 1H), 4.58 (s, 2H), 4.24-4.11 (m, 2H), 4.06-3.92 (m, 2H), 1.38 (d, J = 6.3 Hz, 3H), 1.28-1.12 (m, 6H). |
| 60 | N-((2S,3R)-3-cyano-2-methyloxetan-3-yl)-1,3-diethyl-2,4-dioxo-1,2,3,4-tetrahydroquinazoline-6-sulfonamide (stereochemistry assumed) | 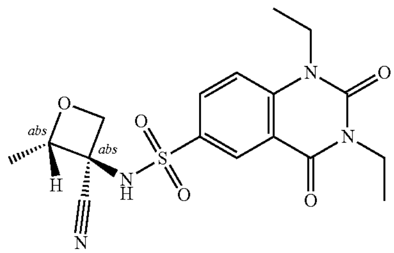 [SMILES: CCn1c(=O)c2cc(S(=O)(=O)N[C@]3(C#N)CO[C@H]3C)ccc2n(CC)c1=O] | LCMS (ES, m/z): 393.15 [M + H]+; RT: 0.800 min. $^1$H NMR (300 MHz, DMSO-d6) δ = 8.42 (s, 1H), 8.08 (d, J = 9.0 Hz, 1H), 7.70 (d, J = 9.0 Hz, 1H), 4.95-4.83 (m, 1H), 4.58 (s, 2H), 4.24-4.11 (m, 2H), 4.06-3.93 (m, 2H), 1.38 (d, J = 6.3 Hz, 3H), 1.28-1.12 (m, 6H). |
| 61 | N-((2S,3S)-3-cyano-2-methyloxetan-3-yl)-1,3-diethyl-2,4-dioxo-1,2,3,4-tetrahydroquinazoline-6-sulfonamide (stereochemistry assumed) | 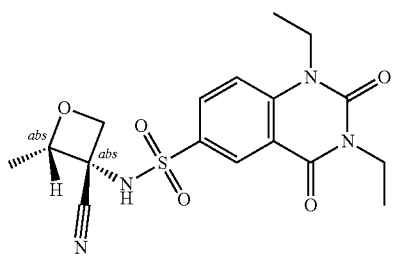 [SMILES: CCn1c(=O)c2cc(S(=O)(=O)N[C@@]3(C#N)CO[C@H]3C)ccc2n(CC)c1=O] | LCMS (ES, m/z): 393.15 [M + H]+; RT: 0.795 min. $^1$H NMR (300 MHz, DMSO-d6) δ = 9.26 (br, 1H), 8.47 (s, 1H), 8.10 (m, d, J = 8.7 Hz, 1H), 7.72 (d, J = 9.0 Hz, 1H), 5.09-4.97 (m, 1H), 4.80-4.64 (m, 2H), 4.24-4.11 (m, 2H), 4.05-3.92 (m, 2H), 1.42 (d, J = 6.3 Hz, 3H), 1.28-1.12 (m, 6H). |
| 62 | N-((2R,3R)-3-cyano-2-methyloxetan-3-yl)-1,3-diethyl-2,4-dioxo-1,2,3,4-tetrahydroquinazoline-6-sulfonamide (stereochemistry assumed) | 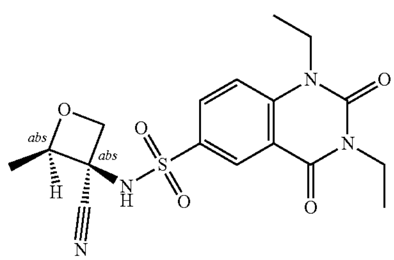 [SMILES: CCn1c(=O)c2cc(S(=O)(=O)N[C@]3(C#N)CO[C@@H]3C)ccc2n(CC)c1=O] | LCMS (ES, m/z): 393.15 [M + H]+; RT: 0.790 min. $^1$H NMR (300 MHz, DMSO-d6) δ = 9.28 (br, 1H), 8.46 (d, J = 2.4 Hz, 1H), 8.11 (d, J = 8.7 Hz, 1H), 7.70 (d, J = 9.0 Hz, 1H), 5.08-4.95 (m, 1H), 4.77-4.63 (m, 2H), 4.24-4.11 (m, 2H), 4.05-3.92 (m, 2H), 1.41 (d, J = 6.3 Hz, 3H), 1.27-1.12 (m, 6H). |
| 63 | 4-chloro-N-(3-cyanooxetan-3-yl)-1-(5-(difluoromethyl)-1,3,4-thiadiazol-2-yl)-1H-indazole-6-sulfonamide | 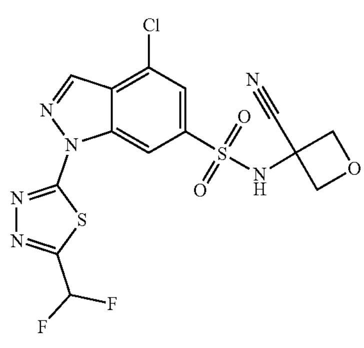 [SMILES: N#CC1(NS(=O)(=O)c2cc(Cl)c3cnn(-c4nnc(C(F)F)s4)c3c2)COC1] | LCMS (ES, m/z): 447.00 [M + H]+, RT: 0.957 min. $^1$H NMR (300 MHz, Chloroform-d) δ = 9.04 (s, 1H), 8.45 (s, 1H), 7.90 (s, 1H), 7.22-6.66 (m, 1H), 5.12-4.79 (m, 4H). |

-continued

| Ex. No. | Compound Name | Compound Structure | Characterization Data |
|---|---|---|---|
| 64 | 4-chloro-N-(1-cyano-2-(2-hydroxyethyl)cyclopropyl)-1-(5-(difluoromethyl)-1,3,4-thiadiazol-2-yl)-1H-indazole-6-sulfonamide | 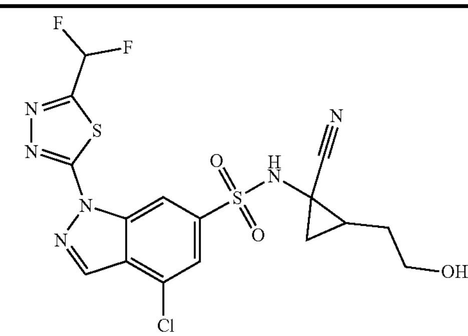 | LCMS (ES, m/z): 475.00 [M + H]+, RT: 1.513 min. $^1$H NMR (400 MHz, Chloroform-d) δ = 9.07 (s, 1H), 8.44 (s, 1H), 7.93 (s, 1H), 7.13-6.86 (m, 2H), 3.93-3.81 (m, 2H), 2.68-2.51 (m, 1H), 2.06-1.91 (m, 2H), 1.51-1.38 (m, 2H), 1.29-1.21 (m, 1H). |
| 65 | 4-chloro-1-(5-(difluoromethyl)-1,3,4-thiadiazol-2-yl)-N-(2-(2-hydroxyethyl)-1-methylcyclopropyl)-1H-indazole-6-sulfonamide | 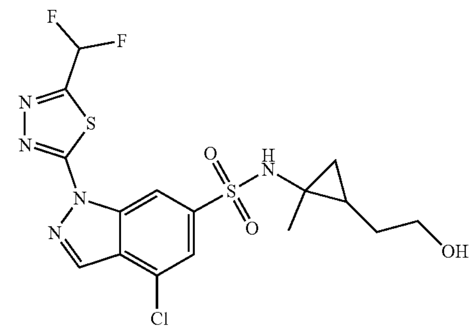 [SMILES: CC1(NS(=O)(=O)c2cc(Cl)c3cnn(-c4nnc(C(F)F)s4)c3c2)CC1CCO] | LCMS (ES, m/z): 464.05, 466.05 [M + H]+, RT: 0.974 min. $^1$H NMR (400 MHz, Chloroform-d) δ = 9.12 (s, 1H), 8.43 (s, 1H), 7.91 (s, 1H), 7.20-6.93 (m, 1H), 6.37 (s, 1H), 3.97-3.81 (m, 1H), 3.81-3.65 (m, 1H), 1.95-1.85 (m, 1H), 1.51-1.38 (m, 1H), 1.26 (s, 3H), 0.95-0.74 (m, 1H), 0.73-0.61 (m, 2H). |
| 66 | 1,3-diethyl-N-((1R,2S)-1-(hydroxymethyl)-2-vinylcyclopropyl)-2,4-dioxo-1,2,3,4-tetrahydroquinazoline-6-sulfonamide (stereochemistry assumed) | 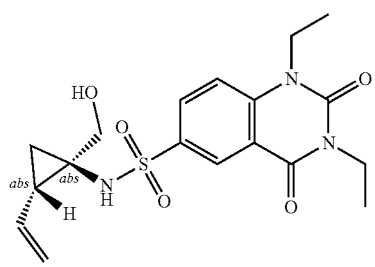 [SMILES: C=C[C@@H]1C[C@@]1(CO)NS(=O)(=O)c1ccc2c(c1)c(=O)n(CC)c(=O)n2CC] | LCMS (ES, m/z): 394.20 [M + H]+, RT: 0.771 min. $^1$H NMR (400 MHz, DMSO-d6) δ = 8.42 (s, 1H), 8.34 (s, 1H), 8.05 (d, J = 8.8 Hz, 1H), 7.68 (d, J = 8.8 Hz, 1H), 5.68-5.43 (m, 1H), 5.06-4.94 (m, 2H), 4.53 (t, J = 5.2 Hz, 1H), 4.24-4.13 (m, 2H), 4.08-3.94 (m, 2H), 3.35 (d, J = 4.8 Hz, 2H), 1.68-1.52 (m, 1H), 1.33-1.13 (m, 6H), 1.02-0.88 (m, 1H), 0.88-0.73 (m, 1H). |
| 67 | N-((1S,2S)-1-cyano-2-(2-hydroxyethyl)cyclopropyl)-1-(5-(difluoromethyl)-1,3,4-thiadiazol-2-yl)-4-(4-isobutyrylpiperazin-1-yl)-1H-indazole-6-sulfonamide (stereochemistry assumed) | 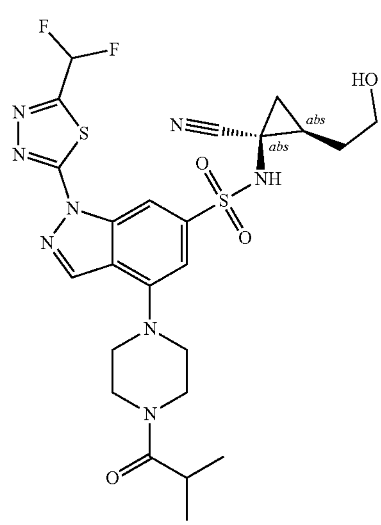 [SMILES: CC(C)C(=O)N1CCN(c2cc(S(=O)(=O)N[C@@]3(C#N)C[C@H]3CCO)cc3c2cnn3-c2nnc(C(F)F)s2)CC1] | LCMS (ES, m/z): 595.15 [M + H]+, RT: 0.858 min. $^1$H NMR (400 MHz, DMSO-d6) δ 9.29 (s, 1H), 8.97 (s, 1H), 8.49 (s, 1H), 7.74-7.47 (m, 1H), 7.16 (s, 1H), 4.59-4.52 (m, 1H), 3.83-3.71 (m, 4H), 3.54-3.41 (m, 6H), 2.99-2.91 (m, 1H), 1.62-1.53 (m, 2H), 1.52-1.34 (m, 2H), 1.29-1.15 (m, 1H), 1.05 (d, J = 6.4 Hz, 6H). |

| Ex. No. | Compound Name | Compound Structure | Characterization Data |
|---|---|---|---|
| 68 | N-((1R,2R)-1-cyano-2-(2-hydroxyethyl)cyclopropyl)-1-(5-(difluoromethyl)-1,3,4-thiadiazol-2-yl)-4-(4-isobutyrylpiperazin-1-yl)-1H-indazole-6-sulfonamide (stereochemistry assumed) | 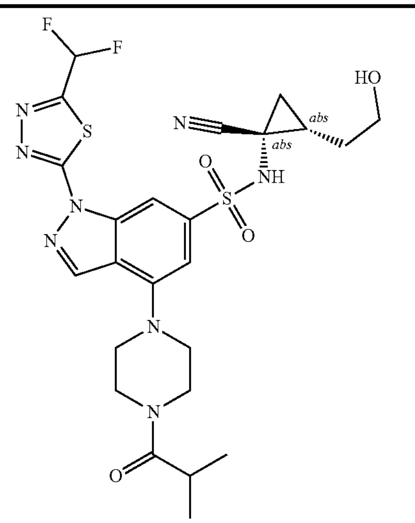 | LCMS (ES, m/z): 595.15 [M + H]+, RT: 0.850 min. $^1$H NMR (400 MHz, DMSO-d6) δ 9.29 (s, 1H), 8.97 (s, 1H), 8.49 (s, 1H), 7.74-7.47 (m, 1H), 7.17 (s, 1H), 4.59-4.52 (m, 1H), 3.83-3.71 (m, 4H), 3.54-3.41 (m, 6H), 2.99-2.91 (m, 1H), 1.62-1.53 (m, 2H), 1.52-1.34 (m, 2H), 1.29-1.15 (m, 1H), 1.05 (d, J = 6.4 Hz, 6H). |
| 69 | 1-(5-(difluoromethyl)-1,3,4-thiadiazol-2-yl)-N-((1S,2S)-2-(2-hydroxyethyl)-1-methylcyclopropyl)-4-(4-isobutyrylpiperazin-1-yl)-1H-indazole-6-sulfonamide (stereochemistry assumed) | 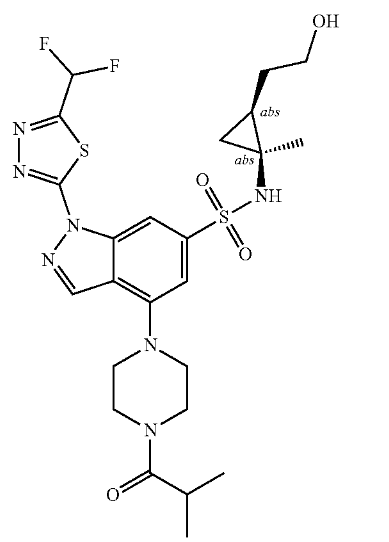 [SMILES: CC(C)C(=O)N1CCN(c2cc(S(=O)(=O)N[C@@]3(C)C[C@H]3CCO)cc3c2cnn3-c2nnc(C(F)F)s2)CC1] | LCMS (ES, m/z): 584.20 [M + H]+, RT: 0.885 min. $^1$H NMR (400 MHz, DMSO-d6) δ 8.94 = (s, 1H), 8.45 (s, 1H), 8.24 (s, 1H), 7.79-7.41 (m, 1H), 7.15 (s, 1H), 4.31 (t, J = 5.2 Hz, 1H), 3.90-3.69 (m, 4H), 3.58-3.39 (m, 4H), 3.05-2.89 (m, 1H), 2.06-1.94 (m, 1H), 1.41-1.32 (m, 1H), 1.21-1.18 (m, 1H), 1.09 (s, 3H), 1.05 (d, J = 6.8 Hz, 6H), 0.95-0.86 (m, 1H), 0.86-0.81(m, 1H), 0.79-0.75 (m, 1H), 0.15-0.05 (m, 1H). |
| 70 | 1-(5-(difluoromethyl)-1,3,4-thiadiazol-2-yl)-N-((1R,2R)-2-(2-hydroxyethyl)-1-methylcyclopropyl)-4-(4-isobutyrylpiperazin-1-yl)-1H-indazole-6-sulfonamide (stereochemistry assumed) | 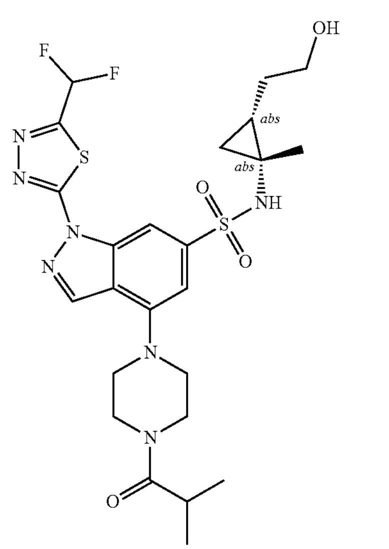 [SMILES: CC(C)C(=O)N1CCN(c2cc(S(=O)(=O)N[C@]3(C)C[C@@H]3CCO)cc3c2cnn3-c2nnc(C(F)F)s2)CC1] | LCMS (ES, m/z): 584.20 [M + H]+, RT: 1.497 min. $^1$H NMR (400 MHz, DMSO-d6) δ = 8.94 (s, 1H), 8.45 (s, 1H), 8.24 (s, 1H), 7.80-7.40 (m, 1H), 7.15 (s, 1H), 4.31 (t, J = 5.2 Hz, 1H), 3.90-3.69 (m, 4H), 3.58-3.38 (m, 4H), 3.03-2.89 (m, 1H), 2.05-1.96 (m, 1H),1.41-1.32 (m, 1H), 1.20-1.18 (m, 1H), 1.09 (s, 3H), 1.05 (d, J = 6.4 Hz, 6H), 0.95-0.86 (m, 1H), 0.86-0.81 (m, 1H), 0.79-0.72 (m, 1H), 0.15-0.05 (m, 1H). |

| Ex. No. | Compound Name | Compound Structure | Characterization Data |
|---|---|---|---|
| 71 | 4-chloro-1-(5-(difluoromethyl)-1,3,4-thiadiazol-2-yl)-N-(2,3-dimethyloxetan-3-yl)-1H-indazole-6-sulfonamide | 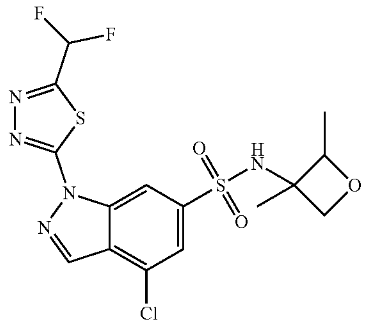 [SMILES: CC1OCC1(C)NS(=O)(=O)c1cc(Cl)c2cnn(-c3nnc(C(F)F)s3)c2c1] | $^1$H NMR (400 MHz, DMSO-d6) δ = 9.12 (s, 1H), 9.10 (s, 1H), 8.44 (s, 1H), 7.88 (s, 1H), 7.15-6.88 (m, 1H), 5.30-5.20 (m, 1H), 4.65-4.61 (m, 1H), 4.36-4.14 (m, 1H), 1.55 (s, 3H), 1.31-1.25 (m, 3H). |
| 72 | 1-methyl-N-(3-methyloxetan-3-yl)-1H-indazole-6-sulfonamide | 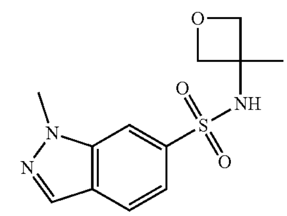 [SMILES: Cn1ncc2ccc(S(=O)(=O)NC3(C)COC3)cc21] | LCMS (ES, m/z): 282.15 [M + H]+. RT: 0.633 min. $^1$H NMR (300 MHz, DMSO-d6) δ = 8.22 (s, 1H), 8.15 (s, 1H), 7.99 (d, J = 8.4 Hz, 1H), 7.55 (d, J = 8.4 Hz, 1H), 6.27 (br, 1H), 4.56 (d, J = 6.3 Hz, 2H), 4.15-4.10 (m, 5H), 1.41 (s, 3H). |
| 73 | 1-(5-(difluoromethyl)-1,3,4-thiadiazol-2-yl)-4-methoxy-N-(3-methyloxetan-3-yl)-1H-indazole-6-sulfonamide | 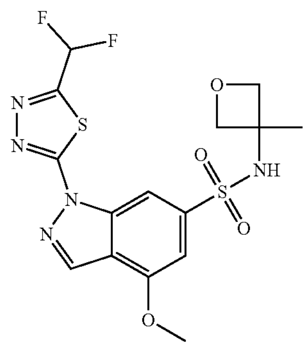 [SMILES: COc1cc(S(=O)(=O)NC2(C)COC2)cc2c1cnn2-c1nnc(C(F)F)s1] | LCMS (ES, m/z): 432.05 [M + H]+, RT: 1.464 min. $^1$H NMR (400 MHz, DMSO-d6) δ = 8.80 (s, 1H), 8.72 (s, 1H), 8.53 (s, 1H), 7.71-7.47 (m, 1H), 7.31 (s, 1H), 4.59 (d, J = 6.0 Hz, 2H), 4.15 (d, J = 6.3 Hz, 2H), 4.09 (s, 3H), 1.45 (s, 3H). |
| 74 | 1,3-diethyl-N-((1R,2R)-2-(hydroxymethyl)cyclobutyl)-2,4-dioxo-1,2,3,4-tetrahydroquinazoline-6-sulfonamide (stereochemistry assumed) | 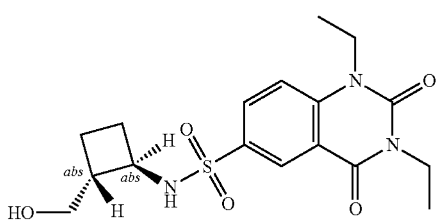 [SMILES: CCn1c(=O)c2cc(S(=O)(=O)N[C@@H]3CC[C@H]3CO)ccc2n(CC)c1=O] | LCMS (ES, m/z): 382.15 [M + H]+, RT: 0.683 min. $^1$H NMR (400 MHz, DMSO-d6) δ = 8.40 (s, 1H), 8.11 (s, 1H), 8.05 (d, J = 8.8 Hz, 1H), 7.69 (d, J = 8.8 Hz, 1H), 4.53 (t, J = 5.3 Hz, 1H), 4.18-4.16 (m, 2H), 4.00-3.98 (m, 2H), 3.73-3.71 (m, 1H), 3.30 (t, J = 5.6 Hz, 2H), 2.08-2.05 (m, 1H), 1.80 (t, J = 8.0 Hz, 4H), 1.23-1.18 (m, 6H). |
| 75 | 1,3-diethyl-N-((1S,2S)-2-(hydroxymethyl)cyclobutyl)-2,4-dioxo-1,2,3,4-tetrahydroquinazoline-6-sulfonamide (stereochemistry assumed) | 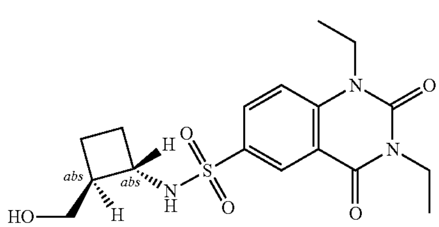 [SMILES: CCn1c(=O)c2cc(S(=O)(=O)N[C@H]3CC[C@@H]3CO)ccc2n(CC)c1=O] | LCMS (ES, m/z): 382.20 [M + H]+, RT: 0.692 min. $^1$H NMR (400 MHz, DMSO-d6) δ = 8.40 (s, 1H), 8.06 (d, J = 8.9 Hz, 1H), 8.01 (s, 1H), 7.69 (d, J = 8.8 Hz, 1H), 4.53 (t, J = 5.3 Hz, 1H), 4.18-4.16 (m, 2H), 4.00-3.98 (m, 2H), 3.51-3.49 (m, 1H), 3.20 (t, J = 5.6 Hz, |

| Ex. No. | Compound Name | Compound Structure | Characterization Data |
|---|---|---|---|
| | | | 2H), 1.93-1.82 (m, 3H), 1.46 (t, J = 8.0 Hz, 2H), 1.23-1.18 (m, 6H). |
| 76 | 4-(4-(cyclopentanecarbonyl)piperazin-1-yl)-1-(5-(difluoromethyl)-1,3,4-thiadiazol-2-yl)-N-(3-methyloxetan-3-yl)-1H-indazole-6-sulfonamide | 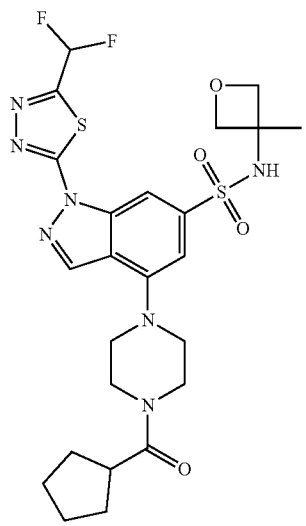 [SMILES: CC1(NS(=O)(=O)c2cc(N3CCN(C(=O)C4CCCC4)CC3)c3cnn(-c4nnc(C(F)F)s4)c3c2)COC1] | $^1$H NMR (300 MHz, DMSO-d6) δ = 8.95 (s, 1H), 8.64 (s, 1H), 8.45 (s, 1H), 7.78-7.43 (m, 1H), 7.15 (s, 1H), 4.58 (d, J = 6.0 Hz, 2H), 4.13 (d, J = 6.3 Hz, 2H), 3.84-3.71 (m, 4H), 3.51-3.42 (m, 4H), 3.12-3.01 (m, 1H), 1.89-1.51 (m, 8H), 1.44 (s, 3H). |
| 77 | N-(2,2-difluoroethyl)-4-(1-(5-(difluoromethyl)-1,3,4-thiadiazol-2-yl)-6-(N-(3-(fluoromethyl)oxetan-3-yl)sulfamoyl)-1H-indazol-4-yl)-N-methylpiperazine-1-carboxamide | 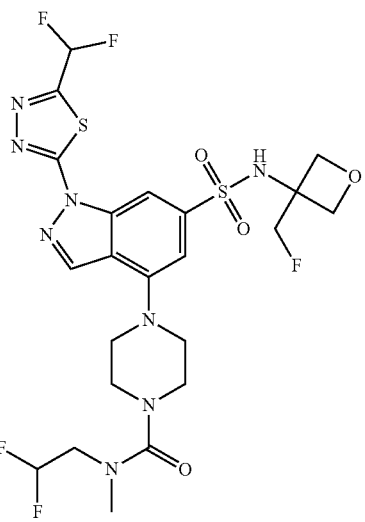 | $^1$H NMR (300 MHz, DMSO-d6) δ = 8.95 (s, 2H), 8.47 (s, 1H), 7.78-7.43 (m, 1H), 7.19 (s, 1H), 6.41-6.01 (m, 1H), 4.70 (s, 1H), 4.58-4.54 (m, 3H), 4.35 (d, J = 6.9 Hz, 2H), 3.69-3.55 (m, 2H), 3.54-3.39 (m, 2H), 3.00 (s, 3H). |
| 78 | N-((1S,2S)-1-cyano-2-(hydroxymethyl)cyclopropyl)-1,3-diethyl-2,4-dioxo-1,2,3,4-tetrahydroquinazoline-6-sulfonamide (stereochemistry assumed) | 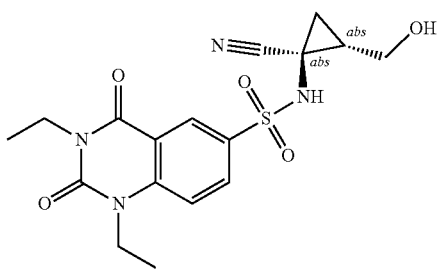 [SMILES: CCn1c(=O)c2cc(S(=O)(=O)N[C@@]3(C#N)C[C@@H]3CO)ccc2n(CC)c1=O] | LCMS (ES, m/z): 393.10 [M + H]+, RT: 1.088 min. $^1$H NMR (300 MHz, Chloroform-d) δ = 8.78 (s, 1H), 8.23 (d, J = 8.7 Hz, 1H), 7.37 (d, J = 9.0 Hz, 1H), 6.40 (s, 1H), 4.30-4.02 (m, 5H), 3.42-3.30 (m, 1H), 2.21-2.06 (m, 1H), 1.85-1.76 (m, 1H), 1.42-1.21 (m, 7H). |

| Ex. No. | Compound Name | Compound Structure | Characterization Data |
|---|---|---|---|
| 79 | (S)-1-(5-(difluoromethyl)-1,3,4-thiadiazol-2-yl)-4-(4-isobutyryl-3-methylpiperazin-1-yl)-N-(3-methyloxetan-3-yl)-1H-indazole-6-sulfonamide (stereochemistry assumed) | 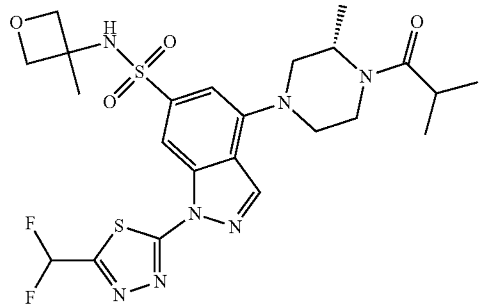 [SMILES: CC(C)C(=O)N1CCN(c2cc(S(=O)(=O)NC3(C)COC3)cc3c2cnn3-c2nnc(C(F)F)s2)C[C@@H]1C] | LCMS (ES, m/z): 570.15 [M + H]+, RT: 0.924 min. $^1$H NMR (400 MHz, Chloroform-d) δ = 8.74 (s, 1H), 8.32 (s, 1H), 7.20 (s, 1H), 7.14-6.87 (m, 1H), 5.40 (s, 1H), 5.06-4.56 (m, 3H), 4.43-3.84 (m, 3H), 3.77-3.58 (m, 3H), 3.28-3.23 (m, 1H), 3.14-3.09 (m, 1H), 2.86-2.81 (m, 1H), 1.67 (s, 3H), 1.49-1.44 (m, 3H), 1.19 (d, J = 7.8 Hz, 6H). |
| 80 | 4-(4-isobutyrylpiperazin-1-yl)-N-(3-methyloxetan-3-yl)-1-(5-vinyl-1,3,4-thiadiazol-2-yl)-1H-indazole-6-sulfonamide | 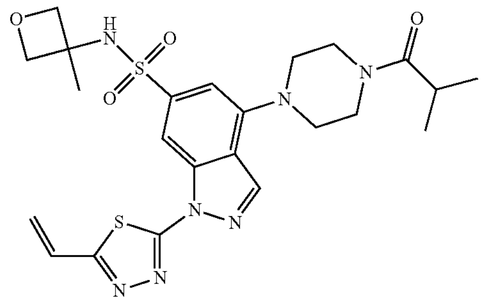 [SMILES: C=Cc1nnc(-n2ncc3c(N4CCN(C(=O)C(C)C)CC4)cc(S(=O)(=O)NC4(C)COC4)cc32)s1] | LCMS (ESI, m/z): 532.20 [M + H]+, RT: 0.900 min $^1$H NMR (400 MHz, Chloroform-d) δ = 8.78 (s, 1H), 8.28 (s, 1H), 7.19 (s, 1H), 7.11-7.01 (m, 1H), 6.08-6.00 (m, 1H), 5.86-5.82 (m, 1H), 5.67 (s, 1H), 4.78 (d, J = 6.8 Hz, 2H), 4.34 (d, J = 6.8 Hz, 2H), 3.92-3.79 (m, 4H), 3.47-3.38 (m, 4H), 2.91-2.79 (m, 1H), 1.66 (s, 3H), 1.19 (d, J = 6.8 Hz, 6H). |
| 81 | 1-(5-bromo-1,3,4-thiadiazol-2-yl)-4-(4-isobutyrylpiperazin-1-yl)-N-(3-methyloxetan-3-yl)-1H-indazole-6-sulfonamide | 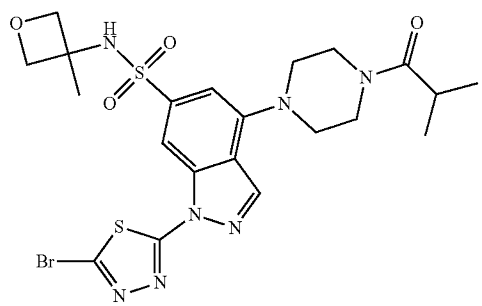 [SMILES: CC(C)C(=O)N1CCN(c2cc(S(=O)(=O)NC3(C)COC3)cc3c2cnn3-c2nnc(Br)s2)CC1] | LCMS (ESI, m/z): 586.10 [M + H]+, RT: 0.908 min $^1$H NMR (300 MHz, Chloroform-d) δ = 8.66 (s, 1H), 8.29 (s, 1H), 7.20 (s, 1H), 5.64 (s, 1H), 4.77 (d, J = 6.6 Hz, 2H), 4.34 (d, J = 6.6 Hz, 2H), 3.98-3.79 (m, 4H), 3.51-3.34 (m, 4H), 2.91-2.82 (m, 1H), 1.66 (s, 3H), 1.19 (d, J = 6.6 Hz, 6H). |

Example A. Inhibition of PARG Target Engagement Cellular Assay

The ability of the compounds of the Examples to inhibit PARG was determined as described below. After treating HCC1806 cells with cisplatin, followed by PARG inhibitor compound titration for 1 h, the cells were fixed in formaldehyde. The cells were permeabilized, blocked, and incubated with antibody against poly (ADP) ribose (PAR) polymer. The cells were then washed and incubated with IR 800 conjugated secondary antibody together with TO-PRO3 iodide nuclear stain. After washing, images of the cells were captured and analyzed on Odyssey CLx instrument and analyzed using LI-COR image studio software.

Example B. Inhibition of PARG Cellular Viability Assay

HCC1806 cells were plated in 384 well cell culture plates and incubated at 37° C. 5% $CO_2$. PARG inhibitors were added starting at 20 μM for a 10-point dose response curve at 1:2 dilutions. The compounds were added to the plate for 168 h and then Cell Titer-Glo reagent (Promega) was added. After incubation with the reagent, luminescence was read.

Compounds of the present disclosure, as exemplified in Examples 1-20, showed $IC_{50}$ values in the following ranges: *=$IC_{50}$<10 μM; =10 μM≤$IC_{50}$≤100 μM; *=100 μM<$IC_{50}$.

Data obtained for the Example compounds using the target engagement cellular assay described in Example A is provided in Table A.

TABLE A

| Example No. | PARG target engagement ($IC_{50}$ μM) |
|---|---|
| 1 | * |
| 2 | * |
| 3 | * |
| 4 | ** |

TABLE A-continued

| Example No. | PARG target engagement (IC$_{50}$ µM) |
|---|---|
| 5 | * |
| 6 | *** |
| 7 | * |
| 8 | * |
| 9 | ** |
| 10 | ** |
| 11 | *** |
| 12 | * |
| 13D | * |
| 14 | ** |
| 15A | * |
| 16 | * |
| 17A | ** |
| 18 | * |
| 19 | * |
| 20 | ** |

Example C. Inhibition of PARG TFMU Assay

The ability of the compounds of the Examples to inhibit PARG activity in 4-(trifluoromethyl)umbelliferone (TFMU) assay was determined as described below. PARG inhibitors were added into 384 well plate for a 10-point dose response curve at 1:3 dilutions. TFMU PARG substrate and PARG (250 pM or 2 nM) were then added to the plate to initiate enzymatic reaction. After incubation with the reagent, luminescence was read. IC$_{50}$ values were calculated using set control points for 100% inhibition as no enzyme and 0% inhibition 250 pM or 2 nM of PARG enzyme.

Compounds of the present disclosure showed IC$_{50}$ values in the following ranges: **=IC$_{50}$<50 nM; *=50 nM≤IC$_{50}$<500 nM; **=500 nM≤IC$_{50}$<5000 nM; *=5000 nM≤IC$_{50}$.

Data obtained for the Example compounds using the TFMU assay described in Example C is provided in Table B.

TABLE B

| Example No. | PARG TFMU Assay (IC$_{50}$ nM) |
|---|---|
| 1 | * |
| 2 | * |
| 3 | ** |
| 4 | *** |
| 5 | ** |
| 6 | **** |
| 7 | * |
| 9 | ** |
| 10 | ** |
| 11 | ** |
| 12 | ** |
| 13A | * |
| 13D | * |
| 14 | **** |
| 15A | ** |
| 16 | * |
| 17A | *** |
| 18 | ** |
| 19 | ** |
| 20 | *** |
| 21 | *** |
| 22 | **** |
| 23 | *** |
| 24 | *** |
| 25A | *** |
| 25B | *** |
| 26 | *** |
| 27 | **** |
| 28A | *** |
| 28B | **** |
| 29 | *** |
| 30 | **** |
| 31 | **** |
| 32 | *** |
| 33 | **** |
| 34 | **** |
| 35 | **** |
| 36 | **** |
| 37 | **** |
| 38 | **** |
| 39 | **** |
| 40 | **** |
| 41 | **** |
| 42 | **** |
| 43 | **** |
| 44 | **** |
| 45 | **** |
| 46 | **** |
| 47 | **** |
| 48 | *** |
| 49 | ** |
| 51 | * |
| 52 | * |
| 61 | ** |
| 63 | ** |
| 65 | ** |
| 71 | *** |
| 72 | * |
| 73 | *** |
| 74 | * |
| 75 | * |
| 76 | **** |
| 77 | **** |
| 78 | * |
| 79 | **** |
| 80 | **** |
| 81 | **** |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

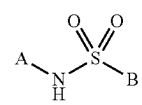

or a pharmaceutically acceptable salt thereof, wherein:

A is a group having the formula:

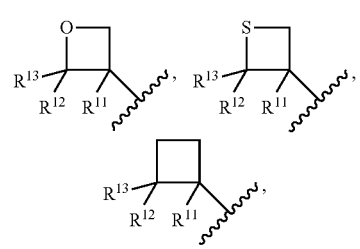

-continued

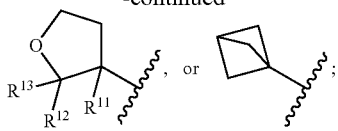

B is a group of formula (b) or formula (c):

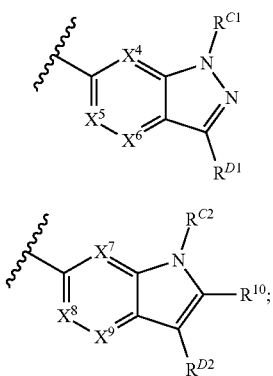

$X^4$ is N or $CR^4$;
$X^5$ is N or $CR^5$;
$X^6$ is N or $CR^6$;
$X^7$ is N or $CR^7$;
$X^8$ is N or $CR^8$;
$X^9$ is N or $CR^9$;
wherein no more than two of $X^4$, $X^5$, and $X^6$ are simultaneously N;
wherein no more than two of $X^7$, $X^8$, and $X^9$ are simultaneously N;
$R^4$, $R^5$, $R^7$, and $R^8$ are each independently selected from H, halo, and $C_{1-4}$ alkyl;
$R^6$ and $R^9$ are each independently selected from H, halo, $NR^cR^d$, $OR^a$, $C_{6-10}$ aryl, $C_{3-7}$ cycloalkyl, 5-10 membered heteroaryl, and 4-10 membered heterocycloalkyl, wherein said $C_{6-10}$ aryl, $C_{3-7}$ cycloalkyl, 5-10 membered heteroaryl, and 4-10 membered heterocycloalkyl of $R^6$ and $R^9$ are each optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
$R^{10}$ is H, halo, $C_{1-4}$ alkyl, or $C_{1-4}$ haloalkyl;
$R^{C1}$ and $R^{C2}$ are independently selected from $C_{1-6}$ alkyl, $C_{2-6}$ alkenyl, and 5-membered heteroaryl, wherein said $C_{1-6}$ alkyl, $C_{1-6}$ alkyl substituted with R', $C_{2-6}$ alkenyl, and 5-membered heteroaryl of $R^{C1}$ and $R^{C2}$ are each optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each R' is independently selected from halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^{D1}$ and $R^{D2}$ are independently selected from H, halo, and $C_{1-4}$ alkyl;
$R^{11}$ is H, CN, CCR", $CH_3$, $CH_2CN$, $CH_2OH$, $CHF_2$, or $CH_2F$;
R" is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $C(O)R^{b3}$, $C(O)NR^{c3}R^{d3}$, $C(O)OR^{a3}$, or $NR^{c3}R^{d3}$;
$R^{12}$ is H or F;
$R^{13}$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, or $S(O)_2NR^{c3}R^{d3}$, wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^{13}$ is optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^3$, $SR^{a3}$, $C(O)R^{b3}$, $C(O)NR^{c3}R^{d3}$, $C(O)OR^3$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, or $R^{12}$ and $R^{13}$, together with the C atom to which they are attached, form a $C_3$ cycloalkyl or 3-membered heterocycloalkyl group comprising one heteroatom selected from N and O, optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $R^a$, $R^b$, $R^c$, $R^d$, $R^{a2}$, $R^{b2}$, $R^{c2}$, $R^{d2}$, $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^a$, $R^b$, $R^c$, $R^d$, $R^{a2}$, $R^{b2}$, $R^{c2}$, $R^{d2}$, $R^{a3}$, $R^{b3}$, $R^{c3}$, and $R^{d3}$ is optionally substituted with 1, 2, 3, 4, or 5 substituents independently selected from halo, $C_{1-4}$ alkyl, $C_{1-4}$haloalkyl, $C_{1-6}$ haloalkyl, $C_{2-6}$ alkenyl, $C_{2-6}$ alkynyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or $R^c$ and $R^d$, together with the N atom to which they are attached, form a 4-7 membered heterocycloalkyl group optionally substituted with 1, 2, or 3 substituents independently selected from halo, $C_{1-4}$ alkyl, $C_{1-4}$ haloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or $R^{c2}$ and $R^{d2}$, together with the N atom to which they are attached, form a 4-7 membered heterocycloalkyl group optionally substituted with 1, 2, or 3 substituents independently selected from halo, $C_{1-4}$ alkyl, $C_{1-4}$ haloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or $R^{c3}$ and $R^{d3}$, together with the N atom to which they are attached, form a 4-7 membered heterocycloalkyl group optionally substituted with 1, 2, or 3 substituents independently selected from halo, $C_{1-4}$ alkyl, $C_{1-4}$ haloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy; and each $R^e$, $R^{e2}$, $R^{e3}$, and $R^{e4}$ is independently selected from H, $C_{1-4}$ alkyl, and CN.

2. A compound of Formula I:

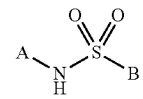
I or a pharmaceutically acceptable salt thereof, wherein:
A is a group having the formula:

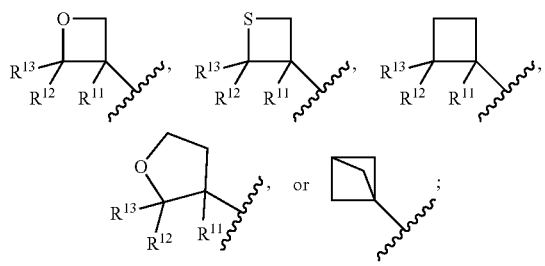

B is a group of formula (b) or formula (c):

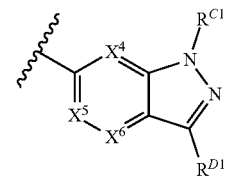
(b)

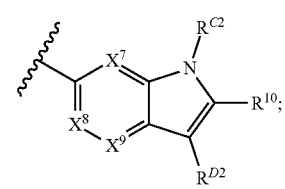
(c)

$X^4$ is N or $CR^4$;
$X^5$ is N or $CR^5$;
$X^6$ is N or $CR^6$;
$X^7$ is N or $CR^7$;
$X^8$ is N or $CR^8$;
$X^9$ is N or $CR^9$;
wherein no more than two of $X^4$, $X^5$, and $X^6$ are simultaneously N;
wherein no more than two of $X^7$, $X^8$, and $X^9$ are simultaneously N;
$R^4$, $R^5$, $R^7$, and $R^8$ are each independently selected from H, halo, and $C_{1-4}$ alkyl;
$R^6$ and $R^9$ are each independently selected from H, $C_{6-10}$ aryl, $C_{3-7}$ cycloalkyl, 5-10 membered heteroaryl, and 4-10 membered heterocycloalkyl, wherein said $C_{6-10}$ aryl, $C_{3-7}$ cycloalkyl, 5-10 membered heteroaryl, and 4-10 membered heterocycloalkyl of $R^6$ and $R^9$ are each optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

$R^{10}$ is H, halo, $C_{1-4}$ alkyl, or $C_{1-4}$ haloalkyl;

$R^{C1}$ and $R^{C2}$ are independently selected from $C_{1-6}$ alkyl, $C_{2-6}$ alkenyl, and 5-membered heteroaryl, wherein said $C_{1-6}$ alkyl, $C_{2-6}$ alkenyl, and 5-membered heteroaryl of $R^{C1}$ and $R^{C2}$ are each optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})R^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^{D1}$ and $R^{D2}$ are independently selected from H, halo, and $C_{1-4}$ alkyl;

$R^{11}$ is CN, $CH_3$, $CHF_2$, or $CH_2F$;

$R^{12}$ is H or F;

$R^{13}$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, or $S(O)_2NR^{c3}R^{d3}$, wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^{13}$ is optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, or $R^{12}$ and $R^{13}$, together with the C atom to which they are attached, form a $C_3$ cycloalkyl or 3-membered heterocycloalkyl group comprising one heteroatom selected from N and O, optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $NR^{c3}S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $R^a$, $R^b$, $R^c$, $R^d$, $R^{a2}$, $R^{b2}$, $R^{c2}$, $R^{d2}$, $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^a$, $R^b$, $R^c$, $R^d$, $R^{a2}$, $R^{b2}$, $R^{c2}$, $R^{d2}$, $R^{a3}$, $R^{b3}$, $R^{c3}$, and $R^{d3}$ is optionally substituted with 1, 2, 3, 4, or 5 substituents independently selected from halo, $C_{1-4}$ alkyl, $C_{1-4}$haloalkyl, $C_{1-6}$ haloalkyl, $C_{2-6}$ alkenyl, $C_{2-6}$ alkynyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or $R^c$ and $R^d$, together with the N atom to which they are attached, form a 4-7 membered heterocycloalkyl group optionally substituted with 1, 2, or 3 substituents independently selected from halo, $C_{1-4}$ alkyl, $C_{1-4}$ haloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or $R^{c2}$ and $R^{d2}$, together with the N atom to which they are attached, form a 4-7 membered heterocycloalkyl group optionally substituted with 1, 2, or 3 substituents independently selected from halo, $C_{1-4}$ alkyl, $C_{1-4}$haloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or $R^{c3}$ and $R^{d3}$, together with the N atom to which they are attached, form a 4-7 membered heterocycloalkyl group optionally substituted with 1, 2, or 3 substituents independently selected from halo, $C_{1-4}$ alkyl, $C_{1-4}$haloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy; and each $R^e$, $R^{e2}$, $R^{e3}$, and $R^{e4}$ is independently selected from H, $C_{1-4}$ alkyl, and CN.

3. The compound of claim 1, or a pharmaceutically acceptable salt thereof, wherein A is

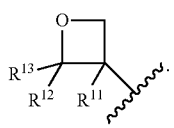

4. The compound of claim 1, or a pharmaceutically acceptable salt thereof, wherein A is

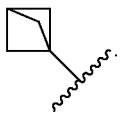 [SMILES: *C12CC(C1)C2]

5. The compound of claim 1, or a pharmaceutically acceptable salt thereof, wherein A is selected from

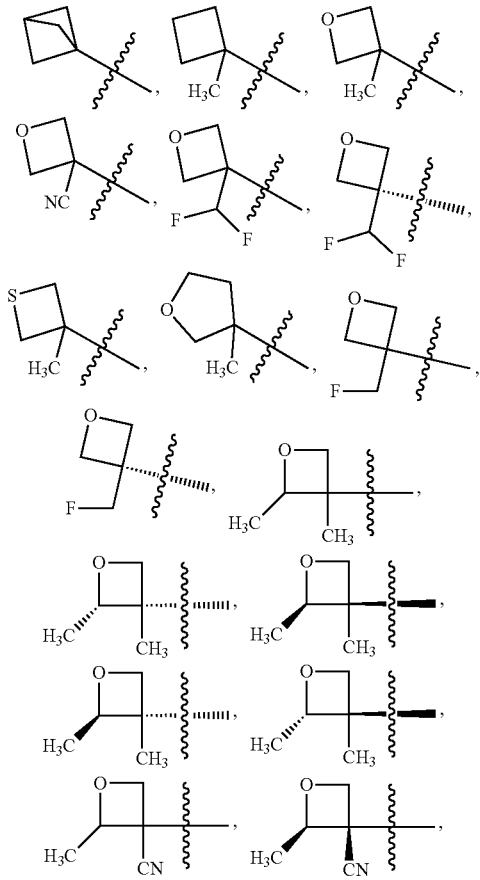

-continued

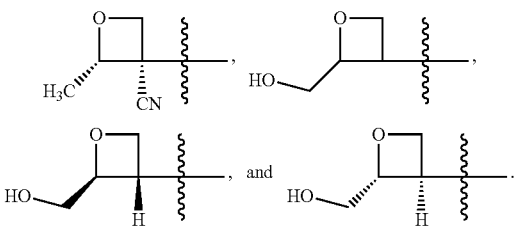

6. The compound of claim 1, or a pharmaceutically acceptable salt thereof, wherein A is selected from

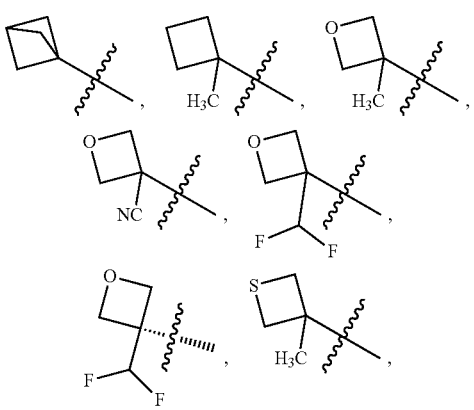

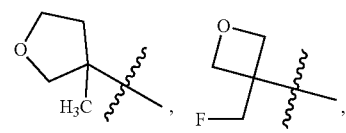

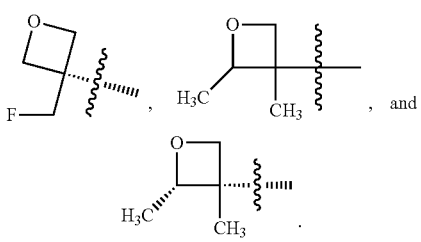

7. The compound of claim 1, or a pharmaceutically acceptable salt thereof, wherein B is of formula (b):

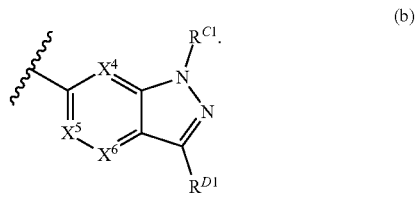

(b)

8. The compound of claim 1, or a pharmaceutically acceptable salt thereof, wherein B is of formula (c):

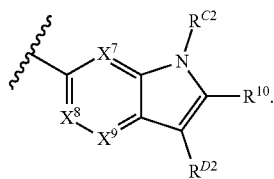

(c)

9. The compound of claim 1, or a pharmaceutically acceptable salt thereof, wherein A is

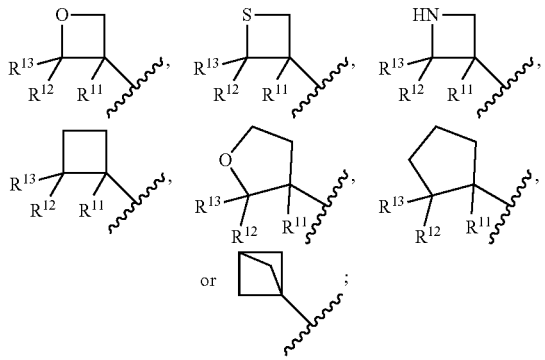

and
B is of formula (b):

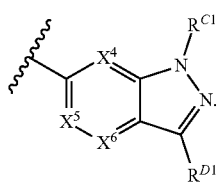

(b)

10. The compound of claim 1, or a pharmaceutically acceptable salt thereof, wherein $X^4$ is $CR^4$, $X^5$ is $CR^5$, and $X^6$ is $CR^6$.

11. The compound of claim 10, or a pharmaceutically acceptable salt thereof, wherein $R^4$ is H, $R^5$ is H, and $R^6$ is H.

12. The compound of claim 1, or a pharmaceutically acceptable salt thereof, wherein $R^6$ is selected from H, halo, $NR^cR^d$, $OR^a$, $C_{6-10}$ aryl, $C_{3-7}$ cycloalkyl, 5-10 membered heteroaryl, and 4-10 membered heterocycloalkyl, wherein said $C_{6-10}$ aryl, $C_{3-7}$ cycloalkyl, 5-10 membered heteroaryl, and 4-10 membered heterocycloalkyl of $R^3$, $R^6$, and $R^9$ are each optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

13. The compound of claim 1, or a pharmaceutically acceptable salt thereof, wherein $R^6$ is $C_{6-10}$ aryl, $C_{3-7}$ cycloalkyl, 5-10 membered heteroaryl, and 4-10 membered heterocycloalkyl, wherein said $C_{6-10}$ aryl, $C_{3-7}$ cycloalkyl, 5-10 membered heteroaryl, and 4-10 membered heterocycloalkyl, optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

14. The compound of claim 12, or a pharmaceutically acceptable salt thereof, wherein $R^6$ is 4-10 membered heterocycloalkyl, optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

15. The compound of claim 12, or a pharmaceutically acceptable salt thereof, wherein $R^6$ is piperazinyl optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

16. The compound of claim 1, or a pharmaceutically acceptable salt thereof, wherein $X^7$ is $CR^7$, $X^8$ is $CR^8$, and $X^9$ is $CR^9$.

17. The compound of claim 16, or a pharmaceutically acceptable salt thereof, wherein $R^7$ is H, $R^8$ is H, and $R^9$ is H.

18. The compound of claim 1, or a pharmaceutically acceptable salt thereof, wherein $R^{C1}$ is 5-membered heteroaryl, optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $R^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

19. The compound of claim 1, or a pharmaceutically acceptable salt thereof, wherein $R^{C1}$ is 1,3,4-thiadiazyl, optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

20. The compound of claim 1, or a pharmaceutically acceptable salt thereof, wherein $R^{C1}$ is 1,3,4-thiadiazyl substituted with $C_{1-6}$ haloalkyl.

21. The compound of claim 1, or a pharmaceutically acceptable salt thereof, wherein $R^{C1}$ is selected from $CH_3$,

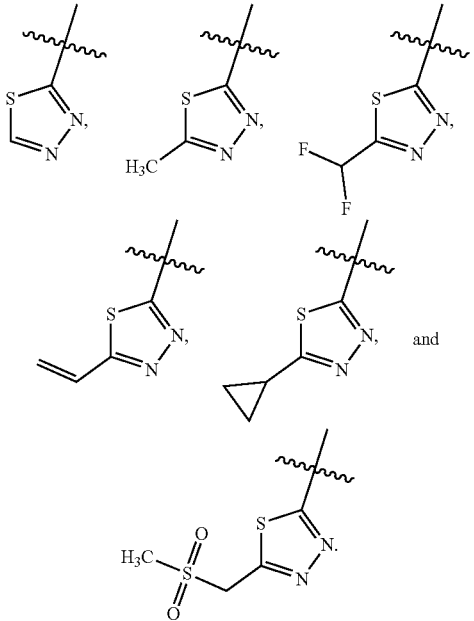

and

22. The compound of claim 1, or a pharmaceutically acceptable salt thereof, wherein $R^{C1}$ is

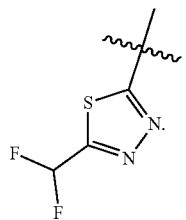 [SMILES: *c1nnc(C(F)F)s1]

23. The compound of claim 1, or a pharmaceutically acceptable salt thereof, wherein $R^{D1}$ is H.

24. The compound of claim 1, or a pharmaceutically acceptable salt thereof, wherein $R^{11}$ is CN, $CH_3$, $CHF_2$, or $CH_2F$.

25. The compound of claim 1, or a pharmaceutically acceptable salt thereof, wherein $R^{11}$ is CN.

26. The compound of claim 1, or a pharmaceutically acceptable salt thereof, wherein $R^{11}$ is $CH_3$.

27. The compound of claim 1, or a pharmaceutically acceptable salt thereof, wherein $R^{11}$ is $CHF_2$.

28. The compound of claim 1, or a pharmaceutically acceptable salt thereof, wherein $R^{11}$ is $CH_2F$.

29. The compound of claim 1, or a pharmaceutically acceptable salt thereof, wherein $R^{11}$ is H.

30. The compound of claim 1, or a pharmaceutically acceptable salt thereof, wherein $R^{11}$ is $CH_2OH$.

31. The compound of claim 1, or a pharmaceutically acceptable salt thereof, wherein $R^{12}$ is H.

32. The compound of claim 1, or a pharmaceutically acceptable salt thereof, wherein $R^{13}$ is selected from H and $C_{1-6}$ alkyl, wherein said $C_{1-6}$ alkyl is optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

33. The compound of claim 1, or a pharmaceutically acceptable salt thereof, wherein $R^{13}$ is H.

34. The compound of claim 1, or a pharmaceutically acceptable salt thereof, wherein $R^{13}$ is $C_{1-6}$ alkyl, optionally substituted with 1, 2, 3, or 4 substituents independently selected from CN and $OR^{a3}$.

35. The compound of claim 1, or a pharmaceutically acceptable salt thereof, wherein $R^{13}$ is selected from H, methyl, ethyl, ethenyl, $CH_2CN$, $CH_2OH$, $CH_2CH_2OH$, and $CH_2CH_2OCH_3$.

36. The compound of claim 1, or a pharmaceutically acceptable salt thereof, wherein $R^{13}$ is selected from H, ethyl, $CH_2CN$, and $CH_2CH_2OH$.

37. The compound of claim 1, or a pharmaceutically acceptable salt thereof, wherein $R^{12}$ and $R^{13}$ are each H.

38. The compound of claim 1, or a pharmaceutically acceptable salt thereof, wherein $R^{11}$, $R^{12}$, and $R^{13}$ are each H.

39. The compound of claim 1, or a pharmaceutically acceptable salt thereof, wherein:

$R^{11}$ is CN, $CH_3$, or $CH_2F$;

$R^{12}$ is H; and $R^{13}$ is H, ethyl, $CH_2CN$, and $CH_2CH_2OH$.

40. The compound of claim 1 having Formula IIB or IIC:

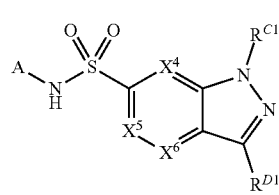

IIB

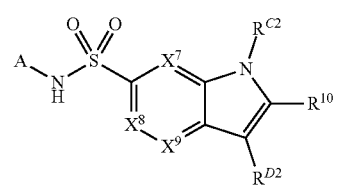

IIC or a pharmaceutically acceptable salt thereof.

41. The compound of claim 40 having Formula IIB-1 or IIB-2:

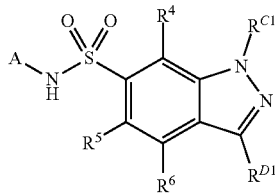

IIB-1

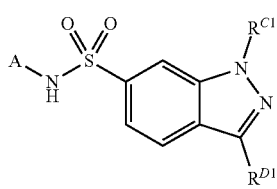

IIB-2 or a pharmaceutically acceptable salt thereof.

42. The compound of claim 40 having Formula IIB-3:

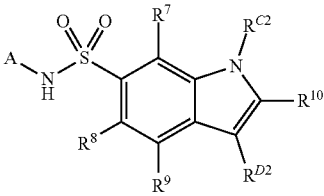

IIB-3 or a pharmaceutically acceptable salt thereof, wherein $R^{C'}$ is selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)R$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$.

43. The compound of claim 40 having Formula IIC-1 or IIC-2:

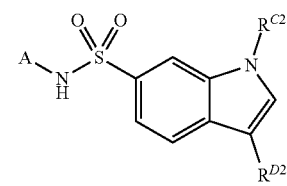

IIC-1

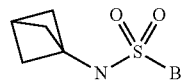

IIC-2 or a pharmaceutically acceptable salt thereof.

44. The compound of claim 1 having Formula IIIA, IIIB, IIIC, IIID, or IIIE:

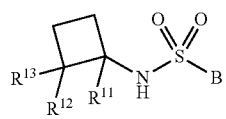

IIIA

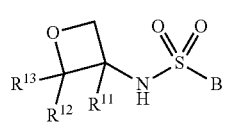

IIIB

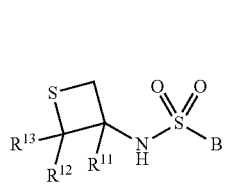

IIIC

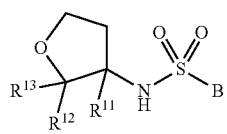

IIID

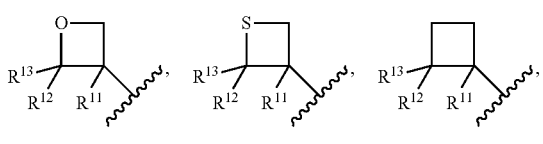

IIIE or a pharmaceutically acceptable salt thereof.

45. The compound of claim 1, or a pharmaceutically acceptable salt thereof, wherein:

A is a group having the formula:

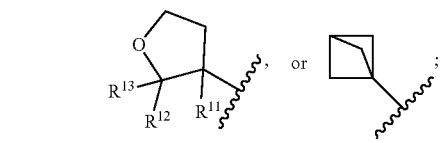

B is a group of formula (b) or formula (c):

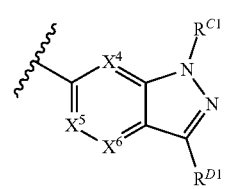

(b)

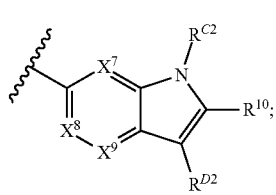

X⁴ is CR⁴;
X⁵ is CR⁵;
X⁶ is CR⁶,
X⁷ is CR⁷;
X⁸ is CR⁷;
X⁹ is CR⁹;
R⁴, R⁵, R⁷, and R⁸ are each independently selected from H, halo, and $C_{1-4}$ alkyl;
R⁶ and R⁹ are each independently selected from H, halo, NR$^c$R$^d$, OR$^a$, $C_{6-10}$ aryl, $C_{3-7}$ cycloalkyl, 5-10 membered heteroaryl, and 4-10 membered heterocycloalkyl, wherein said $C_{6-10}$ aryl, $C_{3-7}$ cycloalkyl, 5-10 membered heteroaryl, and 4-10 membered heterocycloalkyl of R⁶ and R⁹ are each optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;
R¹⁰ is H;
R$^{C1}$ and R$^{C2}$ are 5-membered heteroaryl, wherein said 5-membered heteroaryl of R$^{C1}$ and R$^{C2}$ are each optionally substituted with 1, 2, 3, or 4 substituents independently selected from halo, $C_{1-6}$ alkyl, $C_{1-6}$ alkyl substituted with R', $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;
each R' is S(O)$_2$R$^{b2}$;
R$^{D1}$ and R$^{D2}$ are H;
R¹¹ is H, CN, CH$_3$, CH$_2$OH, CHF$_2$, or CH$_2$F;
R¹² is H;
R¹³ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O) NR$^{c3}$R$^{d3}$, C(=NR$^{e3}$)NR$^{c3}$R$^{d3}$, NR$^{c3}$C(=NR$^{e3}$) NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$ R$^{b3}$, or S(O)$_2$NR$^{c3}$R$^{d3}$, wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of R¹³ is optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O) NR$^{c3}$R$^{d3}$, S(O)$_2$R$^{b3}$, and S(O)$_2$NR$^{c3}$R$^{d3}$, or R¹² and R¹³, together with the C atom to which they are attached, form a $C_3$ cycloalkyl or 3-membered heterocycloalkyl group comprising one heteroatom selected from N and O, optionally substituted with 1, 2, or 3 substituents independently selected from halo, $C_{1-4}$ alkyl, $C_{1-4}$ haloalkyl, CN, OR$^{a3}$, SR$^{a3}$, C(O)R$^{b3}$, C(O) NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C (O)OR$^{a3}$, C(=NR$^{e3}$)NR$^{c3}$R$^{d3}$, NR$^{c3}$C(=NR$^{e3}$) NR$^{c3}$R$^{d3}$, S(O)R$^{b3}$, S(O)NR$^{c3}$R$^{d3}$, S(O)$_2$R$^{b3}$, NR$^{c3}$S (O)$_2$R$^{b3}$, NR$^{c3}$S(O)$_2$NR$^{c3}$R$^{d3}$, and S(O)$_2$NR$^{c3}$R$^{d3}$;
each R$^a$, R$^b$, R$^c$, R$^d$, R$^{a2}$, R$^{b2}$, R$^{c2}$, R$^{d2}$, R$^{a3}$, R$^{b3}$, R$^{c3}$, and R$^{d3}$ is independently selected from H and $C_{1-6}$ alkyl;
each R$^e$, R$^{e2}$, R$^{e3}$, and R$^{e4}$ is independently selected from H and $C_{1-4}$ alkyl.
46. The compound of claim 1, or a pharmaceutically acceptable salt thereof, wherein:
A is a group having the formula:

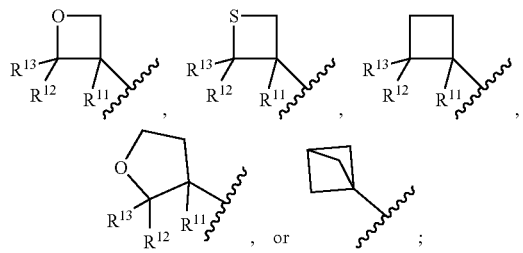

B is a group of formula (b) or formula (c):

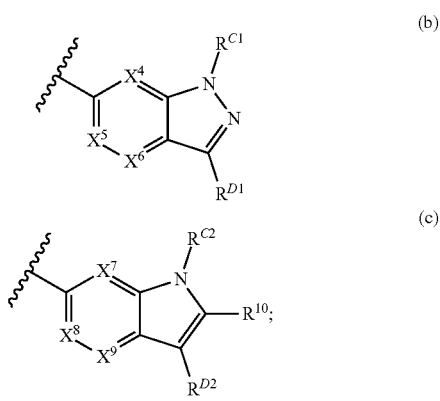

$X^4$ is $CR^4$;
$X^5$ is $CR^5$;
$X^6$ is $CR^6$;
$X^7$ is $CR^7$;
$X^8$ is $CR^8$;
$X^9$ is $CR^9$;
$R^4$, $R^5$, $R^7$, and $R^8$ are each independently selected from H, halo, and $C_{1-4}$ alkyl;
$R^6$ and $R^9$ are each independently selected from H, $C_{6-10}$ aryl, $C_{3-7}$ cycloalkyl, 5-10 membered heteroaryl, and 4-10 membered heterocycloalkyl, wherein said $C_{6-10}$ aryl, $C_{3-7}$ cycloalkyl, 5-10 membered heteroaryl, and 4-10 membered heterocycloalkyl of $R^6$ and $R^9$ are each optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
$R^{10}$ is H;
$R^{C1}$ and $R^{C2}$ are 5-membered heteroaryl, wherein said 5-membered heteroaryl of $R^{C1}$ and $R^{C2}$ are each optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;
$R^{D1}$ and $R^{D2}$ are H;
$R^{11}$ is CN, $CH_3$, $CHF_2$, or $CH_2F$;
$R^{12}$ is H;
$R^{13}$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2$ $R^{b3}$, or $S(O)_2NR^{c3}R^{d3}$, wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^{13}$ is optionally substituted with 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, or $R^{12}$ and $R^{13}$, together with the C atom to which they are attached, form a $C_3$ cycloalkyl or 3-membered heterocycloalkyl group comprising one heteroatom selected from N and O, optionally substituted with 1, 2, or 3 substituents independently selected from halo, $C_{1-4}$ alkyl, $C_{1-4}$haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^3R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $R^a$, $R^b$, $R^c$, $R^d$, $R^{a2}$, $R^{b2}$, $R^{c2}$, $R^{d2}$, $R^{a3}$, $R^{b3}$, $R^{c3}$, and $R^{d3}$ is independently selected from H and $C_{1-6}$ alkyl;
each $R^e$, $R^{e2}$, $R^{e3}$, and $R^{e4}$ is independently selected from H and $C_{1-4}$ alkyl.

47. The compound of claim 1, or a pharmaceutically acceptable salt thereof, wherein:
A is a group having the formula:

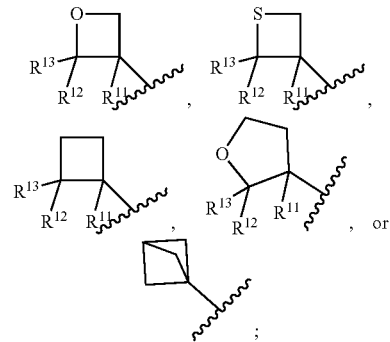

;

B is a group of formula (b):

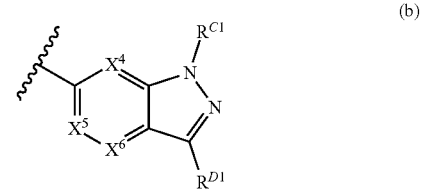

(b)

$X^4$ is $CR^4$;
$X^5$ is $CR^5$;
$X^6$ is $CR^6$;
$R^4$ and $R^5$ are each H;
$R^6$ is selected from H, halo, $NR^cR^d$, $OR^a$, and 4-10 membered heterocycloalkyl, wherein said 4-10 membered heterocycloalkyl of $R^6$ is each optionally substituted with $C(O)R^b$;
$R^{C1}$ is $C_{1-6}$ alkyl or 5-membered heteroaryl, wherein the 5-membered heteroaryl is optionally substituted with $C_{1-6}$ alkyl, $C_{1-6}$ alkyl substituted with R', $C_{2-6}$ alkenyl, $C_{3-7}$ cycloalkyl, or $C_{1-6}$ haloalkyl;
each R' is $S(O)_2R^{b2}$;
$R^{D1}$ is H;

R$^{11}$ is CN, CH$_3$, or CH$_2$F;
R$^{12}$ is H;
R$^{13}$ is H or C$_{1-6}$ alkyl, wherein said C$_{1-6}$ alkyl is optionally substituted with 1, 2, 3, or 4 substituents independently selected from CN and OR$^{a3}$;
each R$^b$ is independently selected from H and C$_{1-6}$ alkyl.

48. The compound of claim 1, or a pharmaceutically acceptable salt thereof, wherein:

A is a group having the formula:

[chemical structures]

B is a group of formula (b):

[chemical structure (b)]

X$^4$ is CR$^4$;
X$^5$ is CR$^5$;
X$^6$ is CR$^6$;
R$^4$ and R$^5$ are each H;
R$^6$ is selected from H and 4-10 membered heterocycloalkyl, wherein said 4-10 membered heterocycloalkyl of R$^6$ is each optionally substituted with C(O)R$^b$;
R$^{C1}$ is 5-membered heteroaryl, optionally substituted with C$_{1-6}$ haloalkyl;
R$^{D1}$ is H;
R$^{11}$ is CN, CH$_3$, or CH$_2$F;
R$^{12}$ is H;
R$^{13}$ is H or C$_{1-6}$ alkyl, wherein said C$_{1-6}$ alkyl is optionally substituted with 1, 2, 3, or 4 substituents independently selected from CN and OR$^{a3}$;
each R$^b$ is independently selected from H and C$_{1-6}$ alkyl.

49. The compound of claim 1, or a pharmaceutically acceptable salt thereof, wherein the compound is
1-[5-(difluoromethyl)-1,3,4-thiadiazol-2-yl]-N-(3-methyloxetan-3-yl)-4-[4-(2-methylpropanoyl)piperazin-1-yl]indazole-6-sulfonamide.

50. The compound of claim 1, or a pharmaceutically acceptable salt thereof, selected from:
1-(5-(difluoromethyl)-1,3,4-thiadiazol-2-yl)-4-(4-isobutyrylpiperazin-1-yl)-N-(1-methylcyclobutyl)-1H-indazole-6-sulfonamide;
1-(5-(difluoromethyl)-1,3,4-thiadiazol-2-yl)-N-(3-(fluoromethyl)oxetan-3-yl)-4-(4-isobutyrylpiperazin-1-yl)-1H-indazole-6-sulfonamide;
1-(5-(difluoromethyl)-1,3,4-thiadiazol-2-yl)-N-(3-methyloxetan-3-yl)-1H-indazole-6-sulfonamide;
4-chloro-N-(3-cyanooxetan-3-yl)-1-(5-(difluoromethyl)-1,3,4-thiadiazol-2-yl)-1H-indazole-6-sulfonamide;
1-(5-(difluoromethyl)-1,3,4-thiadiazol-2-yl)-4-(dimethylamino)-N-(3-methyloxetan-3-yl)-1H-indazole-6-sulfonamide;
1-(5-(difluoromethyl)-1,3,4-thiadiazol-2-yl)-N-((2S,3S)-2,3-dimethyloxetan-3-yl)-4-(4-isobutyrylpiperazin-1-yl)-1H-indazole-6-sulfonamide;
1-(5-(difluoromethyl)-1,3,4-thiadiazol-2-yl)-4-(4-isobutyrylpiperazin-1-yl)-N-(oxetan-3-yl)-1H-indazole-6-sulfonamide;
N-(3-cyanooxetan-3-yl)-1-(5-(difluoromethyl)-1,3,4-thiadiazol-2-yl)-4-(4-isobutyrylpiperazin-1-yl)-1H-indazole-6-sulfonamide;
4-(4-isobutyrylpiperazin-1-yl)-N-(3-methyloxetan-3-yl)-1-(5-((methylsulfonyl)methyl)-1,3,4-thiadiazol-2-yl)-1H-indazole-6-sulfonamide;
N-(3-cyano-2-methyloxetan-3-yl)-1-(5-(difluoromethyl)-1,3,4-thiadiazol-2-yl)-4-(4-isobutyrylpiperazin-1-yl)-1H-indazole-6-sulfonamide;
1-(5-(difluoromethyl)-1,3,4-thiadiazol-2-yl)-4-(4-(isopropylsulfonyl)piperazin-1-yl)-N-(3-methyloxetan-3-yl)-1H-indazole-6-sulfonamide;
4-(4-(cyclopentanecarbonyl)piperazin-1-yl)-1-(5-(difluoromethyl)-1,3,4-thiadiazol-2-yl)-N-(3-(fluoromethyl)oxetan-3-yl)-1H-indazole-6-sulfonamide;
1-(5-(difluoromethyl)-1,3,4-thiadiazol-2-yl)-N-(3-methyloxetan-3-yl)-4-(4-(pyrrolidine-1-carbonyl)piperazin-1-yl)-1H-indazole-6-sulfonamide;
1-(5-(difluoromethyl)-1,3,4-thiadiazol-2-yl)-N-(3-(fluoromethyl)oxetan-3-yl)-4-(4-(pyrrolidine-1-carbonyl)piperazin-1-yl)-1H-indazole-6-sulfonamide;
N-(2,2-difluoroethyl)-4-(1-(5-(difluoromethyl)-1,3,4-thiadiazol-2-yl)-6-(N-(3-methyloxetan-3-yl)sulfamoyl)-1H-indazol-4-yl)-N-methylpiperazine-1-carboxamide;
N-(3-cyanooxetan-3-yl)-1-(5-(difluoromethyl)-1,3,4-thiadiazol-2-yl)-4-(4-(pyrrolidine-1-carbonyl)piperazin-1-yl)-1H-indazole-6-sulfonamide;
N-(3-cyanooxetan-3-yl)-4-(4-(cyclopropanecarbonyl)piperazin-1-yl)-1-(5-(difluoromethyl)-1,3,4-thiadiazol-2-yl)-1H-indazole-6-sulfonamide;
N-(3-cyanooxetan-3-yl)-4-(4-(cyclopentanecarbonyl)piperazin-1-yl)-1-(5-(difluoromethyl)-1,3,4-thiadiazol-2-yl)-1H-indazole-6-sulfonamide;
4-(6-(N-(3-cyanooxetan-3-yl)sulfamoyl)-1-(5-(difluoromethyl)-1,3,4-thiadiazol-2-yl)-1H-indazol-4-yl)-N-(2,2-difluoroethyl)-N-methylpiperazine-1-carboxamide;
N-(3-(fluoromethyl)oxetan-3-yl)-4-(4-isobutyrylpiperazin-1-yl)-1-(5-methyl-1,3,4-thiadiazol-2-yl)-1H-indazole-6-sulfonamide;
1-(5-cyclopropyl-1,3,4-thiadiazol-2-yl)-N-(3-(fluoromethyl)oxetan-3-yl)-4-(4-isobutyrylpiperazin-1-yl)-1H-indazole-6-sulfonamide;
N-(3-(fluoromethyl)oxetan-3-yl)-4-(4-isobutyrylpiperazin-1-yl)-1-(1,3,4-thiadiazol-2-yl)-1H-indazole-6-sulfonamide;
4-(4-isobutyrylpiperazin-1-yl)-1-(5-methyl-1,3,4-thiadiazol-2-yl)-N-(3-methyloxetan-3-yl)-1H-indazole-6-sulfonamide;
4-(4-isobutyrylpiperazin-1-yl)-N-(3-methyloxetan-3-yl)-1-(1,3,4-thiadiazol-2-yl)-1H-indazole-6-sulfonamide;
N-(3-(fluoromethyl)oxetan-3-yl)-4-(4-isobutyrylpiperazin-1-yl)-1-(5-vinyl-1,3,4-thiadiazol-2-yl)-1H-indazole-6-sulfonamide;
1-(5-(difluoromethyl)-1,3,4-thiadiazol-2-yl)-N-(3-methyloxetan-3-yl)-4-(4-methylpiperazin-1-yl)-1H-indazole-6-sulfonamide;

1-(5-(difluoromethyl)-1,3,4-thiadiazol-2-yl)-N-(3-methyloxetan-3-yl)-1H-indazole-6-sulfonamide;

4-chloro-N-(3-cyanooxetan-3-yl)-1-(5-(difluoromethyl)-1,3,4-thiadiazol-2-yl)-1H-indazole-6-sulfonamide;

4-chloro-1-(5-(difluoromethyl)-1,3,4-thiadiazol-2-yl)-N-(2,3-dimethyloxetan-3-yl)-1H-indazole-6-sulfonamide;

1-methyl-N-(3-methyloxetan-3-yl)-1H-indazole-6-sulfonamide;

1-(5-(difluoromethyl)-1,3,4-thiadiazol-2-yl)-4-methoxy-N-(3-methyloxetan-3-yl)-1H-indazole-6-sulfonamide;

4-(4-(cyclopentanecarbonyl)piperazin-1-yl)-1-(5-(difluoromethyl)-1,3,4-thiadiazol-2-yl)-N-(3-methyloxetan-3-yl)-1H-indazole-6-sulfonamide;

N-(2,2-difluoroethyl)-4-(1-(5-(difluoromethyl)-1,3,4-thiadiazol-2-yl)-6-(N-(3-(fluoromethyl)oxetan-3-yl)sulfamoyl)-1H-indazol-4-yl)-N-methylpiperazine-1-carboxamide;

(S)-1-(5-(difluoromethyl)-1,3,4-thiadiazol-2-yl)-4-(4-isobutyryl-3-methylpiperazin-1-yl)-N-(3-methyloxetan-3-yl)-1H-indazole-6-sulfonamide;

4-(4-isobutyrylpiperazin-1-yl)-N-(3-methyloxetan-3-yl)-1-(5-vinyl-1,3,4-thiadiazol-2-yl)-1H-indazole-6-sulfonamide; and 1-(5-bromo-1,3,4-thiadiazol-2-yl)-4-(4-isobutyrylpiperazin-1-yl)-N-(3-methyloxetan-3-yl)-1H-indazole-6-sulfonamide.

51. A pharmaceutical composition comprising a compound of claim 1, or a pharmaceutically acceptable salt thereof, and at least one pharmaceutically acceptable carrier.

52. A method of inhibiting the activity of PARG comprising contacting a compound of claim 1, or a pharmaceutically acceptable salt thereof, with said PARG.

53. The method of claim 52, wherein the contacting is contacting in vitro.

54. A method of treating a disease or disorder in a patient in need of treatment comprising administering to said patient a therapeutically effective amount of a compound of claim 1, or a pharmaceutically acceptable salt thereof, wherein the disease or disorder is characterized by overexpression or increased activity of PARG.

55. The method of claim 54, wherein the disease or disorder is cancer.

56. The method of claim 55, wherein the cancer is a stress-dependent cancer.

57. The method of claim 55, wherein said cancer is selected from lung cancer, colon cancer, breast cancer, ovarian cancer, prostate cancer, liver cancer, pancreatic cancer, brain cancer, skin cancer, bladder cancer, esophageal cancer, head and neck cancer, kidney cancer, rectal cancer, stomach cancer, thyroid cancer, uterine cancer, mantle cell lymphoma, and renal cell carcinoma.

* * * * *